United States Patent
Duffy et al.

(10) Patent No.: US 8,318,183 B2
(45) Date of Patent: Nov. 27, 2012

(54) *PLASMODIUM* LIVER STAGE ANTIGENS

(75) Inventors: Patrick Duffy, Seattle, WA (US); Stefan H. I. Kappe, Seattle, WA (US); Urszula Krzych, Washington, DC (US); Donald G. Heppner, Vienna, VA (US); Lawrence W. Bergman, Landsdale, PA (US); Vladislav A. Malkov, Seattle, WA (US); Alice Tarun, Shoreline, WA (US); Jason P. Wendler, Lincoln, NE (US); Igor Bacik, Rockville, MD (US)

(73) Assignees: Seattle Biomedical Research Institute, Seattle, WA (US); The United States of America, as Represented by the Secretary of the Army, on Behalf of the Walter Reed Army Institute of Research, Washington, DC (US); Philadelphia Health & Education Corporation, Philadelphia, PA (US)

( * ) Notice: Subject to any disclaimer, the term of this patent is extended or adjusted under 35 U.S.C. 154(b) by 0 days.

(21) Appl. No.: 12/722,439

(22) Filed: Mar. 11, 2010

(65) Prior Publication Data

US 2010/0166794 A1 Jul. 1, 2010

Related U.S. Application Data

(62) Division of application No. 12/088,065, filed as application No. PCT/US2006/037851 on Sep. 29, 2006, now Pat. No. 7,722,889.

(60) Provisional application No. 60/722,254, filed on Sep. 30, 2005, provisional application No. 60/748,382, filed on Dec. 8, 2005.

(51) Int. Cl.
*A61K 39/015* (2006.01)
*C12P 21/06* (2006.01)
*C07H 21/04* (2006.01)

(52) U.S. Cl. .............. 424/268.1; 424/265.1; 424/191.1; 435/69.1; 536/23.1; 536/23.7

(58) Field of Classification Search .................... None
See application file for complete search history.

(56) References Cited

FOREIGN PATENT DOCUMENTS

WO 92/05193 A1 4/1992

OTHER PUBLICATIONS

Accession: JQ2124; dated 1994.*
"Hypothetical Protein," Database Accession No. Q8ILR5, Database UniProt EBI, Mar. 1, 2003 [retrieved Nov. 1, 2007], 2 pages.
Lederman, S., et al., "A Single Amino Acid Substitution in a Common African Allele of the CD4 Molecule Ablates Binding of the Monoclonal Antibody, OKT4," Molecular Immunology 28(11):1171-1181, Nov. 1991.
Li, C.H., et al., "β-Endorphin Omission Analogs: Dissociation of Immunoreactivity From Other Biological Activities," PNAS (Proceedings of the National Academy of Sciences of the United States of America) 77(6):3211-3214, Jun. 1980.
Matuschewski, K., "Vaccine Development Against Malaria," Current Opinions in Immunology 18(4):449-457, Aug. 2006.
Gardner, M.J., et al. "Genome Sequence of the Human Malaria Parasite *Plasmodium falciparum*," Nature 419(6906):498-511, Oct. 2002.
McAndrew, M.B., et al., "Characterisation of the Gene Encoding an Unusually Divergent TATA-Binding Protein (TBP) From the Extremely A+T-Rich Human Malaria Parasite *Plasmodium falciparum*," Gene 124(2):165-171, Feb. 1993.
European Search Report mailed Oct. 11, 2010, issued in corresponding European Application No. 10171776.7, filed Sep. 29, 2006, 4 pages.

* cited by examiner

*Primary Examiner* — Padma Baskar
(74) *Attorney, Agent, or Firm* — Christensen O'Connor Johnson Kindness PLLC

(57) ABSTRACT

The invention provides isolated liver stage *Plasmodium* polypeptides comprising an amino acid sequence selected from the group consisting of SEQ ID NOs:1-48 and immunogenic derivatives thereof. The invention also provides isolated nucleic acid molecules encoding the liver stage *Plasmodium* polypeptides of the invention, compositions comprising one or more liver stage *Plasmodium* polypeptides of the invention, methods for inducing an immune response against the liver stage *Plasmodium* polypeptides, and methods for treating and diagnosing liver stage malaria.

5 Claims, No Drawings

PLASMODIUM LIVER STAGE ANTIGENS

CROSS-REFERENCES TO RELATED APPLICATIONS

This application is a divisional of U.S. application Ser. No. 12/088,065, filed Jul. 30, 2008, now issued as U.S. Pat. No. 7,722,889, which is a national phase of International Application No. PCT/US2006/037851, filed Sep. 29, 2006, which claims the benefit of U.S. Provisional Application No. 60/722,254, filed Sep. 30, 2005, and U.S. Provisional Application No. 60/748,382, filed Dec. 8, 2005, all of which are incorporated herein by reference.

STATEMENT OF GOVERNMENT LICENSE RIGHTS

This invention was made by employees of the United States Army Medical Research and Material Command, which is an agency of the United States Government. The Government has certain rights in this invention.

FIELD OF THE INVENTION

This invention relates to proteins that are specifically expressed by liver stage *Plasmodium* parasites and their use in the prevention, diagnosis, and treatment of malaria.

BACKGROUND

Malaria has a tremendous impact on human health, killing millions annually, and the disease is a major impediment for social and economic development of nations in malaria-endemic areas, particularly in sub-Saharan Africa (Sachs & Malaney, *Nature* 415:680-685, 2002). Malaria infection begins when the Anopheline female injects infective sporozoites into the mammalian host. Sporozoites travel through different cells before settling into their final host hepatocyte. The sporozoite moves into a parasitophorous vacuole created by invagination of the hepatocyte plasma membrane. Inside this compartment, the sporozoite transforms into a liver stage. The liver stage grows rapidly and undergoes multiple rounds of nuclear division. The mature liver stage releases thousands of merozoites that will establish red blood cell infection. Liver stages are predicted to express many different proteins, some possibly unique to this stage, but only a few of those unique molecules have been identified so far. Identification of liver stage-specific molecules is important because the infected hepatocyte has been established as the primary target of the sterile protective immune response in the radiation attenuated sporozoite vaccine model and recently in the genetically attenuated sporozoite vaccine model (reviewed in Matuschewski, *Curr. Op. Immunol.* 18:1-9, 2006). In addition, liver stage molecules that can be detected in human diagnostic sample may be useful for diagnosing early stage malaria.

There is a need in the art for vaccines that protect against malaria infection and disease. There is also a need in the art for diagnostic markers for malaria. The present invention addresses these needs and others.

SUMMARY

One aspect of the invention provides isolated liver stage *Plasmodium* polypeptides. In some embodiments, the isolated liver stage *Plasmodium* polypeptides comprise an amino acid sequence selected from the group consisting of SEQ ID NOs:1-48. In some embodiments, the liver stage *Plasmodium* proteins are preferentially targeted by immune responses associated with protection from *Plasmodium* infection. The isolated liver stage *Plasmodium* polypeptides of the invention may be recombinant or synthetic polypeptides. In some embodiments, the polypeptides of the invention are immunogenic derivatives of polypeptides comprising an amino acid sequence selected from the group consisting of SEQ ID NOs:1-48. Such immunogenic derivatives include, but are not limited to, peptides comprising an amino acid sequence selected from SEQ ID NOs:49-52.

Another aspect of the invention provides isolated nucleic acid molecules encoding the liver stage *Plasmodium* polypeptides of the invention. Thus, some embodiments provide an isolated nucleic acid molecule encoding a polypeptide comprising an amino acid sequence selected from the group consisting of SEQ ID NOs:1-48 and immunogenic derivatives thereof.

A further aspect of the invention provides compositions comprising one or more liver stage *Plasmodium* polypeptides of the invention and a pharmaceutically acceptable carrier. Thus, some embodiments provide an immunogenic composition comprising a liver stage *Plasmodium* polypeptide and a pharmaceutically acceptable carrier, wherein the liver stage *Plasmodium* polypeptide comprises an amino acid sequence selected from the group consisting of SEQ ID NOs:1-48 and immunogenic derivatives thereof. In some embodiments, the compositions of the invention are immunogenic compositions for inducing immune responses, such as vaccine compositions.

In another aspect, the invention provides methods for inducing an immune response against *Plasmodium* parasites, comprising administering an immunogenic composition comprising an effective amount of one or more liver stage *Plasmodium* polypeptides of the invention. Thus, in some embodiments the invention provides a method for inducing an immune response in a mammalian subject against *Plasmodium* falciparum, comprising administering to a mammalian subject a composition comprising an effective amount of at least one liver stage *Plasmodium* polypeptide selected from the group consisting of SEQ ID NOs:1-48 and immunogenic derivatives thereof.

Yet another aspect of the invention provides methods for treating a mammalian subject in need thereof, comprising administering to a mammalian subject in need thereof an immunogenic composition comprising an effective amount of one or more liver stage *Plasmodium* polypeptides of the invention. Thus, in some embodiments, the invention provides a method for treating a human subject in need thereof, comprising administering to a human subject an immunogenic composition comprising at least one isolated polypeptide selected from the group consisting of SEQ ID NOs:1-48 and immunogenic derivatives thereof.

In addition, the invention provides genetically attenuated sporozoites from which at least one gene coding for a liver stage polypeptides of the invention has been eliminated. Thus, in some embodiments, the invention provides genetically attenuated *Plasmodium* sporozoites lacking a gene coding for a liver stage polypeptide selected from the group consisting of SEQ ID NOs:1-48.

The invention also provides expression vectors encoding the liver stage *Plasmodium* polypeptides of the invention, host cells comprising such expression vectors, antibodies that bind specifically to the liver stage *Plasmodium* polypeptides of the invention or immunogenic derivatives thereof, and diagnostic assays for detecting the presence of the liver stage *Plasmodium* polypeptides of the invention or nucleic acid molecules encoding them.

DETAILED DESCRIPTION OF THE PREFERRED EMBODIMENT

In one aspect, the invention provides novel proteins expressed by liver stage *Plasmodium* parasites. Some of these proteins are expressed specifically in liver stage parasites, as shown in EXAMPLES 1-3 (see Tables 2 and 3, SEQ ID NOs:1-28). Some of the liver stage proteins of the invention are expressed both in sporozoites and liver stage parasites, but are expressed at significantly lower levels in blood stage parasites, as shown in EXAMPLE 3 (see Table 4, SEQ ID NOs:29-48).

In some embodiments, the liver stage *Plasmodium* proteins are preferentially targeted by immune responses associated with protection from *Plasmodium* infection. For example, the liver stage proteins or immunogenic derivatives thereof may be antigenic targets of T cell immunity that correlates with protection, as shown in EXAMPLE 4. The liver stage *Plasmodium* proteins of the invention may also be preferentially recognized by sera from subjects that have acquired immunity to *Plasmodium* infection than by sera from pre-immune or non-immune subjects (see, e.g., Doolan et al., *Proc. Natl. Acad. Sci. USA* 100(17):9952-9957, 2003; Sundaresh et al., *Bioinformatics* 22(14):1760-1766, 2006).

Thus, one aspect of the invention provides isolated liver stage *Plasmodium* polypeptides. In some embodiments, the isolated liver stage *Plasmodium* polypeptides comprise an amino acid sequence selected from the group consisting of SEQ ID NOs:1-48. The sequences of these proteins, the nucleotide sequences encoding them, and annotation information may be obtained from the *Plasmodium* Genome Database (http://plasmodb.org/; Kissinger et. al., *Nature* 419:490-492, 2002) under the protein/gene ID numbers provided in Tables 1-4, and are herein incorporated by reference. The isolated liver stage *Plasmodium* polypeptides of the invention may be recombinant or synthetic full-length polypeptides, or immunogenic derivatives thereof, as further described below. Accordingly, some embodiments of the invention provide an isolated *Plasmodium* polypeptide comprising an amino acid sequence selected from the group consisting of SEQ ID NOs: 1-48 and immunogenic derivatives thereof. For example, the isolated polypeptide may be a *P. falciparum* polypeptide selected from the group consisting of SEQ ID NOs:11-44 and immunogenic derivatives thereof.

As used herein, the term "polypeptide" refers to a polymer of amino acids and does not refer to a specific length of the product; thus, peptides, oligopeptides, and proteins are included within the definition of polypeptide. This term also includes post-expression modifications of the polypeptide, for example, glycosylations, acetylations, phosphorylations, and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The liver stage *Plasmodium* polypeptides of the invention may be full-length polypeptides, immunogenic derivatives, or domains of full-length polypeptides, or immunogenic variants thereof. As used herein, the term "immunogenic" refers to the ability of a polypeptide to elicit a humoral and/or cellular immune response, whether alone or when linked to a carrier, in the presence or absence of an adjuvant. Thus, an immunogenic portion of a full-length liver stage *Plasmodium* polypeptide of the invention refers to a portion of the full-length polypeptide that is capable of eliciting an immune response against the corresponding full-length polypeptide. The term "immunogenic derivative or domain" encompasses any polypeptide that includes at least 5 to 8 amino acids (such as, for example, 10 to 50 amino acids, 30 to 200 amino acids, or 100 to 500 amino acids) and that is capable of inducing an immune response to the full-length polypeptide. Thus, immunogenic derivative include truncated forms, epitopes, or other derivatives of full-length polypeptides.

The term "epitope" refers to a linear array of 3 to 10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g., cysteines involved in disulfide bonding, glycosylation sites, etc.). A conformational epitope may also be formed by two or more essential regions of subunits of a homo-oligomer or hetero-oligomer.

Other immunogenic derivatives may be prepared by the addition, deletion, substitution, or rearrangement of amino acids or by chemical modifications thereof. Exemplary epitopes of liver stage *Plasmodium* polypeptides are described in EXAMPLES 1 and 4. Thus, immunogenic derivatives include, but are not limited to, peptides comprising an amino acid sequence selected from SEQ ID NOs:49-52.

Methods of predicting immunogenic regions in a polypeptide are well known in the art. For example, a polypeptide sequence may be analyzed by using several algorithms, including prediction of hydrophilicity according to the Kyte-Doolittle method, surface probability according to the Emini method, and antigenicity according to the Jameson-Wolf method (for example, the Protean software, available from DNASTAR, http://www.dnastar.com/). Other epitope prediction approaches are known in the art (see, e.g., Moise & De Groot, *Nat. Biotechnol.* 24(7):791-792, 2006).

In some embodiments, the immunogenic derivatives of the liver stage *Plasmodium* proteins of the invention include 5 to 10, 10 to 50, 20 to 200, 40 to 300, or 100 to 600 contiguous amino acids of a full-length polypeptide comprising an amino acid sequence selected from the group consisting of SEQ ID NOs:1-48. Exemplary immunogenic derivatives of the polypeptides of the invention are described in EXAMPLES 1 and 4 and include, but are not limited to, peptides comprising an amino acid sequence selected from SEQ ID NOs:49-52, polypeptides comprising amino acids 59-300 of SEQ ID NO:13, amino acids 72-230 of SEQ ID NO:14, amino acids 1-545 or amino acids 660-1073 of SEQ ID NO:17, amino acids 28-184 of SEQ ID NO:18, amino acids 151-326 of SEQ ID NO:20, amino acids 6-529 or amino acids 587-842 of SEQ ID NO:21, amino acids 1-346 of SEQ ID NO:23, amino acids 92-578 of SEQ ID NO:25, amino acids 76-130 of SEQ ID NO:30, amino acids 415-885 of SEQ ID NO:31 amino acids 84-229 of SEQ ID NO:33, amino acids 22-291 of SEQ ID NO:34, amino acids 208-512 or amino acids 716-1026 of SEQ ID NO:35, amino acids 1-135 of SEQ ID NO:36, amino acids 181-306 or amino acids 47-457 of SEQ ID NO:39, amino acids 585-1018 of SEQ ID NO:40, amino acids 230-843 of SEQ ID NO:41, amino acids 236-683 of SEQ ID NO:44, amino acids 26-182 of SEQ ID NO:45, and amino acids 23-459 or amino acids 488-813 of SEQ ID NO:48.

Immunogenic derivatives of the polypeptides of the invention, which may be useful in the preparation of vaccines, may be prepared by expression of the appropriate gene fragments or by peptide synthesis, using methods well known in the art, as further described below. Exemplary methods for recombinant expression of immunogenic derivatives of the invention are provided in EXAMPLE 6.

An immunogenic derivative may be a fusion polypeptide containing additional sequences encoding one or more epitopes for other *Plasmodium* immunogens, or other non-*Plasmodium* immunogens. Alternatively, the immunogenic derivative of the invention may be fused to a carrier polypeptide (such as Hepatitis B surface or core antigen) or to another carrier that has immunostimulating properties, as in the case of an adjuvant, or that otherwise enhances the immune response to the protein or derivative thereof, or that is useful in expressing, purifying, or formulating the protein or derivative thereof. The liver stage *Plasmodium* proteins or immunogenic derivatives thereof may be chemically conjugated to a macromolecule using a conventional linking agent such as glutaraldehyde (Geerlings et al., *J. Immunol. Methods* 106:239-244, 1988).

In some embodiments, the liver stage *Plasmodium* polypeptides of the invention include immunogenic derivatives with more than 80% amino acid sequence identity (such as more than 90% sequence identity, more than 95% amino acid sequence identity, or more than 99% sequence identity) to the sequences defined in SEQ ID NOs:1-48. The terms "identical" or percent "identity" in the context of two or more amino acid sequences, refer to two or more sequences or subsequences that are the same or have a specified percentage of amino acid residues that are the same, when compared and aligned for maximum correspondence over a comparison window, as measured using one of the following sequence comparison algorithms or by manual alignment and visual inspection.

It is recognized that amino acid positions that are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. The scoring of conservative substitutions can be calculated according to, for example, the algorithm of Meyers & Millers, *Computer Applic. Biol. Sci.* 4:11-17, 1988.

A "comparison window" refers to a segment of contiguous positions, such as between about 25 and about 600 positions, or between about 50 to 200 positions, or between about 100 and 150 positions, over which a sequence may be compared to a reference sequence of the same number of contiguous positions after the two sequences are optimally aligned. Methods of alignment of sequences for comparison are well known in the art. Optimal alignment of sequences for comparison can be conducted, for example, by a local homology algorithm (Smith & Waterman, *Adv. Appl. Math.* 2:482, 1981), by a global alignment algorithm (Needleman & Wunsch, *J. Mol. Biol.* 48:443, 1970), by search for similarity methods (Pearson & Lipman, *Proc. Natl. Acad. Sci. U.S.A.* 85:2444, 1988; Altschul et al., *Nucl. Acids Res.* 25(17):3389-402, 1997), by computerized implementations of these algorithms (e.g., GAP, BESTFIT, FASTA, and BLAST in the Wisconsin Genetics Software Package, Genetics Computer Group, 575 Science Dr., Madison, Wis.), typically using the default settings, or by manual alignment and visual inspection (see, e.g., *Current Protocols in Molecular Biology*, Ausubel et al. (eds.), 1994). For example, BLAST protein searches can be performed using the XBLAST program, score=50, wordlength=3 to obtain amino acid sequences that are more than 80% identical to the amino acid sequence of SEQ ID NOs:1-48.

One example of a useful algorithm implementation is PILEUP. PILEUP creates a multiple sequence alignment from a group of related sequences using progressive pairwise alignments. It can also plot a dendrogram showing the clustering relationships used to create the alignment. PILEUP uses a simplification of the progressive alignment method of Feng & Doolittle, *J. Mol. Evol.* 35:351-360, 1987. The method used is similar to the method described by Higgins & Sharp, *CABIOS* 5:151-3, 1989. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. A series of such pairwise alignments that includes increasingly dissimilar sequences and clusters of sequences at each iteration produces the final alignment.

In some embodiments, the liver stage *Plasmodium* polypeptides of the invention include variants of the wild-type polypeptides. These variants fall into one or more of three classes: substitutional, insertional, or deletional variants. These variants may be naturally occurring allelic or interspecies variants (e.g., variants from different *P. falciparum* strains) or they may be prepared by site-specific mutagenesis of nucleotides in the DNA encoding protein. Site-specific mutagenesis may be performed using cassette or PCR mutagenesis or other techniques well known in the art to produce DNA encoding the variant and, thereafter, expressing the DNA in recombinant cell culture. Variant target protein fragments having up to about 100-150 amino acid residues may be prepared by in vitro synthesis using established techniques. Conservative substitution tables providing functionally similar amino acids are well known in the art (Henikoff & Henikoff, *Proc. Natl. Acad. Sci. U.S.A.* 89:10915-10919, 1992)

Amino acid substitutions are typically of single residues. Insertions usually will be on the order of from about 1 to about 20 amino acids, although considerably longer insertions may be tolerated. Deletions range from about 1 to about 20 residues, although in some cases, deletions may be much longer. Substitutions, deletions, and insertions or any combinations thereof may be used to arrive at a final derivative.

In some embodiments, the liver stage *Plasmodium* polypeptides of the invention are recombinant polypeptides. The term "recombinant polypeptide" refers to a protein produced by recombinant expression methods such as, for example, in prokaryotic or eukaryotic host cells or in cell-free in vitro expression systems, as described in detail below.

The liver stage *Plasmodium* polypeptides of the invention are typically expressed using an expression vector and purified. Expression vectors may be either self-replicating extra-chromosomal vectors or vectors that integrate into a host genome. Generally, expression vectors include transcriptional and translational regulatory nucleic acid sequences operably linked to the nucleic acid encoding the target protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers. A nucleic acid sequence is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Operably linked DNA sequences may be contiguous or non-contiguous. Methods for linking DNA sequences are well-known in the art and include use of the polymerase chain reaction and ligation. The transcriptional and translational regulatory nucleic acid will generally be appropriate to the host cell used to express the target protein; for example, transcriptional and translational regulatory nucleic acid sequences from *E. coli* are preferably used to express the target protein in *E. coli*.

Numerous types of appropriate expression vectors, and suitable regulatory sequences are known in the art for a variety of host cells. Methods for expressing polypeptides are well known in the art (e.g., Sambrook et al., *Molecular Cloning: A Laboratory Manual*, 2nd ed., Vol. 1-3, Cold Spring Harbor Laboratory, 1989; Berger and Kimmel, *Guide to Molecular Cloning Techniques, Methods in Enzymology*, Vol. 152, Academic Press, Inc., San Diego, Calif., 1987; Ausubel et al., *Current Protocols in Molecular Biology*, John Wiley & Sons, Inc., N.Y., 1995).

In general, the transcriptional and translational regulatory sequences may include, but are not limited to, promoter sequences, ribosomal binding sites, transcriptional start and stop sequences, translational start and stop sequences, and enhancer or activator sequences. Promoter sequences encode either constitutive or inducible promoters. The promoters may be either naturally occurring promoters or hybrid promoters. Hybrid promoters, which combine elements of more than one promoter, are well known in the art.

An expression vector may comprise additional elements. For example, the expression vector may have two replication systems, thus allowing it to be maintained in two organisms, for example, in mammalian or insect cells for expression and in a prokaryotic host for cloning and amplification. Furthermore, for integrating expression vectors, the expression vector contains at least one sequence homologous to a sequence in the host cell genome and, preferably, two homologous sequences that flank the expression construct. The integrating vector may be directed to a specific locus in the host cell by selecting the appropriate homologous sequence for inclusion in the vector. Constructs for integrating vectors are well known in the art.

In addition, an expression vector may include a selectable marker gene to allow the selection of transformed host cells. Selection genes are well known in the art and will vary depending on the host cell used.

The liver stage *Plasmodium* polypeptides of the invention may be produced by culturing a host cell transformed with an expression vector containing nucleic acid encoding a liver stage *Plasmodium* polypeptide, under the appropriate conditions to induce or cause expression of the liver stage *Plasmodium* polypeptide. The conditions appropriate for protein expression will vary with the choice of the expression vector and the host cell, and may be easily determined by one skilled in the art using routine experimentation. For example, the growth and proliferation of the host cell may be optimized for the use of constitutive promoters in the expression vector, and appropriate growth conditions for induction are provided for use of an inducible promoter. In addition, in some embodiments, the timing of the harvest is important, for example, when using baculoviral systems. One of skill in the art will recognize that the coding sequences may be optimized for expression in the selected host cells.

Appropriate host cells include yeast, bacteria, archaebacteria, fungi, insect cells, and animal cells, including mammalian cells (such as human cells and cells lines). Thus, host cells include, but are not limited to, *Drosophila melanogaster* cells, *Tetrahymena, Saccharomyces cerevisiae* and other yeasts, *E. coli, Bacillus subtilis*, Sf9 cells, C129 cells, 293 cells, *Neurospora*, BHK, CHO, COS, HeLa cells, Hep G2 cells, THP1 cell line (a macrophage cell line), and human embryonic kidney cell lines (e.g., HEK293).

In some embodiments, the liver stage *Plasmodium* polypeptides are expressed in mammalian cells. Mammalian expression systems are well known in the art and include retroviral systems. Promoters from viral genes are frequently used in mammalian expression systems, because the viral genes are often highly expressed and have a broad host range. Examples include the SV40 early promoter, the mouse mammary tumor virus LTR promoter, the adenovirus major late promoter, the herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenylation signals include those derived from SV40.

Nucleic acid molecules encoding the liver stage *Plasmodium* polypeptides of the invention may be cloned using standard molecular biological methods, including DNA amplification methods such as the polymerase chain method (PCR) (see e.g., Sambrook et al., *Molecular Cloning: A Laboratory Manual,* 2nd ed., Cold Spring Harbour, N.Y., 1989; Berger and Kimmel, *Methods in Enzymology.*, Vol. 152: *Guide to Molecular Cloning Techniques*, Academic Press, Inc., San Diego, Calif., 1987; Co et al., *J. Immunol.* 148:1149, 1992). Thus, for example, a nucleic acid molecule encoding a liver stage *P. falciparum* polypeptide may be PCR-amplified using a sense primer containing one restriction site and an antisense primer containing another restriction site. This will produce a nucleic acid encoding the desired sequence or subsequence having terminal restriction sites. This nucleic acid can then easily be ligated into a vector having appropriate corresponding restriction sites. Suitable PCR primers may be readily chosen by one of skill in the art based on the sequence to be expressed. Appropriate restriction sites can also be added by site-directed mutagenesis (see Gillman & Smith, *Gene* 8:81-97, 1979; Roberts et al., *Nature* 328:731-4, 1987).

The methods of introducing exogenous nucleic acids into host cells are well known in the art and will vary with the host cell used. Suitable techniques include, but are not limited to, dextran-mediated transfection, calcium phosphate precipitation, polybrene mediated transfection, protoplast fusion, electroporation, viral infection, encapsulation of the nucleic acids in liposomes, and direct microinjection of nucleic acids into nuclei.

In some embodiments, the liver stage *Plasmodium* polypeptides of the invention are expressed in bacterial systems. Bacterial expression systems are well known in the art.

Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally-occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the expressed protein in bacteria. The expressed protein may be secreted into the growth medium (gram-positive bacteria) or into the periplasmic space, located between the inner and outer membrane of the cell (gram-negative bacteria). A bacterial expression vector may also include an epitope tag providing for affinity purification of the target protein. The bacterial expression vector may also include a selectable marker gene to allow for the selection of bacterial strains that have been transformed. Suitable selectable markers include genes that render transformed bacteria resistant to drugs such as ampicillin, chloramphenicol, erythromycin, kanamycin, neomycin and tetracycline. Selectable markers also include biosynthetic genes, such as those in the histidine, tryptophan, and leucine biosynthetic pathways. These components are assembled into expression vectors. Expression vectors for bacteria are well known in the art and include vectors for *Bacillus subtilis*, *E. coli, Streptococcus cremoris*, and *Streptococcus lividans*, among others. The bacterial expression vectors are transformed into bacterial host cells using techniques well known in the art such as calcium chloride treatment, electroporation, and others. An exemplary method for expressing placental *P. falciparum* polypeptides of the invention using a bacterial expression system is described in EXAMPLE 5.

The liver stage *Plasmodium* polypeptides of the invention may also be produced in insect cells. Expression vectors for the transformation of insect cells, and in particular, baculovirus-based expression vectors, are well known in the art. The liver stage *Plasmodium* polypeptides may also be produced in yeast cells. Yeast expression systems are well known in the art and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The liver stage *Plasmodium* polypeptides of the invention may be produced in a cell-free expression system in vitro using an expression vector containing nucleic acid encoding a liver stage *Plasmodium* polypeptide, under the appropriate conditions to induce or cause expression of the liver stage *Plasmodium* polypeptide in vitro. Cell-free in vitro expression systems are well known in the art. If necessary, conditions for co-translational sulfide-sulfide exchange and correct folding of disulfide bonds can be customized for the cell-free system (Lyubov et al., *Nat. Biotechnol.* 15(1):79-84, 1993). An exemplary method for expressing placental *P. falciparum* polypeptides of the invention using a cell-free in vitro expression system is described in EXAMPLE 5.

Historically, expression of *P. falciparum* proteins in heterologous organisms was found to be a significant challenge. The *P. falciparum* genome is one of the most A+T-rich of any genome known. As a consequence, *P. falciparum* uses a different repertoire of codons, which may result in low levels of expression in heterologous systems. In addition, in *Saccharomyces cerevisiae* or *Pichia pastoris* certain A+T-rich stretches of sequence can act as polyadenylation or transcription termination signals, resulting in the expression of low-level or truncated mRNA (Romanos et al., *Nucl. Acids Res.* 19(7):1461-7, 1991).

Advances made in the last seven years have drastically changed the situation for the better. What used to be a challenging and low success rate effort for some *Plasmodium* proteins is now a routine, mainstream molecular biological exercise. For example, *Plasmodium* coding sequences with an appropriate codon usage and increased G+C content may be synthesized. The principles of creation of synthetic genes are explicitly described in (Withers-Martinez et al., *Protein Eng.* 12(12):1113-20, 1999). These principles include: (1) decreasing the overall A+T content with the elimination of potential transcription termination signals, (2) eliminating palindromic sequences conducive to stable hairpins, and (3) minimizing tandem or inverted repeats (<10 by in length) that are likely to give rise to non-specific priming. Additionally, at the synthesis step putative N-linked glycosylation sites are removed to mimic *P. falciparum* polypeptide structures lacking any glycosylation.

There is a long list of *P. falciparum* proteins successfully expressed in *Pichia pastoris* (see, e.g., Withers-Martinez et al., *Protein Eng.* 12(12):1113-1120, 1999; Milek et al., *Vaccine* 18(14):1402-11, 2000; Brady et al., *Protein Expr. Purif.* 23(3):468-475, 2001; Kocken et al., *Infect. Immun.* 70(8): 4471-4476, 2002; Zhang et al., *J. Biol. Chem.* 277(51): 49767-49775, 2002; Yadava & Ockenhouse, *Infect. Immun.* 71(9):4961-4969, 2003; Wang et al., *Biotechnol. Bioeng.* 90(7):838-847, 2005; Pan et al., *J. Immunol.* 172(10):6167-6174, 2004; Tsai et al., *J. Biotechnol.* 121(4):458-470, 2006). Moreover, malarial proteins produced in *P. pastoris* can be purified to produce clinical grade products (see, e.g., Malkin et al., *Infect. Immun.* 73(6):3677-3685, 2005). A detailed protocol describing how to clone and express protein in *Pichia pastoris* is available from Invitrogen as a part of Easy-Select *Pichia* Expression Kit, product #K1740-01. This commercially available kit facilitates the whole expression procedure starting with a DNA sequence and finishing with the expressed protein. An exemplary method for expressing liver stage *Plasmodium* polypeptides of the invention in *P. pastoris* is described in EXAMPLE 6.

Bacterial expression is another promising approach to produce clinical grade recombinant *Plasmodium* proteins for potential vaccine applications (see, e.g., Dutta et al., *Infect. Immun.* 70(6):3101-3110, 2006; Shimp et al., *Protein Expr. Purif.*, [Epub ahead of print], Jun. 27, 2006; Hillier et al., *Infect. Immun.* 73(4):2109-2115, 2005; Darko et al., *Infect. Immun.* 73(1):287-297, 2005; Nardin et al., *Infect. Immun.* 73(11):6519-6527, 2004; Chen et al., *Vaccine* 22(21-22): 2701-2712, 2004; Zhou et al., *Protein Expr. Purif.* 34(1):87-94, 2004; Singh et al., *Infect. Immun.* 71(12):6766-6774, 2003). Similar to yeast expression, re-synthesis of the gene to optimize codon representation improved the yield and solubility of recombinant proteins (Hillier et al., *Infect. Immun.* 73(4):2109-2115, 2005). Refolding of the recombinant proteins may be used to produce functional epitopes.

The liver stage *Plasmodium* polypeptides of the invention and immunogenic derivatives thereof may also be made as a fusion proteins, using techniques that are well known in the art. For example, a liver stage *Plasmodium* polypeptides may be made as a fusion protein to increase expression or to link it with a tag polypeptide that provides an epitope to which an anti-tag antibody can selectively bind. An epitope tag is generally placed at the amino-or carboxyl-terminus of the target protein. The presence of such epitope-tagged forms of an expressed protein can be detected using an antibody against the tag polypeptide. Thus, the epitope tag enables the expressed proteins to be readily purified by affinity purification using an anti-tag antibody or another type of affinity matrix that binds to the epitope tag. Various tag polypeptides and their respective antibodies are well known in the art. Exemplary tags include, but are not limited to, poly-histidine (poly-his) or poly-histidine-glycine (poly-his-gly) tags; the influenza HA tag polypeptide and its antibody 12CA5 (Field et al., *Mol. Cell. Biol.* 8:2159-2165, 1988); the c-myc tag and the 8F9, 3C7, 6E10, G4, B7, and 9E10 antibodies thereto (Evan et al., *Mol. Cell. Biol.* 5:3610-3616, 1985); and the Herpes Simplex virus glycoprotein D (gD) tag and its antibody (Paborsky et al., *Prot. Eng.* 3(6):547-553, 1990). Other tag polypeptides include the Flag-peptide (Hopp et al., *BioTechnol.* 6:1204-1210, 1988); the KT3 epitope peptide (Martin et al., *Science* 255:192-194, 1992); tubulin epitope peptide (Skinner et al., *J. Biol. Chem.* 266:15163-15166, 1991); and the T7 gene 10 protein peptide tag (Lutz-Freyermuth et al., *Proc. Natl. Acad. Sci. USA* 87:6393-6397, 1990).

Covalent modifications of liver stage *Plasmodium* polypeptides (including immunogenic derivatives thereof) are included within the scope of this invention. One type of covalent modification includes reacting targeted amino acid residues of a protein with an organic derivatizing agent that is capable of reacting with selected side chains or the N- or C-terminal residues of the protein. Derivatization with bifunctional agents is useful, for instance, for crosslinking a protein to a water-insoluble support matrix or surface for use in screening assays. Commonly used crosslinking agents include, but are not limited to, 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

The liver stage *Plasmodium* polypeptides of the invention (including immunogenic derivatives thereof) may be purified or isolated after expression. The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is considered to be substantially purified. The term "purified" denotes that a protein gives rise to essentially one band in an electrophoretic gel. For example, it means that the protein is at least 85% pure, such as at least 95% pure or at least 99% pure. The term "isolated polypeptides" also includes polypeptides in situ within recombinant host cells, since at least one component of the polypeptide natural environment will not be present. Generally, however, an isolated polypeptide is prepared using at least one purification step.

The liver stage *Plasmodium* polypeptides of the invention may be isolated or purified in a variety of ways known to those skilled in the art, depending on what other components are present in the sample. Standard purification methods include electrophoretic, molecular, immunological, and chromatographic techniques including ion exchange, hydrophobic, affinity, and reverse-phase HPLC chromatography, and chromatofocusing. For example, a protein may be purified using an antibody column. Ultrafiltration and diafiltration techniques, in conjunction with protein concentration, are also useful. Suitable purification techniques are standard in the art (see, generally, R. Scopes, *Protein Purification*, Springer-Verlag, N.Y., 1982; Deutcher, *Methods in Enzymology Vol.* 182: *Guide to Protein Purification*, Academic Press, Inc., N.Y., 1990). The degree of purification necessary will vary, depending on the use of the polypeptide. In some instances, no purification may be necessary.

Some embodiments of the invention provide synthetic liver stage *Plasmodium* polypeptides. Polypeptides having up to about 100-150 amino acid residues may be prepared by in vitro synthesis using established techniques. Synthetic polypeptides may be prepared by chemical synthesis (such as solid phase peptide synthesis) using methods known in the art, such as those described in Merrifield et al., *J. Am. Chem. Soc.* 85:2149, 1964; Houghten et al., *Proc. Natl. Acad. Sci. USA* 82:51:32, 1985, and Stewart & Young, *Solid Phase Peptide Synthesis*, Pierce Chem Co., Rockford, Ill, 1984. Such polypeptides may be synthesized with or without a methionine at the amino terminus. Chemically-synthesized liver stage *Plasmodium* proteins of the invention and immunogenic derivatives thereof may be oxidized using methods set forth in these references to form disulfide bridges. Further, peptidomimetics that structurally and/or functionally resemble a polypeptide embodiment may be made. Several approaches to make peptidomimetics that resemble polypeptides have been described (see, e.g., U.S. Pat. Nos. 5,288,707; 5,552,534; 5,811,515; 5,817,626; 5,817,879; 5,821,231; and 5,874,529).

Another aspect of the invention provides isolated nucleic acid molecules encoding the liver stage *Plasmodium* polypeptides of the invention. Thus, some embodiments provide an isolated nucleic acid molecule encoding a polypeptide comprising an amino acid sequence selected from the group consisting of SEQ ID NOs:1-48 and immunogenic derivatives thereof. For example, the nucleic acid molecule may encode a *P. falciparum* polypeptide selected from the group consisting of SEQ ID NOs:11-44 and immunogenic derivatives thereof. The term "isolated nucleic acid molecule" refers to a nucleic acid molecule, DNA, or RNA, that has been removed from its native environment. For example, recombinant nucleic acids contained in a vector are considered isolated for the purposes of the present invention. Examples of isolated nucleic acid molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) encoding liver stage *Plasmodium* polypeptides or immunogenic derivatives thereof. The sequence of these nucleic acid molecules may be different to the any naturally-occurring sequences encoding the liver stage *Plasmodium* polypeptides of the invention but that, due to the degeneracy of the genetic code, still encode a liver stage *Plasmodium* polypeptide. Of course, the genetic code is well known in the art. Thus, it would be routine for one skilled in the art to generate such degenerate variants. Another aspect of the invention provides expression vectors encoding the liver stage *Plasmodium* polypeptides of the invention. Another aspect of the invention provides host cells comprising expression vectors encoding the liver stage *Plasmodium* polypeptides of the invention.

Yet another aspect of the invention provides antibodies that bind specifically to the liver stage *Plasmodium* polypeptides of the invention (including immunogenic derivatives thereof). The term "antibody" refers to an intact immunoglobulin or to an antigen-binding portion of an immunoglobulin that competes with the intact antibody for specific binding to a protein or fragment of a protein of the present invention. Exemplary antibodies include polyclonal, monoclonal, humanized, bispecific, and heteroconjugate antibodies. Antigen-binding portions of an immunoglobulin of the present invention may be produced by various techniques including, but not limited to recombinant DNA techniques and enzymatic or chemical cleavage of intact antibodies.

An "isolated antibody," as used herein, is an antibody that (1) is not associated with components that are naturally associated with it, including other antibodies that accompany it in its native state, (2) is free of other proteins from the same species, (3) is expressed by a cell from a different species, or (4) does not occur in nature. The terms "bind specifically" and "specific binding" refer to the ability of an antibody of the present invention to bind to a first molecular species in preference to binding to other molecular species with which the antibody and first molecular species are admixed. An antibody is said specifically to "recognize" a first molecular species when it can bind specifically to that first molecular species. In the present invention, the first molecular species is a liver stage *Plasmodium* polypeptide of the invention.

Methods of preparing polyclonal antibodies are known to the skilled artisan. Polyclonal antibodies may be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include a full-length liver stage *Plasmodium* polypeptide of the invention or an immunogenic derivative thereof. It may be useful to conjugate the immunizing agent to a protein known to be immunogenic in the mammal being immunized. Examples of such immunogenic proteins include, but are not limited to, keyhole limpet hemocyanin, serum albumin, bovine thyroglobulin, and soybean trypsin inhibitor. Examples of adjuvants that may be used include Freund's complete adjuvant and MPL-TDM adjuvant (monophosphoryl Lipid A, synthetic trehalose dicorynomycolate). The immunization protocol may be selected by one skilled in the art without undue experimentation.

Monoclonal antibodies may be prepared using hybridoma methods, such as those described by Kohler & Milstein, *Nature* 256:495, 1975. In a hybridoma method, a mouse, hamster, or other appropriate host animal is typically immunized with an immunizing agent to elicit lymphocytes that produce or are capable of producing antibodies that will specifically bind to the immunizing agent. Alternatively, the lymphocytes may be immunized in vitro. Suitable immortalized cell lines for the production of monoclonal antibodies are well-known in the art (see, e.g., Goding, *Monoclonal Antibodies: Principles and Practice*, Academic Press, pp. 59-103, 1986; Kozbor, *J. Immunol.* 133:3001, 1984; Brodeur et al., *Monoclonal Antibody Production Techniques and Applications*, Marcel Dekker, Inc., N.Y., pp. 51-63, 1987).

The binding specificity of monoclonal antibodies produced by the hybridoma cells may be determined by immunoprecipitation or by an in vitro binding assay such as radioimmunoassay (RIA) or enzyme-linked immunoabsorbent assay (ELISA). Such techniques and assays are well known in the art. The binding affinity of the monoclonal antibody may, for example, be determined by the Scatchard analysis of Munson & Pollard, *Anal. Biochem.* 107:220, 1980.

The monoclonal antibodies may be isolated or purified from the culture medium or ascites fluid by conventional immunoglobulin purification procedures such as, for example, protein A- sepharose, hydroxylapatite chromatography, gel electrophoresis, dialysis, or affinity chromatography.

The monoclonal antibodies may also be made by recombinant DNA methods, such as those described in U.S. Pat. No. 4,816,567, herein incorporated by reference. Monoclonal antibodies may be isolated using phage display libraries (Hoogenboom & Winter, *J. Mol. Biol.* 227:381, 1991; Marks et al., *J. Mol. Biol.* 222:581, 1991).

The antibodies of the invention may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

The antibodies may also be human or humanized antibodies, bispecific antibodies, or heteroconjugate antibodies. Methods for preparing human or humanized antibodies, bispecific antibodies, or heteroconjugate antibodies are well known in the art and described, for example, in Desnoyers et al., U.S. Pat. No. 7,084,258, herein incorporated by reference.

The antibodies that specifically bind to the liver stage *Plasmodium* polypeptides of the invention may be used in diagnostic assays, for example, to detect the presence of liver stage malaria parasites, or as therapeutic or prophylactic agents for treating or preventing infection by *Plasmodium*. The term "therapeutic agent" refers to an agent capable of treating a malaria infection. The term "prophylactic agent" refers to an agent capable of preventing an infection by *P. falciparum*.

In some embodiments, the antibodies may be used to treat subjects at risk of developing or suffering from malaria by passive immunization. In general, this will comprise administering a therapeutically or prophylactically effective amount of one or more antibodies of the present invention to a subject susceptible to malaria or a subject exhibiting a malaria infection. Any active form of the antibody may be administered, including Fab and F(ab')$_2$ fragments. Treatment of individuals having a malaria infection may comprise the administration of a therapeutically effective amount of antibodies of the present invention. The dosage of administered antibodies will vary depending upon such factors as the patient's age, weight, height, sex, general medical condition, previous medical history, as well as other factors known to those of skill in the art. An appropriate effective amount may be readily determined using only routine experimentation. Effective amounts and routes of administration for therapeutic and prophylactic applications are further described below.

Another aspect of the invention provides compositions comprising one or more liver stage *Plasmodium* polypeptides of the invention and a pharmaceutically acceptable carrier. Thus, some embodiments provide an immunogenic composition comprising a liver stage *Plasmodium* polypeptide and a pharmaceutically acceptable carrier, wherein the liver stage *Plasmodium* polypeptide comprises an amino acid sequence selected from the group consisting of SEQ ID NOs:1-48 and immunogenic derivatives thereof. For example, the isolated polypeptide may be a *P. falciparum* polypeptide selected from the group consisting of SEQ ID NOs:11-44 and immunogenic derivatives thereof. In some embodiments, the immunogenic compositions comprise at least two liver stage *Plasmodium* polypeptides selected from the group consisting of SEQ ID NOs:1-48, and immunogenic derivatives thereof.

In some embodiments, the compositions of the invention are immunogenic compositions for inducing immune responses, such as vaccine compositions. A "vaccine" is an immunogenic composition capable of eliciting protection against infection by *Plasmodium* parasites and/or malarial disease, whether partial or complete. A vaccine that is used for treatment of an infected individual may be referred to as a therapeutic vaccine. The immunogenic compositions of the invention may also be used to elicit antibodies in a species that is not infectable by *P. falciparum*, for example, to raise antibodies in rabbits or mice.

In addition to one or more liver stage *Plasmodium* polypeptides of the invention, the compositions of the invention may include other antigens. For example, the compositions may include antigens based on the *Plasmodium* circumsporozoite protein used currently in the RTS,S vaccine (see Matuschewski, *Curr. Op. Immunol.* 18:1-9, 2006).

The invention further provides methods for preparing an immunogenic composition, by suspending and packaging one or more liver stage *P. falciparum* polypeptides of the invention in a suitable pharmaceutically acceptable carrier. Suitable pharmaceutically acceptable carrier include sterile water or sterile physiological salt solution, particularly phosphate buffered saline (PBS), as is well known in the art.

The immunogenic compositions of the invention generally also include an adjuvant. Suitable adjuvants are well known in the art (see, for example, *Vaccine Design—The Subunit and Adjuvant Approach*, Pharmaceutical Biotechnology, Vol. 6, M. F. Powell & M. J. Newman (eds.), Plenum Press, N.Y. and London, ISBN 0-306-44867-X, 1995). Exemplary adjuvants include complete Freund's adjuvant (CFA) that is not used in humans, incomplete Freund's adjuvant (IFA), squalene, squalane and alum (e.g., Alhydrogel™, Superfos, Denmark), which are materials well known in the art and are available commercially from several sources. Other exemplary adjuvants include the adjuvants described in Lanar et al., U.S. Pat. No. 7,029,685, and U.S. Patent Application Publication No. 2006/0073171, herein incorporated by reference.

In some embodiments, the immunogenic composition is a vaccine composition. Vaccine preparation is generally described in *New Trends and Developments in Vaccine*, Voller et al., (eds.), University Park Press, Baltimore, Md., 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945, and by Armor et al., U.S. Pat. No. 4,474,757.

The amount of immunogen(s) present in each vaccine dose is selected as an amount that induces an immune response (such as an immunoprotective response) without significant adverse side effects. The term "immune response" refers to an acquired and enhanced degree of protective immunity against *Plasmodium* infection or malarial disease, for example, complete or partial protection against infection or disease following subsequent exposure to malaria parasites. The amount of immunogen present in each dose will vary, depending upon which specific immunogens are employed and other factors. Generally, it is expected that each dose will comprise a total of 1-1000 micrograms of protein, such as 1-200 micrograms or 10-100 micrograms or 5-50 micrograms of protein. Following an initial vaccination, subjects will generally receive one or more boosts. An optimal amount for a particular vaccine, as well as the number and frequency of boosts, may be determined empirically by standard studies involving observation of immune responses in subjects.

The vaccine compositions of the invention may be administered by any suitable method of administration known in the art including, but not limited to, intradermally, subcutaneously, intramuscularly, intraperitoneally, orally, ocularly (e.g., as an eye spray), and intravenously. Vaccines are conventionally administered parenterally, by injection, for example, either subcutaneously or intramuscularly. Additional formulations that are suitable for other modes of administration include suppositories and, in some cases, oral formulations, or nasal sprays. For suppositories, traditional binders and carriers may include, for example, polyalkalene glycols or triglycerides. Oral formulations include such normally employed excipients as, for example, pharmaceutical grades of mannitol, lactose, starch, magnesium stearate, sodium saccharine, cellulose, magnesium carbonate, and the like.

In some embodiments, the vaccine compositions of the invention are DNA vaccines comprising a nucleic acid molecule encoding one or more liver stage *P. falciparum* polypeptides of the invention. Thus, some embodiments provide an immunogenic composition comprising a nucleic acid molecule encoding a polypeptide and a pharmaceutically acceptable carrier, wherein the polypeptide comprises an amino acid sequence selected from the group consisting of SEQ ID NOs:1-48 and immunogenic derivatives thereof. For example, the nucleic acid molecule may encode a *P. falciparum* polypeptide selected from the group consisting of SEQ ID NOs:11-48 and immunogenic derivatives thereof. The immunogenic composition may additionally comprise a nucleic acid coding for other antigens, for example, antigens based on the Plasmodium circumsporozoite protein used currently in the RTS,S vaccine (see Matuschewski, *Curr. Op. Immunol.* /8:1-9, 2006).

Methods for preparing and administering a DNA vaccine expressing *Plasmodium* proteins are known in the art and have been previously described (see, e.g., Doolan & Hoffman, *Int. J. Parasitol.* 31:753-762, 2001; Narum et al., U.S. Pat. No. 7,078,507, herein incorporated by reference. In some embodiments, the vaccine compositions of the invention are viral vaccines comprising a viral vector encoding one or more liver stage *P. falciparum* polypeptides of the invention. Exemplary viral vectors for use in the vaccine compositions of the invention include, but are not limited to, vaccinia viral vectors (such as vectors based on modified vaccinia virus or avian pox viruses), adenoviral vectors, and yellow fever viral vectors (see, e.g., Imoukhuede et al., *Vaccine*, in press, 2006; Miao et al., *Vaccine*, in press, 2006; Tao et al., *J. Exp. Med.* 201:201-209, 2005). Methods for preparing and administering viral vaccines expressing *Plasmodium* proteins are known in the art and have been previously described (see, e.g., Imoukhuede et al., *Vaccine*, in press, 2006; Miao et al., *Vaccine*, in press, 2006; Tao et al., *J. Exp. Med.* 201:201-209, 2005). An exemplary method for preparing a DNA vaccine encoding a liver stage *Plasmodium* polypeptide of the invention is provided in EXAMPLE 7.

In another aspect, the invention provides genetically attenuated sporozoites from which at least one gene coding for a liver stage polypeptides of the invention has been eliminated. Thus, in some embodiments, the invention provides genetically attenuated *Plasmodium* sporozoites lacking a gene coding for a liver stage polypeptide selected from the group consisting of SEQ ID NOs:1-48. The gene coding for a liver stage polypeptide may be a gene coding for a *P. falciparum* polypeptide selected from the group consisting of SEQ ID NOs:11-44. Methods for preparing genetically attenuated *Plasmodium* sporozoites lacking a liver stage gene have been previously described (see, e.g., Mueller et al., *Nature* 433:164-167, 2005; Mueller et al., *Proc. Natl. Acad. Sci. USA* 102:3022-3027, 2005; Kappe et al., U.S. Patent Application Publication No. 2005/0226896, herein incorporated by reference).

Another aspect of the invention provides methods for inducing an immune response against liver stage *P. falciparum* parasites, comprising administering an immunogenic composition comprising an effective amount of one or more liver stage *P. falciparum* polypeptides of the invention. Thus, in some embodiments the invention provides a method for inducing an immune response in a mammalian subject against *Plasmodium* falciparum, comprising administering to a mammalian subject a composition comprising an effective amount of at least one isolated polypeptide selected from the group consisting of SEQ ID NOs:1-48 and immunogenic derivatives thereof. For example, the isolated polypeptide may be a *P. falciparum* polypeptide selected from the group consisting of SEQ ID NOs:11-44 and immunogenic derivatives thereof. As used herein, the term "mammalian subjects" includes, but is not limited to, humans, goats, rabbits, and mice. In some embodiments, the mammalian subject is a human subject.

Another aspect of the invention provides methods for treating a mammalian subject in need thereof, comprising administering to a mammalian subject in need thereof an immunogenic composition comprising an effective amount of one or more liver stage *P. falciparum* polypeptides of the invention. Thus, in some embodiments the invention provides methods for treating a human subject in need thereof, comprising administering to a human subject an immunogenic composition comprising at least one isolated polypeptide selected from the group consisting of SEQ ID NOs:1-48 and immunogenic derivatives thereof. For example, the isolated polypeptide may be a *P. falciparum* polypeptide selected from the group consisting of SEQ ID NOs:11-44 and immunogenic derivatives thereof.

The invention also provides methods for inducing an immune response against *P. falciparum* parasites, comprising administering a live, genetically attenuated *Plasmodium* organism that is genetically engineered to disrupt a gene encoding a liver stage *P. falciparum* polypeptides of the invention. Methods for administering live, genetically attenuated *Plasmodium* organisms and inducing an immune response against *Plasmodium* parasites have been previously described (see, e.g., Mueller et al., *Nature* 433:164-167, 2005; Mueller et al., *Proc. Natl. Acad. Sci. USA* 102:3022-3027, 2005; Kappe et al., U.S. Patent Application Publication No. 2005/0226896, herein incorporated by reference).

The term "treating" refers to both therapeutic treatment and prophylactic or preventative measures, wherein the object is to prevent or slow down (lessen) the targeted pathologic condition or disease. Those in need of treatment include those already with the disease as well as those prone to have the disease or those in whom the disease is to be prevented. In some embodiments, the subjects to be treated are human subjects suffering from malaria, such as, for example, liver stage malaria. In some embodiments, the subjects to be treated are human subjects at risk for contracting malaria. The subjects to be treated may or may not have previously been infected by *Plasmodium* parasites.

The term "effective amount" for a therapeutic or prophylactic treatment refers to an amount or dosage of a composition sufficient to induce a desired response (e.g., an immunogenic response) in the individual to which it is administered. Preferably, the effective amount is sufficient to effect treatment, as defined above. The effective amount and method of administration of a particular therapeutic or prophylactic treatment may vary based on the individual patient and the stage of the disease, as well as other factors known to those of skill in the art. Therapeutic efficacy and toxicity of such compounds may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosages for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the prevalence of *P. falciparum* in the geographical vicinity of the patient, the severity of the disease state of the patient, age and weight of the patient, diet, time, and frequency of administration, drug combination(s), reaction sensitivities, and tolerance/response to therapy. An appropriate effective amount may be readily determined using only routine experimentation. Several doses may be needed per individual in order to achieve a sufficient response to effect treatment. Suitable regimes for initial administration and follow-up administration (e.g., booster shots) are also variable, but are typified by an initial administration followed in intervals (weeks or months) by a subsequent administration.

The production of antibodies elicited by a treatment is readily ascertained by obtaining a plasma or serum sample from the subject to which an immunogenic composition is administered, and assaying the antibodies therein for their ability to bind to the polypeptide(s) used to elicit the immune response to *P. falciparum* parasites, such as liver stage parasites. Exemplary methods include, but are not limited to, ELISA assays, immunofluorescence assays (IFA), or other immunoassays such as a Western blots, as is well known in the art.

Antibodies to one or more of the liver stage *P. falciparum* parasites of the invention may be isolated from the blood of the mammalian subject using well-known techniques, and then reconstituted into a second vaccine for passive immunization, as is also well known. Similar techniques are used for gamma-globulin immunizations of humans. For example, antiserum from one or a number of immunized subjects may be precipitated in aqueous ammonium sulfate (typically at 40-50 percent of saturation), and the precipitated antibodies purified chromatographically (e.g., affinity chromatography).

In another aspect, the invention provides diagnostic and screening agents and assays, which may be protein-based or nucleic acid-based. These agents and assays may be used to detect the presence of the liver stage *Plasmodium* polypeptides of the invention, or nucleic acid molecules encoding them, in order to determine whether a subject is suffering from or is likely to suffer from malaria. Many techniques may be used, including, but not limited to, ELISA, sandwich assays, immunoprecipitation, immunoblots, hybridization techniques, and PCR.

In some embodiments, the liver stage *Plasmodium* polypeptides of the invention are used for the detection of antibodies in a mammalian subject. In some embodiments, antibodies to the liver stage *Plasmodium* polypeptides of the invention are used to detect the presence of these polypeptides. Diagnostic immunoassay procedures are standard in the art (see, e.g., D. Stites and A. Terr, *Basic and Clinical Immunology*, 7th ed., 1991). Exemplary methods may, for example, use solid supports, or immunoprecipitation. Most assays involve the use of labeled antibody or polypeptide. Such labels may be, for example, enzymatic, fluorescent, chemiluminescent, radioactive, or dye molecules. Assays that amplify the signals from the immune complex are also known, such as assays that utilize biotin and avidin or streptavidin, and enzyme-labeled and mediated immunoassays, such as ELISA assays.

Some embodiments provide methods for the in vitro diagnosis of malaria in a subject likely to be infected by *P. falciparum*, comprising (a) contacting a biological sample comprising antibodies from a mammalian subject with one or more liver stage *P. falciparum* polypeptides of the invention under conditions enabling the formation of antigen/antibody complexes between the polypeptides and the antibodies, and (b) detecting the formation of antigen/antibody complexes. Examples of biological samples that may be used to perform this method are red blood cells, white blood cells, serum or urine. Conditions enabling the formation of antigen/antibody complexes are well known in the art.

The invention also provides methods for monitoring the immune status of a subject vaccinated against infection or disease caused by *P. falciparum*, comprising (a) contacting a biological sample comprising antibodies from a subject with one or more liver stage *P. falciparum* polypeptides of the invention under conditions enabling the formation of antigen/antibody complexes between the polypeptides and the antibodies, and (b) detecting the formation of antigen/antibody complexes.

In the diagnostic and monitoring methods described above, the biological sample may be further contacted with one or several antigenic peptides originating from other *Plasmodium* antigens.

In some embodiments, the diagnostic and screening agents and assays are nucleic acid-based. Exemplary diagnostic and screening agents for use in nucleic acid-based assays include nucleic acid probes complementary to nucleic acid molecules encoding *P. falciparum* polypeptides of the invention. Nucleic-acid based diagnostic and screening assays are well known in the art. Exemplary diagnostic and screening assays to be used in this aspect of the invention are described in Scherf et al., U.S. Pat. No. 6,855,323, herein incorporated by reference.

The invention also provides kits that are useful for carrying out the present invention. The kits may include a first container means containing the polypeptides, nucleic acid molecules, compositions, and/or antibodies of the invention. The kits may also include other container means containing solutions necessary or convenient for carrying out the invention. The container means may be made of glass, plastic, or foil and can be a vial, bottle, pouch, tube, bag, etc. The kits may also contain written information, such as procedures for carrying out the present invention or analytical information, such as the amount of reagent contained in the first container means. The container means may be in another container means, for example, a box or a bag, along with the written information.

The following examples illustrate representative embodiments now contemplated for practicing the invention, but should not be construed to limit the invention.

EXAMPLE 1

This example describes the identification of a novel conserved *Plasmodium yoelii* protein that is differentially expressed during liver stage development.

One of the most important questions regarding liver stage biology is if this stage differentially expresses a unique set of proteins. However, because the liver stage is difficult to track experimentally this question has remained largely unanswered. This example describes a gene that is differentially expressed in livers stages of the rodent malaria *Plasmodium yoelii* in vivo, and its protein product (PyLSP1). Bioinformatics analysis, PCR and RT-PCR elucidated the complete gene structure and identified a PyLSP1 ortholog in *P. falciparum*. RT-PCR and immunoassays showed that PyLSP1 expression is up-regulated in late liver stages in vivo but that it is not significantly expressed in sporozoites and the parasites blood stages.

Materials and Methods

Microarray Studies:

Liver total RNA was isolated from BALB/c mouse liver infected with >3 million *P. yoelii* wild type sporozoites using Trizol (Invitrogen). Blood stage RNA was obtained from blood stage infections in Swiss-Webster mice when the parasitemia reached 5%. The RNA was treated with DNAse (Invitrogen) to remove genomic DNA contamination. About 20 microgram of total RNA was used for cDNA synthesis and indirectly labeled with fluorescent Cy3 or Cy 5 dyes using the Fairplay labeling kit from Stratagene.

Cy3 and Cy5 labeled cDNA were hybridized overnight to a custom 65-mer oligo array made by Lawrence Bergman's group at Drexel University that had duplicate probes for all ~6500 annotated genes of *P. yoelii*. After washes, the microarray slide was scanned using a GenePix scanner and results were analyzed using Acuity software. Intensity signals of each spot were normalized and compared to a spot with random oligos (negative control). The threshold for detection of an expressed gene was set at four times the intensity signal of the negative control. Microarray analysis was performed on total RNA from infected liver 40 hrs post infection, uninfected liver, and from mixed blood stages.

Our candidate genes for analysis were chosen as follows: high expression in the 40 hrs. infected liver, low or no expression in mixed blood stages, possible orthology with a *P. falciparum* gene, and the presence of a signal peptide. The presence of a signal peptide is an indicator that the protein encoded by the gene may be secreted and thus may play important roles in host-parasite interactions. The candidate genes were then analyzed by quantitative real-time PCR as described in EXAMPLE 2.

Protein Expression Studies:

The location of putative immunogenic peptides were identified using various programs available on the Web for secondary structure prediction of proteins. Peptide 2 (KDDYS-KNNGKDSLVCC, SEQ ID NO:49) and Peptide 5 (CNLKYLLLHHTNAFLC, SEQ ID NO:50) were synthesized by a commercial company (Sigma-Genosys). Two New Zealand white rabbits were used for antibody production by Sigma Genosys. The peptides were injected subcutaneously with Freund's adjuvant following a 77-day schedule with 6 immunizations and 4 bleeds per animal. The peptide antibodies were used for immunofluorescence and immunoblot analysis of LSP1, using standard protocols.

Results

LSP1 Identification and Expression:

Using microarray gene expression profiling, we identified genes that are only expressed at 40 hours of *P. yoelii* LS development in vivo (Tables 1 and 2). One uniquely expressed gene is PyLSP1 encoding a hypothetical protein with a predicted molecular mass of ~380 kDa. The *P. yoelii* gene product contains a predicted cleavable signal peptide and a transmembrane domain. BLAST homology searches with the PyLSP1 amino acid sequence were performed to identify orthologous genes in *P. falciparum* and *P. berghei* using the PlasmoDB and Sanger Center databases, respectively. Potential orthologs were found in both *P. falciparum* and *P. berghei* parasites. The gene identification number for *P. yoelii* PyLSP1 is PY04499 (SEQ ID NO:1), for *P. falciparum* PyLSP1 is Pf14_0179 (SEQ ID NO:11), and for *P. berghei*, PyLSP1 is gi 68075600.

LSP1 is Expressed in Late Liver Stages:

We investigated the expression of PyLSP1 by RT-PCR and qRT-PCR in different stages of parasite development using specific primers. PyLSP1 was detected in infected liver samples taken at 40 hours post-infection. These results showed also that PyLSP1 is down-regulated in sporozoites, early liver stages and blood stages (see Table 1, below). To study the protein expression pattern of PyLSP1, we raised antisera against two independent peptides in a region of high predicted antigenicity. Immuno-colocalization analysis showed that PyLSP1 is highly expressed by LS in liver sections taken at 44 hours post-infection. A faint internal staining is present in LS 24 hours after infection. PyLSP1 appears to localize to the parasitophorous vacuole. No expression was detected in sporozoites, blood stages, or early LS. Immuno-colocalization data are in concordance with the RT-PCR data; PyLSP1 is present in the late LS but not early LS.

EXAMPLE 2

This example describes the identification of novel *Plasmodium yoelii* proteins that are differentially expressed during liver stage development.

Materials and Methods a. RNA Preparation: Total RNA was prepared from mixed blood stages, salivary gland sporozoites and *Plasmodium yoelii* infected mouse liver using Trizol (Invitrogen) according to manufacturer's instructions. Total RNA from mixed blood stages and infected mouse liver were treated with Turbo-free RNase (Ambion), while total RNA from sporozoites was treated with RNase-free DNase (Invitrogen) according to manufacturer's instructions. The treated RNA were cleaned using the RNeasy mini kit (Qiagen). The RNA concentration was measured by spectrophotometry and RNA quality was verified using the Agilent Bioanalyzer.

b. Primer Design: Primers were designed using the primer analysis software Primer Express v2.0 and v3.0 (Applied Biosystems). Designs were based on the mRNA sequence of the genes available at PlasmoDB. Amplicons were set to be between 100 and 250 bp.

c. Conventional and Real-Time RT-PCR: For conventional RT-PCR, 2.5 microliter of the diluted cDNA was used for each 25 microliter PCR reaction with 2.5 microliter of diluted cDNA, 25 pmole of each primer, and 12.5 microliter of the Bioline Red PCR mix (Bioline) using the following cycling conditions: initial denaturation at 95° C. for 3 min; 30 cycles at 94° C. for 30 sec, 55° C. for 45 sec, and 72° C. for 1 min; and final extension at 72° C. for 7 min.

Real-time PCR analysis was performed on ABI Prism 7300 Sequence Detection Systems using the SYBR Green PCR Master Mix (Applied Biosystems). The PCR reaction consisted of 12.5 microliter of SYBR Green PCR Master Mix, 20 pmole of forward and reverse primers, and 5 microliter of diluted cDNA in a total volume of 25 microliter. PCR cycling conditions were performed using the default conditions of the ABI Prism 7300 SDS Software. To verify that the PCR amplified product is unique, a dissociation protocol was added after the PCR from 65° C. to 95° C. For each primer pair, no template control, a standard curve of four serial dilutions of a 40 hr infected liver+mixed blood stages cDNA mixture, and each of the test cDNAs (mixed blood stages 12-, 24-, 40-hr liver and salivary gland sporozoite) were included.

d. Normalization and Relative Quantitation: The five different RNA samples were normalized to *P. yoelii* 18S and 14-3-3 protein housekeeping gene using the Relative Standard Curve Method (Applied Biosystems Bulletin). The standard is prepared from a mixture of total RNA from mixed blood stages and infected mouse liver (1:1). First strand cDNA is prepared from this mixture of total RNA. Dilutions of 1, 1:5, 1:10, 1:25, and 1:50 of the resulting cDNA were used as templates for real time PCR for each primer pair. The relative quantity of each amplified gene product from the test cDNAs is interpolated from the corresponding standard curve. Because quantitation is normalized to 18S and 14-3-3 housekeeping gene, standard curves are prepared for both the target as well as the reference genes (18S and 14-3-3). Normalized quantity of each target gene is expressed as the ratio of the relative amount of target gene over each of the reference genes to get the different normalized values. Fold change expression compared to mixed blood stages is then calculated by getting the ratio of the normalized expression value of each gene in the different test cDNAs to the normalized expression value of the gene in mixed blood stages (i.e., fold expression in mixed blood is set at a value of 1).

Results

Ten *P. yoelii* genes were found to be specifically expressed in liver stages. Nine of these genes have orthologs in *P. falciparum*, as shown in Table 1. The expression pattern in liver stages of these ten genes is shown in Table 2.

TABLE 1

Liver Stage Genes Identified in Examples 1 and 2

| P. yoelii gene | SEQ ID NO | P. falciparum ortholog | SEQ ID NO |
|---|---|---|---|
| PY04499 | SEQ ID NO: 1 | PF14_0179 | SEQ ID NO: 11 |
| PY04387 | SEQ ID NO: 2 | PFD0260c | SEQ ID NO: 12 |
| PY02416 | SEQ ID NO: 3 | PFI1125c | SEQ ID NO: 13 |
| PY01586 | SEQ ID NO: 4 | PF13_0128 | SEQ ID NO: 14 |
| PY03769 | SEQ ID NO: 5 | MAL13P1.66 | SEQ ID NO: 15 |
| PY03462 | SEQ ID NO: 6 | PF10_0027 | SEQ ID NO: 16 |
| PY05006 | SEQ ID NO: 7 | MAL8P1.201 | SEQ ID NO: 17 |
| PY00696 | SEQ ID NO: 8 | PFE1450c | SEQ ID NO: 18 |
| PY03269 | SEQ ID NO: 9 | PF11_0480 | SEQ ID NO: 19 |
| PY03831 | SEQ ID NO: 10 | None | |

TABLE 2

Expression Pattern of Liver Stage Genes Identified In EXAMPLES 1 and 2

| | | Fold change compared to mixed blood stages using 18S | | | | | | Fold change compared to mixed blood stages using 14-3-3 gene | | | | | |
|---|---|---|---|---|---|---|---|---|---|---|---|---|---|
| Py Gene | Exp | mixed blood | schizont | sporozoite | 12 hr liver | 24 hr liver | 40 hr liver | mixed blood | schizont | sporozoite | 12 hr liver | 24 hr liver | 40 hr liver |
| PY04499 | 40 | 1 | 0.6 | 12.8 | 443.0 | 1274.7 | 884.5 | 1.0 | 0.9 | 12.0 | 126.7 | 909.3 | 95.8 |
| PY04387 | 40 | 1 | 1.7 | 41.4 | 83.8 | 3095.7 | 12518.4 | 1.0 | 2.5 | 30.6 | 22.4 | 974.5 | 3847.6 |
| PY02416 | 40 | 1 | 1.0 | 146.0 | 80.1 | 209.4 | 1072.2 | 1.0 | 1.1 | 66.6 | 18.1 | 51.5 | 565.3 |
| PY01586 | 40 | 1 | 2.7 | 77.2 | 194.5 | 108.7 | 153.1 | 1.0 | 3.6 | 20.1 | 11.6 | 17.7 | 47.1 |
| PY03769 | 24 | 1 | 1.5 | 3015.6 | 56.9 | 86.3 | 45.1 | 1.0 | 1.9 | 1194.1 | 14.6 | 21.7 | 14.4 |
| PY03462 | 40 | 1 | 9.6 | 67.1 | 45.0 | 59.2 | 8.3 | 1.0 | 10.6 | 30.6 | 10.2 | 14.6 | 4.4 |
| PY05006 | 40 | 1 | 6.9 | 21.8 | 49.0 | 28.4 | 5.7 | 1.0 | 9.9 | 16.1 | 13.1 | 8.9 | 1.7 |
| PY00696 | 24 | 1 | 0.4 | 1.0 | 6.6 | 6.7 | 3.7 | 1.0 | 0.3 | 0.3 | 0.9 | 1.9 | 1.2 |
| PY03269 | 40 | 1 | 2.3 | 472.5 | 1006.2 | 740.7 | 389.5 | 1.0 | 3.4 | 350.1 | 268.4 | 233.2 | 119.7 |
| PY03831 | 24 | 1 | 2.8 | 17791.9 | 8421.6 | 2331.9 | 14.9 | 1.0 | 3.2 | 6746.5 | 1496.7 | 639.5 | 5.4 |

EXAMPLE 3

This example describes the identification of novel *Plasmodium falciparum* proteins that are differentially expressed during liver stage development.

We optimized the in vitro infection of HC-04 hepatocytes by *P. falciparum* parasites and employed unbiased amplification of the RNA in order to obtain sufficient material for microarray studies. We applied this material to the microarrays, and compared gene expression profiles of uninfected and infected HC-04 hepatocytes to identify the genes that were uniquely transcribed by the liver stage parasites. We analyzed these genes using bioinformatics tools to determine which may be unique to liver stage parasites. These genes encode the proteins that are now evaluated as vaccines to prevent *P. falciparum* infection by eliciting immune responses targeting liver stage parasites or to develop drugs or diagnostics targeting liver stage parasites.

Materials and Methods a. Optimization of In Vitro Infection of HCO4 Hepatocytes by *P. falciparum*: The human liver cell line, HC-04, was seeded into six-well tissue culture plates and maintained in culture medium supplemented with antibiotics and fetal bovine serum until confluent at 37° C. in a humidified incubator equilibrated with 10% $CO_2$ in air. *P. falciparum* sporozoites, hand-dissected three weeks after feeding, were added to HC-04 cells at a 2:1 (sporozoite:cell) ratio. The medium was changed 3 hrs after sporozoite inoculation and then every 48 hrs until exoerythrocytic merozoites were observed (see Sattabongkot et al., Am. J. Trop. Med. Hyg. 74(5):706-707, 2006). Detection of liver-stage parasite was performed using Giemsa staining.

b. Microarray Studies: Microarray experiments were performed as previously described (Bozdech et al., Genome Biol. 4(2):R9, 2003). Unmodified 70-mer oligonucleotides were printed on Corning UltraGaps poly-L-lysine slides. Slides were blocked by succinic anhydride in 1-methyl-2-pyrrolidinone neutralized with boric acid. RNA was isolated using PureLink Micro-to-Midi Total RNA Purification System (Invitrogen, Catalog No. 12183-018) according to manufacturer instructions. RNA was amplified using Ambion's AminoAllyl MessageAmp II aRNA Kit Amplification (Ambion, Catalog No. 1753) according to manufacturer instructions. The resulting aa-dUTP-containing cDNA was coupled to CyScribe Cy3 or Cy5 (Amersham, Piscataway, N.J.) monofunctional dye in the presence of 0.1 M $NaHCO_3$ pH 9.0. Coupling reactions were incubated for a minimum of 1 hr at room temperature. The hybridization medium contained 3×SSC, 1.5 mg/ml poly(A) DNA, and 0.5% SDS. Hybridizations were performed at 65° C. for 8-16 hrs. Arrays were washed in 2×SSC/0.2% SDS and then 0.1×SSC at room temperature. The microarrays were scanned with a GenePix 4000 scanner and the images analyzed using GenePix software (Axon Instruments, Union City, California).

c. qPCR: qPCR reactions were performed in 0.050 ml volume in the presence of 500 nM of each of forward and reverse primers in 1× SYBR Green PCR Master Mix (Applied Biosystems, Catalog No. 4334973) using the 96-well format of 7000 Sequence Detection System (Applied Biosystems). Typical qPCR conditions were: 2 minutes at 50° C., 10 minutes at 95° C., followed by 45 cycles of amplification. Each amplification cycle consisted of melting step at 95° C. for 15 seconds and annealing/extension step at 60° C. for 45 seconds.

Results

The proportion of *P. falciparum* genes detected as upregulated (in infected versus uninfected HC-04 cells) in 2 or more out of 4 completed microarrays was substantially and significantly greater than the proportion of non-malaria (human or yeast) genes. This establishes our criteria that genes that were detected as upregulated in 2 or more of our 4 arrays are candidate liver stage antigens.

Genes that are transcribed by liver stage parasites have been confirmed by quantitative PCR (qPCR). qPCR detection of liver stage genes was performed using the following quality control procedures to ensure specific identification and quantitation: a) each gene detected with two independent primer pairs/qPCR reactions; b) qPCR-amplified gene fragments was confirmed by size on agarose gel; c) qPCR of infected-HC-04 cells was compared to qPCR of uninfected HC-04 cells to show specificity; d) qPCR of liver stage genes was normalized to qPCR of housekeeping genes to quantify abundance; e) qPCR of genes was compared between liver stage parasites and other stages (sporozoite, late rings, late trophozoite, and late schizont stages) to confirm stage-specificity of transcription.

Table 3 shows the relative amounts (in $\log_2$ scale) of expression of *P. falciparum* genes identified by qPCR to be overexpressed during liver stage compared to sporozoites, late rings, late trophozoites, and late schizonts after normalization using a panel of housekeeping genes. The value of 0 (zero) reflects an estimate of transcription that is not biologically meaningful, based on a level that is 170-fold less than the geometric mean of level of transcription of housekeeping genes. The genes in Table 3 are likely to be unique to liver stage parasites. Other genes whose expression was found to be elevated in liver stages compared to other stages include PFE0935c, PFB0610c, PF11_0480, PFD0270c, PFL1995c, PFA0170c, PF08_0054, and PFI0875w. The sequences of these genes and the proteins encoded by them may be obtained from the *Plasmodium* Genome Database (http://plasmodb.org/; Kissinger et. al, *Nature* 419:490-492, 2002), and are hereby incorporated by reference (version accessed Sep. 28, 2006). All the above genes and the proteins encoding them may be used for developing vaccines that elicit responses against liver stage parasites or as targets for drugs and diagnostics.

The gene at *P. falciparum* locus PFE0305w (SEQ ID NO:20) has a sequence similar to transcription initiation factor TFIID, TATA-binding protein. We show that this transcription initiation factor is liver stage-specific. Therefore, knockout of this gene may represent a powerful strategy to create attenuated malaria parasites.

TABLE 3

Relative Expression Pattern of Liver Stage Specific Genes.

| | SP | Liver Stage | | | | | |
|---|---|---|---|---|---|---|---|
| | 0 h | 24 h | 48 h | 72 h | LR | LT | LS |
| PFE0305w, SEQ ID NO: 20 | 0.9 | 3.0 | 2.9 | 3.2 | −0.9 | −0.7 | −0.8 |
| MAL7P1.164, SEQ ID NO: 21 | −1.1 | 2.3 | 3.3 | 2.8 | −2.4 | −0.5 | −1.1 |
| PF11_0230, SEQ ID NO: 22 | −1.3 | 1.4 | 1.6 | 0.9 | 0.0 | −0.9 | 0.6 |
| PF14_0113, SEQ ID NO: 23 | −0.3 | 3.1 | 3.3 | 2.5 | 1.4 | 1.3 | −1.1 |
| PF14_0534, SEQ ID NO: 24 | −0.8 | 1.7 | 2.8 | 3.3 | −0.7 | −0.6 | −2.8 |
| PF11_0118, SEQ ID NO: 25 | 0.6 | 2.1 | 2.5 | 1.3 | 0.1 | 0.4 | −1.8 |
| PFC0195w, SEQ ID NO: 26 | −0.6 | −0.8 | 2.1 | 4.4 | −2.0 | −0.8 | −1.3 |
| PFC0960c, SEQ ID NO: 27 | 0.6 | 0.2 | 1.2 | 2.8 | −5.4 | −0.8 | 0.5 |
| PF13_0112, SEQ ID NO: 28 | 1.1 | 1.8 | 1.8 | 2.6 | 0.0 | 0.4 | −1.1 |

SP = Sporozoites
LR = Late ring stage
LT = Late Trophozoites
LS = Late Schizonts Table 4 shows the relative amounts (in $\log_2$ scale) of expression of *P. falciparum* genes overexpressed in sporozoite stage parasites (prior to hepatocyte invasion) that continue to be expressed during liver stage parasite development, but that are not expressed during blood stage development or expressed at significantly lower levels during blood stage development. Expression was normalized using a panel of housekeeping genes. The value of 0 (zero) reflects an estimate of transcription that is not biologically meaningful, based on a level that is 170-fold less than the geometric mean of level of transcription of housekeeping genes. These genes also may be important targets for gene knockout attenuation of parasites, for drug and vaccine design, and for development of diagnostics.

TABLE 4

Relative Expression Pattern of Genes Overexpressed
in Liver Stages Compared to Blood Stages.

| | SP | Liver Stage | | | | | |
|---|---|---|---|---|---|---|---|
| | 0 h | 24 h | 48 h | 72 h | LR | LT | LS |
| PF08_0073, SEQ ID NO: 29 | 4.2 | −0.5 | 0.9 | 0.0 | −7.7 | −8.1 | −2.5 |
| PF10_0164, SEQ ID NO: 30 | 9.9 | 7.4 | 7.8 | 7.4 | 4.0 | 4.1 | 6.4 |

TABLE 4-continued

Relative Expression Pattern of Genes Overexpressed
in Liver Stages Compared to Blood Stages.

| | SP | Liver Stage | | | | | |
|---|---|---|---|---|---|---|---|
| | 0 h | 24 h | 48 h | 72 h | LR | LT | LS |
| PF10_0214, SEQ ID NO: 31 | 5.9 | 5.0 | 4.6 | 4.0 | 2.1 | 2.4 | 1.8 |
| PF11_0221, SEQ ID NO: 32 | 0.7 | 0.6 | 1.2 | −1.6 | −0.6 | 0.8 | 0.4 |
| PF13_0012, SEQ ID NO: 33 | 4.1 | 2.7 | 1.8 | 2.0 | −6.2 | −5.5 | −4.6 |
| PF14_0044, SEQ ID NO: 34 | 2.1 | 1.9 | 1.6 | 2.3 | −5.4 | −5.3 | −3.0 |
| PF14_0050, SEQ ID NO: 35 | −0.1 | 1.8 | 2.0 | 2.1 | −1.4 | 0.7 | 0.7 |
| PFA0200w, SEQ ID NO: 36 | 9.4 | 2.5 | 1.3 | 3.5 | −5.3 | −2.9 | 1.4 |
| PFB0690w, SEQ ID NO: 37 | 5.8 | −1.0 | 0.6 | 2.5 | −2.8 | −3.1 | −1.7 |
| PFD0205c, SEQ ID NO: 38 | 0.7 | −0.7 | 0.9 | 3.9 | −2.2 | 0.1 | 1.0 |
| PFD0215c, SEQ ID NO: 39 | 6.9 | 2.8 | 2.8 | 3.6 | −2.2 | −1.1 | 1.8 |
| PFD0285c, SEQ ID NO: 40 | 7.0 | 2.5 | 3.1 | 3.9 | 0.4 | −0.1 | −0.9 |
| PFD0430c, SEQ ID NO: 41 | 10.8 | 0.9 | −0.8 | 0.9 | −6.2 | −3.8 | 0.0 |
| PFE1070c, SEQ ID NO: 42 | 6.2 | 2.3 | 2.1 | 0.6 | 0.1 | 0.3 | 0.0 |
| PFE1200w, SEQ ID NO: 43 | 0.9 | 2.3 | 2.4 | 2.7 | −1.6 | −0.2 | −0.8 |
| PFE1550w, SEQ ID NO: 44 | 0.9 | 1.9 | 1.8 | 1.9 | −2.5 | −0.5 | 0.0 |
| PFL0800c, SEQ ID NO: 45 | 13.6 | 3.9 | 1.7 | 3.6 | −6.4 | −7.8 | −2.6 |
| PF13_0201, SEQ ID NO: 46 | 9.2 | 2.9 | 1.3 | 2.0 | −4.7 | −4.1 | −0.9 |
| PFC0210c, SEQ ID NO: 47 | 12.9 | 4.1 | 2.9 | 4.2 | −1.6 | −1.1 | −1.8 |
| PFD0425w, SEQ ID NO: 48 | 10.0 | −0.2 | 0.7 | 2.0 | −5.2 | −2.0 | −0.7 |

SP = Sporozoites
LR = Late ring stage
LT = Late Trophozoites
LS = Late Schizonts

EXAMPLE 4

This example describes the identification of two liver stage *Plasmodium falciparum* proteins as targets of protective immunity.

Fully protective immunity against liver stage malaria can be induced with attenuated parasites (reviewed in Matuschewski, *Curr. Op. Immunol.* 18:1-9, 2006). This was originally demonstrated with malaria parasites that had been attenuated by irradiation, and more recently with parasites that had been genetically attenuated by removing key virulence genes. In these model systems, protective immunity has been correlated with IFN-gamma producing T cells (Kurds et al., *Trends Parasitol.* 17(5):219-223, 2001; Hoffman et al., *J. Infect. Dis.* 185:1155-1164, 2002; Berenzon et al., *J. Immunol.* 171(4):2024-2034, 2003), although it has been unclear what the antigenic targets of the specific T cells were.

We used a rodent model of protective immunity induced by attenuated parasites to assess whether the liver stage antigens that we have identified in *P. falciparum* may be targets of protective immunity. Mice were inoculated 3 times by intravenous injection with *P. berghei* parasites that had been radiation-attenuated at the sporozoite stage (i.e., in mosquito salivary glands). The immunizations comprised 75,000 attenuated parasites for priming, followed by 20,000 and 20,000 parasites for each boost. Rodents were challenged with 10,000 wild type parasites at 7 days after the final immunization and were shown to be fully protected.

We collected immune cells from the livers and spleens of protected rodents 5 weeks after challenge and examined their specific responses against peptides representing *P. berghei* orthologs of the *P. falciparum* antigens. Liver mononuclear cells were cultured overnight with medium alone, with Peptide 12 (INLQNLNYI, SEQ ID NO:51) from the *P. berghei* ortholog of *P. falciparum* liver stage protein PFE305w (SEQ ID NO:20), or with Peptide 4 (IAVENCNNI, SEQ ID NO:52) from the *P. berghei* ortholog of PF11_0480 (SEQ ID No:19).

We demonstrated that liver T cells, but not spleen T cells, from protected rodents expressed IFN-gamma in response to peptides 12 and 4. These data establish the liver stage proteins PFE0305w (SEQ ID NO:20) and PF11_0480 (SEQ ID No:19) as antigenic targets of immunity that correlate with protection, and as immunogenic antigens expressed by liver stage malaria parasites.

EXAMPLE 5

This Example describes the expression of recombinant liver stage *Plasmodium* proteins.

Materials and Methods a. Analyses of Protein Sequences: Large molecular weight proteins that cannot be expressed as full length proteins may be expressed as predicted immunogenic domains. Such immunogenic domains are predicted from the sequence of the proteins identified in Examples 1-3, and used for animal immunization studies. Protein sequences were analyzed using the DNASTAR program by several algorithms, including prediction of hydrophilicity according to Kyte-Doolittle method, surface probability according to Emini method, and antigenicity according to Jameson-Wolf method (DNASTAR, Inc).

b. Protein Expression in *E. coli*: Protein expression in prokaryotic vector pET28b is carried out by growing bacteria to the logarithmic phase of growth, inducing expression of the recombinant protein with 1 mM IPTG and continuing to grow the bacteria culture to saturation. The culture is spun down and the bacteria cell pellet is washed 3 times in solution A (50 mM Tris, 10 mM EDTA, 5 mM DTT, 2% Triton X-100, 500 mM NaCl pH7.5). Proteins are solubilized for 2 hours in solution B (6 M guandium-HCl, 50 mM Tris pH8.0, 5 mM DTT). Cell debris is removed by centrifugation and the protein solution is loaded onto Nickel columns to purify the His-tagged recombinant protein according to the manufacturer's specification (Novagen).

c. In vitro Protein Expression: Because some of the malaria antigens may be difficult to express in cellular systems and are conformation dependent, an alternative method is also used to express the proteins identified in Examples 1-3, by using a cell-free in vitro protein synthesis system (ENDEXT Technology) produced by CellFree Sciences. This method utilizes wheat germ lysate free of translation inhibitors that allows stable translation of eukaryotic proteins, including conformation-dependent malaria antigens. The genes encoding these proteins are cloned into pEU-E01-His-TEV-MCS vector (Cell Free Systems, Inc.), followed by protein synthesis according to the manufacturer (CellFree Sciences). The His-tag proteins are purified using anti-His beads according to the manufacturer (Dynal).

d. Immune Recognition of Proteins: The recombinant proteins are analyzed for their recognition by T cells and sera from immune and non-immune individuals, for example, as described in EXAMPLE 4, in Doolan et al., *Proc. Natl. Acad. Sci. USA* 100(17):9952-9957, 2003, and in Sundaresh et al., *Bioinformatics* 22(14):1760-1766, 2006.

It is expected that the proteins that are used to immunize rabbits are immunogenic, and elicit antibodies that recognize *Plasmodium* liver stages, as described in EXAMPLE 1, and/or T cell responses, as described in EXAMPLE 4. Proteins that react with T cells and/or sera from immune individuals at significantly higher levels compared with T cells and/or sera from nonimmune individuals are expected to be good immunogens for use in a malaria vaccine.

EXAMPLE 6

This example describes the expression in *P. pastoris* of recombinant liver stage *Plasmodium* falciparum proteins and immunogenic derivatives thereof.

a. Identification of Immunogenic Domains: Protein sequences were analyzed using DNASTAR program by several algorithms, including prediction of hydrophilicity according to Kyte-Doolittle method, surface probability according to Emini method, and antigenicity according to Jameson-Wolf method (DNASTAR, Inc). To improve the solubility of recombinant proteins, highly hydrophobic regions are not included in expression domains.

b. Expression of Liver Stage *Plasmodium* Proteins in *P. pastoris*: Proteins are expressed according to a detailed protocol describing how to clone and express protein in *Pichia pastoris* (available from Invitrogen as a part of EasySelect *Pichia* Expression Kit, product #K1740-01).

c. Expression of High Molecular Weight Liver Stage *P. falciparum* Proteins: High molecular weight proteins that cannot be expressed as full-length proteins may be expressed as predicted immunogenic domains. Some of the large liver stage Plasmodium proteins identified in EXAMPLES 1-3 do not demonstrate any apparent structure in their sequences: PF14_0179 (SEQ ID NO:11) is a predicted 423 kDa protein; PFD0260c (SEQ ID NO:12) is a predicted 233.7 kDa protein; MAL13P1.66 (SEQ ID NO:15) is a predicted 345.7 kDa protein; PF11_0480 (SEQ ID NO:19) is a predicted 348 kDa protein; PFC0195w (SEQ ID NO:26) is a predicted 170.5 kDa protein; PFC0960c (SEQ ID NO:27) is a predicted 231.8 kDa protein; PFE1070c (SEQ ID NO:42) is a predicted 162 kDa protein; and PFE1200w (SEQ ID NO:43) is a predicted 147.8 kDa protein. These proteins are expressed as a number of partially overlapping polypeptides of 40-70 kDa each.

d. Expression of Small and Medium Molecular Weight Liver Stage *P. falciparum* Proteins: The following small and medium molecular weight proteins are expressed as full-length proteins: PF10_0027 (SEQ ID NO:16) is a predicted 49.7 kDa protein; PF11_0230 (SEQ ID NO:22) is a predicted 19.7 kDa protein; PF14_0534 (SEQ ID NO:24) is a predicted 55 kDa protein; PF13_0112 (SEQ ID NO:28) is a predicted 9.2 kDa protein; PF08_0073 (SEQ ID NO:29) is a predicted 44.8 kDa protein; PF11_0221 (SEQ ID NO:32) is a predicted 7.1 kDa protein; PFB0690w (SEQ ID NO:37) is a predicted 29.7 kDa protein; and PFD0205c (SEQ ID NO:38) is a predicted 19.6 kDa protein.

e. Expression of Selected Liver Stage *P. falciparum* Proteins: PFI1125c (SEQ ID NO:13) is a putative 3-oxoacyl-(acyl-carrier protein) reductase of 33 kDa molecular weight. Both the full-length protein and a conserved domain including amino acids 59-300 are expressed.

PF13_0128 (SEQ ID NO:14) is a precursor of beta-hydroxyacyl-acp dehydratase of 26 kDa molecular weight. Both the full-length protein and a conserved domain including amino acids 72-230 are expressed.

MAL8P1.201 (SEQ ID NO:17) is a conserved hypothetical protein of 128.6 kDa molecular weight. This protein is expressed as two domains: the first domain includes amino acids 1-545, the second domain includes amino acids 660-1073. Both domains are hydrophilic and contain multiple antigenic epitopes.

PFE1450c (SEQ ID NO:18) is a conserved hypothetical protein of 22 kDa molecular weight. A domain of this protein starting after putative transmembrane domain, at amino acid 28, is expressed.

PFE0305w (SEQ ID NO:20) is a transcription initiation factor TFIID, TATA-binding protein of 38 kDa molecular weight. The full-length protein is expressed, as well as a conserved domain including amino acids 151-326.

MAL7P1.164 (SEQ ID NO:21) is a putative adapter-related protein of 100 kDa molecular weight. This protein is expressed as two domains: the first domain includes amino acids 6-529, the second domain includes amino acids 587-842. The first domain has extensive sequence homology to N terminal region of Adaptin. The second domain is hydrophilic and contains multiple antigenic epitopes.

PF14_0113 (SEQ ID NO:23) is a hypothetical protein of 113 kDa molecular weight. Based on antigenic surface probability, a domain including amino acids 1-346 is expressed.

PF11_0118 (SEQ ID NO:25) is a hypothetical protein of 72.5 kDa molecular weight with substantial homology to transcription elongation regulator 1, TBP-associated factor. Based on sequence homology, a domain including amino acids 92-578 is expressed.

PF10_0164 (SEQ ID NO:30) is a hypothetical membrane protein. A hydrophilic, non-membrane portion including amino acids 76-130 is expressed.

PF10_0214 (SEQ ID NO:31) is a hypothetical protein of 168 kDa molecular weight. Based on antigenic surface probability, a domain including amino acids 415-885 is expressed.

PF13_0012 (SEQ ID NO:33) is a hypothetical protein of 26.8 kDa molecular weight. This protein is expressed from amino acid 84, without putative transmembrane domains.

PF14_0044 (SEQ ID NO:34) is a hypothetical protein of 33.5 kDa molecular weight. This protein is expressed from amino acid 22, without the putative signal peptide.

PF14_0050 (SEQ ID NO:35) is a hypothetical protein of 124 kDa molecular weight. This protein is expressed as two domains: the first domain includes amino acids 208-512, the second domain includes amino acids from 716 to carboxyl end. Both domains are hydrophilic and contain multiple antigenic epitopes.

PFA0200w (SEQ ID NO:36) is a hypothetical membrane protein of 19 kDa molecular weight. This protein is expressed as a hydrophilic, non-membrane portion including amino acids 1-135.

PFD0215c (SEQ ID NO:39) is a pf52 protein of 56 kDa molecular weight. This protein is expressed as two domains: the first domain includes amino acids 181-306, the second domain includes amino acids 47-457. The first domain has extensive sequence homology to sexual stage antigen s48/45 domain. The second domain excludes hydrophobic transmembrane regions and contains multiple antigenic epitopes.

PFD0285c (SEQ ID NO:40) is a putative lysine decarboxylase of 280.9 kDa molecular weight with substantial homology to the major domain of Lys/Arg decarboxylase. Based on sequence homology, a domain including amino acids 585-1018 is expressed.

PFD0430c (SEQ ID NO:41) is a hypothetical protein of 94.7 kDa molecular weight. Based on antigenic surface probability, a domain beginning at amino acid 230 to the C-terminal end is expressed.

PFE1550w (SEQ ID NO:44) is a hypothetical membrane protein of 85 kDa molecular weight. This protein is expressed as a hydrophilic, non-membrane portion including amino acids 236-683.

PFL0800c (SEQ ID NO:45) is a hypothetical protein of 20 kDa molecular weight. This protein is expressed starting at amino acid 26, after putative transmembrane domains.

PFD0425w (SEQ ID NO:48) is a hypothetical protein of 113 kDa molecular weight. This protein is expressed as two domains: the first domain includes amino acids 23-459, the second domain includes amino acids 488-813. The first domain has extensive sequence homology to N-terminal region of Adaptin. Both domains are hydrophilic and contain multiple antigenic epitopes.

f. Immune Recognition of Proteins: The recombinant proteins are analyzed for their recognition by T cells and sera from immune and non-immune individuals, for example, as described in EXAMPLE 4, in Doolan et al., *Proc. Natl. Acad. Sci. USA* 100(17):9952-9957, 2003; and in Sundaresh et al., *Bioinformatics* 22(14):1760-1766, 2006.

It is expected that the proteins that are used to immunize rabbits are immunogenic, and elicit antibodies that recognize *Plasmodium* liver stages, as described in EXAMPLE 1, and/or T cell responses, as described in EXAMPLE 4. Proteins that react with T cells and/or sera from immune individuals at significantly higher levels compared with T cells and/or sera from nonimmune individuals are expected to be good immunogens for use in a malaria vaccine.

EXAMPLE 7

This example describes the preparation of a DNA vaccine encoding a liver stage *Plasmodium* polypeptide. The development of effective vaccines is one of the most promising approaches for providing cost-effective interventions to complement currently available control strategies for malaria. DNA as vaccines were first reported by Ulmer et al., *Science* 259:1745-1749, 1993, who reported an induced protective immunity against influenza after injection of plasmid DNA encoding a viral protein.

DNA or nucleic acid vaccines are being evaluated for efficacy against a range of parasitic diseases including malaria. Data from studies in rodent model systems have provided proof of principle that DNA vaccines are effective at inducing both humoral and T cell responses to a variety of candidate vaccine antigens. In particular, the induction of potent cellular responses often gives DNA vaccination an immunological advantage over subunit protein vaccination. Protection against parasite challenge has been demonstrated in a number of systems. The use of DNA as a vaccine has been evaluated recently using 302 *P. falciparum* genes (Aguiar et al., *Genome Res.* 14(10B):2076-2082, 2004), 192 *P. yoelii* sporozoite genes (Haddad et al., *Infect. Immun.* 70(8):4329-4335, 2004), and ~2000 *P. berghei* full length cDNA (Shibui et al., *Vaccine* 23(34):4359-4366, 2005).

Materials and Methods (Adapted from Shibui et al., *Vaccine* 23(34):4359-4366, 2005)

cDNA encoding the full length of the gene is inserted in an expression vector.

Plasmid DNA is extracted, purified, and precipitated onto 1 micrometer gold particles using $CaCl_2$ in the presence of spermidine at a loading rate of 2 microgram DNA/mg of gold according to the instructions of the manufacturer. A helium gene gun system is used to inoculate mice with these DNA coated gold particles.

Immunization of mice is carried out by three injections of the gold particles 1 week apart. The immunized mice are challenged after 1 week with either blood stage parasites or infectious sporozoites dissected from infected mosquitoes.

Each of the scientific or patent references cited herein is hereby incorporated by reference.

While the preferred embodiment of the invention has been illustrated and described, it will be appreciated that various changes can be made therein without departing from the spirit and scope of the invention.

---

The invention claimed is:

1. An isolated polypeptide comprising an amino acid sequence with at least 95% amino acid sequence identity to SEQ ID NO:20.

2. The isolated polypeptide of claim 1 comprising the amino acid sequence of SEQ ID NO:20.

3. An immunogenic composition comprising an isolated polypeptide and a pharmaceutically acceptable carrier, wherein the isolated polypeptide comprises an amino acid sequence with at least 95% identity to SEQ ID NO:20.

4. The immunogenic composition of claim 3, wherein the isolated polypeptide comprises the amino acid sequence of SEQ ID NO:20.

5. An immunogenic composition comprising an isolated polypeptide and a pharmaceutically acceptable carrier, wherein the isolated polypeptide comprises an amino acid sequence of amino acids 151-326 of SEQ ID NO:20.

* * * * *

UNITED STATES PATENT AND TRADEMARK OFFICE
CERTIFICATE OF CORRECTION

PATENT NO. : 8,318,183 B2  Page 1 of 1
APPLICATION NO. : 12/722439
DATED : November 27, 2012
INVENTOR(S) : P. Duffy et al.

It is certified that error appears in the above-identified patent and that said Letters Patent is hereby corrected as shown below:

| TITLE PAGE | LINE | ERROR |
|---|---|---|
| Item (73) | Assignee | "Seattle Biomedical Research Institute, Seattle, WA (US); The United States of America, as Represented by the Secretary of the Army, on Behalf of the Walter Reed Army Institute of Research, Washington, DC (US); Philadelphia Health & Education Corporation, Philadelphia, PA (US)," should read |
| | | --Seattle Biomedical Research Institute, Seattle, WA (US); The United States of America, as Represented by the Secretary of the Army, on Behalf of the Walter Reed Army Institute of Research, Washington, DC (US); Philadelphia Health & Education Corporation D/B/A Drexel University College of Medicine "DUCOM," Philadelphia, PA (US)-- |

Signed and Sealed this
Seventeenth Day of September, 2013

Teresa Stanek Rea
*Deputy Director of the United States Patent and Trademark Office*

SEQUENCE LISTING

<160> NUMBER OF SEQ ID NOS: 52

<210> SEQ ID NO 1
<211> LENGTH: 1784
<212> TYPE: PRT
<213> ORGANISM: Plasmodium yoelii

<400> SEQUENCE: 1

```
Met Lys Arg Ile Leu Ala Tyr Ser Leu Phe Phe Leu Tyr Ile Leu Arg
1               5                   10                  15

Asn Asn Val Leu Ser Lys Lys Thr Ile Glu Tyr Asn Leu Leu Gly Ser
            20                  25                  30

Ala His Lys Ser Asp Asn Ile Val Asp Arg Leu Gln Val Ile Thr Glu
        35                  40                  45

Gly Lys Tyr Arg Asp Ile Leu Val Glu Val Asn Lys Pro Leu Leu Ser
    50                  55                  60

Ile Ile Glu Asn Lys Glu Ser Val Ser Leu Asp Ile Leu Leu Ser Thr
65                  70                  75                  80

Ile Lys Leu Leu Asp Asp Lys Asn Lys Glu Thr Asp Asp Leu Ser Lys
                85                  90                  95

Lys Lys Glu Ile Glu Gln Thr Ile Ile Tyr Ile Lys Asp Ala Ile Lys
            100                 105                 110

Asn His Leu Gly Asn Asp Gly Asn Asn Glu Glu Asn Asp Gly Asn Asp
        115                 120                 125

Ile Thr Lys Thr Lys Ser Asn Lys Ser Asn Leu Met Leu Lys Leu Asp
    130                 135                 140

Asn Tyr Tyr Met Lys Arg Asp Leu Glu Asn Leu Lys Lys Lys Ser Asn
145                 150                 155                 160

Asp Ile Ala Leu Arg Lys Ala Asn Leu Gly Lys Lys Leu Lys Ala Tyr
                165                 170                 175

Ser Thr Ser Ser Glu Ser Leu Leu Phe Gly Ala Pro Gly Asp Leu Asn
            180                 185                 190

Leu Ser Asp Asp Ser Val Lys Glu Leu Asn Asn Met Ile Ser Ile Lys
        195                 200                 205

Ile Leu Arg Gln Arg Ile Tyr Lys Asp Asn Met Pro Phe Thr Thr Glu
    210                 215                 220

Ser Val Pro Lys Thr Phe Asn Lys Leu Val Asp Leu Tyr Thr Pro Leu
225                 230                 235                 240

Leu Asp Phe Asn Leu Asp Ser Leu Glu Lys Tyr Lys Asn Asn Glu Ile
                245                 250                 255

Lys Tyr Tyr Thr Asp Ser Lys Ser Glu Phe Phe Tyr Leu Leu Arg Asn
            260                 265                 270

Asn Met Asp Leu Glu Lys Phe Met Leu Lys Leu Pro Ile Ser Lys Met
        275                 280                 285

Pro Asn Pro Lys Pro Asn Asp Asp Val Ser Glu Ser Ser Asp Val Asp
    290                 295                 300

Asn Lys Ile Tyr Thr Tyr Val Asn Asn Leu Glu Lys Glu Lys Asn
305                 310                 315                 320
```

```
Ala Lys Glu Tyr Ser Leu Gly Ala Tyr Asn Thr Asp Pro Val Tyr Thr
            325                 330                 335

Tyr Ser Ser Lys Ile Lys Lys Asn Pro Ile Ser Lys Gln Asn Glu Gln
            340                 345                 350

Ser Asp Ser Val Ser Arg Ile Asn His Leu Leu Gln Lys Lys Met Gly
            355                 360                 365

His Thr Tyr Leu Asn Lys Pro Glu Lys Tyr Tyr Asn His Gln Asn Gly
            370                 375                 380

Leu Ile His Lys Asn Arg Pro Asn Gly Tyr Asn Ser Gln Phe Ile Asn
385                 390                 395                 400

Ser Asn Asn Glu Asn Glu Thr Cys Tyr Lys Lys His Asn Asn Asn Ile
                405                 410                 415

Leu Phe Glu Ile Ile Ile Lys Ser His Leu Leu Thr Asn Asn Asp Val
            420                 425                 430

Cys Lys Lys Ile Ile Ile Lys Lys Ala Asp Gly Asn Asp Ser Ser Glu
            435                 440                 445

Asn Asn Ile Ser Glu Asp Ala Arg Ile Ile Tyr Asp Asn Asp Ser Ala
450                 455                 460

Lys Asn Cys Ile Gln Tyr Ser Lys Lys Asn Asp Glu Leu Tyr Tyr Val
465                 470                 475                 480

Ile Pro Leu Ile His Phe Asn Gly Pro Ser Lys Ser Met Arg Cys Leu
                485                 490                 495

Ser Cys Asp Asp Tyr Glu Lys Asn Ile His Asn Lys Cys Pro Phe Asn
            500                 505                 510

Glu Asn Phe Val His Leu Thr Tyr Asp Asn Lys Cys Ile Val Cys Met
            515                 520                 525

Pro Ser Ser Ala Ile Ser Asn Cys Leu Ile Asn Ser Gln Lys Val Asn
            530                 535                 540

Ile Asp Ser Cys Lys Gly Tyr Cys Asn Cys Ser Asn Cys Phe Ser Pro
545                 550                 555                 560

Asn Asn Glu Phe His Thr Phe Lys Tyr Val Phe Pro Ser Tyr Lys Tyr
                565                 570                 575

Thr His Arg Val Arg Asp Thr His Asn Pro Asn Asn Cys Asn Cys Glu
                580                 585                 590

Ser Phe Arg Tyr Ser Gly Gln Gly Asp Pro Tyr Phe Lys Val Arg Asp
            595                 600                 605

Met Asn Lys His Arg Asp Lys Arg Leu Tyr Glu Ser Ile His Lys Gln
            610                 615                 620

Met Glu Gly Arg Asp Lys Thr Tyr Tyr Glu Gln Ser Asn Glu Tyr Gln
625                 630                 635                 640

Ile Gly Glu Gly Ala Ser Glu Asn Asp Val Gly Glu Cys Leu Phe Phe
                645                 650                 655

Gly Cys Ile His Asp Asp Gly Tyr Asn Asp Phe Asp Asn Tyr Asn Ile
                660                 665                 670

Lys Met Arg Glu Thr Ile Lys Leu Asn Ser Ser Ile Phe Asp Pro Ile
            675                 680                 685

Ser Leu Lys Lys Asn Asn Ser Asp Tyr Ala Tyr Ala Asp Glu Glu Ile
            690                 695                 700

Ile Glu Asn Val Asn Lys Glu Arg Tyr Ile Lys Asn Asp Arg Lys Lys
705                 710                 715                 720

Asn Val Asp Ile Lys Ile Leu His Glu Asn Val Asp Asn Asn Ser Glu
                725                 730                 735

Asn Glu Lys Asn Glu Lys Asn Glu Lys Asn Glu Lys Asn Glu Glu Asn
```

-continued

```
                    740                 745                 750
Lys Glu Asn Glu Glu Asn Lys Glu Asn Lys Glu Asn Arg
            755                 760                 765
Asp Ile Val Lys Gly Ser Asp Ser Asp Asn Tyr Asp Asp Asn Asp
            770                 775                 780
Ile Ser Gln Glu Ala Asn Asn Ile Glu Tyr Phe Lys Lys Met Tyr Tyr
785                 790                 795                 800
Asp Ile Leu Asn Asn Asn Thr Asp Asp Glu Ser Asp Val Ser Glu Asn
                    805                 810                 815
Asp Asp Asp Asp Asp Asp Asp Asp Asn Gly Tyr Tyr Asp Gly Asn
                    820                 825                 830
Ile Asp Asn Phe Tyr Ser Leu Arg Phe Leu Tyr Lys Thr Arg Ile Phe
                    835                 840                 845
Thr Lys Lys Lys Thr Val Ile Asn Ala Tyr Ile Lys Thr Asn Lys Ile
                    850                 855                 860
Ser Ala Asp Asp Asn Lys Lys Asn Ile Leu Phe Leu Phe Lys Lys Leu
865                 870                 875                 880
Phe Asn Thr Val Phe Lys Asp Val His Tyr Lys Ile Lys Asp Ser Ala
                        885                 890                 895
Val Ser Leu Phe Pro Val Ile Thr Asp Ser Asn Ile Ile Gly Phe Asp
                    900                 905                 910
Val Asp Phe Gly Arg Ile Gln Val Gln Tyr Ala Gly Cys Ile Asn Met
                    915                 920                 925
Leu Arg Tyr Ser Val Phe Asp Thr Gln Asn Met Ala Ile Tyr Phe Ile
                    930                 935                 940
Thr Pro Asp Lys Lys Tyr Ile Leu Leu Glu Asp Val Ile Lys Glu Ile
945                 950                 955                 960
Ser Glu Gly Asn Glu Asn Tyr Tyr Tyr Asn Glu Asn Val Glu Gly
                        965                 970                 975
Asn Ser Asn Glu Asn Val Glu Asn Ser Asn Glu Asn Val Glu Glu
                        980                 985                 990
His Ser Asn Glu Asn Asn Glu Ile Ile Asn Asn Glu Asn Asp Leu Ala
                    995                 1000                1005
Leu Tyr Glu Asn Thr Ser His Ser Ser Phe Glu Asn Leu Glu Ser
            1010                1015                1020
Glu Leu Asp Asp Gly Tyr Asn Lys Thr Asp Lys Pro Ser Ile Gln
            1025                1030                1035
Asp Glu Lys Gln Glu Leu Asp Asp Lys Glu Asn Thr His Glu Pro
            1040                1045                1050
Ser Lys Asp Asp Tyr Ser Lys Asn Asn Gly Lys Asp Ser Leu Val
            1055                1060                1065
Glu Leu Asn Lys Asp Asn Glu Glu Lys His Glu Leu Leu Asp Thr
            1070                1075                1080
Ile Leu Lys Glu Phe Asn Asn Glu Arg Glu Lys Thr Pro Ala Gln
            1085                1090                1095
Asn Glu Leu Ser Lys Val Leu Ser Glu Tyr Gly Asp Leu Leu Ser
            1100                1105                1110
Lys Glu Asp Leu Lys Glu Ile Lys Asn Asn His Lys Asn Val Asp
            1115                1120                1125
Val Asn Lys Gly Asn Ala Glu Asn Gly Asp Ala Ile Glu Ile Ile
            1130                1135                1140
Ile Lys Lys Asn Ser Lys Glu Asn Gly Ile Asn Gly Lys Thr Asn
            1145                1150                1155
```

-continued

```
Asp Lys Asp Asn Ile Val Asn Glu Ser Asp Asp Gln Ser Glu Phe
1160                1165                1170
Ile Thr Ile Asp Gln Asn Gly Cys Glu Ile Ile Asn Glu Thr Met
1175                1180                1185
Arg Lys Tyr Met Asp Lys Tyr Phe Ser Val His Asn Ile Pro Ile
1190                1195                1200
His Tyr Ile Glu Asn Asn Asn Ile Ser Lys Lys Ala Ile His Ile
1205                1210                1215
Thr Ser Asp Ile Asp Ser Asp Leu Asn Met Leu Lys Ser Ser Ile
1220                1225                1230
Leu Ala Ile Ser Asn Thr Asn Gly Lys Ser Ile Asp Asp Phe Lys
1235                1240                1245
Leu Phe Leu Ile Pro Asn Asp Ile Glu Lys Tyr Asp Pro Asn Lys
1250                1255                1260
Leu Glu Asp Ile Pro Ser Ser Ile Arg Thr Ala Asn Asp Leu Tyr
1265                1270                1275
Asn Tyr Ile Lys Arg Met Asn Met Lys Ile Leu Ile Ala Ser Val
1280                1285                1290
His Asp Asp Ala Gly Ile Ser Ile Glu Pro Gln Ile Phe Asn Tyr
1295                1300                1305
Leu Tyr Glu Ser Asn Asn Asp Thr Pro Tyr Ile Glu Ser Ala Leu
1310                1315                1320
Asp Val Lys Glu Gly Lys Glu Ala Thr Asn Thr Glu Leu Glu Leu
1325                1330                1335
Asn Lys Ser Gln Tyr Gly Asp Lys Glu Lys Leu Arg Asp Ser Ser
1340                1345                1350
Ile Leu Lys Asn Gln Gln Leu Ser Asn Ala Leu Leu Lys Asn Glu
1355                1360                1365
Ile Tyr Tyr Thr Thr Lys Lys Glu Ile Lys Ala Asp Gly Ile Met
1370                1375                1380
Lys Asn Gly Ile Glu Asp Thr Asn Leu Arg Gly Lys Ile Ser Gly
1385                1390                1395
Cys Ser Glu Asp Ser Asn Ile Ser Ser Asn Ser Thr Glu Ala Lys
1400                1405                1410
Thr Ile Asp Glu Asn Asn Ala Asp His Lys Asn Glu Glu Glu Thr
1415                1420                1425
Val Phe Glu Ser Asp Asn Gln Tyr Thr Thr Pro Asn Asn Tyr Asn
1430                1435                1440
Lys Ile Asp Ile Tyr Ile Asp Asn Thr Asp Arg Lys Ile Thr Val
1445                1450                1455
Leu Asp Gly Ile Leu Phe Lys His Tyr Thr Phe Lys Leu Phe Ile
1460                1465                1470
Met Asp Ile Met Asn Lys Ile His Val Pro Ser Asn Phe Ile
1475                1480                1485
Asp Leu Lys Ser Tyr Lys Lys Gly Ile Ser Pro Phe Asp Ile Phe
1490                1495                1500
Asp Cys Leu Glu Tyr Tyr Ser Tyr Asn Lys Lys Ser Asn Ile Ile
1505                1510                1515
Ser Ala Leu Phe Phe Glu Lys His Ile Lys Leu Leu Asp Ile Leu
1520                1525                1530
Lys Asn Leu Asn Ser Lys Asp Glu Tyr Leu Leu Ile Lys Asn Lys
1535                1540                1545
Asn Ser Glu Tyr Cys Ser Gly Val Asp Asn Leu Lys Tyr Ile Lys
1550                1555                1560
```

```
Ile Pro Leu Thr Ile Asn Leu Lys Lys Ser Lys Asp Ile Tyr Leu
    1565                1570                1575

Glu Phe Pro Ile Phe His Ile Asp Glu His Tyr Asn Phe Val Tyr
    1580                1585                1590

Asn Lys Ile Ser Phe Met Asn Val Pro Glu Asn Tyr Thr Ala Ser
    1595                1600                1605

Lys Leu Cys Asn Thr Val Lys Asn Ile Leu Asn Glu Ala Leu Asp
    1610                1615                1620

Ile Tyr Glu Leu Asp Ile Ile Thr Ser Leu Gln Ile Tyr Asn Leu
    1625                1630                1635

Ile Asp Asn Glu Trp Glu Tyr Ile Glu Asp Asn Val Leu Ile His
    1640                1645                1650

Glu Ile Lys Met Asp Asn Asn Tyr Leu Tyr Thr Met Phe Ile His
    1655                1660                1665

Asp Lys Phe Leu Thr Lys Arg Tyr Tyr Gln Ala Met Ser Asn Leu
    1670                1675                1680

Ile Ile Asp Leu Ser Asn Asn Ile Tyr Ile Lys Lys Leu Asp
    1685                1690                1695

Ile Tyr Ile Asp Tyr Asn Tyr Ser Pro Tyr Thr Leu Tyr Asn Ile
    1700                1705                1710

Pro Ile His Met Ser Phe Met Asn Leu Lys Tyr Leu Leu Leu His
    1715                1720                1725

His Thr Asn Ala Phe Leu Ser Asp Ser Phe Leu Asn Glu Asn Ser
    1730                1735                1740

Asn Lys Thr Tyr Asn Leu Phe Leu Leu Asn Met Val Asn Thr Phe
    1745                1750                1755

Tyr Lys Ile Lys Leu Asn Ser Asn Lys Met Met Gln Pro Ile Leu
    1760                1765                1770

Glu Asp Leu Leu Lys Ile Ser Gly Lys Cys Ser
    1775                1780

<210> SEQ ID NO 2
<211> LENGTH: 3009
<212> TYPE: PRT
<213> ORGANISM: Plasmodium yoelii

<400> SEQUENCE: 2

Ser Glu Asn Asn Ser Lys Asn Lys Ser Glu Thr Lys Ser Lys Ile Lys
1               5                   10                  15

Lys Val

```
Asp Asn Lys Asn Glu Asp Ser Asn Tyr Asp Asn Pro Ala Ser Pro Ala
145                 150                 155                 160

Pro Asn Asp Ser Asn Tyr Asp Ser Pro Ala Ser Pro Ala Pro Asn Asp
                165                 170                 175

Val Pro Glu Gly Asn Ile Gln Arg Pro Ser Arg Leu Ile Ala Glu Lys
            180                 185                 190

Glu Ser Glu Asn Ser Glu Asn Lys Ser Glu Asp Lys Lys Gln Asp
        195                 200                 205

Lys Glu Thr Asn Thr Ser Asp Asn Asn Gly Asp Asn Pro Ala Ser
    210                 215                 220

Pro Ala Pro Asn Asp Ser Asn Tyr Asp Ser Pro Ala Ser Pro Ser Pro
225                 230                 235                 240

Asn Asp Val Pro Glu Gly Asn Ile Lys Arg Pro Ser Arg Leu Ile Ala
                245                 250                 255

Glu Lys Glu Ser Glu Asn Asn Ser Glu Asn Lys Ser Glu Asp Lys Glu
            260                 265                 270

Gln Asn Lys Lys Gln Asp Lys Glu Thr Asn Thr Ser Asp Asn Asn Asn
        275                 280                 285

Gly Asp Asn Pro Ala Ser Pro Ala Pro Asn Asp Val Pro Glu Gly Asn
        290                 295                 300

Ile Gln Arg Pro Ser Arg Leu Ile Ala Glu Lys Glu Ser Glu Asn Asn
305                 310                 315                 320

Ser Glu Asn Lys Ser Glu Asn Lys Glu Thr Asn Thr Ser Asp Asn Lys
                325                 330                 335

Asn Gly Asp Ser Asn Tyr Asp Asn Pro Ala Ser Pro Ala Pro Asn Asp
            340                 345                 350

Ser Asn Tyr Asp Asn Pro Ala Ser Pro Ala Pro Asn Asp Val Pro Glu
        355                 360                 365

Gly Asn Ile Gln Arg Pro Ser Arg Leu Ile Ala Glu Lys Glu Ser Glu
    370                 375                 380

Asn Asn Ser Lys Asn Lys Ser Glu Asp Lys Lys Gln Asn Lys Glu Ser
385                 390                 395                 400

Asn Thr Ser Asn Asn Asn Asn Glu Asp Ser Asn Tyr Asp Asn Pro Ala
                405                 410                 415

Ser Pro Ala Pro Asn Asp Ser Asn Tyr Asp Asn Pro Ala Ser Pro Ala
            420                 425                 430

Pro Asn Asp Ser Asn Tyr Asp Ser Pro Ala Ser Pro Ala Pro Asn Asp
        435                 440                 445

Val Pro Glu Gly Asn Ile Lys Arg Pro Ser Arg Leu Ile Ala Glu Lys
    450                 455                 460

Glu Ser Glu Asn Asn Ser Lys Asn Lys Ser Glu Asp Lys Lys Gln Asn
465                 470                 475                 480

Lys Glu Thr Asn Thr Ser Asp Asn Asn Asn Gly Asp Ser Asn Tyr Asp
                485                 490                 495

Asn Pro Ser Ser Pro Ala Pro Asn Asp Ile Pro Glu Gly Asn Ile Lys
            500                 505                 510

Arg Pro Ser Arg Leu Ile Ala Glu Lys Glu Ser Glu Asn Lys Ser Glu
        515                 520                 525

Ser Asn Ser Glu Asn Lys Ser Glu Asp Lys Lys Gln Asp Lys Glu Ser
    530                 535                 540

Asn Thr Ser Asp Asn Asn Asn Gly Glu Arg Pro Ala Thr Pro Phe Pro
545                 550                 555                 560

Asn Asp Leu Pro Glu Asp Lys Pro Lys Arg Pro Thr Arg Leu Phe Ala
```

-continued

```
                565                 570                 575
Glu Lys Glu Ser Glu Asn Asn Gly Glu Asn Lys Asn Glu Asp Lys Lys
            580                 585                 590
Gln Asp Lys Glu Thr Asn Thr Ser Asp Asn Asn Asn Gly Asp Arg Pro
            595                 600                 605
Ala Ser Pro Ala Pro Asn Asp Ser Asn Tyr Asp Ser Pro Ala Ser Pro
            610                 615                 620
Ala Pro Asn Asp Val Pro Glu Gly Asn Ile Lys Arg Pro Ser Arg Leu
625                 630                 635                 640
Ile Ala Glu Asn Glu Ser Glu Asn Lys Glu Asn Glu Lys Lys Lys
                645                 650                 655
Ile Lys Val Tyr Asn Thr Ser Gly Asn Asn Gly Asp Ser Pro Ala
            660                 665                 670
Ser Pro Ala Pro Asn Asp Val Pro Glu Gly Asn Ile Lys Arg Pro Ser
            675                 680                 685
Arg Leu Ile Ala Glu Lys Glu Ser Glu Asn Asn Ser Glu Asn Lys Ser
            690                 695                 700
Glu Asp Lys Lys Gln Asp Lys Glu Thr Asn Thr Ser Asp Asn Asn Asn
705                 710                 715                 720
Gly Asp Asn Pro Ala Ser Pro Ala His Lys Asp Ser Asn Tyr Asp
                725                 730                 735
Asn Pro Ala Ser Pro Ala Pro Asn Asp Val Pro Glu Gly Asn Ile Gln
            740                 745                 750
Arg Pro Ser Arg Leu Ile Ala Glu Lys Glu Ser Glu Asn Asn Ser Glu
            755                 760                 765
Asn Lys Asn Glu Asp Lys Lys Gln Asp Lys Glu Thr Asn Thr Ser Asp
            770                 775                 780
Asn Asn Asn Gly Asp Ser Asn Tyr Asp Asn Pro Ser Ser Pro Ala Pro
785                 790                 795                 800
Asn Asp Val Pro Glu Gly Asn Ile Lys Arg Pro Ser Arg Leu Ile Ala
                805                 810                 815
Glu Lys Glu Ser Glu Asn Lys Ser Glu Ser Asn Ser Glu Asn Lys Ser
            820                 825                 830
Glu Asp Lys Lys Gln Asp Lys Glu Ser Asn Thr Ser Asp Asn Asn Asn
            835                 840                 845
Gly Asp Arg Pro Ala Ser Pro Ala Asn Asp Ser Asn Tyr Asp Ser
            850                 855                 860
Pro Ala Ser Pro Ala Pro Asn Asp Ser Asn Tyr Asp Ser Pro Ala Ser
865                 870                 875                 880
Pro Ala Pro Asn Asp Val Pro Glu Gly Asn Ile Lys Arg Pro Ser Arg
                885                 890                 895
Leu Ile Ala Glu Asn Glu Ser Glu Asn Lys Glu Asn Glu Lys Lys Lys
            900                 905                 910
Lys Ile Lys Val Tyr Asn Thr Ser Gly Asn Asn Gly Asp Ser Pro
            915                 920                 925
Ala Ser Pro Ala Pro Asn Asp Val Pro Glu Gly Asn Ile Gln Arg Pro
            930                 935                 940
Ser Arg Leu Ile Ala Glu Lys Glu Ser Glu Asn Lys Ser Glu Ser Asn
945                 950                 955                 960
Ser Glu Asn Lys Ser Glu Asp Lys Lys Gln Asp Lys Glu Thr Asn Thr
                965                 970                 975
Ser Asp Asn Asn Asn Gly Asp Asn Pro Ala Ser Pro Ala Pro Lys Asp
            980                 985                 990
```

-continued

```
Val Pro Glu Asp Lys Pro Lys Arg  Pro Thr Arg Leu Phe  Ala Glu Lys
        995              1000              1005

Glu Ser  Glu Asn Asn Ser Glu  Asn Lys Asn Glu Asp  Lys Lys Gln
    1010             1015              1020

Asp Lys  Glu Thr Asn Thr Ser  Asp Asn Lys Asn Asp  Asp Ser Asn
    1025             1030              1035

Tyr Glu  Asn Pro Ala Ser Pro  Ala Pro Lys Asp Val  Pro Glu Asp
    1040             1045              1050

Lys Pro  Lys Arg Pro Thr Arg  Leu Phe Ala Glu Lys  Glu Ser Glu
    1055             1060              1065

Asn Asn  Ser Glu Asn Lys Gln  Asn Lys Glu Ser  Asn Thr Ser
    1070             1075              1080

Asp Asn  Asn Asn Gly Asp Asn  Ser Ala Ser Ser Val  Ser Ile Asp
    1085             1090              1095

Ile Pro  Glu Gly Asn Ile Lys  Ile Pro Ser Ile Leu  Ile Ser Glu
    1100             1105              1110

Ser Glu  Ser Glu Asn Lys Ser  Lys Thr Asn Gly Glu  Asp Lys Glu
    1115             1120              1125

Gln Asn  Lys Glu Ser Asn Thr  Ser Asp Asn Asn Gly  Asp Asn Ser
    1130             1135              1140

Ala Ser  Ser Val Ser Ile Asp  Ile Pro Glu Gly Asn  Ile Gln Arg
    1145             1150              1155

Pro Ser  Arg Leu Ile Ala Glu  Lys Ser Glu Asn  Asn Ser Glu
    1160             1165              1170

His Asn  Ser Lys Asn Lys Asn  Glu Asp Lys Lys Gln  Asp Lys Glu
    1175             1180              1185

Thr Asn  Thr Ser Asn Asn Lys  Thr Asp Asp Asn Pro  Ala Ser Pro
    1190             1195              1200

Ala Pro  Asn Asp Val Pro Glu  Asp Lys Pro Lys Arg  Pro Thr Arg
    1205             1210              1215

Leu Phe  Ala Glu Lys Glu Ser  Glu Asn Asn Glu  Asn Lys Asn
    1220             1225              1230

Glu Asp  Lys Lys Gln Asn Lys  Glu Ser Asn Thr Ser  Asp Asn Lys
    1235             1240              1245

Asn Glu  Asp Ser Asn Tyr Asp  Asn Pro Ala Ser Pro  Ala Pro Asn
    1250             1255              1260

Asp Ser  Asn Tyr Asp Asn Pro  Ala Ser Pro Ala Pro  Asn Asp Val
    1265             1270              1275

Pro Glu  Gly Asn Ile Lys Arg  Pro Ser Arg Leu Ile  Ala Glu Lys
    1280             1285              1290

Glu Ser  Glu Asn Asn Ser Glu  Asn Lys Asn Glu Tyr  Lys Glu Gln
    1295             1300              1305

Asn Lys  Glu Tyr Asn Thr Ser  Asp Asn Asn Ser Gly  Asp Ile Pro
    1310             1315              1320

Glu Ser  Pro Val Pro Asn Tyr  Val Pro Glu Gly Lys  Phe Lys Lys
    1325             1330              1335

Ile Ser  Arg Leu Ile Ala Lys  Lys Glu Ser Glu Asn  Asn Arg Glu
    1340             1345              1350

Asn Lys  Ser Glu Asp Lys Lys  Gln Asp Lys Glu Thr  Asn Thr Ser
    1355             1360              1365

Asp Asn  Lys Asn Asp Asp Arg  Pro Ala Thr Pro Val  Pro Asn Asp
    1370             1375              1380

Val Pro  Glu Gly Asn Ile Lys  Arg Pro Ser Arg Leu  Ile Ala Glu
    1385             1390              1395
```

```
Lys Glu Thr Glu Asn Asn Gly Glu Asn Lys Ser Glu Asp Lys Lys
            1400                1405                1410
Gln Asp Lys Glu Thr Asn Thr Ser Asp Asn Asn His Asp Asp Arg
    1415                1420                1425
Pro Ala Thr Pro Ala Pro Asn Asp Val Pro Glu Ala Asn Ile Lys
        1430                1435                1440
Arg Pro Ser Arg Leu Ile Ala Glu Lys Glu Ser Glu Asn Asn Ser
    1445                1450                1455
Glu Asn Lys Ser Glu Asn Lys Glu Thr Asn Thr Ser Asp Asn Lys
    1460                1465                1470
Asn Gly Asp Ser Asn Tyr Asp Asn Pro Ala Ser Pro Ala Pro Asn
        1475                1480                1485
Asp Asp Ser Asn Tyr Asp Asn Pro Ala Ser Pro Ala Pro Asn Asp
    1490                1495                1500
Val Pro Glu Gly Asn Ile Lys Arg Pro Ser Arg Leu Ile Ala Glu
    1505                1510                1515
Lys Glu Ser Glu Asn Asn Ser Glu Asn Asn Ser Glu Asn Lys Glu
    1520                1525                1530
Ser Asn Thr Ser Asp Asn Asn Asn Gly Asp Asp Ser Ala Ser Ser
    1535                1540                1545
Val Ser Ile Asp Ile Pro Glu Gly Asn Ile Lys Trp Tyr Ser Arg
    1550                1555                1560
Pro Thr Ala Glu Lys Lys Ser Glu Asn Asn Ser Glu Asn Asn Ser
    1565                1570                1575
Glu Asn Lys Glu Ser Asn Thr Ser Asp Asn Asn Asn Gly Asp Asp
    1580                1585                1590
Ser Ala Ser Ser Val Ser Ile Asp Ile Pro Glu Gly Asn Ile Lys
    1595                1600                1605
Trp Tyr Ser Arg Pro Thr Ala Glu Lys Lys Ser Glu Asn Asn Ser
    1610                1615                1620
Glu Asn Asn Ser Lys Asn Lys Glu Ser Asn Thr Ser Asp Asn Asn
    1625                1630                1635
Asn Gly Asp Asp Ser Ala Ser Ser Val Ser Val Asp Ile Pro Glu
    1640                1645                1650
Gly Asn Ile Lys Arg Pro Ser Arg Leu Ile Ala Glu Lys Glu Ser
    1655                1660                1665
Glu Asn Asn Ser Glu Asn Lys Asn Asp Asp Lys Lys Gln Asp Lys
    1670                1675                1680
Glu Thr Asn Thr Ser Asp Asn Lys Asn Glu Asp Ser Asn Tyr Asp
    1685                1690                1695
Asn Pro Ala Ser Pro Ala Pro Asn Asp Ser Asn Tyr Asp Asn Pro
    1700                1705                1710
Ala Ser Pro Ala Pro Asn Asp Ile Pro Glu Gly Asn Ile Lys Arg
    1715                1720                1725
Pro Ser Arg Leu Ile Ala Glu Lys Glu Tyr Glu Asn Asn Ser Glu
    1730                1735                1740
Asn Lys Asn Glu Tyr Lys Glu Gln Asn Lys Glu Tyr Asn Thr Ser
    1745                1750                1755
Asp Asn Asn Ser Gly Asp Ile Pro Glu Ser Pro Val Pro Asn Tyr
    1760                1765                1770
Val Pro Glu Gly Lys Phe Lys Arg Phe Ser Arg Leu Ile Ala Glu
    1775                1780                1785
Lys Glu Ser Glu Asn Asn Ser Glu Asn Lys Asn Asp Asp Lys Lys
```

```
                    1790                1795                1800

Gln Asp Lys Glu Thr Asn Thr Ser Asp Asn Asn Asn Glu Val Ser
    1805                1810                1815

Asn Tyr Asp Asn Pro Ala Ser Pro Ala Pro Asn Asp Ser Asn Tyr
    1820                1825                1830

Asp Asn Pro Ala Ser Pro Val Ser Val Asp Ile Pro Glu Gly Asn
    1835                1840                1845

Ile Lys Arg Pro Ser Arg Leu Ile Ala Glu Lys Glu Ser Glu Asn
    1850                1855                1860

Asn Asn Lys Asn Lys Asn Glu Asp Lys Lys His Asp Lys Glu Thr
    1865                1870                1875

Asn Thr Ser Asp Asn Lys Asn Glu Asp Ser Asn Tyr Asp Asn Pro
    1880                1885                1890

Ala Ser Pro Ala Pro Asn Asp Ser Asn Tyr Asp Asn Pro Ala Ser
    1895                1900                1905

Pro Val Ser Val Asp Ile Pro Glu Gly Asn Ile Lys Arg Pro Ser
    1910                1915                1920

Arg Leu Ile Ala Glu Lys Glu Ser Glu Asn Lys Asn Glu Asp Lys
    1925                1930                1935

Lys Gln Asp Lys Lys Gln Asp Asn Glu Thr Asn Asn Ser Asp Asn
    1940                1945                1950

Asn His Asp Asp Arg Pro Ala Thr Pro Ala Pro Asn Asp Val Pro
    1955                1960                1965

Glu Asp Lys Pro Lys Arg Pro Thr Arg Leu Phe Ala Glu Lys Glu
    1970                1975                1980

Ser Glu Asn Asn Ser Glu Asn Lys Asn Glu Asp Lys Lys Gln Asn
    1985                1990                1995

Lys Glu Ser Asn Thr Ser Asp Asn Asn His Asp Asp Arg Pro Ala
    2000                2005                2010

Thr Pro Ala Pro Asn Asp Val Pro Glu Asp Lys Pro Lys Arg Pro
    2015                2020                2025

Thr Arg Leu Phe Ala Glu Lys Glu Ser Glu Asn Asn Ser Glu Asn
    2030                2035                2040

Lys Asn Glu Asp Lys Lys Gln Asn Lys Glu Ser Asn Thr Ser Asp
    2045                2050                2055

Asn Lys Asn Glu Asp Ser Asn Tyr Asp Asn Pro Ala Ser Pro Ala
    2060                2065                2070

Pro Asn Asp Asp Ser Asn Tyr Asp Asn Pro Ala Ser Pro Ala Pro
    2075                2080                2085

Asn Asp Val Pro Glu Gly Lys Phe Lys Arg Leu Ser Arg Leu Ile
    2090                2095                2100

Ala Glu Lys Glu Phe Glu Asn Lys Ser Glu Lys His Ile Ser Gly
    2105                2110                2115

Lys Asn Lys Ala Asn Lys Ser Thr Phe Val Glu Asn Gly Gln Lys
    2120                2125                2130

Trp Asn Leu Asp Glu Glu Arg Lys Ser Met Phe Glu Lys Ile Lys
    2135                2140                2145

Lys Lys Lys Gln Lys Tyr Lys Lys Tyr Tyr Ala Tyr Asp Met
    2150                2155                2160

Ile Glu Lys Met Glu Tyr Leu Ser Ser Leu Ser Asp Asp Glu Tyr
    2165                2170                2175

Phe Thr Asn Asp Gly Ala Pro Asn His Ala Gln Thr Ser Ser Val
    2180                2185                2190
```

```
Leu Gly Lys Tyr Leu Lys His Pro Asn Thr Tyr Asn Lys Tyr Leu
2195                2200                2205
Asp Ile Asn Leu Phe Phe Asp Glu Lys Pro Tyr Gln Tyr Arg Lys
2210                2215                2220
Gly Asn Tyr Tyr Phe Ile Asn Pro Phe Pro Tyr Ser Ile Ile Lys
2225                2230                2235
Met Lys Lys Asn Glu Gly Leu Ser Asn Ser Glu Lys Ile Lys Tyr
2240                2245                2250
Asp Gly Val Tyr Cys Tyr Ser Leu Ser Phe Asn Asn Tyr Ser Ser
2255                2260                2265
Leu Thr Tyr Thr Ile Glu Asn Ser Phe Arg Asn Val Lys Pro Ile
2270                2275                2280
Glu Glu Ile Ile Pro Gly Thr Leu Thr Gly Phe Lys Ser Asp Asp
2285                2290                2295
Gly Tyr Gln Lys Met Leu Thr Pro Met Phe Val Glu Gln Asp Met
2300                2305                2310
Phe Leu His Cys Ala Phe Lys Asn Glu Tyr Asp Glu Ile Glu Asn
2315                2320                2325
Lys Ile Ala Ser Phe Pro Val Lys Ile Phe Leu Lys Lys Asn Leu
2330                2335                2340
Asn Lys Thr Lys Gly Cys Ser Phe Gln Ile Asn Lys Asn Gly Ser
2345                2350                2355
Ile Tyr Lys Glu Tyr Ala Glu Arg Glu Ser Phe Leu Ser Lys Lys
2360                2365                2370
Val Ile Leu Asn Asp Glu Ser Thr Ser Asn Glu Cys Asp Ile Thr
2375                2380                2385
Ala Thr Asn Glu Ile Ile Gly Phe Gln Cys Gly Pro Pro Tyr Lys
2390                2395                2400
Tyr Tyr Thr Asn Asp Ser Asn Thr Ser Tyr Ile Asp Lys Ile Phe
2405                2410                2415
Phe Asn Thr Val Asn Asn Glu Asp Ile Lys Ile Gly Glu Tyr Phe
2420                2425                2430
Lys Val Glu Pro Ala His Cys Phe Glu Glu Val Asn Ala Asn Glu
2435                2440                2445
His Ile Glu Asp Ile Ala Pro Gly Ser Phe Pro Phe Pro Asn Phe
2450                2455                2460
Glu Met Ile Asn Gly Gly Leu Lys Ser His His Thr Arg Tyr Ile
2465                2470                2475
Lys Leu Lys Ile Arg Asp Pro Asn Ala Ile Ile Ser Cys Tyr Cys
2480                2485                2490
Asn Tyr Tyr Asn Asn Gly Lys Ile Ile Tyr Ser Gly Ile Met Thr
2495                2500                2505
Ile Asn Gly Lys Lys Lys Tyr Asn Asp Gln Ser Tyr Ser Asp Tyr
2510                2515                2520
Pro Pro Gln Asp Ile Asn Lys Thr Ser Asp Asn Ala Lys Gly Thr
2525                2530                2535
Gly His Lys Thr Ile Asn Ser Asn Lys Lys Ser Lys Ile Asp Asn
2540                2545                2550
Thr Glu Asn Tyr Asp Asn Asp Tyr Lys Tyr Phe Phe Asn Phe Leu
2555                2560                2565
Pro Tyr Tyr Asn Pro Tyr Leu Met Gln Tyr Lys Lys Gln Pro Glu
2570                2575                2580
Tyr Val Val Lys Asn Asp Phe Ile Tyr Asp Ser Lys Tyr Ser Asp
2585                2590                2595
```

```
Thr Asn Asn Asp Glu Phe Leu Lys Lys Ile Lys Asn Asn Leu Ser
    2600                2605            2610
Asp Leu Lys Leu Thr Asp Asn Asn Glu Tyr Ile His Asp Met Asp
    2615                2620            2625
Asp Asn Leu Arg Tyr Lys Tyr Asp Asn Arg Asp Ser Asn Val Tyr
    2630                2635            2640
Pro Ile Ser Glu Tyr Asp Leu Glu Asn His Phe Asp Ser Asp Val
    2645                2650            2655
Leu Ser Asp Ser Tyr Gly His Thr Phe Asn Asp Asp Tyr Ile Ser
    2660                2665            2670
Pro His Ser Asn Ser Tyr Tyr Glu Glu Asn Thr Tyr Asn Ser Asp
    2675                2680            2685
Asp Ile Phe Ser Asn Tyr Asp Asp Val Asn Ile Glu Ala Glu Tyr
    2690                2695            2700
Glu Glu Phe Glu Pro Leu Gln Asn Asn Val Thr Phe Gln Asp Asn
    2705                2710            2715
Lys Ser Tyr Glu Asp Lys Ser Gln Ser Ile Ile Val Ile Asn Lys
    2720                2725            2730
Ser Lys Asn Val Asn Leu Tyr Ile Pro Lys Asn Lys Ile Lys Asn
    2735                2740            2745
Lys Ser Glu Tyr Thr Lys Asn Asn Glu Asp Ile Glu Asp Asn Lys
    2750                2755            2760
Lys Lys Asp Ala Leu Leu Lys Tyr Leu Leu Leu Thr Tyr Glu Glu
    2765                2770            2775
Thr Pro Asp Lys Asn Glu Lys Met Asn Lys Lys Leu Lys Leu Phe
    2780                2785            2790
Lys Glu Tyr Phe Pro Ser Ser Pro Asn His Asn Ile Phe Val Glu
    2795                2800            2805
Glu Lys Glu Asn Asp Asn Thr Ser Asn Lys Ile Lys Ser Ile Phe
    2810                2815            2820
Asp Asn Gln Glu Lys Ser Ile Glu Ser Leu Ser Gly Glu Gln Ile
    2825                2830            2835
Asn Gly Glu Ile Glu Val Ser Glu Asn Asp Ser Thr Leu Asp His
    2840                2845            2850
Asn Lys Ser Tyr Asn Tyr Asp Asn Thr Asn Ser Asn Asn His Glu
    2855                2860            2865
Asn Asn Asn Ala Gly Val Asn Asn Ala Asp Val Asn Asn Asp Gly
    2870                2875            2880
Val Asn Asn Asp Gly Val Asn Asn Ala Gly Val Asn Asn Ala Gly
    2885                2890            2895
Glu Asn Asn Ala Gly Val Asn Asn Ala Gly Glu Asn Asn Ala Gly
    2900                2905            2910
Val Asn Asn Ala Asp Asp Asn Asn Ala Asp Asp Asn Ile Asp Asp
    2915                2920            2925
Asp Thr Thr Asn Phe Ile Met Asp Lys Ile Leu His Asp Leu Phe
    2930                2935            2940
Gly His Asn Glu Tyr Asp Gly Asn Lys Glu Glu Asn Pro Lys Asn
    2945                2950            2955
Lys Lys Ile Tyr Gln Thr Lys Ile Asn Thr Ile Glu Asn Glu Glu
    2960                2965            2970
Asp Asp Glu Glu Glu Glu Glu Glu Glu Asp Leu Ile Glu Lys
    2975                2980            2985
Asp Gly Glu Leu Glu Lys Glu Gly Ile Val Pro Arg Arg Lys Gln
```

```
                      2990               2995             3000
Lys Arg  Val Thr Lys Ile
    3005

<210> SEQ ID NO 3
<211> LENGTH: 311
<212> TYPE: PRT
<213> ORGANISM: Plasmodium yoelii
<220> FEATURE:
<221> NAME/KEY: misc_feature
<222> LOCATION: (103)..(103)
<223> OTHER INFORMATION: Xaa can be any naturally occurring amino acid

<400> SEQUENCE: 3

Met Asn Met Leu Tyr Lys Leu Leu Phe Phe Phe Met Arg Ala
1               5                   10                  15

Leu Glu Cys Tyr Arg Ile Pro Asn Ile Gln Asn Leu Asn Lys Val Asn
                20                  25                  30

Thr Asn Lys Tyr Leu Arg Ser Asn Arg Asp Leu Asn Leu Ser Gly His
            35                  40                  45

Asn Lys Glu Asn Asn Tyr Tyr Cys Gly Glu Asn Lys Val Ala Leu Val
 50                  55                  60

Thr Gly Ala Gly Arg Gly Ile Gly Arg Ser Ile Ala Lys Thr Leu Ala
65                  70                  75                  80

Lys Ser Val Ser His Val Leu Cys Ile Ser Lys Thr Gln Phe Phe Phe
                85                  90                  95

Phe Phe Phe Phe Phe Xaa Gln Lys Ser Cys Asp Ser Val Ser Asp
                100                 105                 110

Glu Ile Asn Ser Leu Gly Tyr Lys Ala Thr Gly Tyr Ala Ala Asp Val
            115                 120                 125

Ser Asn Lys Glu Glu Ile Thr Glu Leu Ile Asn Lys Leu Leu Thr Asp
130                 135                 140

His Lys Ser Ile Asp Ile Leu Val Asn Asn Ala Gly Ile Thr Arg Asp
145                 150                 155                 160

Asn Val Phe Leu Arg Met Lys Asn Glu Glu Trp Glu Asp Val Ile Lys
                165                 170                 175

Thr Asn Leu Asn Ser Leu Phe Tyr Val Thr His Pro Ile Thr Lys Lys
            180                 185                 190

Met Ile Ser Asn Lys Tyr Gly Arg Ile Ile Asn Met Ser Ser Ile Val
            195                 200                 205

Gly Ile Thr Gly Asn Phe Gly Gln Thr Asn Tyr Ser Ala Ser Lys Ala
210                 215                 220

Gly Val Ile Gly Phe Thr Lys Ser Leu Ala Lys Glu Leu Ala Ser Arg
225                 230                 235                 240

Asn Ile Thr Val Asn Ala Ile Ala Pro Gly Phe Ile Ser Ser Asp Met
                245                 250                 255

Thr Asp Lys Ile Ser Asp Ile Lys Gln Ile Ile Ser Asn Ile
            260                 265                 270

Pro Ala Gly Arg Met Gly Thr Pro Glu Glu Ile Ala Asn Met Val Gly
            275                 280                 285

Tyr Leu Ser Ser Glu Ile Ala Gly Tyr Ile Asn Gly Lys Val Phe Ile
            290                 295                 300

Ile Asp Gly Gly Leu Ser Ser
305                 310

<210> SEQ ID NO 4
<211> LENGTH: 231
```

```
<212> TYPE: PRT
<213> ORGANISM: Plasmodium yoelii

<400> SEQUENCE: 4

Met Trp Ile Met Lys Leu Phe Ile Ile Phe Val Tyr Val Leu Phe Pro
1               5                   10                  15

Val Leu Cys Leu Gly Val Lys Lys Gly Phe Asn Phe Leu Phe Pro
            20                  25                  30

Ala Phe Glu His Phe Asn Lys Lys Asn Lys Leu Lys Lys Ser Lys Asn
            35                  40                  45

Gly Val Asn Lys Asn Asp Ser Ile Lys Ile Tyr Met Asn Asn Ile Glu
50                  55                  60

Lys Asp Asp Asn Ile Ser Ala Lys Ile Ile Ser Ser Asn Ile Thr Pro
65                  70                  75                  80

Asn Leu Asn Ser Glu Ile Ile Asp Ile Asp Gln Ile Lys Asn Ile Leu
                85                  90                  95

Pro His Arg Tyr Pro Phe Leu Val Asp Lys Val Leu Tyr Ile Gln
            100                 105                 110

Pro Asn Lys Lys Ile Ile Gly Ile Lys Asn Val Thr Ala Asn Glu His
            115                 120                 125

Phe Phe Asn Gly His Phe Pro Gln Lys Pro Ile Met Pro Gly Val Leu
130                 135                 140

Gln Ile Glu Ala Leu Ala Gln Leu Gly Gly Ile Leu Cys Leu Lys Asn
145                 150                 155                 160

Ser Glu Asn Lys Ser Lys Asp Asn Leu Phe Leu Phe Ala Gly Val Asp
                165                 170                 175

Gly Val Lys Trp Lys Lys Pro Val Leu Pro Gly Asp Thr Leu Val Met
            180                 185                 190

Glu Val Glu Gln Ile Leu Phe Lys Pro Thr Leu Gly Ile Ala Lys Leu
            195                 200                 205

Lys Gly Val Gly Tyr Val Gly Asn His Val Val Ile Glu Ile Glu Asn
210                 215                 220

Met Ile Phe Ala Met Ser Lys
225                 230

<210> SEQ ID NO 5
<211> LENGTH: 2788
<212> TYPE: PRT
<213> ORGANISM: Plasmodium yoelii

<400> SEQUENCE: 5

Met Asn Glu Thr Asn Val Gly Thr Asp Ile Glu Glu Lys Lys Lys His
1               5                   10                  15

Ile Gly Lys Glu Gly Lys His Lys Phe Ser Ile Arg His Lys Lys Ile
            20                  25                  30

Lys Leu Tyr His Lys Ser Lys Ser Gln Glu Lys Arg Lys Lys Lys Val
            35                  40                  45

Lys Gln Phe Lys Asn Tyr Asn Ser Leu Lys Tyr Lys Lys Tyr Glu
50                  55                  60

Lys Pro Lys Lys Lys Lys Lys Thr Ser Met Leu Leu Asn Lys Lys
65                  70                  75                  80

Asn Asn Ala Asn Leu Glu Lys Lys Ala Ser His Ser Asn Val Val Ile
                85                  90                  95

Ser Glu Lys Thr Gln Ser Phe Ile Asn His Asp Lys Ser Ile Asn Glu
            100                 105                 110

Asn Val Ser Lys Lys Asn Phe Thr Asn Lys Asn Leu Asn Glu Lys Glu
```

```
                115                 120                 125
Pro Ile Pro Pro Asp Asn Ser Ser Thr Lys Tyr Ile Ser Asn Asn Lys
130                 135                 140

Cys Asn Glu Thr His Met Ser Asn Asn Leu Asp Ala Asn Lys Glu Leu
145                 150                 155                 160

Pro Thr Gly Val Lys Lys Asp Gln Asn Gly Ser Ser Asn Tyr Ile Tyr
                165                 170                 175

Glu Lys Ile Thr Cys Lys Arg Ile Leu Gln Asn Tyr Val Glu Lys Thr
                180                 185                 190

Asn Val Lys Glu Asn Lys Asp Ile Cys Lys Ser Ile Glu Asp Asn Asn
                195                 200                 205

Thr Asn His Ser Leu Leu Lys Asn Gln Glu Ile Lys Ser Ile Lys Ile
210                 215                 220

Cys Asn Lys Glu Gln Asn Ile Lys Arg Asn Ile Phe Lys Thr Gln Asn
225                 230                 235                 240

Trp Lys Asn Gly Phe Asn Pro Ser Ile Arg Asn Asn Tyr Gly Ser Arg
                245                 250                 255

Tyr Val Gly Ile Ser Glu Arg Gly Gly Leu Lys Ile Lys Asn Ser Arg
                260                 265                 270

Ile Ile Arg Asn Gly Thr Lys Asn Val Phe Ile Ser Lys Cys Cys Thr
            275                 280                 285

Val Lys Lys Asn Lys Thr Phe Ser Ile Glu Ser Thr Lys Leu Lys
290                 295                 300

Lys Glu Lys Ser Ser Asp Glu Ser Lys Ser Glu Ile Tyr Lys Asn Ile
305                 310                 315                 320

His His Thr Ile Ile Asn Asp Ile Asp Glu Ile Asn Asn Lys Ile Thr
                325                 330                 335

Arg Lys Val Ala Ile Asp Lys Thr Lys Asn Val Lys Asp Ile Asp Met
                340                 345                 350

Asp Lys Lys Asn Met Asn Glu Asn Leu Lys Tyr Phe Asn Thr Leu Pro
                355                 360                 365

Glu Asn Val Ser Leu Val Glu Asp Asn Ala Ser Ile Lys Glu Thr Phe
                370                 375                 380

Glu Ser Thr Ser Lys Asp Thr Thr Phe Ile Glu Leu Glu Lys Val His
385                 390                 395                 400

Leu Thr Asn Phe Lys Glu Leu Pro Ile Pro Leu Lys Asn Asp Thr Asp
                405                 410                 415

Gln Ile Lys Phe Ile Leu Glu Asn Leu Ser Glu Glu Lys Ile Ile Ser
                420                 425                 430

Leu Ser Ile Pro Phe Asp Glu Asn Ser Lys Ile Val Lys Tyr Leu Asn
                435                 440                 445

Leu Leu Ser Ile Glu Lys Ile Glu Lys Ile Ile Lys Leu Leu Asp Val
450                 455                 460

Asp Asn Tyr Lys Ser Phe Ile Phe Ile Phe Lys Glu Asp Lys Ile Val
465                 470                 475                 480

Lys Ile Ile Glu Asn Ile Ser Ile Asn Thr Ser Ile Ser Ile Leu Leu
                485                 490                 495

Asn Leu Pro Gln Asn Lys Leu Thr Tyr Ile Phe Asp Lys Met Thr Glu
                500                 505                 510

Gln Ile Ile Lys Ile Ile Asn Thr Ile Ser Leu Cys Lys Phe Tyr
            515                 520                 525

Tyr Ile Ile Glu Cys Leu Pro Ile Glu Lys Ile Ser Pro Leu Ser Asn
530                 535                 540
```

```
His Ile Ser Tyr Asp Lys Leu Tyr Ile Leu His Asn Ser Leu Thr Cys
545                 550                 555                 560

Lys Asn Leu Ser Leu Ile Thr Asn Asp Leu Tyr Ile Ser Thr Thr Asn
                565                 570                 575

Arg Leu Met Asn Asp Leu Pro Leu His Lys Ser Ile Lys Ile Met Lys
            580                 585                 590

Tyr Leu Ser Ile Lys Lys Met Ala Leu Cys Ile Asn Ile Asn Tyr Met
        595                 600                 605

Ser Val Tyr Phe Ala Ala Glu Ile Cys Lys Ser Phe Asn Ser Pro Glu
    610                 615                 620

Ile Val Asp Ile Leu Phe Tyr Leu Asn Glu Lys Asn Thr Glu Ile Leu
625                 630                 635                 640

Leu Lys Glu Cys Asp Ile Lys Lys Ile Val Tyr Ile Asn Tyr Ile
                645                 650                 655

Pro Val Asn Lys Phe Lys Thr Ile Ile His Lys Phe Pro Thr Ser Phe
                660                 665                 670

Leu Lys Gln Ile Ile Asn Asp Ile Ser Met Lys Tyr Ile Ile Gln Ile
            675                 680                 685

Phe Ile Ser Leu Pro Gln Asn Lys Thr Ile Glu Cys Leu Tyr Ser Leu
        690                 695                 700

Ser Pro Lys Lys Leu Asn Ile Leu Ile Thr Thr Ile Pro Thr Lys Asn
705                 710                 715                 720

Leu Ile Ile Asp Leu Ile Ile Arg Asn Gly Lys Pro Thr Thr Ser Val
                725                 730                 735

Glu Ser Ser Ile Lys Asp His Lys Ile Tyr Lys Asn Lys Arg Lys
                740                 745                 750

Gln Lys Lys Leu Ile Lys Met Leu Asp Tyr Ser Asn Ile Phe Leu Ile
        755                 760                 765

Leu Asn Glu Leu Ser Gly Lys Asn Tyr Asp Thr Phe Cys Lys Leu Leu
        770                 775                 780

Cys Ala Asn Gln Ile Lys Asp Ile Ile Ser Asn His Thr Ile Asp Cys
785                 790                 795                 800

Glu Gln Ala Val Lys Ile Ile Tyr Leu Pro Ile Asn Lys Ile Ile
                805                 810                 815

Glu Ile Leu Gly Asn Leu Glu Lys Asp Lys Phe Thr Ala Ile Ile Lys
                820                 825                 830

His Phe Pro Tyr Val Ile Arg Glu Ile Ile Asn Gln Arg Ile Tyr Asn
            835                 840                 845

Glu Asn His Ala Leu Gln Glu Asn Ser Glu Phe Thr Asn Ser Asn Asn
        850                 855                 860

Val Asp Glu Asn Leu Tyr Asn Asn Asn Asn Phe Lys Asp Asn Ala
865                 870                 875                 880

Glu Asn Gly Ser Asn Lys Ile Lys Arg Ile His Gln Ile Phe Ile Thr
                885                 890                 895

Phe Lys Leu Leu Lys Phe Ile Lys Phe Phe Asn Asp Tyr Tyr Asn Leu
            900                 905                 910

Lys Glu Ile Lys Lys Tyr Ala Tyr Ser Asn Tyr Ile Gln Glu Arg Lys
        915                 920                 925

Lys Asn Asp Ile Ile His Ser Ile Asn Ile Lys Asn Tyr Leu Lys Phe
    930                 935                 940

Leu Asn Cys Thr Pro Cys Ile Lys Ile Met Arg Ile Glu Asn Ala Ile
945                 950                 955                 960

Asn Lys Ala Leu Asn Lys Asn Val Tyr Asn Lys Asn Asn Val Ile Asp
                965                 970                 975
```

```
Ser Ile Phe Ile Phe Asn Ile Tyr His Lys Thr Lys Ile Gln Lys
            980             985             990

Tyr Ile Asn Glu Gln Lys Val Ile Cys Ser Leu Glu Asn Ser Thr Leu
        995             1000            1005

Ile Lys Lys Glu Lys Glu Lys Lys Arg Lys Cys Ile Glu Gly Ser
    1010            1015            1020

Ser Ile Leu Ser Ser Asn Ile Asn Thr Ser Gln Asp His Asn Gln
    1025            1030            1035

Tyr Glu Lys Asn Glu Tyr Ile Asn Glu Asn Asn Ile Asn Glu Asn
    1040            1045            1050

Met Leu His Asn Val Asn Lys Tyr Ser Leu Lys Asn Glu Gln Lys
    1055            1060            1065

Ser Asn Asp Glu Thr Lys Asn Ile Ser Asp Asn Ile Lys Pro Ile
    1070            1075            1080

Glu Asp Ser Lys Gln Ser Ser Ile Leu Lys Ile Lys Asn Asn Tyr
    1085            1090            1095

Tyr Val Phe Ile Ile Tyr Leu Val Ser Phe Ile Lys Lys His Ile
    1100            1105            1110

Gln Lys Cys Ile Ile Leu Ser Thr Gln Ile Ser Ser Glu Asn Cys
    1115            1120            1125

Ser Lys Asn Gln Ile Ile Lys Tyr Cys Asn Ile Val Asn Ala Glu
    1130            1135            1140

Glu Asn Leu Ser Asp Glu Ser Lys Asn Lys Asp Val Lys Asp Asn
    1145            1150            1155

Gln Asn Asn Ile Ile Cys Val Asn Asn Glu Asn Lys Asn Glu Ile
    1160            1165            1170

Asp Gln Thr Asn Ile Arg Lys Glu Tyr Lys Phe Ser Lys Ile Phe
    1175            1180            1185

Phe Asn Ser Val Arg Lys Ile Met Lys Ser Ile Phe Tyr Thr Val
    1190            1195            1200

Lys Lys Ile Asn Lys Met Asp Asn Ser Leu Phe Val Thr Lys Asn
    1205            1210            1215

Asn Ser Ala Ser Asn Ile Ile Arg Thr Lys Ile Ile Tyr Cys Lys
    1220            1225            1230

Asn Val Val Lys Asn Met Ile Phe Asn Glu Leu Asn Ile Lys Glu
    1235            1240            1245

Ser Phe Arg Asn Tyr Leu Thr Phe Glu Asn Asn Lys Arg Glu Asn
    1250            1255            1260

Ile Ala Asp Lys Cys Ile Leu Glu Glu Ser Arg Arg Val His Thr
    1265            1270            1275

Asn Glu Ile Thr Asn Ser Leu Asn Tyr Leu Asp Tyr Ser Ile Val
    1280            1285            1290

Lys Asn Leu Thr Glu Asn Ile Asn Phe Ile Gly Asp Asp Glu Leu
    1295            1300            1305

Gly Gln Met Cys Lys Glu Asn Asp Asn Leu Lys Asn Lys Tyr Ile
    1310            1315            1320

Val Lys Asp Leu Asn Glu Asn Lys Glu Ser Lys Glu Ile Lys Gln
    1325            1330            1335

Ile Val Lys Lys Met Glu Asn Ile Glu Tyr Lys His Asn Asp Glu
    1340            1345            1350

Thr Phe Tyr Asp Phe Pro Asn Asn Ile Leu Leu Leu Asn Lys
    1355            1360            1365

Ser Lys Ile Pro Gln Leu Ser Ser Ser Asn Glu Asn Val Ile Ile
```

-continued

```
            1370                1375                1380
Thr Asp Asn Ile Phe Asp Asn Asn Cys Gly Ile Glu Ile Gln Thr
    1385                1390                1395
His Asn Lys Leu Ile Asn Thr Glu Lys Asn Asn Gly Asn Arg Asn
    1400                1405                1410
Asn Ile His Ser Ile Glu Gly Ser Tyr Lys Asn Asn Ala Lys Asp
    1415                1420                1425
Val Val Lys Asp Ser Ile Lys Asn Arg Thr Val Glu Thr Leu Asp
    1430                1435                1440
Val Phe Glu Lys Glu Arg Asn Phe Asn Ile Ser Ser Lys Gln Ser
    1445                1450                1455
Asn Lys Ile Tyr Leu Lys Asn Ile Lys Lys Glu Tyr Ser Ile Asn
    1460                1465                1470
Arg Asn His Tyr Ser Leu Phe Pro Asn Leu Lys Phe Phe Lys Asn
    1475                1480                1485
Lys Ile Thr Pro Lys Lys Gln Asn Thr Val Thr Ile Asn Asn Asp
    1490                1495                1500
Asn Ser Asn Leu Glu Gln Arg Lys Glu Asn Leu Ser Asn Asn Asp
    1505                1510                1515
Asn Ile Thr Asn Leu Ser Pro Asn Val Gly Ile Ile Lys Asp Lys
    1520                1525                1530
Lys Gln Cys Cys Leu Arg Phe Met Phe Val Leu Asn Asp Ile Asn
    1535                1540                1545
Leu Glu Asn Asn Met Asn Asn Thr Thr Ile Val Ile Asn Phe Tyr
    1550                1555                1560
Phe Gln Lys Thr Asn Lys Tyr Phe Lys Lys Tyr Lys Asn Asn Ile
    1565                1570                1575
Leu Gly Ala Ser Leu Val Ile Asn Thr Asn Ile Asn Gly Lys Asn
    1580                1585                1590
Asn Val Ile Asn Ile Asn Thr Pro Asn Asn Asp Asn Tyr Cys Tyr
    1595                1600                1605
Ile Ser Ser Asn Ile Ile Ser Leu Asn Lys Tyr Asn Ile Asn Asn
    1610                1615                1620
Asp Pro Phe Glu Asn Tyr Trp Lys Asn Ile Asn Leu Gln Asn Ser
    1625                1630                1635
Asn Asp Asn Asn Lys Asn Asn Leu Asn Asp Cys Asn Ser Asp Ile
    1640                1645                1650
Ser Asp Leu Asp Lys Gln Met Phe Glu Asn Ser Phe Leu Val Thr
    1655                1660                1665
Ile Asp Asn Ser Ala Lys Lys Pro Lys Tyr Glu Asn Ile Ile Glu
    1670                1675                1680
Tyr Val Pro Phe Asn Cys Glu His Thr Asn Phe Ile Asp Gln Leu
    1685                1690                1695
Leu Gln Asp Tyr Ile Asn Leu Asn Ile Lys Lys Thr Thr Asn Ile
    1700                1705                1710
Lys Gln Ser Met Lys Lys Val Tyr Lys Asn Phe Tyr Ser Asn Phe
    1715                1720                1725
Ile Leu Leu Trp Thr Cys Lys Asn Ile Gly Tyr Ile Tyr Leu Asp
    1730                1735                1740
Lys Asn Asn Ser Leu Tyr Ile Asn Ile Asn Asp Ser Thr Asn Asn
    1745                1750                1755
Phe Ser Ile Asn Leu His Lys Lys Ile Tyr Asn Val Ile Ser Asp
    1760                1765                1770
```

```
Ile Lys Ser Ser Lys Lys Asn Asp Phe Ile Phe Val Lys Ser Tyr
1775                1780                1785

Lys Asp Lys Ile Ile Phe Gln Lys Ile Lys Thr Leu Phe Ser Lys
1790                1795                1800

Val Phe Leu Lys Lys Asn Asp Thr Ser Asn Asp Ile Leu Asn Lys
1805                1810                1815

Ser Thr Ile Asp Gln Asp Ile Gln Asn Asp Glu Ile Thr Glu Asn
1820                1825                1830

Lys Phe Val Cys Leu Ser Asn Glu His Asn Thr Ser Lys Val Asn
1835                1840                1845

Lys Asn Asn Ile Glu Asn Asn Glu Val Ile Asn Cys Leu Asn Cys
1850                1855                1860

Ile Asn Lys Thr Asn Ile Gln Ile Asn Asn Thr His Asp Asp Gln
1865                1870                1875

Asn Ser Glu Gln Asn Lys Leu Asn Ile Ile Gln Asn Asn Ile Gly
1880                1885                1890

Asp Ser Gln Ser Glu Ile Cys Phe Gly Asp Asp Cys Tyr Asn Thr
1895                1900                1905

Tyr Lys Lys Tyr Asn Pro Ser Tyr Asn Cys Cys Ser Gln Asn Asn
1910                1915                1920

Val Thr Tyr Asn Asp Lys Asn Phe Glu Thr Ser Glu Ile Tyr Lys
1925                1930                1935

Asn Ile Ile Met Thr Cys Lys Asn Leu Asp Leu Pro Tyr Lys Asp
1940                1945                1950

Asn Val Ser Glu Gln Phe Glu Ile Lys Lys Glu Thr Met Leu Asn
1955                1960                1965

Glu Asn Asn Asn Ile Lys Gly Lys Gln Gln Cys Tyr Asn Glu Thr
1970                1975                1980

Gly Tyr Asn Ile Ser Lys Lys Ile Lys Asn Thr Ser Trp Asn Ala
1985                1990                1995

Lys Met Asp Lys Asn Asp Phe Tyr Asn Asn Thr Tyr Ser Lys Ser
2000                2005                2010

Leu Ser Thr Asn Lys Gln Asn Ile Val Thr Asn Arg Phe Asn Asn
2015                2020                2025

Ile Ile Tyr Lys Ala Asn Lys Lys Leu Thr Phe Lys Glu Lys Ile
2030                2035                2040

Ile Asp Asp Lys Leu Leu Lys Thr Tyr Asn Ile Asn Arg Glu Ser
2045                2050                2055

Leu Asn Ser Leu Thr Glu Ser Glu Lys Gln Ile Val Asp Glu Ile
2060                2065                2070

Lys Asn Asp Glu Phe Asn Lys Ile Ile Glu Gln Glu Leu Tyr Asn
2075                2080                2085

Glu Ser Asn Ile Tyr Lys Phe Gln Asp Ser Phe Pro Leu Arg Ser
2090                2095                2100

Ile Gly Tyr Thr Glu Glu Glu Phe Asn Ile Ile Met Tyr Leu Glu
2105                2110                2115

Lys Arg Lys Lys Arg Gln Asn Ser Lys Lys Lys Thr Ile Lys Lys
2120                2125                2130

Asn Ile Asn Cys Leu Ile Ser Ser Leu Asn Asn Ile Lys Met Arg
2135                2140                2145

Lys Leu Asn Phe Ile Pro Leu Leu Glu Asn Ser Leu Cys Asn Tyr
2150                2155                2160

Asn Ile Asn Thr Tyr Phe Ser His Leu Glu Thr Asp Tyr Asn Tyr
2165                2170                2175
```

```
Asp Lys Asn Glu Asn Lys Gly Ser Asp Ile Ile Asp Gln Asn Leu
 2180            2185                2190

Phe Ile Glu Asp Ile Lys Lys Lys His Arg Thr Leu Ser Asn Glu
 2195            2200                2205

His Asn Asn Ile Glu Asp Ser Gln Ser Ser Asn Asn Leu Asn Val
 2210            2215                2220

Gln Asn Gly Asn Ser Leu Phe Leu Thr Phe Gly Asn Asn Lys Lys
 2225            2230                2235

Lys His Ile Tyr Lys Glu Asn Pro Asn Asn Cys Lys Asn Asn
 2240            2245                2250

Asn Pro Pro Lys Leu Met Cys Lys His Ile Leu Thr Asn Glu Phe
 2255            2260                2265

Asp Lys Asn Thr Lys Ile Ser Asp Val Asn Asn Val Ser Gly Glu
 2270            2275                2280

Ser Asp Asp Met Arg Gln Ile His Glu Thr Asn Lys Met His Lys
 2285            2290                2295

Asn Lys Lys Asn Ile Arg Ala Ser Leu Lys Asn Ile Pro Asn Ile
 2300            2305                2310

Tyr Ile His Glu Lys Pro Gln Asn Lys Lys Glu Asn Phe Leu Asn
 2315            2320                2325

Pro Leu His Gln Ser Asn Lys Arg Ile Cys Tyr Ser Glu Ser Ser
 2330            2335                2340

Ser Arg Lys Leu Thr His Lys Lys Ser Asp Ile Tyr Asn Lys Ile
 2345            2350                2355

Ile Asn Glu Ser Asn Arg Thr Arg Ser Ser Asp Phe Ile Arg Gln
 2360            2365                2370

Thr Glu Glu Asn Asn Leu Thr Thr Asn Phe Gln Lys Lys Gly Tyr
 2375            2380                2385

Asn Lys Arg Leu Ile Asn Lys Ala Asn Lys Thr Asn Gln Ala Asn
 2390            2395                2400

Ile Asn Leu Phe Lys Lys Thr Ile Ser Asn Asn Ala His Asp Arg
 2405            2410                2415

Asn Asn Ser Asn Thr Ile Leu Asn Ser Asn Lys Ile Thr His Glu
 2420            2425                2430

Asn Tyr Gly Ser Asn Tyr Arg Thr Arg Gln Glu Lys Ser Val Gly
 2435            2440                2445

Glu Ser Lys Leu Ile Pro Met Lys Asp Thr Leu Glu Tyr Pro Asn
 2450            2455                2460

Glu Thr Ile Pro Ser Val Glu Ser Lys Asn Ala Tyr Ile Asn Asp
 2465            2470                2475

Ser Lys Gln Arg Glu Gln Asn Lys Lys Cys Glu Asn Glu Glu Thr
 2480            2485                2490

Gly Leu Leu Asn Met Tyr Cys Leu Phe Glu Asn Lys Ser Asp Phe
 2495            2500                2505

Phe Tyr Leu Ile Ser Glu Gly Tyr Ser Lys Ala Ser Ser Phe Val
 2510            2515                2520

Asp Asp Asn Met Leu Ile His Ser Lys Leu Tyr Asn Asp Ile Phe
 2525            2530                2535

Asp Ile Lys Lys Asn Asp Met Leu Ile Trp Tyr Asn Gln Ser Ile
 2540            2545                2550

Cys Asn Asp Cys Lys Lys Leu Asp Gly Asp Asn Asn Ser Asn Asn
 2555            2560                2565

Ile Asn Asn Pro Asn Asp Asn Ile Ser Asn Glu Asn Asn Leu Cys
```

-continued

```
                        2570                2575                2580

Ile His Arg Asn Pro Lys Ile Leu Cys Asn Ile Cys  Gly Glu Val
        2585                2590                2595

Phe Lys Lys Ser Leu Leu Asn Asp Leu Phe Phe  Lys Ile Ile
        2600                2605                2610

Ile Ile Asn Lys Lys Asn Ile Phe Leu Lys Arg Leu  Ile Ile Asp
        2615                2620                2625

Ile His Tyr Glu Ser Pro Leu Ile Asn Ala His Phe  Thr Ser Lys
        2630                2635                2640

Asp Asn Ile Lys Tyr Ile Leu Glu Lys Ser Thr Lys  Gln Tyr Lys
        2645                2650                2655

Leu Lys Ile Ile Ala Ile Thr Lys Lys Val His  Lys Lys Leu
        2660                2665                2670

Ser Leu Ser Lys Ser Lys Phe Leu Arg Lys Cys Leu  Glu Ile Glu
        2675                2680                2685

Leu Ile Ser Asn Phe Gln Asn Thr Asn Asn Leu Ile  Ser Thr Gln
        2690                2695                2700

Asn Tyr Asn Asn His Ile Ser Thr Thr Asp Pro Tyr  Tyr Cys Ile
        2705                2710                2715

Asn Val Ser Arg Thr Pro Ser Ile His Asn Met Asp  Glu Tyr Lys
        2720                2725                2730

Gln Asn Ile Ile Asp Glu Gln Ile Glu Thr His Ser  Glu Asp Leu
        2735                2740                2745

Pro Asn Asp Leu Ser Asn Asp Leu Pro Asn Ala Val  Gln Ser Pro
        2750                2755                2760

Gln Phe Asn Phe Asp Thr Phe Asn Ser Ser Ile Ala  Ile Leu Thr
        2765                2770                2775

Phe Ser Ile Leu Asp Asp Lys Asn Lys Lys
        2780                2785

<210> SEQ ID NO 6
<211> LENGTH: 398
<212> TYPE: PRT
<213> ORGANISM: Plasmodium yoelii

<400> SEQUENCE: 6

Met Phe Asn Phe Phe Phe Leu Leu Thr Ile Tyr Leu Leu Phe Ala
1               5                   10                  15

Thr Cys Val Val Asn Val Lys Ala Gln Ser Glu Ser Ile Ile Lys Thr
            20                  25                  30

Glu Ser Ile Glu Ile Ser Tyr Asp Glu Asn Ser Arg His Leu Tyr Ile
        35                  40                  45

Asp Ser Ile Asn Lys Asp Asn Cys Asn Lys Gln Lys Tyr Tyr Ile Asn
    50                  55                  60

Glu Gln Cys Lys Ile Asp Asn Pro Met Glu Asn Asn Ala Glu Asn Glu
65                  70                  75                  80

Arg Met Ser Cys Leu Asn Gly Asp Asn Cys Ser Asp Ile Leu Thr Tyr
                85                  90                  95

Ile Tyr Glu Lys Asn Gly Ile Asp Ile Val His Glu Lys Asp Tyr His
            100                 105                 110

Lys Phe Pro Phe Tyr Asp Asp Leu Ser Tyr Glu Ile Met Gly Cys Asp
        115                 120                 125

Lys Ile Val Tyr Leu Asn Lys Asn Ile Lys Cys Val Cys Cys Ile Glu
    130                 135                 140

Asn Arg Asn Asn Gly Leu Glu Glu Asn Thr Glu Glu Pro Ile Ile Asp
```

```
                 145                 150                 155                 160
Leu Glu Lys Thr Lys Ile Asp Asn Leu Tyr Asn Phe Lys Glu Cys Lys
                165                 170                 175

Cys Ile Leu Asn Tyr Gln Leu Lys Lys Asn Glu Ile Ile Asn Ser Asn
            180                 185                 190

Lys Cys Asp Asn Phe Asn Cys Ala Glu Gly Phe Cys Thr Leu Gln Leu
        195                 200                 205

Asn Gly Gln Pro Tyr Cys Ser Cys Phe Glu Asn Tyr Tyr Phe Asp Lys
    210                 215                 220

Lys Leu Asn Ser Cys Thr Lys His Glu Gln Gln Ile Gln Lys His Asp
225                 230                 235                 240

Asp Asp Ser Ile Pro Lys Ser Leu Ser Ser Asp Pro Ile Asn Asp Pro
                245                 250                 255

Gln Ser Phe Asp Gln Asp Glu Asp Thr Asn Asn His Lys Ser Thr Ser
            260                 265                 270

Gln His Glu Asp Thr Ser Thr Asn Asn Asp Thr Asn Val Leu Ile Pro
        275                 280                 285

Asp Pro Asn Leu Gln Asp Cys Gln Glu Asp Arg Leu Thr Asp Glu Thr
    290                 295                 300

Ser Gln Cys Lys Lys Gly Asn Lys Asp Asn Glu Asn Asn Thr Lys Glu
305                 310                 315                 320

Asn Ile Cys Leu Arg Leu Glu Cys Phe Ile Asn Ser Asn Lys Pro Glu
                325                 330                 335

Cys Val Cys Leu Asn Lys Asn Gly Asp Lys Ile Ser Asn Asn Ile Phe
            340                 345                 350

Asp Leu Ile Tyr Lys Tyr Phe Leu Asn Tyr Leu Phe Cys Ser Ile Phe
        355                 360                 365

Lys Lys Ser Lys Gln Lys Thr Asn Lys Met Ser Tyr Ser Asp Glu Lys
    370                 375                 380

Arg Lys Ser Glu Asp His Asp His Lys Asn Asp Gly Asn Ser
385                 390                 395

<210> SEQ ID NO 7
<211> LENGTH: 1042
<212> TYPE: PRT
<213> ORGANISM: Plasmodium yoelii

<400> SEQUENCE: 7

Met Lys Ser Glu Asp Asn Gly Ser Phe Thr Asn Ile Pro Gly Tyr Tyr
1               5                   10                  15

Tyr Asp Lys Lys Lys Asn Arg Tyr Phe Leu Ile Asp Asn Glu Leu Lys
            20                  25                  30

Lys Lys Leu Lys Lys Glu Glu Phe Asn Asn Leu Ile Asn Glu Ala Lys
        35                  40                  45

Lys Lys Asn His Lys Asn Lys Ala Glu Thr Glu Tyr Ile Lys Lys
    50                  55                  60

Phe His Lys Ile His Gly Ile Lys Glu Met Lys Lys Lys Lys Asn
65                  70                  75                  80

Ile Asn Ala Asn Lys Leu Asn Ile Lys Asn Asn Asp Asn Glu Lys Ser
                85                  90                  95

Thr Leu Leu Asp Lys Asn His Asn Ser Ser Asn Ile Glu Lys Asn
            100                 105                 110

Leu Gln Leu Ile Asn Asn Glu Ile Ile Phe Leu Lys Lys Ser Ile Ser
        115                 120                 125

Glu Asn Gln Asn Ile Tyr Asn Val Ile Lys Ser Ile Arg Asn Cys His
```

-continued

```
                130                 135                 140
Phe Lys Glu Asp Ser Ile Leu Ser Leu Pro Val Phe Ile Asn Ile
145                 150                 155                 160

Asp Asn Cys Glu Tyr Ile Ser Val Glu Asp Leu Cys Glu Leu Gln Leu
                165                 170                 175

Asp Asn Gln Ser Phe Tyr Gln Lys Lys Asp Thr Asn Ile Lys Thr Pro
                180                 185                 190

Asn Phe Leu Asn Ile Lys Arg Ser Asp Ser Pro Ile Phe Leu Asn
        195                 200                 205

Asp Phe Lys Phe Phe Asn Ser Asn Lys Lys Thr Leu Asp Glu Asn Asn
210                 215                 220

Lys Lys Asp Lys Leu Gln Ile Cys Gln His Pro Asn Asn Val Leu Tyr
225                 230                 235                 240

Asp Gly Ser Lys Gln Asn Gln Asn Gln Asn Ile Thr Tyr Asn Ser Lys
                245                 250                 255

Ser Asp Glu Asn Leu Lys Asn Val Tyr Asn Asn Gln Thr Lys Asn Tyr
                260                 265                 270

Ser Tyr Ile Asn Ser Leu Ser Leu Lys Asn Glu Thr Ser Val Pro Ile
        275                 280                 285

Glu His His Ser Ile Glu Lys Ser Ile Leu Ile Pro Lys Leu Tyr Gly
        290                 295                 300

Arg Thr Tyr Glu Lys Ile Asn Ser Tyr Asn Ile Glu Asn Leu Lys Ser
305                 310                 315                 320

Lys Ile Thr Ala Asn Arg Tyr Lys Pro Asn Phe Tyr Phe Tyr Asn
                325                 330                 335

His His Thr Lys Tyr Ser Gly Met Asn Ser Ile Asn Tyr Asn Asp Ala
                340                 345                 350

Tyr Asn Met Ile Leu Ser Glu Asn His Asn Gly Glu Asp Ile Asn Asn
                355                 360                 365

Asn Asn Asn Gly Asn Glu Asn Asp Asn Asn Gly Met Arg Val Ile Glu
        370                 375                 380

Trp Asn Pro Leu Pro Asn Thr Gln Asp Met Ile Tyr Gln Glu Ser
385                 390                 395                 400

His Asn Tyr Phe Glu Asn Asn Thr Glu Thr Gly Thr Thr Asp Glu Ile
                405                 410                 415

Thr Asn Glu Ala Arg Val Ser Lys Ser Tyr Lys Pro Ser Glu Ser Phe
                420                 425                 430

Phe His Leu Phe Ser Asn Pro Leu Tyr Glu Asp Ile Ile Phe Ser Thr
        435                 440                 445

Ser Lys Glu Asn Asn Phe Ser Phe Ser Leu Gly Val Ile Asp Leu Lys
450                 455                 460

Lys Phe Leu Asn Lys Asn Asn Lys Ser Phe Met Asp Asp Ile Ile His
465                 470                 475                 480

Glu Asn Val Tyr Tyr Asn Ser Glu Thr Asn His Leu Cys Ser Tyr Ser
                485                 490                 495

Lys Glu Gln Ser Glu Leu Leu Cys Thr Ser Pro Gln Ile Leu Ser His
                500                 505                 510

Phe Thr Ile Phe Asn Glu Glu Tyr Val Ala Tyr Ser Ser Tyr Pro Asn
        515                 520                 525

Thr Lys Asp Asp Lys Cys Leu Leu Phe Leu Leu Ser Ile Glu Ser Phe
                530                 535                 540

Phe Gln Ser Ser Pro Lys Ile Glu Thr Ile Asn Phe Gln Thr Glu Ile
545                 550                 555                 560
```

-continued

Asn Tyr Phe Lys Leu Phe Pro Ser Ile Glu Thr Asn Tyr Ser Met His
            565             570             575

Glu Asn Cys Tyr Asn Asn Asp Met Asn Phe Pro Ser Asn Ser Glu
        580             585             590

Tyr Ala Tyr His Tyr Asn Asn Glu Leu Asp Lys Ile Phe Ile Cys Gly
        595             600             605

Ser Tyr Pro Cys Phe Ser Phe Ser Thr Ile Lys Asp Ser Thr Pro Tyr
    610             615             620

Cys Ile Trp Asp Ser Lys Lys Leu Lys Val His Asp Leu Leu Leu Leu
625             630             635             640

Asn Glu Asp Ser Thr Ser Tyr Ile Asp Asn Ile Leu Asn Ser Lys Arg
            645             650             655

Tyr Thr Asn Pro Thr Tyr Leu Thr His Gly Asn Thr Ser Gln Thr Val
        660             665             670

Ile Lys Ala Cys Ser Lys Lys Gly Lys Glu Lys Lys Asn Glu Ile
    675             680             685

Glu Lys Gly Lys Lys His Glu Asn Asn Lys Pro Ser Asn Gln Ala Lys
    690             695             700

Lys Ile Gln Thr Asn Gln His Cys Asn Thr Thr Lys Arg Lys Asn
705             710             715             720

Asp Asn Lys Arg Lys His Ser Thr Lys Asp Ser Lys Ser Glu Asp Tyr
            725             730             735

Thr Asp Glu Asp Ile Asn Asn Asn Lys Tyr Glu Phe Ser Lys Lys Gly
        740             745             750

Asn Asn Asn Ser Thr Glu Lys Asn Ser Cys Asn Arg Leu Ser Lys Asn
        755             760             765

Asn Ser Ser Lys Ser Ser Leu Leu Tyr Ser Thr Glu Lys Pro Lys Ser
770             775             780

Lys His Asn Thr Thr Tyr Asn Pro Gln Ser Pro Asn Tyr Val Lys Cys
785             790             795             800

Asn Tyr Asn Asp Asn Lys Lys Gly Ile Cys Cys Glu Asn Ile Lys
            805             810             815

Lys Thr Asn Asn Asn Ile Phe Leu Leu Cys Asn Thr Gly Asn Leu Tyr
        820             825             830

Leu Cys Asp Leu Arg Cys Asn Val Leu Asn Ala Ile Ser Lys Leu Lys
    835             840             845

Pro Asn Glu Gly Tyr Val Asn Lys Leu Tyr Ser Leu Asn Asn Tyr
    850             855             860

Gln Tyr Ile Leu Ser Lys Thr Asn Asn His Ile Gly Leu Tyr Asp Met
865             870             875             880

Arg Tyr Ile Pro Tyr Lys Cys Asn Asp Glu Leu Lys Asn Asn Leu Val
            885             890             895

Val Ser Tyr Asp Arg Phe Ile Asn Asn Asp Asn Leu Lys Lys His Leu
        900             905             910

Asn Asp Phe Tyr Val Ile Asp Asn Glu Gln Phe Ile Val Ser Leu Asp
    915             920             925

Thr Tyr Thr Asn Ala Val His Ile Tyr Asp Ile Met Asn Thr Ala Asn
    930             935             940

Lys Ile Ile Asn Leu Asp Gly His Glu His Ser Lys Asn Asn Thr Leu
945             950             955             960

His Ser Tyr Ile Asn Leu Ser Arg Ile Pro Tyr Ile Tyr Ala Ser Pro
            965             970             975

Glu Asn Glu Asp Tyr Tyr Tyr Asn Tyr Tyr Lys Arg Lys Ala Ser Glu
        980             985             990

Thr Lys Ala Thr Asp Ser Lys His Thr Asn His Leu Asn Pro Leu Lys
995 1000 1005

Ser Tyr Pro Lys Lys Asp Leu Phe Ile Gly Leu Asn Val Gln Ser
1010 1015 1020

Ile Leu Pro Leu Phe Tyr Ile His Lys Thr Asn Val Met Arg Ile
1025 1030 1035

Met Ile Ile Arg
1040

<210> SEQ ID NO 8
<211> LENGTH: 176
<212> TYPE: PRT
<213> ORGANISM: Plasmodium yoelii

<400> SEQUENCE: 8

Met Phe Phe Leu Pro Leu Phe Thr Ile Ala Ile Val Tyr Leu Phe Ile
1 5 10 15

Gln Asn Ser Leu Leu Ser Tyr Ile Phe Leu Lys His Asn Asn Val Val
20 25 30

Asn Cys Leu Ser Lys Arg Asn Gln Thr Ile Trp Ser Asn Ile Leu Ser
35 40 45

Glu Lys Thr Leu Ser Thr Asn Asn Lys Asn Met Ile Trp Glu Lys Asn
50 55 60

Tyr Ser Ala Arg Lys Arg Asn Lys Ile Asn Ser Leu Phe Phe Leu Asn
65 70 75 80

Leu Lys Lys Lys Lys Leu Pro His Leu Leu Ala Phe His Ser Glu Asp
85 90 95

Cys Glu Tyr Cys Asn Ser Met Glu Pro Leu Leu Lys Lys Leu Lys Asp
100 105 110

Glu Glu Gly Ile Glu Phe Leu Lys Leu Glu Met Tyr Glu Asn Ser Tyr
115 120 125

Asn Phe Glu Leu Leu Gln Gln Leu Asp Tyr Asn Asn Leu Cys Gly Gly
130 135 140

Leu Pro Tyr Tyr Tyr Asn Leu Lys Thr His Tyr Asn Ile Cys Gly Ala
145 150 155 160

Thr Thr Tyr His Asn Leu Arg Lys Trp Ala Phe Asp Lys Lys Cys Lys
165 170 175

<210> SEQ ID NO 9
<211> LENGTH: 2694
<212> TYPE: PRT
<213> ORGANISM: Plasmodium yoelii
<220> FEATURE:
<221> NAME/KEY: misc_feature
<222> LOCATION: (881)..(881)
<223> OTHER INFORMATION: Xaa can be any naturally occurring amino acid

<400> SEQUENCE: 9

Met Asn Leu Lys Leu Phe Asp Gly Gln Leu Asn Gly Gln Ile Asn Glu
1 5 10 15

Asn Asn Leu Asn Asp Leu Thr Asn Leu Leu Lys Ser Lys Asn Lys Ala
20 25 30

Pro Phe His Ile Asn Asn Ser Ala Asn Asn Asn Ile Ser Ser Asn Thr
35 40 45

Asn Ser Tyr Ile Ser Ser Asn Asp Asn Phe Asn Ile Pro Ser Ser Tyr
50 55 60

Phe Ile Tyr Asp Tyr Thr Asn Thr Asp Lys Phe Ala Tyr Thr Leu Asn
65 70 75 80

```
Asn Val Glu Asn Leu Glu His Ile His Asn Tyr Gln Asn Val His Asn
                85                  90                  95
Asn Phe Tyr Pro Thr Ser Pro Glu Tyr Thr Ser Asn Asn Ile Asn
            100                 105                 110
Asn Asn Thr Phe Ile Arg Asn Ser Phe Asn Asn Lys Asn Asp Ala Val
            115                 120                 125
Asn Phe Asn Ile Asn Gln Asn Ile Asp Asn Cys Ser Asn Lys Ser Lys
            130                 135                 140
Thr Asp Ile Lys Asp Glu Leu Asn Ser Thr Pro Ile Tyr Ser Ser Asn
145                 150                 155                 160
Tyr Gln Pro Thr Val Thr Thr Phe Asn Asn Asn Lys Lys Thr Tyr Ile
                165                 170                 175
Lys Thr Glu Lys Thr Lys Asn Asn Ser Lys Asn Gly Asn Thr Ile Lys
                180                 185                 190
Ala Gln Thr Asp Asp Asn Ile Ile Lys Gln Gln Asp Val Lys Gln Asn
                195                 200                 205
Ser Tyr Gln Asn Phe Tyr Ile Asn Gln Ile Lys Asn Glu His Ile Thr
                210                 215                 220
Asn Thr Ile Asn Ser Gln Asn Ile Lys Asn Val Asn Phe His Ser
225                 230                 235                 240
Asn Asn Ile Pro Leu Ile Lys Asn Met Pro Asn Gly Cys Leu Phe Tyr
                245                 250                 255
Gln Asn Asp Thr Phe Gly Asn Thr Ile His Asn Asn Ser Tyr Asn Asn
                260                 265                 270
Asp Ile Asn Ala Ala Ile Ser Ser Ala Thr Thr Ser Ser Ile Ala Ile
                275                 280                 285
Pro Thr Ala Thr Asn Ala Ser Ile Ser Ser Pro Thr Ser Thr Thr Ile
                290                 295                 300
Asn Ile Asp Gln Cys Tyr Asn Gln Ile Phe Glu Ser Asn Gly Ile Ile
305                 310                 315                 320
His Ser Asn Pro Ile Ser Asn Asn Asp Ser Asn Asn Asn Met Val Asp
                325                 330                 335
Leu Asn His Ile Asp His Lys Ala Lys Asn Ile Asn Met Thr Trp Gly
                340                 345                 350
Asp His Asn Ser Lys Asn Thr His Asn His Pro Asn Leu Asn Ile Gln
                355                 360                 365
Thr Glu Thr Thr Ser Ile Asn Asn Asp Tyr Tyr His Thr Asn Asn Pro
                370                 375                 380
Asp Ile Asn Glu Asn Ser Ser Leu His Thr Asp Glu Glu Asn Asn Leu
385                 390                 395                 400
Glu Asp Asn Asn Asn Met Glu Asn Ala Ser Cys Leu Lys Lys Gly Ile
                405                 410                 415
Asn Arg Lys Cys Tyr Ser Asn Asn Ser Thr Ile Asn Asn Asn Asn
                420                 425                 430
Ser Asp Asn Asn Pro Glu Asn Arg Asn Gln Asn Glu Tyr Asn Asp Ser
                435                 440                 445
Cys Asp Gly Gln Asn Asn Tyr Cys Gln Gln Asn Asn Asn Asp Asp
                450                 455                 460
Asn Asn Tyr Asp Lys Lys Tyr Ser Ala Thr Tyr Ile Arg Ser Asn Asn
465                 470                 475                 480
Tyr Ser Asn Gly Asn Ile Tyr Asp Asp Ile Asn Tyr Glu Thr Lys Gln
                485                 490                 495
Ser Glu Gly Ile Ile Ser Lys Asn Gln Met Lys Asn Asn Cys Phe Arg
```

```
                500             505             510
Asp Asn Asn Lys Phe Asn Pro Thr Asp Phe Lys Glu Val Ser Pro Lys
            515                 520             525

Ser Thr Ser Ile Asn Asn Ile Ser Asn Ser Met Thr Ser Asn Asp Ser
530             535                 540

Ser Met Asn Gln Tyr Asn Asn Ala Asn Ser Arg Cys Asn Asn Ser Val
545                 550                 555                 560

Gly Asn Asn Asn Thr Asp Ser Asn Gln Phe Lys Gln Asn Ile Asn Arg
                565                 570                 575

Tyr Asn Asn Ser Asn Ser Ile Glu Leu Lys Thr Asn Ser Gln Leu Asn
            580                 585                 590

Asp Tyr Ser Ser Asn Ser Asn Thr Ile Leu Leu Met Asp Glu Cys Asp
            595                 600                 605

Ser Asn Glu Leu Leu Asn Pro His Ser Ser Asp Asn Asn Tyr Leu Asn
            610                 615                 620

Asp Lys Asp Leu Leu His Ser Asn Asn Met Thr Arg Asn Cys Ser Tyr
625                 630                 635                 640

Asn Asn Asp Asn Arg Ser Asn Thr Phe Asn Glu Leu Val Asn Asn Met
                645                 650                 655

Leu Phe Gln Asn Asp Gly Ser Pro Gln Ser Ser Lys Asn Val Ile Lys
            660                 665                 670

Asn Tyr Ser Thr Ile Tyr Glu Ser Gln Thr Asn Lys Leu Glu Thr Val
            675                 680                 685

Phe Pro Asn Val Gln Asn Asn Lys Tyr Met Arg Gln Asn Asn Ile
690                 695                 700

His Gln Thr Asn Asp Thr Thr Arg Asn Gly Ile Glu Gln Phe Glu Cys
705                 710                 715                 720

Ile His Asn Ser Asp Asn Tyr Tyr Ile Asn Asp Asn Val Ser Asn
                725                 730                 735

Thr Ser Asn Val Asn Asp Ser Lys Asn Ile Asn Arg Gly Asn Asn Ser
                740                 745                 750

Glu Asp Phe Lys Thr Ile Lys Asn Glu Ile Lys Tyr Pro Ala Ile Asn
            755                 760                 765

Ser Glu Thr Ser Asn Tyr Val Tyr Asn Pro Gln Asn Asn Ile Met Tyr
770                 775                 780

Ile Gln Asn Thr Ser Glu Gln Ile Thr Lys Gly Asn Asn Ser Tyr
785                 790                 795                 800

Ile Gln Tyr Asn Thr Thr Tyr Ser Ile Asn Asn Glu Asn Ile Ser Thr
                805                 810                 815

Asn Tyr Leu Thr Met Asn Ser Leu Ile Asn Asp Gln Asn Lys Leu Glu
            820                 825                 830

Asn Cys Ser Lys Asn Lys Asn Val Asn Asp Ser Lys Ile Asn Ser
            835                 840                 845

Ile Tyr Asp Glu Lys Asn Gln Lys Asn Trp Asp Asn Thr Ser Ile Pro
            850                 855                 860

Ile Lys Asn Lys His Glu Asn Asn Ile Tyr Glu Ile Lys Glu Asn Asp
865                 870                 875                 880

Xaa Asn Ser Gln Glu Ile Glu Leu Asn Asp Lys Thr Thr Gln His Phe
                885                 890                 895

Glu Asn Thr Asp Lys Glu Gly Asn Glu Asn Asn Ser Asp Asn Asn Gly
                900                 905                 910

Asn Pro Asn Phe Val Asn Lys Asn Ile Glu Asn Asn Glu Asn Ile Ala
            915                 920                 925
```

-continued

Asn Ser Ile Gly Lys Glu Gln Asn Tyr Ile Phe Gln Glu Asn Leu Gln
        930             935             940

His Leu Asp Thr Lys Asn Val Lys Asn Asn Glu Thr Tyr Cys Leu Pro
945             950             955             960

Ser Asn Glu Met Cys Gln Val Ser Gln Lys Gln Asn Asn Asn Ile His
            965             970             975

Val Tyr Asp Glu Lys Asn Ile Glu Glu Asn Gln Thr Val Met Phe Gln
            980             985             990

Asn Asn Leu Gln Tyr Asn Gln Ala Gln Pro Tyr Tyr Gln Pro Lys Thr
        995             1000            1005

Lys Gly Ile Tyr Asp Asp Lys Thr Asn Phe Asn Pro Val Gln Asn
    1010            1015            1020

Thr Asn Asp Leu Gln Arg Asn Thr Asn Asn Ile Ile Thr Asn Asp
    1025            1030            1035

Pro Leu Ile Lys Asn Ile Tyr Glu Asn Lys Asn Ala Ser Phe Ile
    1040            1045            1050

Asn Ser Lys Gln Ser Val Ile Leu Pro Lys Asn Asp Asp Leu Asp
    1055            1060            1065

Asn Ser Asn Phe Lys Gly Asn Asn Glu Asn Asn Ser Lys Thr Lys
    1070            1075            1080

Asn Ile Asn Glu Phe Ser Leu Asn Lys Asn Tyr Lys Asn Ser Ile
    1085            1090            1095

Asn Asn Ser Gln Lys His Gln Arg Asp Ala Asp Ile Asn Cys Tyr
    1100            1105            1110

Asp Ile Asn Thr Lys Tyr Lys Glu Asn Leu Lys Lys Gln Lys Asn
    1115            1120            1125

Ser Ile Val Ser Thr Val Asp Lys Ser Asp Tyr Phe Asp Val Glu
    1130            1135            1140

Asn Asn Glu Ile His Gly Lys Val Asp Asn Asp Gly Tyr Lys Gly
    1145            1150            1155

Ala Glu Ile Asp Lys Gln Asn Asn Gln Glu Met Asn Asn Asn Phe
    1160            1165            1170

Cys Asn Arg Thr Lys Tyr Ile Lys Val Glu Thr Ile Thr Asp Ser
    1175            1180            1185

Ile Asp Asp Lys Asn Asn Ser Ile Ser Ser Ile Arg Asn Asn
    1190            1195            1200

Thr Asn Lys Thr Ile Tyr Asp Ile Tyr Met Asn Asp Thr Met Gln
    1205            1210            1215

Leu Asn Glu Asn Ile Asn Asn Asn Lys Asn Leu Asn Ile Gln Asn
    1220            1225            1230

Asn Ser Asn Asp Ile Ile Thr Lys Asp Asn Asn Thr Asn Asn Leu
    1235            1240            1245

Gly Asn Ile Asp Asn Asn Phe Thr Asn Ser Glu Tyr Ser Gln Phe
    1250            1255            1260

His Thr Asn Asn Ser Val Lys Thr Gln His Asn Pro Glu Leu Ser
    1265            1270            1275

Gln Arg Glu Met Asn Tyr Leu Tyr Thr Asn Lys Met Ala Leu Ile
    1280            1285            1290

Lys Asp Asn Ile Asn Ile Asp Ala Asn Asp Asn Ile Ile Asn Leu
    1295            1300            1305

Gln Asn Phe Asn Tyr Ile Asp Gln Thr Asn Asp Asn Lys Asn
    1310            1315            1320

Arg Lys Met Asn Ser Leu Thr Met Lys Met His Ser Asn Ala Ser
    1325            1330            1335

```
Ser Tyr Ile Phe Asp Asn Lys Thr Asn Asn Ser Glu Glu Gln
    1340            1345            1350

Lys Asn Asn Asp Phe Asn Leu Gly Leu Asn Pro Val Lys Asp Lys
    1355            1360            1365

Tyr Asp Asn Leu Tyr Ala Asn Tyr Tyr Val Asn Asp Asn Asp His
    1370            1375            1380

Ile Asn Ser Asn Asp Gln Gln Ile Lys Asn Ser Asn Leu Glu Thr
    1385            1390            1395

Gln Asp Thr Leu Asn Arg Arg Lys Lys Asn Thr Leu Lys Thr Ile
    1400            1405            1410

Ser Met Glu Gln Leu Pro Phe His Asn Ser Val Asn Asn Phe Glu
    1415            1420            1425

Asn Asn Tyr Glu Ser Asn Ser Ser Cys Tyr Lys Tyr Thr Lys Gly
    1430            1435            1440

Ile Asn Thr Thr Pro Met Leu Asn Glu Asn Ile Asn Asn Ala Cys
    1445            1450            1455

Ile Asn Gln Glu Ile Tyr Asp Asn Asn Arg Gln Asn Ile Glu Thr
    1460            1465            1470

Pro Arg Ser Lys Asn Tyr Pro Val Phe Asn Met Gly Ile Gln Asn
    1475            1480            1485

Asn Lys Ala Asn Ser Glu Ala Leu Asp Glu Asn Gly Gln Ile Gln
    1490            1495            1500

Ser Lys Asn Val Leu Thr Asn Asn Leu Phe Lys Ile Asn Lys Lys
    1505            1510            1515

Tyr Asn Ser Asn Asn Ala Glu Thr Asn Asn Leu Ile Tyr Asp
    1520            1525            1530

Asn Asn Glu Asn Ala Gln Tyr Asn Tyr Leu Asn Asp Leu His Thr
    1535            1540            1545

Asn Gly Arg Asn Ser Ile Tyr Glu Ser His Met Asp Leu Pro Pro
    1550            1555            1560

Asn His Pro His Leu Leu Tyr Leu Asn Asn Leu Asn Ala Lys Asn
    1565            1570            1575

Leu Glu Asn Ile Ser Glu Arg Lys Ile Ser Ile Pro Asn Glu Tyr
    1580            1585            1590

Ile Asn Phe Asn Ser Leu Asn His Ile Tyr Asn Val Pro Gln Phe
    1595            1600            1605

Asp Asn Leu Pro Asn Asn Val Asn Ser Asn Thr Arg Tyr Asn Asn
    1610            1615            1620

Asn Asn Asn Ser Asn Asn Ser Asn Asn Ser Asn Ile Cys Asp Asn
    1625            1630            1635

Ser Ile Asn Asn Thr Asn Asn Ser Ile Asp Pro Asn Asn Asn Asn
    1640            1645            1650

Thr Pro Thr Val Tyr Asn Thr Glu Gly Pro Ile Ser Asn Val Asp
    1655            1660            1665

Asn Asn Tyr Asn Ile Thr Asn Met Pro Leu Asp Lys Asn Ser Ile
    1670            1675            1680

Ile Thr Asn Pro His Tyr Ser Ser Asn Thr Asn Asp Asn Lys Asn
    1685            1690            1695

Ser Ala Ile Tyr Asn Asn Ile Arg Tyr Ser Asn Arg Thr Phe Cys
    1700            1705            1710

Asn Tyr Asn Asn Ile Lys Gly Ser Asn Asp Asn Asn Ile Tyr Ile
    1715            1720            1725

Pro Asn Asn Asn Ile Lys Ser Tyr Asn Asp Asn Ile Met His Asn
```

-continued

```
             1730                1735               1740
Leu Ser  Asn Asn Val Lys Gly  Tyr Asn Asn Ser  Val Tyr Thr
    1745                1750               1755
Tyr Arg  Asn Asn Asn Ile Ala  Thr Asn Gly Lys  Asn Asn Lys Glu
    1760                1765                    1770
Pro Asn  Lys Gly Asn Asn Asn  Leu Tyr Asn Phe  Asn Asn Tyr Lys
    1775                1780                    1785
Asn Tyr  Ile His Asn Asp Ser  Ser Asn Leu Ile  Asn Val Lys Ser
    1790                1795                    1800
Glu His  Pro Glu Lys Phe Asn  Tyr Glu Asn Asn  Leu Leu Asp Asn
    1805                1810                    1815
Val Asp  Lys Thr Asn Lys Asn  Asn Ile Asn Arg  Gln Ile Asp Asn
    1820                1825                    1830
Glu Glu  Leu Asn Ser Leu Ile  Thr Glu Ala His  Met Arg Ser Phe
    1835                1840                    1845
Asp Asn  Phe Lys Ala Ser Glu  Glu Asn Ser Met  Arg Asn Asn Ile
    1850                1855                    1860
Asn Asn  Arg Phe Ile Asn Asn  Asn Asn Asn Asp  His Tyr Gln Met
    1865                1870                    1875
Met Ile  Asn Asn Ile Asn Leu  Tyr Asn Ala Tyr  Lys Tyr Leu Tyr
    1880                1885                    1890
Arg Asn  Asn Asn Lys Tyr Ile  Tyr Asn Thr Asn  Asn Asn Asp Lys
    1895                1900                    1905
Ser Ser  Asn Asn Ile Asn Ile  Tyr Ser Asp Ile  Asn Asn Phe Pro
    1910                1915                    1920
Gln Lys  Lys Ile Asn Thr Tyr  Thr Pro Asn Asn  Leu Leu Thr Ser
    1925                1930                    1935
Gln Asn  Asn Asn Val Phe Asn  Thr Gln Asp Asn  Met His Gln Asp
    1940                1945                    1950
Gln Thr  Asn Pro Ile Ile Leu  Tyr Asn Asn Ile  Asn Gly Thr Lys
    1955                1960                    1965
Asn Asn  Leu Ile Ser His Ile  Lys Ser Asp Ile  Pro Ser Ser Gly
    1970                1975                    1980
Cys Asp  Thr Asn Gln Ser Asn  Asn Asp Met Lys  Asn Glu Asn Gly
    1985                1990                    1995
Phe Asn  Tyr Leu Tyr Asn Gly  Ile Pro Phe Asp  Tyr Phe Lys Asn
    2000                2005                    2010
Asp Met  Ala Phe Ile Tyr Asn  Asn Asn Ile Arg  Asn Thr Gly Asn
    2015                2020                    2025
Ile Ile  Glu Gly Thr Asn Ile  Ile Asn Asp His  Asn Lys Gln Phe
    2030                2035                    2040
Glu Asn  Asn Asp Glu Arg Met  Lys Glu Asn Arg  Asn Asn Asn Met
    2045                2050                    2055
Tyr Ala  Asn Leu Asn Asn Pro  Ser Asn Asn Thr  Ile Ile Cys Lys
    2060                2065                    2070
Asp Pro  Lys Asn Tyr Tyr Ile  Lys Asn Asn Phe  Asp Ile Leu Asn
    2075                2080                    2085
Asn Ile  Asp Asn Leu Asn Asp  Ile Lys Asn Glu  Asn Asn Ile Asn
    2090                2095                    2100
Asn Ser  Asn Thr Ile Ile Asn  Ser Ser Val Asp  Leu Gln Asn Asn
    2105                2110                    2115
Lys Thr  Lys Asn Lys Asp Asn  Pro Asn Tyr Asn  Val Asn Asn Cys
    2120                2125                    2130
```

-continued

```
Asn Glu Asn Asn Asn Asn Ala Asp Leu Lys Tyr Ile His Glu Leu
2135                2140                2145

Asn Lys Phe Tyr Asn Ser Lys Gly Thr Ser Tyr Lys Lys Ile Asn
2150                2155                2160

Asp Arg Ile Asn Asp Thr Met Asn Asn Ile Asn Met Thr Ser Asn
2165                2170                2175

Met Asn Thr Thr Glu Thr Leu Gly Ser Asn Val Asp Asp Thr Tyr
2180                2185                2190

Lys Ser Ile Ser Asn Ile Ser Thr Thr Arg Asn Arg Asn Ser Asn
2195                2200                2205

Phe Asn Met Met Asn Asp Asn Gln Tyr Ile Gln Leu Gln Asp Val
2210                2215                2220

Ala Tyr Lys Ile Ser Asp Asn Tyr Asp Asn Ser Val Asn Lys Glu
2225                2230                2235

Asp Thr Glu Ser Cys Pro Lys Lys Pro Ser Asn Leu Arg Asn Thr
2240                2245                2250

Asn Leu Ile Asp Ser Met Asn Met Met Tyr Leu Asn Lys Ala Asn
2255                2260                2265

Lys Asn Ile Tyr Asn His Pro Tyr Tyr Lys Asn Gly Ile Asp Glu
2270                2275                2280

Asn Tyr Phe Asn Ser Asn Met Asn Ile Ser Leu Gln Ser Glu Phe
2285                2290                2295

Ser Asp Pro Asn Asn Ile Ile His Asn Asn Leu Lys Lys Ile Lys
2300                2305                2310

Thr Asn Lys Pro Tyr Asn Gln Ser Tyr Pro Ser Asn Leu Pro Tyr
2315                2320                2325

Asn Arg Asn Ser Asn Tyr Ser Asn Asn Asn Ile Asn Glu Ile Ser
2330                2335                2340

Gln Ile Asn Glu Gly Lys Asn Arg Asp Thr Ala Asn Asn Tyr Tyr
2345                2350                2355

Ile Pro Pro Tyr Met Asn Pro Asn Asp Gln Ala Pro Asp Phe Lys
2360                2365                2370

Asp Asn Tyr Leu Asn Thr Cys Lys Asn Asn Ile Asp Ile Asp Asn
2375                2380                2385

Ile Asn Tyr Tyr Lys Ala Gln Gln Tyr Tyr Ala Asn Asn Lys Phe
2390                2395                2400

Ile Asn Val Asn Tyr Asp Lys Asn Ile Tyr Thr Asn Glu Pro Asn
2405                2410                2415

Lys Tyr Ser Lys Asn Tyr Pro Asn Glu Gly Phe Arg Glu Asn Ile
2420                2425                2430

Asp Gly Thr Tyr Asn Tyr Asn Leu Gly Met Gln Asn Glu His His
2435                2440                2445

Asn Pro Asn Tyr Pro Leu Asn Ile Leu Asn Asn Asn Asn Leu Tyr
2450                2455                2460

Asn Asn Tyr Val Tyr Leu Asn Met Leu Asn Asn Ala Tyr Asn Thr
2465                2470                2475

Asn Asn Asn Asn Leu Lys Leu His Asn Leu Glu Glu Asn Asn Lys
2480                2485                2490

Leu Ile Leu Tyr Asn Asn Lys Lys Asp Thr Tyr Thr Asp Phe Asn
2495                2500                2505

Asn Ser Asn His Asn Val Asn Asn Pro Asn Asp Leu Phe Gln Leu
2510                2515                2520

Lys Ile Met Asp Pro Asn Glu Asn Arg Ile Met Asn Pro Leu Asn
2525                2530                2535
```

```
Asn Ile Gln Ile Pro Ile Lys Asn Tyr Tyr Asn Leu Gln Leu Leu
    2540                2545                2550

Leu Asn Tyr Leu Arg Gly Arg Gln Val Gln Gln Ser Phe Asn His
    2555                2560                2565

Ser Ala Ser Asn Thr Asn Asn Asn Asn Leu Arg Ser Asp Thr
    2570                2575                2580

Lys Arg Asn Tyr Ser Ile Ser Ser Val Gly Phe Ser Asn Arg Ser
    2585                2590                2595

Lys Arg Trp Thr Ile Cys Pro Ser Tyr Ile Cys Cys Asn Ser Ala
    2600                2605                2610

Leu Cys Arg Phe Lys Leu Thr Cys Asn Phe Lys Phe Leu Gln Phe
    2615                2620                2625

Asn His Ser Asn Tyr Ser Phe Asn Ile Pro Tyr Ala Ile Tyr Asn
    2630                2635                2640

Cys Tyr Lys Asn Leu Met Asn Phe Tyr Asn Tyr Phe Thr Ser Thr
    2645                2650                2655

Leu Cys Pro Gln Gln Thr Tyr Leu Ser Lys His Ser Thr Gln His
    2660                2665                2670

Tyr Phe Phe Lys Leu Ile Tyr Ile His Phe Phe Asn Leu Asp Ile
    2675                2680                2685

Phe Leu His Leu Val Thr
    2690

<210> SEQ ID NO 10
<211> LENGTH: 200
<212> TYPE: PRT
<213> ORGANISM: Plasmodium yoelii

<400> SEQUENCE: 10

Met Asn Thr Lys Leu Tyr Ser Leu Phe Phe Phe Ile Tyr Leu Ile Ile
1               5                   10                  15

Val Tyr Cys Ala Thr Val Gln Gly Asn Lys Asn Ser Asn Gly Lys Ala
                20                  25                  30

Asp Gly His Gly Leu Ser Phe Ile Lys Lys Val Tyr Gln Asn Ser Asn
            35                  40                  45

Asn Lys Asp Lys His Met Leu Arg Thr Asp Glu Asp Gly Ile Gly Thr
        50                  55                  60

Phe Asn Ile Lys Tyr Leu Tyr Lys Cys Val Tyr Tyr Thr Tyr Ile Gln
65                  70                  75                  80

Ile Ile Gln Asn Cys Ser Ser Tyr Phe Ile Leu His Glu Ile Val
                85                  90                  95

Leu Cys Ile Ile Asn Asn Phe Cys Phe Ile Asn Pro Ser Gly Asp Val
            100                 105                 110

Val Ile Asp Ile Leu Lys Lys Glu Tyr Val Asp Pro His Ile Ile Lys
        115                 120                 125

Leu Val Asp Ile Val Asn Lys Lys Glu Ile Ile Asn Phe Phe Asn Val
    130                 135                 140

Leu Lys Asn Arg Pro Tyr Val Thr Thr Asp Asn Phe Ile Glu Lys Thr
145                 150                 155                 160

Lys His Lys Asn Ile Leu Ile Lys Met Asp Asp Ala Tyr Leu Val Asp
                165                 170                 175

Asn Phe Phe Leu Phe Ile Leu Leu Tyr Phe Tyr Asn Ile Leu Ile His
            180                 185                 190

Leu Phe Ile Phe Val Pro Phe Leu
        195                 200
```

<210> SEQ ID NO 11
<211> LENGTH: 3597
<212> TYPE: PRT
<213> ORGANISM: Plasmodium falciparum

<400> SEQUENCE: 11

```
Met Lys Leu Ser Val Leu Tyr Leu Val Val Ser Leu Tyr Phe Phe Asp
1               5                   10                  15

Arg Lys Ile Val Cys Asn Lys Lys Asn Gly Lys Ser Lys Ser Asn Asn
            20                  25                  30

His Asn Tyr Phe Asn Asn Thr Thr Lys His Ile Asp Lys Gln Val Ile
        35                  40                  45

Tyr Asn Leu Pro Glu Asn Asp Asn Leu Phe His Val Leu Lys Tyr Leu
    50                  55                  60

Ile His Gly Glu Asn Lys Asn Ile Leu Tyr Asp Val Asp Glu Ser Leu
65                  70                  75                  80

Tyr Thr Lys Ile Glu Asn Lys Glu Tyr Ile Thr Lys Glu Asp Leu Leu
                85                  90                  95

Arg Thr Leu Ala Leu Ile Glu Lys Lys Asn Val Asp Cys Asn Asp Asn
            100                 105                 110

Ile Lys Lys Val Lys Ile Ala Lys Leu Leu Ile Asp Ile Asn Asp Leu
        115                 120                 125

Leu Arg Thr Asn Tyr Ile Ile Leu Asp Asp Tyr Lys Glu Ile Asn Lys
    130                 135                 140

Asn Asp Leu Thr Lys Asn Gly Phe Leu Leu Lys Leu Gln Asn Ser Leu
145                 150                 155                 160

Asn Lys Arg Asp Met Val Asn Ser Lys Arg Val Asn Gln Asp Ile Ile
                165                 170                 175

Leu Arg Asn Gln Tyr Leu Glu Lys Asn Tyr Lys Leu Cys Ser Ile Ser
            180                 185                 190

Ser Asp Met Leu Ile Ile Ser Thr Pro Arg Asn Leu Asn Ile Ser Asp
        195                 200                 205

Thr Ser Ile Lys Glu Ile Lys His Pro Ser Ser Ile Asn Ile Met Asn
    210                 215                 220

Glu Ile Phe Cys Asp Asn Val Ile Ser Ser Asn Val Ser Asn Ile Ser
225                 230                 235                 240

Pro Leu Gln Leu Asn Lys Ser Ile Gly Leu Tyr Lys Pro Leu Leu Asp
                245                 250                 255

Leu Asp Ile Lys Ser Arg Ile Asp Glu Tyr Arg Lys Lys Ile Ile Thr
            260                 265                 270

Tyr Tyr Gln Asp Ser Met Asn Glu Ile Phe Tyr Leu Ile Arg Asp Glu
        275                 280                 285

Phe Asn Glu Ile Lys Lys Lys Phe Tyr Leu Tyr Ile His Pro Ser Lys
    290                 295                 300

Met Pro Glu Ala Lys Pro Asn Asn Asp Ile Phe Lys Lys Glu Asp Met
305                 310                 315                 320

Glu Gly Asn Glu Ile Ile Thr Tyr Val Ser Lys Ile Glu Asn Lys
                325                 330                 335

Glu Asn Ile Lys Asn Lys Glu Glu Tyr Ile Leu Lys Ser Asn Asn Asn
            340                 345                 350

Asn Val Ile Lys Ile Ser Ser Lys Arg Thr Lys Lys Val Ile Asn Ile
        355                 360                 365

Pro Ile Lys Lys Lys Lys Leu Ser Asn Asp Ile Lys Glu Asn Val Asn
    370                 375                 380
```

```
Ser Ser Thr Lys Ser Asp Asn Asn Ile Ile Ser Asn Glu Thr Val
385                 390                 395                 400

Asp Ala Cys Thr Lys Ile Glu Ser Glu Asn Gly Asn Lys Lys Lys Asp
            405                 410                 415

Asp Asn Val Lys Asn Ile Asn Arg Ile Tyr His Ile Phe Leu Lys Lys
            420                 425                 430

Lys Asn Asn Glu Lys Lys Cys Asp Ile Ser Lys Gln Thr Leu Tyr Asn
            435                 440                 445

Asn Ser Phe Lys Glu Asn Asp Val Ile Lys Thr Phe Thr His Asn Asp
        450                 455                 460

Asn Ile Leu Lys Lys Ile Ile Ile Lys Asp Val Ser Arg Glu Lys
465                 470                 475                 480

Pro Thr Ile Lys Glu Ile Ile His Gln Gln Pro Leu Pro Val Glu Asn
                485                 490                 495

Ser Glu Leu Tyr Asn Ile Ser Glu His Ile Gln Asn Lys Cys Asn Cys
            500                 505                 510

Cys Phe Tyr Ser Ile Pro Leu Ile His Ile Tyr His Pro Asn Gly Ser
        515                 520                 525

Met His Cys Leu Ser Cys Ser Gln Tyr Glu Lys Asn Val Asn Arg Lys
        530                 535                 540

Cys Pro Ile Tyr Glu Lys Tyr Ile Thr Phe Asn Tyr Asn Asp Thr Cys
545                 550                 555                 560

Leu Leu Cys Val Pro Ser Ser Tyr Ile Thr Asn Asn Cys Phe Cys Asn
                565                 570                 575

Leu Ile His Ser Lys Gly Leu Gly Glu Lys Thr Asn Asp Val Pro Lys
            580                 585                 590

Lys Leu Asn Met Met Pro His Phe Ser Ile Ile Asp Val Tyr Gly
        595                 600                 605

Asn Lys Asn Ile Asp Gly Tyr Asn Asn Phe Glu Asn Asp Asn Leu
610                 615                 620

Leu Val Tyr Ser Asn Asn Asp Glu Pro Ile Leu Lys Lys Asn His Lys
625                 630                 635                 640

Glu Arg Pro Asn Lys Lys Cys Ser Asn Arg Tyr Lys Leu Lys Cys Pro
            645                 650                 655

Val Gly Asn Gly Ser Ser Asp Met Phe Ser Gly Gln Ser Ile Ser Ile
            660                 665                 670

Phe Pro Ile Ile Gly Asp Asp Ile Asn Arg Gly His Tyr Glu Asn Cys
        675                 680                 685

Pro Tyr Tyr Asp Glu Glu Asp Val Met Cys Tyr Asn Thr Ile Thr Asn
        690                 695                 700

Lys Lys Ile Asn Ile Asn Asn Glu Asp Asp Asn Tyr Glu Lys Ile Leu
705                 710                 715                 720

Tyr Asp Lys Asp Lys Ile Val Tyr Leu Asn Ser Ser Phe Asp Thr
            725                 730                 735

Ile Asn Ile Lys Ile Glu Gly Glu Asp Leu Asn Met Asn Asp Arg Asn
            740                 745                 750

Glu Glu Asn Asp Leu Leu Asp Lys Glu Ser Ile Glu Tyr Ile Asn Glu
        755                 760                 765

Ile Asn Glu Lys Glu Tyr Tyr Asp Ser Ile Glu Ala Cys Lys Asp Tyr
        770                 775                 780

Arg Tyr His Thr Phe Glu Glu Ser Ile Lys Asn Val Asn Asn Arg Glu
785                 790                 795                 800

Cys Tyr Lys Asn Val Tyr Tyr Ser Thr Val His Lys Lys Glu Asp Asn
```

```
                      805                 810                 815
Ile Asp Lys Lys Cys Ser His Asp Ile Glu Ser Arg Asn Lys Arg Val
                820                 825                 830

Asn Glu Tyr Glu Asp Glu Cys Glu Asn Asp Asn Asn Asn Asn Asn Asn
            835                 840                 845

Asn Asn Asp Asp Asp Asp Gly Glu Glu Arg Asn Tyr Phe Leu Phe Asp
        850                 855                 860

Leu Arg Phe Ile Tyr Lys Thr Gly Phe Phe Thr Lys Arg Lys Thr Ile
865                 870                 875                 880

Ile Asn Ser Tyr Leu Lys Thr Asn Lys Ile Asp Ile Thr Tyr Asn Lys
                885                 890                 895

Glu Lys Ile Leu Tyr Leu Phe Lys Asn Leu Phe Glu Lys Thr Phe Lys
            900                 905                 910

Asp Ile Asn Tyr Gln Ile Lys Glu Ser Leu Val His Met Phe Pro Ile
        915                 920                 925

Val Gln Asn Ser Glu Ile Gln Gly Phe Asp Ile Asp Phe Gly Lys Val
    930                 935                 940

Lys Leu His Tyr Ala Thr Ser Ile Asn Met Phe Lys Tyr Ser Val Phe
945                 950                 955                 960

Asp Leu Ile Asn Met Lys Ile Tyr Phe Ile Ser Pro Asp Lys Thr Tyr
                965                 970                 975

Ile Leu Leu Glu Asp Ile Arg Glu Ile Arg Glu Glu Lys Glu Asn
            980                 985                 990

Ser Asn Asn Asp Gly Ser Arg Arg  Lys Asn Lys Ile Ile  Asn Lys Tyr
        995                 1000                1005

Leu His  Glu Met Asp Ile Thr  Asn Ile Glu Trp Ser  Thr Glu Asn
    1010                1015                1020

Ser Lys  Thr Asn Thr Thr Asn  Ser Glu Ser Lys Thr  Thr Thr Thr
    1025                1030                1035

Arg Glu  Asn Thr Ile Val Ile  Lys Glu Lys Ile Gly  Thr His Asp
    1040                1045                1050

Glu Lys  Lys Lys Lys Cys Asp  Asn Thr Lys Asn Asn  Arg Asn Asn
    1055                1060                1065

Asn Asp  Asp Asn Asp Asp Asn  Asp Asn Asp Asn Asp  Asn Asn Asn
    1070                1075                1080

Asp Asn  Asn Asn Asp Asn Asn  Asn Asn Asn Asn Asn  Asn Asn Asn
    1085                1090                1095

Asn Asn  Asn Asn Asn Asn Asn  Asn Asn Asn Asn Asn  Ser Asn Ser
    1100                1105                1110

Asn Ser  Cys Asp Asn Asn Asn  Lys Arg Asp Asn Asp  Ser Phe Glu
    1115                1120                1125

His Val  Asp Ile Gln Lys Asn  Asp Thr Ile Thr Thr  Asn Ile Asp
    1130                1135                1140

Cys Asn  Ile Ile His Asn Asn  Thr Ile Asp Ser Ser  Asn Lys Asn
    1145                1150                1155

Arg Ile  Lys Tyr Asn Leu Asn  Ile Leu Lys Phe Leu  Leu Lys Tyr
    1160                1165                1170

Lys Asp  Leu Leu Ser Lys Glu  Asp Ile Asn Met Ile  Ser Asp Lys
    1175                1180                1185

Asn Asn  Leu Val Thr Ile Asn  Lys Asn Asp Lys Thr  Asn Ile Gly
    1190                1195                1200

Asp Glu  Ile Ile Glu Ile Thr  Ile Arg Lys Asn Glu  Lys Arg Asn
    1205                1210                1215
```

```
Ile Glu Asn Asn Cys Thr Tyr Thr Asn Ser Ile Ile Asn Asn
1220                1225                1230

Ile Asp Asn Asn Ile Ser Glu Ser Ile Asn Ile Asn Gly Gly Glu
1235                1240                1245

Gly Ile Asn Ala Val Ile Glu Thr Val Asp Lys Tyr Leu Asp Lys
1250                1255                1260

Tyr Phe Ser Val His Asn Met Pro Ile Tyr Tyr Met Glu Asn Met
1265                1270                1275

Lys Ile Ser Lys Asn Ile Ile Tyr Val Thr Ser Asp Val Asn Ser
1280                1285                1290

Asp Leu Asp Met Leu Lys Met Ser Ile Leu Gly Ile Cys Asn Ile
1295                1300                1305

Thr Asn Lys Ser Ile Asp Asn Phe Asn Phe Phe Leu Val Arg Asn
1310                1315                1320

Glu Ala Glu Leu Tyr Asp Pro Asn Lys Cys Gln Lys Ile Pro Glu
1325                1330                1335

His Ile Lys Asn Val Gln Asp Leu Tyr Asn Tyr Ser Lys Met Leu
1340                1345                1350

Asp Met Lys Ile Ile Ala Pro Val Tyr Ala Glu Asp Ile Asp
1355                1360                1365

Ile Ile Pro Lys Ser Phe Asp Tyr Leu Phe Lys Leu Tyr Lys Asp
1370                1375                1380

Gly Asp Asp Glu Lys Gly Val Thr Thr Asp Ser Arg Asp Asn Asp
1385                1390                1395

Cys Gln Gln Lys Gly Asn Val Asp Thr Gln Glu Arg Asn Lys Thr
1400                1405                1410

Glu Asn Asp Thr Thr Arg Ile Thr Leu Ser Asn Ile Lys His Asn
1415                1420                1425

Asn Ile Ile Lys Asn Asn Asn Lys Asn Asn Asn Asn Asn Asn
1430                1435                1440

Asn Ser His Asn Asn Asn His Ser Tyr Tyr Asn His Glu Leu Ser
1445                1450                1455

Leu Phe Asn Asp Ala Glu Ser Asn Lys Pro Asn Asp Asn Thr Thr
1460                1465                1470

Thr Ser Asn Asp Lys Asn Tyr Tyr Phe Phe Asn Tyr Asp Asn Lys
1475                1480                1485

Lys Ser Leu Ile Leu Asn Asp Pro Glu Asn Asp Glu Asn Ile Glu
1490                1495                1500

Tyr Leu Ser Glu Glu Ile Ser Ile Tyr Glu Asp Glu His Ile Tyr
1505                1510                1515

Asp Glu Gly Asn Leu Tyr Asn Ser Phe Val Ile Tyr Ile Asp Asn
1520                1525                1530

Pro Phe Lys Arg Ile Asn Ile Glu Asn Ala Pro Ile Leu Lys Gly
1535                1540                1545

Tyr Thr Leu Asn Leu Phe Ile Asn Asp Ile Met Asn Lys Leu Ile
1550                1555                1560

His Ile Pro Ser Thr Phe Ile Asn Thr Gln Ser Tyr Lys Lys Gly
1565                1570                1575

Met Cys Val Met Ser Ile Cys Tyr Cys Phe Asn Tyr Tyr Ser Leu
1580                1585                1590

Asn Ile Tyr Thr Asn Asn Ile Ile Leu Leu Asn Phe Asp Lys Asp
1595                1600                1605

Val Thr Leu Tyr Glu Val Ile Lys Glu Phe Lys Ser Arg Glu Asn
1610                1615                1620
```

Glu Tyr Leu Leu Ile Lys Asn Lys Met Asn Glu Cys Gln Asp
    1625                1630                1635

Val Asp Asn Leu Ser Asn Ile Lys Leu Pro His Thr Ile Asp Leu
    1640                1645                1650

Ile Asp Ser Lys Tyr Ile His Leu Glu Phe Pro Leu Leu Tyr Ile
    1655                1660                1665

Asp Glu His Ser Asn Phe Phe Gln Asp Lys Ile Thr Leu Met Asn
    1670                1675                1680

Val Pro Glu Asn Leu Thr Val Tyr Glu Leu Cys Lys Ser Met Lys
    1685                1690                1695

Asn Ile Leu Asn Glu Ser Leu Ile Ser Phe Asn Leu Ser Thr Ile
    1700                1705                1710

Asn Asp Ile Lys Ile Tyr Thr Ile Arg Gly Arg Gln Trp Glu Met
    1715                1720                1725

Val Leu Asp Asn Leu Leu Val Phe Gly Leu Lys Ile Asn Tyr Glu
    1730                1735                1740

Asp Ile Phe Thr Ile Leu Ile Asp Asn Asn Leu Leu Thr Lys Asn
    1745                1750                1755

Tyr Tyr Glu Leu Leu Ser Asn Ile Ile Ile Asp Phe Arg Asp Asn
    1760                1765                1770

Asn Met Tyr Ile Lys Lys Leu Asp Ile Tyr Ile Asp Tyr Ile Phe
    1775                1780                1785

Gln Pro Tyr Thr Ile Tyr Asn Ile Pro Ile Tyr Ile Thr Pro Asn
    1790                1795                1800

Asn Leu Lys Tyr Ile Leu Leu Gln Tyr Thr Asn Thr Phe Leu Ser
    1805                1810                1815

Asn Ser Leu Leu Asp Glu Phe Phe Phe Thr Tyr Asn Lys Arg His
    1820                1825                1830

Thr Thr Ile Asn Val Val Pro Glu Val Arg Asn Trp Glu His Val
    1835                1840                1845

Glu Asp Ser Asp Val Tyr Ile Tyr Glu Glu Asn Asp Ile Asn Asp
    1850                1855                1860

Lys Lys Lys Glu Gln Lys Arg Asn Ile Ser Phe Ile Tyr Val Leu
    1865                1870                1875

Asn Met Leu Ser Thr Phe Tyr Lys Ile Lys Phe Asn Ser Ser Lys
    1880                1885                1890

Leu Leu Glu Ser Val Met Gly Glu Ile His Gln Leu Cys Gly Lys
    1895                1900                1905

Arg Phe Asn Glu Asn Leu Trp Leu Asp Ile Lys Lys Ser Thr Lys
    1910                1915                1920

Asn Glu Lys Asp Ile Glu Ile Tyr Leu Glu Asn Ser Ser Lys Lys
    1925                1930                1935

Val Leu Ile Lys Asn Val Pro Leu Asp Leu Leu Val Trp Lys Leu
    1940                1945                1950

Ile Asn Ile Ile Met Arg Gly Ser Phe Asn Ile Pro Ile Glu Asp
    1955                1960                1965

Lys Glu Lys Leu Tyr Asn Leu Phe Met Leu Val Pro Lys Asn Lys
    1970                1975                1980

Asp Lys Ile Lys Asp Lys Asn Val Asp Tyr Tyr Phe Leu Ser Thr
    1985                1990                1995

Pro Gly Tyr Thr Val Glu Glu Met Leu Arg Val Phe Glu Lys Lys
    2000                2005                2010

Lys Lys Pro Lys Lys Lys Gly Lys Glu Lys Asn Ser Ala Asn Asp

-continued

```
               2015                2020                2025

Asn  Asn  Asn  Asn  Asn  Asn  Asp  Asn  Asn  Asp  Asn  Tyr  Asn
               2030                2035                2040

Asp  Asn  Tyr  Asn  Asn  Asp  Asn  Ile  Asn  Ser  Asn  Asn  Tyr
               2045                2050                2055

Gly  Asp  Met  Lys  Gln  Thr  Tyr  Tyr  Lys  Ile  Leu  Leu  Ile  Lys  Ala
               2060                2065                2070

Tyr  Pro  Gln  His  Leu  His  Gly  Ile  Gln  Asn  Asn  Glu  Arg  Phe  Asn
               2075                2080                2085

Glu  Tyr  Leu  Thr  Phe  Asn  Leu  Glu  Ala  Leu  Pro  Ser  Val  Ile  Asp
               2090                2095                2100

Val  Lys  Asn  Pro  Thr  Thr  Cys  Leu  Ser  Phe  Tyr  Val  Asn  Tyr  Lys
               2105                2110                2115

Asn  Glu  Asn  Lys  Met  Thr  His  Ile  Ile  Asn  Val  Pro  Glu  Asn  Ile
               2120                2125                2130

Ser  Thr  Asp  Met  Leu  Leu  Lys  Thr  Ile  Leu  Ser  Asp  Asn  Phe  Cys
               2135                2140                2145

Arg  Trp  Lys  Lys  Leu  Pro  Asn  Glu  Glu  Lys  Met  Lys  Phe  Ser  Leu
               2150                2155                2160

His  Leu  Asn  Lys  Lys  Glu  Ile  Thr  Asn  Ile  Lys  Asp  Tyr  Ile  Asn
               2165                2170                2175

Asn  Gly  Asp  Ile  Ala  Gln  Leu  Lys  Thr  Phe  Ile  Leu  Ile  Asn  Asn
               2180                2185                2190

Lys  Lys  Arg  Arg  Val  Gln  Glu  Lys  Tyr  Ile  Asp  Leu  Asp  Asn  Thr
               2195                2200                2205

Thr  Glu  Leu  Gly  Ser  Asn  Val  Asn  Asn  Ile  Ser  Lys  Glu  Glu  Leu
               2210                2215                2220

Lys  Glu  Ile  Gln  Leu  Tyr  Asp  Asn  Val  Leu  Arg  Glu  Ile  Leu  Asn
               2225                2230                2235

Lys  Asn  Tyr  Ile  Asp  Tyr  Asn  Asn  Ile  Ser  Leu  Ser  Gly  Tyr  Thr
               2240                2245                2250

Ile  Thr  Val  Tyr  Val  Phe  Asp  Gly  Asn  Lys  Tyr  Glu  Pro  Leu  Thr
               2255                2260                2265

Ile  Tyr  Asn  Val  Pro  Leu  Asn  Ile  Thr  Asn  Lys  Asp  Ile  Ile  Asn
               2270                2275                2280

Phe  Leu  Leu  Ile  Lys  Ser  Asn  His  Ile  Asn  Ile  Thr  Lys  Leu  Ile
               2285                2290                2295

Asp  Glu  Phe  Leu  Leu  Leu  Asn  Glu  Lys  Leu  Tyr  Asn  Thr  Tyr  Ile
               2300                2305                2310

Val  Lys  Asn  Lys  Asn  Lys  Asn  Met  Leu  Glu  Gln  Asn  Val  Leu
               2315                2320                2325

Phe  Ile  Lys  Lys  Leu  Asn  Glu  Glu  Glu  Glu  Val  Phe  Gln  Leu  Asn
               2330                2335                2340

Glu  Ser  Lys  Phe  Tyr  Leu  Val  His  Asn  Pro  Leu  Phe  Asn  Pro  Leu
               2345                2350                2355

Asp  Asn  Leu  Leu  Gln  Asn  Ile  Val  His  Lys  Lys  Tyr  Asp  Phe  Lys
               2360                2365                2370

Ser  Glu  Lys  Ile  Asp  Ile  His  Ser  Val  Gly  Glu  Lys  Phe  Glu  Ile
               2375                2380                2385

Leu  Thr  Leu  Asn  Ile  Leu  Ile  Asn  Asn  Asp  Ile  Asn  Asn  Met  His
               2390                2395                2400

Asn  Asn  Asn  Val  Asn  Asn  Asn  Tyr  Val  Asn  Asn  Asn  Asn  Ile  Asn
               2405                2410                2415
```

```
Asn Asn Asn Ile Asn Asn Asn Asn Ile Asn Asn Asn Ile Asn
2420                2425                2430
Asn Asn Asn Ile Asn Asn Asn Asn Phe Ser Phe Gly Lys Lys Lys
2435                2440                2445
Phe Val Ile Thr Val Leu Asn Ile Pro Tyr Asn Met Tyr Ile Thr
2450                2455                2460
Glu Phe Leu Arg Tyr Ser Ile Gly Tyr Gln Arg Lys Trp Ile Tyr
2465                2470                2475
Lys Phe Val Leu Phe Tyr Ile Ile Lys Gly Ser Glu Lys Tyr Ile
2480                2485                2490
Leu Asn Asp Gly Asn Asp Ile Ile Arg His Gly Lys Thr Val Ser
2495                2500                2505
Glu Ile Phe Gln Ile Cys Lys Ser Gly Asp Leu Cys Thr Leu His
2510                2515                2520
Ile Asp Ile Asn Phe Asn Glu Ala Asp Asn Asn Leu Glu Asn Asp
2525                2530                2535
Ile Phe Asn Glu Glu Ile Asn Ala Lys Glu Met Lys Asn Val Asp
2540                2545                2550
Val Asp Ser His Ala Asp Val Asp Val Asp Leu Asp Ala Asn Val
2555                2560                2565
Tyr Leu Asp Ala Asn Ala Asp Val Glu Gly Asn Ile Asn Lys Phe
2570                2575                2580
Val Asn Ser Leu His Asn Asp Asn Glu Asn Arg Phe Ile Val Leu
2585                2590                2595
Lys Glu Leu Ser Lys Lys Ile Tyr Thr Asp Asp Tyr Glu Asn Lys
2600                2605                2610
Lys Ile Asp Met Ser Ile Ile Cys Phe Glu Tyr Asn Ala Gly Leu
2615                2620                2625
Tyr Glu Arg Asn Leu Phe Gly Ser Ser Arg Ile Cys Asn Ile Pro
2630                2635                2640
Lys Asn Tyr Thr Val Gly Asp Val Leu Arg Tyr Val Lys Asn Lys
2645                2650                2655
Ile Ile Glu Asp Thr Asn Ile Ser Met Leu Asn Asp Leu Gln Leu
2660                2665                2670
Lys Ile Ile His Asn Asp Asn Tyr Ile Asp Ile Pro Lys Asp Met
2675                2680                2685
Asn Ile Glu Tyr Ala Ile Asn Tyr Leu Phe Ile Tyr Thr Pro Phe
2690                2695                2700
Ile Val Tyr Pro Ser Asp Asp Ile Leu Lys Tyr Asn Asn Ile Ile
2705                2710                2715
Asp Leu Ile Leu Tyr Asn Thr Ile Ile Asp Ile Lys Glu Asn Ser
2720                2725                2730
Phe Val Lys Lys Asp Ile Pro Ile Tyr Val Lys Lys Gly Asn Ile
2735                2740                2745
Phe Lys Asn Val Ser Leu Lys Tyr Ile Pro Ile Asn Ile Lys Glu
2750                2755                2760
Asp Glu Leu Leu Thr Tyr Leu Leu His Tyr Leu Thr Asp Asn His
2765                2770                2775
Glu Val Val Ser Phe Ile Arg Asp Ile Thr Cys Ile Cys Val Tyr
2780                2785                2790
Pro Leu Cys Asp Ser Ile Tyr Ile Phe His Glu Lys Lys Gln Leu
2795                2800                2805
Ser Leu Ile Pro Ser Ile Ser Tyr His Ile Gln Leu Lys Asn Val
2810                2815                2820
```

Tyr Tyr Ile Ser Thr Val Glu Thr Tyr Glu Asn Phe Tyr Asn Ile
    2825            2830            2835

Leu Gly His Met Glu Leu Asn Leu Asn Lys Phe Leu His Ile Gln
    2840            2845            2850

Asn Asp Gly Asn Asn Tyr Lys Lys Lys Glu Ala Tyr Asn Asn Ile
    2855            2860            2865

Tyr Tyr Met Asn Asn Val Asp Glu Leu Ile His Ile Asp Val Asn
    2870            2875            2880

Ile Ile Phe Pro Ser Ile Gln Lys Ile Ile Arg Val Lys Asn Leu
    2885            2890            2895

Asn Val Asn Ile Lys Met Glu Glu Leu Leu Tyr Lys Ile Phe Gly
    2900            2905            2910

Cys Ile Thr Asn Lys Ile Tyr Lys Trp Gly Glu Leu Phe Arg Asn
    2915            2920            2925

Phe Val Gly Lys Lys Glu Lys Ile Asn Ile Val Asn Asn Asp Ile
    2930            2935            2940

Lys Asn Asn Ser Asn Asn Ile Asn Ser Ile Asn Asn Met Asn Ser
    2945            2950            2955

Ile Asn Asn Met Asn Asn Ile Asn Asn Met Asn Ser Ile Asn Asn
    2960            2965            2970

Ile Asn Asn Ile Asn Ser Ile Asn Asn Ile Asn Asn Cys Asp Asn
    2975            2980            2985

Ile Asp Arg Ile Asp Asn Lys Val Leu Lys Asp Tyr Leu Cys Glu
    2990            2995            3000

Glu Gln Asn Ile Ile Thr Phe Ile Phe Cys Ser His Asp Asn Ser
    3005            3010            3015

Ile His Asp Tyr Leu Thr Ser Arg Met Ile Tyr Leu Pro Ala Ile
    3020            3025            3030

Ile Asn Tyr Gln Thr Asn Tyr Ile Thr Phe Tyr Ser Ser Ile Asn
    3035            3040            3045

Gly Phe Ala Asn Asn Glu Thr Thr Phe His Gly Phe Pro Asn Tyr
    3050            3055            3060

Leu Ser Pro Glu Thr Met Leu Thr Met Leu Gln Tyr Asn Phe Phe
    3065            3070            3075

His Val Ile Gly Lys Asn Tyr Leu Lys Leu Tyr Gly Ser Leu Tyr
    3080            3085            3090

Asp Lys Gly Thr Asp Glu Asp Ile Ile Tyr Asn Thr Asn Asp Ile
    3095            3100            3105

Arg Lys Ser Glu Asn Lys Asp Ile Tyr Asn Lys Asn Leu Ile Ala
    3110            3115            3120

Met Arg Gly Ala Ile Lys Phe Ile Leu Arg Ile Lys Asn Lys Gly
    3125            3130            3135

Lys Lys Lys Ser Leu Asp Thr Ile Gln Asn Leu Ile Asn Asn Glu
    3140            3145            3150

Leu Asn Ile Ala Cys Glu Asn Val Glu Asn Asp Val Asp Met Glu
    3155            3160            3165

Glu Cys Asn Asp Phe Leu Ser Ser Leu Asn Asn Ser Ser Ile Phe
    3170            3175            3180

Trp Lys Asn Gly Ile Leu Gly Phe Met Ala Asn Ser Ile Val Thr
    3185            3190            3195

Arg Asp Asn Met Asn Asn Ser Leu Ile Leu Pro Tyr Val Asp Phe
    3200            3205            3210

Glu Ile Asn Glu Lys Met Phe Leu Gln Asn Ile Leu Tyr His Ile

```
                    3215                3220                3225

Asn Ile Ser Pro Tyr Leu Tyr Lys Leu Phe Glu Leu Thr His Ile
    3230                3235                3240

Asp Lys Lys Cys Asn Thr Tyr Lys Lys Lys Leu Lys Asn Ser Val
    3245                3250                3255

Ala His Ile Gln Cys Leu Leu Ser Tyr Gly Phe Ser Ile Tyr Phe
    3260                3265                3270

Asp Leu His Tyr Asp Ser Thr Phe Asp Lys Tyr Lys Gly Phe Thr
    3275                3280                3285

Leu Gly Asp Asn Ser Phe Asp Ile Thr Gln Ile His Ser Phe Gln
    3290                3295                3300

Asn Leu His Glu Gln Asn Phe Val Asp Leu Ile Leu Tyr Asn His
    3305                3310                3315

Asp Asn Thr Phe Ile Thr Ile Lys Asn Val Tyr Arg Asp Met Thr
    3320                3325                3330

Val Ala Thr Phe Leu Asn Asp Leu Ser Lys Thr Arg Cys His Ile
    3335                3340                3345

Leu Gly Leu Thr Tyr Asn Gln Ile Ser Thr Tyr Lys Leu Thr
    3350                3355                3360

Tyr Glu Ile Tyr Asn Glu Thr His Asp Ile Ser Pro Asn Leu Ser
    3365                3370                3375

Ile Ala Asp Val His Asn Ile Val Ile Ser Phe Ser Lys Ser Ser
    3380                3385                3390

Ile Leu Leu Lys Ile Arg Lys Ile Asp Ile Thr Asn Asp Ile Ser
    3395                3400                3405

His Asn Asn Asn Asn Asn Asn Asn Asp Ser Asp Phe Ile Ile
    3410                3415                3420

Asn Ser Asp Asn Ile Asp Tyr Ile Asn Ala Leu Pro Asp Leu Tyr
    3425                3430                3435

Leu Ser Pro Tyr Pro Pro Val Ile Asp Leu Ser Gln Asn Asn Phe
    3440                3445                3450

Gln Val Asn Ile Tyr Met His Ser Lys Phe Ile Pro Asn Asp Tyr
    3455                3460                3465

Ser Leu Arg Lys Asp Ile Val Pro His Ile Thr Ile Asn Asn Val
    3470                3475                3480

Pro Ser Asn Val Phe Ile Leu Ser Leu Lys Glu Leu Leu Lys Thr
    3485                3490                3495

Ile Phe Ile Gln His Met Glu Lys Ser Gln Thr Thr Thr Phe Gln
    3500                3505                3510

Leu Asn Leu Tyr Asp Phe Glu Val Glu Phe Phe Ile Leu Thr Phe
    3515                3520                3525

Asn Arg Phe Thr Ser Lys Phe His Lys Met Asn Ser Asn Val Leu
    3530                3535                3540

Ser Asn Leu Thr Ile Ser Asn Phe Tyr Ser Thr Tyr Ile His Gly
    3545                3550                3555

Gly Leu Phe Leu Asn Ile Asp Lys Ile Lys Ile Asp Ile Pro Asn
    3560                3565                3570

Leu Leu Asn Asp Phe Ile Asp His Phe Ser Lys Val Val Ile Asp
    3575                3580                3585

Phe Ser His His Asn Ile Val Lys Gln
    3590                3595

<210> SEQ ID NO 12
<211> LENGTH: 1964
```

<212> TYPE: PRT
<213> ORGANISM: Plasmodium falciparum

<400> SEQUENCE: 12

```
Met Glu Lys Gly Ser Ile Leu Ser Phe Ile Phe Phe Cys Ser Val Val
1               5                   10                  15

Ile Phe Ile Arg Phe Ile Gly Tyr Phe Phe Cys Asn Arg Tyr Met Thr
            20                  25                  30

Glu Glu Pro Tyr Asn Asn Ile Phe Glu Ile Ile Lys Pro Glu Asn Leu
        35                  40                  45

Tyr Ser Ser Leu Leu Leu Ser Asn Glu Lys Glu Asn Asp Phe Pro
    50                  55                  60

Ser Ser Thr Asn Cys Asn Gly Tyr Met Lys Cys Ile Pro Phe Tyr Asn
65                  70                  75                  80

Asn Val Ser Glu Arg Trp Lys Arg Tyr Asn Phe Ile Gln Leu Tyr Ile
                85                  90                  95

Ile Arg Ser Ala Leu Asn Ile His Val Met Ser Lys Tyr Asn Met Leu
            100                 105                 110

Asn Lys Tyr Asn Lys Glu Thr Asn Arg Leu Leu Lys Arg Asn Asn Asn
        115                 120                 125

Val Glu Asn Arg Ile Asn Asn Ile Ser Asn His Tyr Leu Cys Ser Gly
130                 135                 140

Phe Lys Lys Glu Asn Arg Leu Phe Phe Leu Leu Phe Tyr Lys Thr Ile
145                 150                 155                 160

Lys Met Met Lys Leu Tyr Ile Arg Asn Leu Phe Met Lys Tyr Ile Lys
                165                 170                 175

Ile Tyr Tyr Lys Thr Lys His Phe Glu Lys Asn Ile Glu Thr Asn Lys
            180                 185                 190

Lys Val Val Tyr Val Glu Arg Asp Asn Leu Phe Asp Ile Glu Arg Asn
        195                 200                 205

Asn Leu Phe Asp Ile Leu Tyr Met Leu Lys Arg Ile Asp Ser Tyr Val
    210                 215                 220

Lys Asn Ile Tyr Ser Ile Ile Ser Asn Asn Phe Leu Tyr Val Ile Arg
225                 230                 235                 240

Ile Ile Phe Leu Pro Phe Glu Lys Ile Tyr Phe Ser Leu Lys Ser Leu
                245                 250                 255

Ile Met Ile Lys Lys Met Asn Met Ser Ser Tyr Tyr Tyr Tyr
            260                 265                 270

Val Asn Met Phe Ser Leu Tyr Lys Lys Asn Tyr Asn Lys Tyr Glu Glu
        275                 280                 285

Ile Phe Ile His Glu Gln Arg Val Ile Tyr Pro Asn Glu Tyr Leu Lys
    290                 295                 300

Asn Glu Met Leu Asp Lys Tyr Arg Arg Val Ile Arg Ile Leu Ser Gly
305                 310                 315                 320

Gln His Asp Asn Pro Phe Ile Asp Ser Leu Leu Ile Asn Pro Glu Lys
                325                 330                 335

Ile Glu Lys Asp Asp Leu Asp Val Lys Gln Lys Lys Lys Ile Ile
            340                 345                 350

Glu Glu Leu Lys Lys Lys Lys Glu Asn Thr Asn Thr Asn Thr
        355                 360                 365

Ser Thr Asn Thr Ser Ala Asn Thr Thr Ser Thr Asn Thr Ser Ala
    370                 375                 380

Asn Thr Asn Thr Ser Thr Lys Glu Ser His Ile Leu Asp Glu Ser Lys
385                 390                 395                 400
```

```
Leu Glu Thr Phe Tyr Arg Asp Glu Leu Asp Lys Met Gly Lys Glu
            405                 410                 415

Ile Glu Thr Tyr Phe Lys Gly Asn Ile Asp Lys Lys Ser Leu Asp Glu
            420                 425                 430

Phe His Lys Ile Leu Leu Glu Glu Leu Asn Lys Met Asp Lys Asp Glu
            435                 440                 445

Leu Tyr Glu Met Tyr Arg Glu Glu Leu Asn Arg Ile Glu Gln Glu Lys
            450                 455                 460

Ile Arg Asn Met Asn Lys Glu Glu Ile Asn Lys Thr Tyr Lys Asp Glu
465                 470                 475                 480

Ile Asn Asn Met Asn Ser Asp Gln Val Asp Lys Ile His Arg Glu Glu
                485                 490                 495

Leu Glu Lys Ile Glu Lys Glu Lys Ile Asn Lys Met Asp Lys Asp Glu
            500                 505                 510

Ile Asp Lys Ile Tyr Arg Glu Glu Leu Asp Lys Met Asp Arg Asp Ala
            515                 520                 525

Ile Tyr Ser Met Tyr Ile Glu Asp Ile Ser Asn Lys Asn Ile Lys Asp
            530                 535                 540

Leu Ile Lys Asn Glu Lys Glu Thr Asn Lys Asp Lys Asn Lys Lys Lys
545                 550                 555                 560

Asp Ile Asp Ile Asn Lys Lys Lys Lys Asp Ile Asp Ile Asp Val
                565                 570                 575

Asp Ile Asp Lys Asp Ile His Lys Asp His Val Glu Glu Leu Tyr Gly
            580                 585                 590

Glu Val Lys Asn Lys Leu Ser Lys Glu Glu Leu Asp Arg Met Asp Arg
            595                 600                 605

Asp Ala Leu Tyr Arg Val Tyr Leu Glu Glu Leu Asp Arg Met Asn Arg
            610                 615                 620

Asp Glu Leu Tyr Arg Val Tyr Leu Glu Glu Leu Glu Lys Ile Asp Lys
625                 630                 635                 640

Glu Glu Lys Glu Lys Ile His Arg Glu Lys Leu His Lys Ile Glu Lys
                645                 650                 655

Glu Lys Ile Asn Lys Met Asp Lys Asp Gln Ile Asp Lys Ile Tyr Glu
            660                 665                 670

Glu Glu Leu Asn Lys Met Asp Ser Asp Glu Ile Gln His Val Arg Arg
            675                 680                 685

Ala Ile Leu Gln Asp Ile Gln Lys Glu Lys Ile Gln Asn Leu Glu Leu
            690                 695                 700

Glu Glu Ile Asp Arg Leu Tyr Lys Glu Glu Leu Asp Arg Met Asp Arg
705                 710                 715                 720

Glu Ala Arg Tyr Glu Ile Pro Met Arg Asn Leu Ser Arg Asn Glu Lys
            725                 730                 735

Asp Asn Ile Ile His Arg Asn Ile Lys Asn Glu Ser Asn Gln Lys Asn
            740                 745                 750

Lys Lys Glu Asn Val Asn Val Phe Ile Ile His Asp Asn Asn Asp Ser
            755                 760                 765

Asn Asn Asn Asn Asn Asn Asn Arg Asp Val Asn Asn Leu Asn Asn
            770                 775                 780

Lys His Thr Asn Asn Tyr Asn Glu Asn Val Glu Val Glu Leu Val
785                 790                 795                 800

Val Arg Asn Leu Asp Lys Asp Lys Gly Ala Lys Ile Glu Asp Ile Ile
                805                 810                 815

Asp Tyr Phe Asn Lys Glu Ile Lys Lys Asp Lys Asn Val Asn Val Ser
            820                 825                 830
```

-continued

Asn Ile Val Asn Phe Leu Asn Ser Lys Val Gly Lys Asp Asn Thr Pro
                835                 840                 845

Ile Gln His Lys Lys Glu Asn Gln Val Asp Val Val Arg Lys Asn Ile
850                 855                 860

Gln Ile Ile Gln Glu Asp Asn Ile Lys Asn Lys Gly Gln Lys Asp Asn
865                 870                 875                 880

Thr Glu Met Leu Asp Asn Asn Lys Glu Ile Thr Asn Ile Asp Ile Lys
                885                 890                 895

Asn Val Asp Asp Ile Lys Asn Val Gly Asp Ile Lys Ser Val Gly Asp
                900                 905                 910

Ile Lys Ser Val Asp Asp Ile Asn Asn Val Asp Gly Ile Lys Asn Val
                915                 920                 925

Asp Gly Ile Lys Asn Val Asp Gly Ile Lys Asn Val Asp Gly Ile Asn
                930                 935                 940

Asn Val Gly Asp Ile Asn Asn Ala Gly Asp Thr Asn Asn Ala Gly Asp
945                 950                 955                 960

Ile Asn Asn Val Gly Asp Ile Asn Asn Ser Val Asp Ile Tyr Asn Val
                965                 970                 975

Glu His Ile Asp Glu Ala Glu Lys Lys Pro Asn Leu Asp Asn Pro Lys
                980                 985                 990

Lys Phe Asp Trp Thr Gln Val Phe Lys Asp Lys Val Thr Glu Lys Ile
                995                 1000                1005

Lys Asn Glu Glu Lys Phe Asn Ser Lys Glu Asn Ile Gln Asn
1010                1015                1020

Asp Ile Arg Asp Lys Glu Ile His Lys Asp Asp Arg Ile Lys Gly
1025                1030                1035

Ile Thr Ser Arg Glu Lys Asn Ala Glu Glu Ile Asn Asn Asn Glu
1040                1045                1050

Lys Lys Asp Lys Phe Val Tyr Glu Phe Tyr Thr Ser Asn Lys Lys
1055                1060                1065

Glu Asn Ile Asp Lys Glu Glu Asn Asn Ile Asp Asp Lys Asn
1070                1075                1080

Ile Lys Ile Glu Ile Glu Pro Asn Tyr Glu Ile Asn Asn Asn Phe
1085                1090                1095

Glu Glu Glu Asn Lys Asn Glu Ile Asn Val Ile Ile Asp Lys Glu
1100                1105                1110

Ala Lys Asn Asn Met Asp Lys Asp Asp Ser Asn Asn Asn Asn Asn
1115                1120                1125

Ile Gln Lys Asn Asn Ile Ile Ile Lys Asp Asn Thr Asn Val Ser
1130                1135                1140

Glu Glu Val His Ile Thr Glu Ser Ser Lys Glu Ile Ala Glu Phe
1145                1150                1155

Phe Asn Asn Ile Ile Lys Asn Ser Asn Ile Leu Asp Met Cys Ser
1160                1165                1170

Lys Met Asn Ala Ser Asp Ser Glu Lys Gly Phe Ile Cys Ile Asn
1175                1180                1185

Gly Asn Asn Tyr Ile Ile Asn Pro Gly Thr Tyr His Ile Ile Asn
1190                1195                1200

Ile Lys Tyr Pro Asp Tyr Asn Val Arg Lys Lys Trp Tyr Asp
1205                1210                1215

Ser Met Asp Cys Ile Ser Ile Asn Asn Lys Asp Glu Asn Asn Asn
1220                1225                1230

Asn Lys Glu His Asn Tyr Tyr Asn Lys Asn Asp Asp Asp Leu Tyr

```
                        1235                1240                1245

Leu Lys Lys Ser Val Glu Glu Phe Ile Pro Gly Phe Leu Ser Asn
    1250                1255                1260

Ile Asn Lys Val Asp Asp Leu Ala Arg Ile Phe Thr Pro Ser Phe
    1265                1270                1275

Ile Gln Asn Asp Ile Phe Leu Asn Cys Ile Tyr Lys Tyr Arg Asn
    1280                1285                1290

Asp Phe Asp Lys Asn Asn Ile Tyr Ser Phe Pro Met Lys Ile
    1295                1300                1305

Phe Leu Arg Lys Asn Ser Thr Lys Ile Lys Gly Cys Ser Phe Gln
    1310                1315                1320

Ile Asp Glu Asp Pro Leu Leu Tyr Lys Asp Tyr Ser Glu Lys Glu
    1325                1330                1335

Ser Phe Leu Ser Asn Lys Ile Ile Leu Asn Asn Ser Asn Arg Asn
    1340                1345                1350

Thr Glu Cys Val Leu His Ala Ser Asn Glu Ile Val Gly Phe Gln
    1355                1360                1365

Cys Gly Pro Pro Tyr Lys Ser Tyr Asp Asn Ile Gln Tyr Arg His
    1370                1375                1380

Leu Thr Asn Lys Ser Asn Asp Ile Gln Lys Asn Ile Phe Gly Ile
    1385                1390                1395

Tyr Ser Asn Asn Asn Ser Ser Tyr Ser His Leu Phe Lys Asn Ile
    1400                1405                1410

Phe Asn Asn Glu His Lys Leu Tyr Asn Val Gly Gly Tyr Phe Gln
    1415                1420                1425

Thr Glu Pro Ile Asn Cys Phe Glu Phe Val Asn Asp Asn Ile Asn
    1430                1435                1440

Val Glu Asp Ile Leu Pro Gly Ala Val Pro Phe Pro Arg Phe Asp
    1445                1450                1455

Leu Ile His His Asp Leu Asp Val Asn Gln Thr Arg Tyr Ile Leu
    1460                1465                1470

Leu Asn Glu Thr Asn Gln Asp Lys Thr Ile Ser Cys Thr Cys Asn
    1475                1480                1485

Tyr Phe Thr Glu Pro Asn Ile Val Tyr Thr Gly Lys Ile Ile Ile
    1490                1495                1500

Lys Val Glu Glu Glu Lys Ile Tyr Lys Thr Lys Lys Leu Gln Thr
    1505                1510                1515

Glu Phe Asn Asp Ile Ile Asn Asn Lys Lys Glu Ile Tyr His Glu
    1520                1525                1530

Lys Lys Met Asn His Ile Ile Lys Glu Lys Lys Asp Glu Asp Glu
    1535                1540                1545

Asn Asp Met Ser Phe Asn Lys Asn Tyr Val Asn Asn Tyr Asn Glu
    1550                1555                1560

Asn Phe Lys Ile Asn Asp Ile Asn Asn Phe Tyr Asn Arg Asn Asn
    1565                1570                1575

His Pro Asn Asn Asn Tyr His Asn Asp Tyr His Asn Asn His Ser
    1580                1585                1590

Ser Lys Gly Asn His Thr Asn Lys Ile His Asp Thr Phe Leu Lys
    1595                1600                1605

Asn Lys Tyr Asn Ile Ser Phe Asn Asn Leu Lys Phe Tyr Asn Ile
    1610                1615                1620

Lys His Glu Asn Lys Asn Asn Gln Asp Val Ile Asn Tyr Glu Tyr
    1625                1630                1635
```

```
Asn Val Asp Asp Tyr His Glu Val Gln Asp Gly Gln Asp Glu Ser
    1640            1645                1650

Phe Lys Glu Glu Glu Asp Phe Ile Asp Phe Lys Glu Asn Ile Ile
    1655            1660                1665

Asn Asp Asn Thr Asn His Asn Asn Thr Asp Leu Asp Asp Asp Lys
    1670            1675                1680

Tyr Asn Lys Tyr His Asn Asn Asn Asn Asn Asn Asn Asn Asn Ser
    1685            1690                1695

Ser Phe Lys Ser Ile Glu Ser Asn Leu Asp Leu Gln Arg Ser Ile
    1700            1705                1710

Leu Gln Ser Gly Asp Thr Gln Gln Val Val Val Ile Asn Lys Ser
    1715            1720                1725

Lys Asn Val Asn Val Leu Phe Pro Asp Lys Lys Lys Asn His Thr
    1730            1735                1740

His Pro Asn Glu Glu Lys Arg Thr Phe Pro Lys Tyr Ile Ser Leu
    1745            1750                1755

Val Tyr Lys Glu Lys Asn Lys Asp Asn Glu Lys Ile Asp Lys Thr
    1760            1765                1770

Leu Thr Phe Ile Lys Glu Phe Tyr Pro Pro Leu Leu Arg Gly Gly
    1775            1780                1785

Lys Asp Ser Asp Pro Glu Asn Lys Gln Thr Gly Val Glu Ile Asn
    1790            1795                1800

Asn Gly Val Glu Lys Lys Asn Asp Val Gln Ile Lys Asn Asp Val
    1805            1810                1815

Glu Ile Lys Asn Asp Val Glu Ile Lys Asn Asp Val Glu Ile Asn
    1820            1825                1830

Asp Asp Val Glu Ile Lys Asn Asp Val Glu Ile Lys Asn Asp Val
    1835            1840                1845

Glu Ile Lys Asn Asp Val Glu Ile Asn Asp Val Glu Ile Asn
    1850            1855                1860

Asp Asp Val Glu Ile Asn Asn Gly Val Glu Ile Asn Asp Gly Val
    1865            1870                1875

Glu Asn Lys Asp Asn Ile His Glu Gly Asn Asn Asn Leu Glu Asn
    1880            1885                1890

Asp Ser Phe Asn Glu Asp Thr Ile Glu Glu Pro Phe Glu Asn Ile
    1895            1900                1905

Phe Asp Phe Ile Asn Glu Glu Thr Ser Ser Asn Glu Asn Ser Glu
    1910            1915                1920

Ile Ile Leu Asp Ser Ala Asp Ser Ile Lys Arg Lys Leu Gly His
    1925            1930                1935

Asn Phe Leu Asp Ile Ile Ser Ala Gly Lys Phe Lys Ile Arg His
    1940            1945                1950

Lys Glu Lys Lys Thr Lys Asn Lys Lys Lys Lys
    1955            1960

<210> SEQ ID NO 13
<211> LENGTH: 301
<212> TYPE: PRT
<213> ORGANISM: Plasmodium falciparum

<400> SEQUENCE: 13

Met Ser Val Leu His Arg Phe Tyr Leu Phe Leu Phe Thr Lys Phe
1               5                   10                  15

Phe His Cys Tyr Lys Ile Ser Tyr Val Leu Lys Asn Ala Lys Leu Ala
                20                  25                  30
```

```
Pro Asn His Ala Ile Lys Asn Ile Asn Ser Leu Asn Leu Leu Ser Glu
         35                  40                  45

Asn Lys Lys Glu Asn Tyr Tyr Tyr Cys Gly Glu Asn Lys Val Ala Leu
 50                  55                  60

Val Thr Gly Ala Gly Arg Gly Ile Gly Arg Glu Ile Ala Lys Met Leu
 65                  70                  75                  80

Ala Lys Ser Val Ser His Val Ile Cys Ile Ser Arg Thr Gln Lys Ser
                 85                  90                  95

Cys Asp Ser Val Val Asp Glu Ile Lys Ser Phe Gly Tyr Glu Ser Ser
                100                 105                 110

Gly Tyr Ala Gly Asp Val Ser Lys Lys Glu Ile Ser Glu Val Ile
            115                 120                 125

Asn Lys Ile Leu Thr Glu His Lys Asn Val Asp Ile Leu Val Asn Asn
130                 135                 140

Ala Gly Ile Thr Arg Asp Asn Leu Phe Leu Arg Met Lys Asn Asp Glu
145                 150                 155                 160

Trp Glu Asp Val Leu Arg Thr Asn Leu Asn Ser Leu Phe Tyr Ile Thr
                165                 170                 175

Gln Pro Ile Ser Lys Arg Met Ile Asn Asn Arg Tyr Gly Arg Ile Ile
                180                 185                 190

Asn Ile Ser Ser Ile Val Gly Leu Thr Gly Asn Val Gly Gln Ala Asn
                195                 200                 205

Tyr Ser Ser Ser Lys Ala Gly Val Ile Gly Phe Thr Lys Ser Leu Ala
210                 215                 220

Lys Glu Leu Ala Ser Arg Asn Ile Thr Val Asn Ala Ile Ala Pro Gly
225                 230                 235                 240

Phe Ile Ser Ser Asp Met Thr Asp Lys Ile Ser Glu Gln Ile Lys Lys
                245                 250                 255

Asn Ile Ile Ser Asn Ile Pro Ala Gly Arg Met Gly Thr Pro Glu Glu
                260                 265                 270

Val Ala Asn Leu Ala Cys Phe Leu Ser Ser Asp Lys Ser Gly Tyr Ile
                275                 280                 285

Asn Gly Arg Val Phe Val Ile Asp Gly Gly Leu Ser Pro
290                 295                 300

<210> SEQ ID NO 14
<211> LENGTH: 230
<212> TYPE: PRT
<213> ORGANISM: Plasmodium falciparum

<400> SEQUENCE: 14

Met Arg Phe Leu Ile Ile His Ile Ala Val Ile Val Leu Pro Phe Val
 1               5                  10                  15

Leu Met Ile Asp Val Lys Arg Glu Asn Ser Phe Phe Leu Arg His Ser
             20                  25                  30

Pro Lys Arg Leu Tyr Lys Lys Ala Asp Tyr Asn Asn Met Tyr Asp Lys
         35                  40                  45

Ile Ile Lys Lys Gln Gln Asn Arg Ile Tyr Asp Val Ser Ser Gln Ile
 50                  55                  60

Asn Gln Asp Asn Ile Asn Gly Gln Asn Ile Ser Phe Asn Leu Thr Phe
65                  70                  75                  80

Pro Asn Tyr Asp Thr Ser Ile Asp Ile Glu Asp Ile Lys Lys Ile Leu
                 85                  90                  95

Pro His Arg Tyr Pro Phe Leu Leu Val Asp Lys Val Ile Tyr Met Gln
                100                 105                 110
```

```
Pro Asn Lys Thr Ile Ile Gly Leu Lys Gln Val Ser Thr Asn Glu Pro
            115                 120                 125

Phe Phe Asn Gly His Phe Pro Gln Lys Gln Ile Met Pro Gly Val Leu
130                 135                 140

Gln Ile Glu Ala Leu Ala Gln Leu Ala Gly Ile Leu Cys Leu Lys Ser
145                 150                 155                 160

Asp Asp Ser Gln Lys Asn Asn Leu Phe Leu Phe Ala Gly Val Asp Gly
                165                 170                 175

Val Arg Trp Lys Lys Pro Val Leu Pro Gly Asp Thr Leu Thr Met Gln
            180                 185                 190

Ala Asn Leu Ile Ser Phe Lys Ser Leu Gly Ile Ala Lys Leu Ser
                195                 200                 205

Gly Val Gly Tyr Val Asn Gly Lys Val Val Ile Asn Ile Ser Glu Met
210                 215                 220

Thr Phe Ala Leu Ser Lys
225                 230

<210> SEQ ID NO 15
<211> LENGTH: 2900
<212> TYPE: PRT
<213> ORGANISM: Plasmodium falciparum

<400> SEQUENCE: 15

Met Arg Ser Tyr Glu Arg Lys Lys Lys Lys Thr Ala Lys Thr Ser
1               5                   10                  15

Ser His Gly Arg Asn Lys Trp Thr Ser Asn Lys Ser Lys Ser Ser Tyr
                20                  25                  30

Lys Lys Lys Lys Lys Asn Leu Val Asn Ser Asn Tyr Asn Leu Leu Asn
            35                  40                  45

Tyr Leu Gln Arg Glu His Ile Asn Glu Asn Ile Lys Asn Leu Gly Glu
50                  55                  60

Tyr Leu Asn His Ser Asp Val Asn Ile Cys Glu Lys Asn Ile Lys Lys
65                  70                  75                  80

Val Asp Lys Ser Lys Asn Ile Pro Cys Val Thr Ser Lys Asp Ile Asn
                85                  90                  95

Ile Val Asn Gly Asn Ile Asn Lys Glu Lys Lys Ile Lys Ile Lys Gln
            100                 105                 110

Lys Lys Lys Arg Arg Arg Thr Asn Lys Glu Ser Val Cys Ile Pro Tyr
            115                 120                 125

Val Lys Glu Glu Lys Asp Val Pro Ile Leu Tyr Ser Asn Lys Glu Ile
            130                 135                 140

Ile Leu Tyr Lys Lys Asn Glu Ser Asp Ile Ile Asn Arg Ala Asn Ile
145                 150                 155                 160

Asn Arg Lys Asn Ile Asp Asn Asp Asn Val Asp Lys Asn Asn Val Asp
                165                 170                 175

Lys Tyr Asn Met Asn His Lys Glu Lys Lys Arg Asn Cys Ser Ser Asn
            180                 185                 190

Thr Asn Lys Asn Asn Ile Ser Ile Glu Asn Lys Ile Arg Asn Asn Lys
            195                 200                 205

Trp Ile Asn Lys Arg Asn Ile Phe Glu Gln Lys His Lys Lys Ile Tyr
            210                 215                 220

His Asn Met Phe Lys Ser Glu Asp Ile Ser Asn Gln Asn Phe Lys Asn
225                 230                 235                 240

Val Ile Ile Gln His Glu His Ser Ser Glu Cys Ser Asn Arg Ser His
                245                 250                 255
```

```
Glu Lys Lys Lys Lys Leu Tyr Tyr Ser Ser Thr Leu His Thr Asn
                260             265             270

Phe Gly Arg Ile Lys Glu Asn Thr Leu Phe Gln Glu Tyr Glu Glu
            275             280             285

Lys Gln Asn Glu Ile Ile Asn Lys Lys Tyr Tyr Met Phe His Ser Thr
290             295             300

Asp Ile Thr Asn Asn Asn Ala Asn Leu Tyr Asp Asn Gln Ile Asn Asn
305             310             315             320

Asn Tyr Glu Glu Glu Lys Asn Glu Lys Thr Ile Ser Asn Asp Phe
            325             330             335

Leu Asp Asn Ile Leu Pro Val Glu Lys Ile Ile Gln Tyr Val Asp Asp
            340             345             350

Ile Ser Ile Glu Ala Leu Val Tyr Ile Leu Asn Thr Leu Asp Ile Thr
            355             360             365

Asn Ser Thr Ser Leu Ile Glu Arg Leu Pro His Arg Tyr Tyr Lys Glu
            370             375             380

Tyr Leu Met Phe Thr Asn Asn Ile Lys Arg Ile Ile Glu Leu Met Glu
385             390             395             400

Asn Ile Ser Asn Glu Lys Leu Gly Ser Phe Phe Ile Thr Tyr Lys Glu
            405             410             415

Glu Lys Asp Ile Cys Lys Tyr Ile Asn Ile Leu Ser Leu Gly Lys Leu
            420             425             430

Asn Asn Ile Leu Asn Cys Phe Pro Ile Asp Asn Tyr Lys Glu Phe Ile
            435             440             445

Leu Leu Phe Asp Glu Tyr Lys Leu Leu Glu Ile Leu Asn Thr Leu Ser
            450             455             460

Ile Ser Thr Cys Leu His Ile Leu Leu Asn Ile Ser Gln Lys Lys Leu
465             470             475             480

Arg Tyr Ile Phe Asp Asn Ile Asn Glu Glu Lys Leu Ile Met Leu Ile
            485             490             495

Asn Glu Val Pro Leu Cys Lys Phe Tyr Tyr Ile Asn Glu Cys Ile Pro
            500             505             510

Ile Gln Lys Ile Gly Thr Leu Ser Asn Asn Ile Cys Tyr Glu Lys Leu
            515             520             525

Tyr His Leu His Asn Ser Leu Ser Asn Ser Lys Asn Ile His His Ile
            530             535             540

Thr Cys Asn Leu Ser Ile His Ile Ile Gln Leu Ile Ile Asp Leu
545             550             555             560

Pro Ile Tyr Lys Ala Ile Gln Ile Leu Lys Thr Ile Ser Leu Glu Lys
            565             570             575

Ile Ala Gln Cys Ile Met Phe Asn Lys Asn Cys Phe Asn Ile Tyr Asp
            580             585             590

Ile Leu Tyr Lys Ala Phe His Ile Asp Lys Ile Val Gln Ile Ile Ile
            595             600             605

His Leu Asp Asn Asp Val Asn Asn Ile Asn Leu Leu Asn Leu Ala
            610             615             620

Asn Tyr Thr Asp Ile Ile His Tyr Ile Asn Tyr Ile Ser Phe Asn Lys
625             630             635             640

Phe Lys Ser Phe Ile Asp Lys Leu Pro Ile Pro Phe Leu Lys Lys Ile
            645             650             655

Ile Asn Asp Ile Ser Leu Lys Lys Ile Ile Gln Phe Met Asn Asn
            660             665             670

Lys Asn Glu Lys Lys Val Ile Ile Cys Phe Tyr Gln Leu Thr Ile Lys
            675             680             685
```

```
Asn Leu Asn Ser Val Val Gln Leu Leu Pro Val Lys Asn Val Leu Arg
    690                 695                 700

Leu Val Ile Pro Ser His Met Asp Ile His Ser Lys Glu Thr Lys Lys
705                 710                 715                 720

Ile Met Asn Arg Leu Asp Ala Lys Asn Met Val His Leu Leu Asn Asp
                725                 730                 735

Leu Asn Asp Asn Glu Tyr Lys Tyr Ile Cys Asn Tyr Ile Pro Leu Glu
            740                 745                 750

Lys Ile Pro Asn Leu Leu Asn Asn Ser Thr Phe Ala Asn Tyr Glu Lys
        755                 760                 765

Cys Tyr Ile Val Ile Leu Tyr Leu Pro Ile Arg Lys Leu Ile Asp Thr
770                 775                 780

Phe His Thr Leu Asn Glu Glu Lys Lys Phe Gly Ile Leu Glu Arg Met
785                 790                 795                 800

Pro Tyr Tyr Ile Lys Asp Thr Ile Ile Cys Asn Ile Tyr Asp Thr Thr
                805                 810                 815

Lys Lys Phe Ile Tyr Leu Met Asn Pro Ile Gln Gln Ile Phe Ile Ser
            820                 825                 830

Cys Met Leu Phe Lys Leu Asn Arg Ile Phe Gly Asn His Tyr Lys Lys
        835                 840                 845

Lys Asn Ile Asn Lys Gln Lys Asn Lys Lys Asp Asp Lys Lys Asn Thr
850                 855                 860

Lys Lys Tyr Ile Thr Leu Tyr Ser Ile Arg Asn Lys Phe Tyr Asp Ile
865                 870                 875                 880

Ile Lys Asn Ile Asn Ile Lys Lys Tyr His Leu Phe Leu Asn Gln Val
                885                 890                 895

Thr Cys Asn Lys Ile Ile Glu Thr Gln Asn Ile Ile His Asn Ile Arg
            900                 905                 910

Asn Lys Lys Lys Tyr Glu His Glu Gln Ile Val Gln Asp Leu Phe Phe
        915                 920                 925

Tyr Phe Asn Ile Tyr Gln Tyr Val Lys Lys Lys Lys Glu Lys Ile
930                 935                 940

Leu His Ile Lys Lys Asn Ile Pro Leu Asn Val Gln Asn His Asp Lys
945                 950                 955                 960

Val Arg Pro Lys Ile Phe Asn Asn Ile Asn Ser Ala Ile Thr Cys Ile
                965                 970                 975

Ser Asp Pro Ile Leu Ser Asn Asp Thr Ser Tyr Lys Asn Ser Ser Leu
            980                 985                 990

Tyr Asn Lys Ser Tyr Ile Thr Lys Lys Arg Asn Ser Asn Asp Leu Leu
        995                 1000                1005

Asn Asn Ile Lys Ser Asn Asn Asn Asn Asn Met Tyr Ile Tyr Lys
    1010                1015                1020

Asp Gly Ile Ala Pro Asn Asn Asn Glu Asn His Tyr Ile Asp Leu
    1025                1030                1035

Ser Lys Arg Glu Lys Ile Leu Pro Ile Lys Thr Tyr Asn Ile Lys
    1040                1045                1050

Asn Lys Ala Ser Thr Asn Ile Tyr Tyr Asn Gln Asn Ser Ser Leu
    1055                1060                1065

Asn Asn Ile Cys His Glu Lys Asn Ile Asn Lys Asp Met Thr Lys
    1070                1075                1080

His Val Lys Lys Lys Lys Lys Lys Asn Ser Tyr His Pro Lys
    1085                1090                1095

Ser Arg His Gly Leu Tyr Ile Phe Leu Ile His Leu Ile Ile Val
```

```
            1100                1105                1110
Ile Lys Lys His Ile Gln Asp Glu Asn Asp Arg Lys Ile Asn Glu
            1115                1120                1125
Lys Lys Ser Tyr Asp Ile Asn Tyr Thr Thr Asp Asn Asn Asn
            1130                1135                1140
Asn Asn Asn Asn Asn Tyr Asn Tyr Asn Tyr Asn Asn Asn His
            1145                1150                1155
Asn Asn Asn His Ser Asn Leu Leu Ser Asn Thr Ser Ser Thr Asn
            1160                1165                1170
His Asn Asp Tyr Asn Lys Phe Ile Phe Tyr His Val Arg Lys Ile
            1175                1180                1185
Met Lys Asn Ile Phe Phe Ser Val Arg Lys Ile Leu Gln Met Lys
            1190                1195                1200
Asn Arg Ser Asn Val Ile Lys Asn Ile Ser Ile Phe His Ile Met
            1205                1210                1215
Asn Ala Asn Leu Leu Pro Tyr Met Ile Asn Glu Asn Tyr Asn Asn
            1220                1225                1230
Ile Phe Tyr Asp Ile Ser Asn Asn Ile Lys His Thr Glu Lys Ile
            1235                1240                1245
Asn His Asn Pro Asn Ile Ser Asp Asn Arg Asn His Leu Gln Glu
            1250                1255                1260
Tyr Lys Ile Phe Asn Met Ile Gln Asp Ser Thr Glu Phe Phe Asp
            1265                1270                1275
Ala Asn Asn Thr Cys Val Val Ile Glu Asn Glu His Thr Asn Ile
            1280                1285                1290
Met Asp Thr Ser Lys Glu Asn Glu Asn Ile Phe Ser Leu Lys Asp
            1295                1300                1305
Asp Ile Pro Ile Ile Glu Asp Thr Asn Asn Val Ile Glu Phe Asp
            1310                1315                1320
Asn Glu Gln Ile Ile Asn Asp Ile Cys Val Gln Lys Asn Lys Asn
            1325                1330                1335
Arg Asn Pro Leu Tyr Tyr Val Ser Leu Leu Phe Asn Lys Pro Asn
            1340                1345                1350
Ser Phe Pro Tyr Leu Ile Lys Lys Asn Ile Leu Arg Ile Glu Lys
            1355                1360                1365
Asn Asp Lys Arg Tyr Lys Asn Phe Phe Phe Phe Lys Thr Ala Thr
            1370                1375                1380
Ile Cys Asp Thr Ile Lys Asn Glu Glu Cys Glu Ser Asn Thr Gln
            1385                1390                1395
Gly Asp Asn Ile Lys Asp Tyr Ile Leu Thr Thr Ser Asn Ile Phe
            1400                1405                1410
Lys Lys Asn Arg Asn Asn Ile Leu Asn Ile Tyr Asn Lys Asp Thr
            1415                1420                1425
Lys Ile Asp Asn Asp Ile Asp Lys Glu Glu Ser Glu Gln Ile Asn
            1430                1435                1440
Ser Asp Asn Ile Asn Ile Leu Tyr Cys Asn Thr Asn Val Glu Ser
            1445                1450                1455
His Asn Asn Asn Asn Asn Asn Asn Asn Lys Asn Asn Asn
            1460                1465                1470
Lys Asn Lys Asn Asn Asp Arg Asn Asn Asn Asn Arg Lys Lys Lys
            1475                1480                1485
Asp Ile Gln Lys Ser Lys Phe Ser Asp Leu Arg Tyr Lys Trp Lys
            1490                1495                1500
```

-continued

```
Phe Ser His Ile Ser Glu Lys Tyr Lys Asn Lys Ile Tyr Lys Ile
1505                1510                1515

Asn Asn Asn Ile Asn Gly Glu Lys Lys Asn Val Tyr Cys Leu Lys
1520                1525                1530

Phe Ile Phe Val Leu Asn Asn Val Cys Asp Leu Asp Lys Arg Asn
1535                1540                1545

Asn Asp Asn Ile Asn Leu Thr Leu Asn Phe Phe Ile Ser Lys Lys
1550                1555                1560

Lys Lys Lys Arg Leu Leu Asn Ile Tyr Lys Gln Lys Ile Leu Asp
1565                1570                1575

Ser Ser Leu Asp Ile Gln Ile Asn Asn Glu Lys Tyr Lys Asn Lys
1580                1585                1590

Ile Ile Asn Phe Ser Thr Asn Ile Ser Asp Thr Thr Cys Tyr Ile
1595                1600                1605

Asn Ser Asn Ile Val Asn Ile Lys Phe Asn Lys Glu Gln Lys Asn
1610                1615                1620

Lys Leu Glu Tyr Leu Tyr Ser Leu Ile Asn Glu Glu Asp Pro Ser
1625                1630                1635

Asn Lys Asn Leu Phe Asn Lys Thr Lys Cys Asp Thr Tyr Ile Lys
1640                1645                1650

His Asp Gly Asn Met Asn Val Asp Asn Val His Tyr Asp Tyr Lys
1655                1660                1665

Arg Asp Asp His Ile Asn Asn Asp Lys Tyr Asn Tyr Asn Tyr Asn
1670                1675                1680

Tyr Ser Tyr Asn Tyr Asn Tyr Asp Glu Lys Val Ser Phe Asn Gln
1685                1690                1695

Leu Lys Asn Asn Thr Leu Asp His Asn Glu Asn Lys Asn Asn Asn
1700                1705                1710

Ile Leu Ser Glu Lys Phe Ile Ser Asn Leu Leu Asn Lys Asn Ile
1715                1720                1725

Ile Leu Leu Trp Ser Cys Lys Asn Ile Gly Tyr Ile Phe Leu Asn
1730                1735                1740

Thr Asp Asn Ser Leu His Ile Asn Ile Gln Asp Ile Ser His Asn
1745                1750                1755

Leu Tyr Ile Gln Ile Asp Lys Tyr Asn Tyr Asn Thr His Lys Asn
1760                1765                1770

Tyr Phe Phe Asn Asn Asn Asn Asn Tyr Lys Lys Gly Thr Tyr Ile
1775                1780                1785

Phe Leu Asn Arg Leu Phe Val Lys Glu Lys Ile His Phe Arg Lys
1790                1795                1800

Leu Lys Glu Ala Phe Ser Lys Ile Ile Glu Asn Lys Lys Gln Lys
1805                1810                1815

Lys Lys Gly Val Cys Lys Ser Leu Leu Glu Glu Asn Asn Asn Glu
1820                1825                1830

Asn Phe Tyr Lys Cys Lys Asp Ser Glu Asn Lys Ile Lys Tyr Lys
1835                1840                1845

Asn Val Asn Asn Val Thr Asn Lys Asn Gly Ser Val Glu Asn Asn
1850                1855                1860

Asn Ser Leu Asn Lys Tyr Glu Asn Ser Thr Asn Thr Asp Ile Leu
1865                1870                1875

Lys Phe Ile His Ile Asn Met Glu Asn Asn Tyr Lys Ser Glu Gln
1880                1885                1890

Asn Ser Ala Glu Asp Asn Met Asn Glu Asp Ile Ile Tyr Phe Gly
1895                1900                1905
```

Asp Asp Lys Tyr Glu Phe Phe Asn Asp Thr Asn Ile Leu Glu Lys
1910                1915                1920

Lys Asn Ile Asn Gln Lys Asn Asn Glu Ile Ser Ile Ile Asp Lys
1925                1930                1935

Gln Val Tyr His Asp Ile Asp Ile Asp Lys Asp Asn Tyr Leu Ile
1940                1945                1950

Gln Tyr Asp Lys Asn Ile Lys Arg Lys Asn Ser Leu Ile Phe Met
1955                1960                1965

Asn Asn Thr Asn Asp Thr Cys Ser Asn Asn Met Phe Tyr Glu Gln
1970                1975                1980

Ser Lys Arg Asp Asp Pro Ile Asn Glu Tyr Tyr Lys His His
1985                1990                1995

Asn Ser Ile Val Val Asn Tyr Phe Asn Asn Val Ile Arg Glu Ser
2000                2005                2010

Asn Lys Ile Leu Ser Glu Lys Arg Asn Asn Ile Asn Lys Gln Ile
2015                2020                2025

Arg Glu Glu Ile Ile Asn Ile Asn Glu Lys Ser Ile His Ser Leu
2030                2035                2040

Asp Ser Asn Glu Lys Glu Lys Val His Gln Ile Ile Ser Asn Glu
2045                2050                2055

Tyr Asn Asn Ile Met Glu His Glu Leu Arg Lys Ile Arg Asn Pro
2060                2065                2070

Tyr Leu Cys Asp Met Tyr Gln Phe Leu Lys Tyr Ser Tyr Thr Lys
2075                2080                2085

Glu Glu Phe Asn Ile Ile Leu Tyr Leu Lys Lys Arg Asn Lys Lys
2090                2095                2100

Leu Asn Lys Ile Lys Asp Met Ser Asn Ile Lys Met Asn Val Ser
2105                2110                2115

Lys Lys Ile Ile Asn Asn Gly Asn Asn Ile Ile Asp Val Gln Arg
2120                2125                2130

Asn Gly Lys Phe Val Pro His Ile Phe Asn Asp Asn His Ile Leu
2135                2140                2145

Lys Leu Lys Leu Val Thr Leu Val Asp Asn Glu Leu Cys Asp Tyr
2150                2155                2160

Lys Leu Tyr Asn Asn Lys Ile Ile Asn Asn Asn Asn Lys Glu
2165                2170                2175

Thr Leu Arg Phe Glu Glu Asn Leu Arg Lys Ile Asn Leu Ser Phe
2180                2185                2190

His Ser Ser His Ile Phe Ala Ser Asn Pro Phe Ile Val Ser Arg
2195                2200                2205

Glu His Phe Leu Leu Asp Gln Lys Thr Gln Asn Asn Ser Thr Ala
2210                2215                2220

Gln Ile Ile Gln Asp Asn Asn Asn Asn Asn Asn Asn Asn Gly Asp
2225                2230                2235

Arg Lys Lys Glu Asn Asn Ile Tyr Asn Glu Asn Glu Glu Gly Ile
2240                2245                2250

Ile Asn Asn Asn Ile Phe Val Lys Gly Ile Asn Lys Asn Thr Ser
2255                2260                2265

Phe Tyr Asn Glu Lys Tyr Asn Ile Gln Thr Gln Asn Asn Lys Asp
2270                2275                2280

Tyr Lys Asn Glu Met Leu Ser Leu Ser Asn Ile Ser Tyr Asn Glu
2285                2290                2295

Ile Met Ile Gln Lys Cys Ile Glu Lys Asp Glu Val Phe Lys Asn

-continued

```
                2300                2305                2310
Gly Asn Asn Leu Glu Asn Ser Lys Asn Leu Gln Asn Glu Glu Lys
                2315                2320                2325
Ser Pro Thr Ile Lys Glu Lys Asn Ile Pro Asn Asn Asn Asn Asn
                2330                2335                2340
Asn Asn Asn Asn Asn Lys Asn Asn Ile Tyr Asp Ile Leu Asp
                2345                2350                2355
Asn Asn Leu Phe Lys Gly Leu Phe Ile Lys Asp Asp Ile Lys Leu
                2360                2365                2370
Ser Lys Arg Thr Ile Gln Asp Ile Leu Thr Ser Ser Asp Thr Asn
                2375                2380                2385
Asn Leu Tyr Lys Asn Lys Ala Phe Ser Asn His Lys Glu Glu Ile
                2390                2395                2400
Gln Ser Leu Asn Thr Glu Gln Lys Ile Asn Lys Ile Tyr Ile Pro
                2405                2410                2415
Asn Tyr Ser Ser Asp Val Val Arg Lys Val Ser Asn Asn Phe Ser
                2420                2425                2430
Cys Ile Asn Gln Ser Thr Asn Met Pro Asn Ile Phe Ser Asn Ser
                2435                2440                2445
Ile Gly Asn Ile Lys Arg Ile Lys Glu Lys Asn Lys Ile Met Gln
                2450                2455                2460
Asn Ser Asn Ser Ile Leu Ser Asp Val Ser Asp Ile Phe Ile Asn
                2465                2470                2475
Tyr Asn Asp Ser Asn Lys Glu Val Glu Lys Asn Met Asn Ser Ser
                2480                2485                2490
Tyr Phe Asn Lys Leu Ile Ile Pro Ile Pro Gly Asp Asn Val Asn
                2495                2500                2505
Ile Asn Phe Phe Glu Lys Lys Glu Thr His Leu Asp Asp Asn Tyr
                2510                2515                2520
Ile Asn Ile Asn Ser His Glu Glu Asn Asn Ile Asn Thr Ser His
                2525                2530                2535
Ile Ile Lys Lys Ser His Val Val Ser Asn Leu Asn Tyr Lys Asn
                2540                2545                2550
Ile Ser Asp Asn Ser Leu Lys Asn Lys Leu Cys Phe Glu Phe Ser
                2555                2560                2565
Lys Thr Asn His His His Asn Asn Asn Asn Asn Asn Asn Asn Val
                2570                2575                2580
Asp Asp Tyr Ile Asn Asn Ser Asn Asn Asn Ile Tyr Ile Asn Asp
                2585                2590                2595
Thr His Lys Asn Ile Asn Gly Ile Met Tyr Asn Leu Gly Phe Leu
                2600                2605                2610
Asn Leu His Cys Leu Leu Glu Asn Lys Asn Lys His Phe Tyr Leu
                2615                2620                2625
Ile Thr Gln Gly Tyr Ile Lys Ala Ser Asn Tyr Ile Asn Asp Gln
                2630                2635                2640
Met Leu Ile His Thr Lys Ile Tyr Asn Glu Ile Phe His Thr Lys
                2645                2650                2655
Lys Tyr Ile Asp Ala Lys Lys Asn Thr Ser Ile Ile Ser Ser Ser
                2660                2665                2670
Phe Asp Ser Val Thr Lys Gln Asn Asp Lys Leu Tyr Cys Leu His
                2675                2680                2685
Lys Lys Lys Arg Met Phe Cys Asn Ile Cys Gly Tyr Ile Leu Lys
                2690                2695                2700
```

-continued

```
Gln Asn Phe Leu Asn Asp Phe Phe Phe Phe Lys Ile Phe Ile Val
2705                2710                2715

Thr Lys Arg Ala Ile Phe Ser Asn His Ser Thr Ile Asn Ile Ile
2720                2725                2730

Tyr Gln Ser Pro Leu Ile Lys Ala Val Phe His Glu Lys Asp Asn
2735                2740                2745

Ile Lys Tyr Lys Leu Glu Gln Thr Asn Asn Gln Tyr Ile Leu
2750                2755                2760

Lys Ile Ile Ala Ile Lys Lys Lys Ile His Lys Thr Phe Ser
2765                2770                2775

Leu Ser Lys Asn Lys His Phe Arg Lys Cys Leu Glu Ile Glu Leu
2780                2785                2790

Ile Asn Thr Glu Lys Lys Asn Ile Glu Asn Glu Met Tyr Glu Arg
2795                2800                2805

Lys Glu Asn Val Leu Asp Lys Lys Ile Tyr Gly Lys Gln Val Phe
2810                2815                2820

His Lys Lys Ser Phe Asp Asn Leu Tyr Asn Thr Thr Lys Asp Ser
2825                2830                2835

Leu Ile Ile Asn Asn Glu Lys Tyr Lys Ser Glu Val Lys Lys Lys
2840                2845                2850

Lys Tyr Ser Ser Tyr Glu Asn Ile Lys Asn Tyr Ser Gln Ser Leu
2855                2860                2865

Ser Asn Thr Ser Tyr Ser Asn His Leu Ser Thr Ser Ile Cys Lys
2870                2875                2880

Ala Asn Lys Ala Ile Leu Asn Phe Ser Ile Leu Asp Asp Lys Asn
2885                2890                2895

Lys Lys
2900

<210> SEQ ID NO 16
<211> LENGTH: 427
<212> TYPE: PRT
<213> ORGANISM: Plasmodium falciparum

<400> SEQUENCE: 16

Met Ser Ser Val Leu Arg Thr Ile Leu Ile Ala Ser Phe Phe Tyr Tyr
1               5                   10                  15

Phe Ser Ile Tyr Lys Ile Ser Pro Trp Ala Ile Ile Lys Asn Val Asp
                20                  25                  30

Phe Gln Ile Thr Tyr Asp Glu Leu Ser Arg Asn Leu Tyr Ile His Ser
            35                  40                  45

Ser Gly Lys Gly Lys Cys Thr Ser His Asn Tyr Tyr Ile Asn Asp Lys
        50                  55                  60

Cys Lys Ile Ile Asn Thr Ser Lys Lys Thr Asn Glu Asn Asn Lys Ala
65                  70                  75                  80

Gln Cys Leu Tyr Asn Gln Lys Cys Leu Thr Ile Ala Lys Tyr Ile Phe
                85                  90                  95

Gln His Thr Gly Ile Glu Ala Val Thr Glu Asp Ile Phe Leu Gln Pro
            100                 105                 110

Phe Val Ile Asn Asn Lys Leu Asn Ile Leu Gln Lys Glu Lys Cys Asn
        115                 120                 125

Arg Glu Val Tyr Ile Asn Asp Lys Lys Cys Leu Cys Cys Ile Asn
    130                 135                 140

Asp Val Val Lys Asn Ile Gln Gly Asp Glu Asn Glu Lys Ile Lys Glu
145                 150                 155                 160
```

-continued

Asn Val Thr Tyr Gln Tyr Asn Lys Cys Lys Cys Leu Leu Asn Tyr Gln
            165                 170                 175

Asp Ile Tyr Gly Asp Ser Asn Phe Phe Asn Lys Cys Glu Asn Phe Glu
            180                 185                 190

Cys Asn Asn Gly Leu Cys Thr Ile Gln Ala Asn Gly Gln Pro Phe Cys
            195                 200                 205

Ser Cys Phe Glu Asn Tyr Tyr Phe Glu Lys Lys Ser Asn Thr Cys Lys
            210                 215                 220

Lys His Glu Gln Asn Val Glu Asn Ile His His Ile Asn Ser Asn Arg
225                 230                 235                 240

Asp Ile Ile Glu Asn Thr Glu Asn Asp Thr Arg Thr Ile Val Ser Ile
            245                 250                 255

Lys Asn Asn Pro Pro Asn Tyr Asn Asn Ser His Asn Tyr Asn Asn Ala
            260                 265                 270

Asn Asn Ile Ile His Asn Ile Glu Asp Leu Glu His Asn Lys Ser
            275                 280                 285

Ser Asn Ile Thr Thr Asn Gly Asn Thr Ile Ile Ser Gln Arg Asn Tyr
            290                 295                 300

Asn Ser Cys Pro Leu Asn Gln Ile Lys Asn Lys Lys Gly Ile Cys Glu
305                 310                 315                 320

Thr Ile Ile Asn Tyr Glu Glu Thr Val Cys Leu Arg Ile Asp Cys Ser
            325                 330                 335

Ile Ser Thr Asn Glu Phe Gln Cys Phe Cys Thr Asn Val Asn Gly Glu
            340                 345                 350

His Ile Lys Thr Asp Thr Phe Asp Val Ser Tyr Ile Asn Ile Cys Thr
            355                 360                 365

Leu Asn Asn Ile Asn Cys Asn Asn Gly Ile Cys Asn Asn Ile Leu Ile
            370                 375                 380

Lys Asp Glu Leu Gly Cys Ile Cys Asp Glu Asn Tyr Ile Tyr Asp Tyr
385                 390                 395                 400

Asp Leu Lys Val Cys Leu Ile Lys Thr Leu Thr Asn Asn Ile Tyr Gln
            405                 410                 415

Asp Glu Ile Lys Ile Leu Phe Thr Thr Asn Asn
            420                 425

<210> SEQ ID NO 17
<211> LENGTH: 1083
<212> TYPE: PRT
<213> ORGANISM: Plasmodium falciparum

<400> SEQUENCE: 17

Met Asn Glu Glu Thr Thr Thr Arg Thr Leu Leu Asp Ile Pro Gly Tyr
1               5                   10                  15

Tyr Tyr Asp Lys Lys Asn Arg Tyr Phe Leu Ile Asn Asn Glu Leu
            20                  25                  30

Lys Lys Glu Leu Lys Lys Glu Glu Phe Asn Lys Ser Val Asn Asn Ala
            35                  40                  45

Lys Lys Lys Asn Arg Asp Thr Asn Asn Ala Glu Thr Lys Lys Trp Gly
            50                  55                  60

Lys Lys Lys Phe His Gln Ile His Gly Ile Lys Glu Met Lys Lys
65                  70                  75                  80

Lys Lys Asn Ala Asn Asn Lys Leu Asn Asn Ile Lys Asn Tyr
            85                  90                  95

Asn Glu Glu Asp Gly Ile Asn Thr Ile Tyr Thr Lys Lys Lys Ser Tyr
            100                 105                 110

```
Asn Ile Ile Asn Ser Lys Glu Thr Lys Leu Glu Leu Ile Asn Asn Glu
    115                 120                 125

Leu Asn Phe Leu Lys Lys Asn Ile Cys Glu Asn Gln Asn Ile Phe Asn
    130                 135                 140

Leu Ile Lys Arg Ile Lys Asn Tyr Asn Phe Lys Glu Asp Ser Ile Leu
145                 150                 155                 160

Ser Leu Pro Pro Ile Phe Ile Asn Ser Asn Cys Glu Tyr Ile Gln
                165                 170                 175

Val Glu Asp Leu Cys Glu Tyr Ser Ser Asn Lys Asn Ser Phe Cys His
                180                 185                 190

Lys Glu Asn Asp Cys Leu Asp Ile Leu Lys Ser Pro Arg Ser Phe Asn
        195                 200                 205

Asn Lys Arg Thr Asp Asn Ile Asp Val Ser Leu Asn Asp Tyr Asn Tyr
        210                 215                 220

Phe Asn Ser Ser Gln Lys Leu Ile Asp Lys Tyr Lys Arg Lys Asn Lys
225                 230                 235                 240

Asn Glu Phe Asp Asn Phe Asn Lys Asn Glu Ser Phe Asp Thr Tyr Arg
                245                 250                 255

Lys Tyr Arg Lys Asn Ser Ile Phe Ser Asn Gln Thr Asp Glu Tyr Asn
            260                 265                 270

Val Ser Asn Tyr Asn Tyr Thr Asn Lys Lys Tyr Tyr Cys Asp Asn Lys
            275                 280                 285

Tyr Asn Leu Thr Tyr Cys Lys Asn Gly Asn Asn Met Phe Ser Cys Ile
        290                 295                 300

Asn Pro Asp Tyr Ile Glu Glu Asn Leu Leu Ile Pro Lys Leu Tyr Gly
305                 310                 315                 320

Arg Thr Tyr Glu Lys Leu Asn Ser Cys Asn Ile Lys Asn Ile Lys Ser
                325                 330                 335

Lys Ile Arg Val Asn Arg Tyr Lys Ala Asn Phe Tyr Tyr Phe Tyr Asn
            340                 345                 350

Asn Thr Tyr Asp Ala Phe Ala Leu Glu Ala Asn Asn Thr Ser Arg Glu
        355                 360                 365

Met Asn Met Asn Asn Asn Asp Asn Asp Ala Asn Asn Asp Ser Asn
    370                 375                 380

Asp Asn Asn Asn Asn Asn Asn Asn Asn Ser Asn Ile Tyr Asn
385                 390                 395                 400

Asn Asn Ile Tyr Asn Asn Asn Ile Tyr Asn Asn Asn Ile Tyr Asn Asn
            405                 410                 415

Asn Ser Gly Arg His Phe Ile Ser Phe Asn Asn Ile Ser Ser Asp Thr
        420                 425                 430

Ile Tyr Gln Glu Met Glu Val Gln Ser Leu Gly Asp Ser His Met Pro
    435                 440                 445

Ile Gly His Leu Asp Ala Val Thr Asn Glu Thr Arg Ile Ser Lys Thr
    450                 455                 460

His Lys Pro Ser Glu Ser Phe Phe His Leu Phe Ser Asn Pro Gln Tyr
465                 470                 475                 480

Asp Asp Ile Val Phe Ser Thr Thr Lys Glu Asn Phe Ser Phe Ser
                485                 490                 495

Leu Gly Ala Ile Asp Met Asn Asn Phe Val Gln Lys Asn Lys Lys Ser
            500                 505                 510

Ser Ile Tyr Asp Val Ile His Glu Asn Val Tyr Tyr Ser Thr Asp Thr
        515                 520                 525

Lys Tyr Leu Cys Ser Tyr Ser Lys Glu Lys Ser Glu Leu Leu Cys Ile
    530                 535                 540
```

```
Ser Pro Gln Ile Leu Ser His Phe Asn Ile Phe Asn Gly Glu Tyr Val
545                 550                 555                 560

Ala Tyr Ser Ser Tyr Pro Asn Thr Lys Asp Glu Lys Ser Leu Leu Cys
                565                 570                 575

Leu Leu Ser Ile Lys Ser Phe Phe Gln Cys Asn Pro Lys Ile Glu Ile
            580                 585                 590

Tyr Ser Phe Pro Gly Glu Val Asn Tyr Phe Lys Leu Phe Pro Ser Ile
        595                 600                 605

Gln Ser Asp Asn Tyr Asn Asn Asn Tyr Ser Leu His Pro Thr Ser
    610                 615                 620

Asp Asp Tyr Ser Phe Tyr His Asn Asn Glu Ile Asp Lys Ile Phe Ile
625                 630                 635                 640

Cys Gly Ser Tyr Pro Cys Phe Ser Phe Ser Thr Leu Lys Asn Asn Val
                645                 650                 655

Thr Tyr Cys Ile Trp Asp Ser Lys Lys Leu Lys Val Gln Asp Leu Leu
            660                 665                 670

Ser Met Asn Glu Asp Leu Thr Ser Tyr Ile Glu Asn Ile Ile Asn Gly
        675                 680                 685

Lys Gln Phe Asn Val Tyr Gln Gln Phe Glu Asn Asn Ser Gln Lys Lys
690                 695                 700

Leu Arg Leu Phe Ser Ser Lys Lys Arg Lys Lys Ile Ser Lys Glu
705                 710                 715                 720

Gln Asn Lys Asn Gln His Glu Thr Phe Thr Asp Glu Leu Tyr Glu Asn
                725                 730                 735

Asn Thr Lys Met Asn Asn Asp Asn Lys Ile Lys Phe Cys Lys Lys Glu
            740                 745                 750

Ser Tyr Asn Glu Ser Asp Leu Tyr Lys Gly Asn Ser Glu His Phe Lys
        755                 760                 765

Asn Val His Gly Thr Phe Asn Asn Lys Lys Thr His Asp Tyr Ser Tyr
770                 775                 780

Arg His Phe Asp Asn Asn Asn Asn Asn Asn Tyr Asn Pro Lys
785                 790                 795                 800

Lys Ser Pro Asn Ser Ala Asn Ser Ile Glu Lys Ile Lys Asn Lys Cys
                805                 810                 815

Tyr Phe Ser Tyr Asn His Ser Ser Gln Ser Ser Leu Lys Tyr Asn Tyr
            820                 825                 830

Asn Asp Asn Lys Lys Lys Gly Ile Cys Cys Glu Asn Ile Lys Lys Ser
        835                 840                 845

Asp Asn Asn Ile Phe Leu Cys Cys Asn Thr Glu Tyr Leu Tyr Leu Cys
850                 855                 860

Asp Leu Arg Cys Asn Leu Leu Asn Thr Ile Ser Lys Leu Lys Pro Asn
865                 870                 875                 880

Glu Gly Tyr Val Asn Lys Ile Tyr Ser Leu Asn Asn Asn Val Gln Tyr
                885                 890                 895

Val Ser Ser Lys Thr Asn Asn His Ile Gly Leu Tyr Asp Met Arg Tyr
            900                 905                 910

Ile Asn Tyr Lys His Asn Asp Glu Thr Lys Ser Asn Leu Ile Val Ser
        915                 920                 925

Tyr Glu Arg Phe Ile Asp Asn Asp Asn Leu Lys Lys His Leu Asn Asp
930                 935                 940

Phe Tyr Val Ile Asp Asn Glu Gln Tyr Ile Val Ser Leu Asp Thr Tyr
945                 950                 955                 960

Thr Ser Ser Val Tyr Ile Tyr Asp Ile Met Gly Thr Thr Thr Lys Ile
```

```
                965                 970                 975
Ile Asn Leu Asp Gly Asn Ser Glu Tyr Ser Lys Asn Asn Val Leu His
            980                 985                 990

Cys Tyr Thr Asn Leu Ser Lys Ile  Pro Tyr Ile Tyr Ser  Cys Arg Lys
        995                 1000                1005

Tyr Asp  Asp Tyr Tyr Tyr Asn  Tyr Tyr Lys Gln Lys  Ile Tyr Glu
    1010                1015                1020

Thr Lys  Ala Thr Asp Ser Lys  Tyr Val Asn His Phe  Asn Pro Met
    1025                1030                1035

Lys Ser  Tyr Pro Lys Lys Asp  Leu Phe Ile Gly Leu  Asn Val Gln
    1040                1045                1050

Ser Ile  Leu Pro Leu Phe Tyr  Ile Lys Gln Lys Tyr  Asn Lys His
    1055                1060                1065

Asn Phe  Ile Ser Ile Asn Glu  Gly Gly Phe Ile Leu  Ile Cys Glu
    1070                1075                1080

<210> SEQ ID NO 18
<211> LENGTH: 184
<212> TYPE: PRT
<213> ORGANISM: Plasmodium falciparum

<400> SEQUENCE: 18

Met Phe Cys Pro Phe Met Phe Leu Leu Lys Ile Ile Leu Ile Ile Leu
1               5                   10                  15

Phe Ile Lys Tyr Asn Val Val Asn Gly Leu Leu Lys Thr Pro Cys Asn
            20                  25                  30

Phe Ser Leu Arg Asn Asn Ile Ile Ser Glu Arg Ile Cys Asn Ile Lys
        35                  40                  45

Leu Pro Asn Leu Ser Tyr Lys Asn Ile Leu Phe Ser Arg Tyr Gly Arg
    50                  55                  60

Arg Arg Arg Arg Asn Met Asn Pro Phe Leu Phe Ile Gln Phe Lys Glu
65                  70                  75                  80

Lys Lys Lys Leu Pro His Leu Leu Cys Phe His Ser Lys Asp Cys Glu
                85                  90                  95

Tyr Cys Asn Ser Met Glu Lys Leu Leu Thr Lys Leu Lys Glu Glu Glu
            100                 105                 110

Gln Val His Ile Leu Lys Leu Glu Met Tyr Asp Asn Ser Tyr Asn Phe
        115                 120                 125

Glu Leu Leu Gln Gln Leu Asp Tyr Asn Asn Leu Cys Gly Gly Leu Pro
    130                 135                 140

Tyr Tyr Tyr Asn Leu Lys Thr His Tyr Asn Ile Cys Gly Ala Thr Thr
145                 150                 155                 160

Tyr His Asn Leu Arg Asn Trp Ala Ile Asp Lys Lys Cys Asn Pro Asn
                165                 170                 175

Glu Pro Pro Asn Glu Glu Phe Trp
            180

<210> SEQ ID NO 19
<211> LENGTH: 2941
<212> TYPE: PRT
<213> ORGANISM: Plasmodium falciparum

<400> SEQUENCE: 19

Met Arg Lys Gly Lys Pro Arg His Val Pro Met Phe Leu Arg Ser Glu
1               5                   10                  15

Asn Lys Arg Ile Phe Phe Ser Phe Phe Ser Tyr Phe Met Pro Lys Asn
            20                  25                  30
```

```
Asp Leu Asn Phe Ile Phe Glu His Phe Asp Ile Gly Leu Ile Val Leu
         35                  40                  45

Thr Lys Ile His Asn Ile Arg Lys Lys Tyr Glu Glu Arg Asn Asn
 50                  55                  60

Met Lys Asn Glu Glu Asp Lys Ser Asp Gly Asp Asp Met Lys Ile Phe
 65                  70                  75                  80

Asp Glu Lys Leu Lys Asn Phe Phe Leu Asn Tyr Lys Ile Asn Pro Asn
                 85                  90                  95

Ile Glu Glu Ser Asn Asp Thr Lys Ile Ser Lys Lys Glu Lys Asn Asn
                100                 105                 110

Asn Asn Lys Lys Lys Lys Arg Asn Tyr Pro Leu Asn Asn Glu Cys Lys
            115                 120                 125

Gln Asn Asn Val Asn Lys Lys Val Met Asn Lys Ser Asn Ser Cys Pro
            130                 135                 140

Leu Asn Lys Lys Asn Glu Lys Lys Gln Asp Ile Ile Asp Asp Lys Lys
145                 150                 155                 160

Lys Asn Lys Leu His Asp Met Asn Asn Glu Arg Asp Cys Asn Ile Asn
                165                 170                 175

Lys Glu Ile Asn Asn Asp Ile Gln Lys Met Tyr Met Tyr Asn Asn Glu
                180                 185                 190

Gln Gly Lys Thr His Asn Leu Asp Ile Gln Ser Tyr Met Pro Tyr Asp
            195                 200                 205

Gln Gln Lys Gly Lys Glu Asn Gln Glu Pro Ser Leu Tyr Lys Cys Asp
            210                 215                 220

Glu Ile Leu Lys Met Asn Ser Thr Thr Glu Asp Arg Asn Lys Lys Glu
225                 230                 235                 240

Asp Val Ser Lys Gly Lys Lys Lys Ile Asn Asn Thr Pro Gln Ser
                245                 250                 255

Tyr Asn Thr Pro Gln Ser Tyr Asn Thr Pro Gln Ser Tyr Asn Thr Pro
                260                 265                 270

Gln Ser Tyr Asn Thr Thr Gln Asn Tyr Asn Thr Thr Gln Asn Tyr Asn
            275                 280                 285

Thr Thr Gln Asn Cys Asn Thr Thr Gln Asn Tyr Asn Thr Thr Gln Asn
290                 295                 300

Tyr Asn Thr Thr Gln His Asn Asn Ile Asn Glu Asn Asn Asp Asp
305                 310                 315                 320

Asp Lys Ile Ile Ile Asp Glu Glu Asn Cys Leu Asn Thr Ile Lys His
                325                 330                 335

Asn Glu Arg Glu Met Asn Asn Asn Ile Gln Lys Thr Lys Ser Cys Glu
            340                 345                 350

Asp Asn Gln Tyr Leu Ile Asn Tyr Asn Gly Asn Asn Glu Met Ser Tyr
            355                 360                 365

Asn His Lys His Leu Thr Leu Leu Asp Asn Lys Asn Glu Glu Gln Glu
            370                 375                 380

Asn Ala Phe Ile Leu Asn Asn Met Asn Lys Thr Lys Asn Gly Ile Asn
385                 390                 395                 400

Ile Lys Glu Asn Ile Glu His Ile Lys Asp Asn Lys Lys Asp Glu Ile
                405                 410                 415

Lys Ile Glu Arg Glu Thr Asp Asp Ile Tyr Ile Ser Met Lys Lys Lys
                420                 425                 430

Asn Glu Thr Tyr Lys Lys Phe Ser Lys Arg Met Asn Arg Arg Lys Ile
            435                 440                 445

Ser Glu Leu Val Asn Tyr His Asp Asp Tyr Cys Phe Tyr Ile Thr Asp
```

```
                 450               455               460
Leu Cys Lys Lys Gly Thr Met Leu Ser Leu Lys Lys Asn Glu Leu Phe
465                 470                 475                 480

Asn Gln Lys Asn Asp Lys Ile Asn Ile Leu Ser Ser Val Lys Tyr Phe
                485                 490                 495

Asn Lys Pro Ile Gln Phe Asn Gln Ile Asn Trp Asn Leu Asn Asn Leu
                500                 505                 510

Cys Thr Ile Asn Asn Ile Tyr Thr Lys Leu Tyr Asp Glu His Ile Asn
                515                 520                 525

Asp Lys Ile Asn Thr Thr Pro Asn Met Gln Thr Ile Ile Lys Glu Lys
                530                 535                 540

Tyr Ser Gln Thr Ser Ser Val Ile Leu Gly Asn Glu Gln Ile Gln Asn
545                 550                 555                 560

Gly Tyr Gln Thr Ser Asn Leu Asn Ile Asn Ser Asn Asp Ile Arg Ile
                565                 570                 575

Ile Asn His Asn Lys Asn Asp Asp Ile Ser Ile Asn His Asn Asn Asn
                580                 585                 590

Asn Asp Ile Ser Ile Asn His Asn Asn Asn Asp Ile Ser Ile Asn
                595                 600                 605

His Asn Asn Asn Asn Asp Ile Ser Ile Asn His Asn Asn Asn Asn Asp
610                 615                 620

Ile Ser Ile Ile Asn His Asn Asn Asn Asp Ile Ser Ile Asn His
625                 630                 635                 640

Asn Asn Asn Asn Asn Asn Tyr Tyr Phe Met Asn Asn Tyr Met His Asn
                645                 650                 655

Asn Ile Asn Asn Asn Tyr Tyr Cys Tyr Tyr Met Asn Asn Thr Asn His
                660                 665                 670

Val Asn Asn Tyr Tyr Asn Asn Ile Tyr Ile Gln Asn Asn His Asp Gln
                675                 680                 685

Asn Asn Ala Pro Ile Leu Gln Pro Ile Asn Asn His Leu Ala His Ile
                690                 695                 700

Asn Asp Leu Cys Tyr Ile His Ser Glu Lys Asn Glu Tyr Thr Lys Ile
705                 710                 715                 720

Ser Lys Asn His Gln Met Asn Asn Ile Asn Pro Gln Gln Ser Asn Gly
                725                 730                 735

Lys Asn Gln Asn Asp Ile Ser Asn Asn Ile Asn Lys Asn Asp Glu Tyr
                740                 745                 750

Tyr Asn Leu Asn Glu Gln Lys Ile Leu Cys Asp Lys Asn Lys Ser Tyr
                755                 760                 765

Ile Lys Cys Asp Ile Pro Gln Lys Cys Asp Asn Thr Gln Asp Asp Glu
770                 775                 780

Asn Ser Glu Gln Asn Gln Asn Tyr Ile Thr Asn Pro Ser Asn Gly His
785                 790                 795                 800

Tyr Lys Ile Lys Glu Gln Met Asn Tyr Val Gln His Ile Pro Asp Tyr
                805                 810                 815

Glu His Asp Asn Thr Thr Asn Glu Met Ile Asn Thr Gln Asn Tyr Thr
                820                 825                 830

Asn Ile Asn Leu Asp Pro Tyr Ile Met Asn Gln Asn Asp Asn Asn
                835                 840                 845

Val Tyr Leu Asn Gln Asn Tyr Phe Asp Thr Glu Lys Lys Asn Lys Glu
850                 855                 860

Glu Asp Ile Asn Ile Thr Glu Ala Asn Thr His Tyr Asn Asn Val His
865                 870                 875                 880
```

```
Ile Tyr Gln Asn Asn Ser Asn His Met Asn Lys Met Ile Asn Leu Asn
            885                 890                 895

Asn Asn Thr Asn Ser Lys Ser Thr Gln Asp Tyr Asp Leu Tyr His Asn
            900                 905                 910

Asn Met Glu Asn Phe Asn Asn Thr Asn Tyr Asn Ile Met Lys Glu Lys
            915                 920                 925

Ile His Ile Asn Asp Asp Thr Ser Ser Val Ile Asn Asn Ser Ser Ile
            930                 935                 940

Asn Ser Gln Asn Asn Leu Cys Asn Asn Lys Lys Thr Asn Asn Asp Tyr
945                 950                 955                 960

Gln Asn Arg Asn Ile Lys Asn Asp Asn Ser Ile Pro Asp Ser Ser Ile
            965                 970                 975

Asn Met Asn Glu Leu Lys Asn Asn Ile Gln Met Asn Asp Tyr Tyr Ala
            980                 985                 990

Ser Asn Ile Tyr Asn Asn Asn Asn  Asn Asn Asn Asn  Asn Asn Phe Ile
            995                 1000                1005

Ile Ser Asn Asn Ile Ile Ser  Asn Tyr Asn Asn Tyr  Met Asn Glu
    1010                1015                1020

Ser Asn Val Tyr Pro Gln Ile  Asn Ser Asn Asn Tyr  Ile Pro Tyr
    1025                1030                1035

Ile Asp Pro His Leu Asn Asn  Glu Pro Tyr Lys His  Thr Ile Asn
    1040                1045                1050

Asn Gln Leu Asn Lys Asn Cys  Ile Asn Asn Asn Ile  Ser Met Asp
    1055                1060                1065

Asp Asn Val Tyr Asp Ser Asn  Thr Ile Ser Ile His  Ile Ser Val
    1070                1075                1080

Asn Asp Asn Glu Tyr Asn Asn  Ser Asn Phe Thr Asn  Asp Met Tyr
    1085                1090                1095

Asn Asn Asn Asn Asn Asn Asn  Asn Asn Asn Asn Asn  Cys Asn Asn
    1100                1105                1110

Ser Ser Asn Ser Asn Ser Asn  Ser Asn Gln Val Cys  Leu Tyr Met
    1115                1120                1125

Pro Asn His Glu Leu Tyr Asn  Ser Asn Tyr Asn Ile  Thr Gln His
    1130                1135                1140

Met Pro Ser Ser Asn Asp Val  Pro Lys Ile Gln Lys  His Ile Ala
    1145                1150                1155

Asn Asn Ile Ile Met Asn Gly  His Lys Glu Glu His  Ile Ile Glu
    1160                1165                1170

Lys Lys Ser Lys Glu Glu Thr  Asn Lys Thr Asn Glu  Gln Val Tyr
    1175                1180                1185

Arg Ser Ile Asn Gln Asn Asn  Thr Leu Ile Leu Lys  Glu Asn Glu
    1190                1195                1200

Ile Asp Glu Asn Asp Ile Asn  Thr Leu Asn Gln Asn  Leu Asn Ile
    1205                1210                1215

Lys Asn Asp Met Asn Asn Met  Asp Ile Ile Asn Leu  Lys Asn
    1220                1225                1230

Leu Asn Asn Ile Asn Asn Ile  Tyr Thr Pro Tyr Gln  Asn Asn Ile
    1235                1240                1245

Leu Lys Asn Asn Glu Ile Gln  Phe Leu Asn Asn Asn  Lys Glu Val
    1250                1255                1260

Ile Thr Lys His Ala Tyr Thr  His Ser Ser Asn Glu  Ile Asn Ile
    1265                1270                1275

Asn Val Tyr Lys Asn Ile Asp  Thr Gln Ile Asn Ile  Arg Lys Asn
    1280                1285                1290
```

```
Glu Asn Asn Asn Asp Ile Ile Ile Asn Lys Glu Gln Lys Asp Ile
    1295                1300                1305

Ser Thr Asn Asn Glu Gln Asn Gln Thr Tyr Asn Tyr Ile Thr Ser
    1310                1315                1320

Ser Val Lys Asn Glu Tyr Ser Ile Leu Asp Asn Ser Pro Thr Asp
    1325                1330                1335

Lys Asn Tyr Lys Lys Asn Leu Asn Leu Asn Ile Ser Ser Ser Tyr
    1340                1345                1350

Asn Thr Asn Asp His Ile Asn Asn Tyr His Asp Asp Ile Asp Lys
    1355                1360                1365

Thr Asn Lys Asp Asn Lys Tyr Glu Glu Glu Lys His Lys Asp Ile
    1370                1375                1380

Asn Ile Tyr Ile Asn Asn Ile Asn Ser Asn Gly Asn Lys Asn His
    1385                1390                1395

Asn Phe Ile Asn Ser Tyr Phe Asp Leu Asn Glu Asn Glu Lys Lys
    1400                1405                1410

Lys Lys Ile Asn Ile Phe Tyr His Asp Asn Lys Ser Leu Lys Asn
    1415                1420                1425

Ile Ser Asn Glu Glu Leu Thr Asn Thr Asn Pro Tyr Lys Cys Ile
    1430                1435                1440

Asn Asn Thr Ile Asp Asn Asn Asn Asp His Lys Asn Gly Tyr Ile
    1445                1450                1455

Glu Leu Asn Glu Ile Asn Asn Ser Ile Met Asn Asn Asp Glu Lys
    1460                1465                1470

Ile Ile Thr Ala Tyr Leu Asn Asn Arg Val Val Gln Asn Gly Leu
    1475                1480                1485

Ser His Asp Ile Leu Asn Glu Asp Val Ser Ile Asn Thr His Ser
    1490                1495                1500

Asn Lys Glu Asn Lys Asn Asp Asn His Asn Asn Asn Ser Asn Asn
    1505                1510                1515

Ser Asn Asn Ser Ser Arg Ser Asn Asn His Asn Asn Asn Asn Asn
    1520                1525                1530

Ser Asn Asn Asn Tyr Ala Asn Ser Tyr Asn Val Lys Asn Asp Leu
    1535                1540                1545

Gln Ile Asn Asn Asn Asn Tyr Ser Tyr Ile Lys Asn Glu Lys Asn
    1550                1555                1560

Val His Gln Thr Phe Asn Glu Asn Asn Ile Leu Tyr Lys His Tyr
    1565                1570                1575

Ser Asn His Val His Asn Tyr Ile Thr Lys Asn Thr Ile Gln Glu
    1580                1585                1590

Gln Lys Asn Ile His Ser Asp Asn Lys Tyr Glu Thr Cys Ser Leu
    1595                1600                1605

Pro Glu Lys Lys Asn Ile Tyr Glu Pro Asn Ser Gln Asn Ser Pro
    1610                1615                1620

Asn Ser Gln Lys Leu Pro Asn Ser Gln Asn Leu Ser Asn Ser Gln
    1625                1630                1635

Asn Leu Pro Asn Ser Pro Asn Leu Pro Asn Ser Gln Asn Leu Pro
    1640                1645                1650

Asn Ser Pro Asn Leu Pro Asn Cys Phe Thr Tyr Val Asn Asn Gln
    1655                1660                1665

Thr Asp Ile Leu Ile Ser Asn Leu Val Val Gln Glu Gln Lys Leu
    1670                1675                1680

Asn Asp Gln Lys Lys Glu Met Arg Ser Asn Asn Asn Ile Asn Asn
```

|   |   |   |   |   |   |   |   |   |   |
|---|---|---|---|---|---|---|---|---|---|
|   |   |   |   |   | 1685 |   |   |   | 1690 |   |   |   | 1695 |
| Thr | Lys | Trp | Asn | Asn | Ala | Tyr | Asn | Asn | Glu | Val | Gln | His | Val | Asn |
| 1700 |   |   |   |   | 1705 |   |   |   | 1710 |
| Asn | Asn | Ile | Val | Asn | Glu | Glu | Ile | Asn | Ile | Leu | Pro | Tyr | Pro | Ser |
| 1715 |   |   |   |   | 1720 |   |   |   | 1725 |
| Lys | Asn | Glu | Asn | Asn | Leu | Asn | Glu | His | Asn | Ser | Asn | Ile | Tyr | His |
| 1730 |   |   |   |   | 1735 |   |   |   | 1740 |
| Asp | Lys | Asn | Asn | Gln | His | Asp | Ile | Arg | Thr | Tyr | Tyr | Asn | Asp | Ser |
| 1745 |   |   |   |   | 1750 |   |   |   | 1755 |
| Thr | Lys | Ile | Thr | Asn | Lys | Leu | His | Ile | Glu | Ser | Gly | Asn | Asn | Lys |
| 1760 |   |   |   |   | 1765 |   |   |   | 1770 |
| Leu | Thr | Asn | Asp | Ala | Ile | His | Thr | Asn | Asn | Glu | Tyr | Thr | Ile | Asn |
| 1775 |   |   |   |   | 1780 |   |   |   | 1785 |
| Ser | Arg | Tyr | Pro | Ile | Cys | Gln | Asn | Tyr | Ser | Ala | Ile | Thr | Ala | Pro |
| 1790 |   |   |   |   | 1795 |   |   |   | 1800 |
| Glu | Lys | Met | Asn | Cys | Pro | Gln | Met | Met | Ala | Asn | His | Asn | Phe | Asn |
| 1805 |   |   |   |   | 1810 |   |   |   | 1815 |
| Asn | Ile | Pro | Glu | Tyr | Val | Ile | Gln | Asn | Asn | His | Val | Asn | Val | Asp |
| 1820 |   |   |   |   | 1825 |   |   |   | 1830 |
| Gly | Asn | Asn | Lys | Asn | Asp | Pro | Ile | Asp | Asn | Asn | Asn | Asn | Asn | Asp |
| 1835 |   |   |   |   | 1840 |   |   |   | 1845 |
| Asn | Asp | Asn | Ile | Glu | Ile | Phe | Asn | Ile | Gln | Gln | Thr | Lys | Gln | Ile |
| 1850 |   |   |   |   | 1855 |   |   |   | 1860 |
| Lys | Tyr | Asn | Asn | Asn | Thr | Thr | Asp | Thr | Asn | Asn | Asn | Ser | Leu | Ile |
| 1865 |   |   |   |   | 1870 |   |   |   | 1875 |
| His | Asn | Val | Glu | Asn | Asn | Tyr | Asn | Thr | Asp | Gly | Leu | Asp | Ile | Ser |
| 1880 |   |   |   |   | 1885 |   |   |   | 1890 |
| Asn | Ile | Ser | Tyr | Asn | Asn | Tyr | Thr | Asn | Asn | Met | Tyr | Asn | Leu |
| 1895 |   |   |   |   | 1900 |   |   |   | 1905 |
| Asn | Asn | Asp | Asn | Ile | Asn | Asn | Asn | Tyr | Met | Pro | Gln | Asn | Tyr | Tyr |
| 1910 |   |   |   |   | 1915 |   |   |   | 1920 |
| His | Ile | Asn | Tyr | Asn | Asn | Ile | Ala | Thr | Ser | Glu | Asn | Asn | Gln | Leu |
| 1925 |   |   |   |   | 1930 |   |   |   | 1935 |
| Ile | Gln | Ile | Asn | Asn | Tyr | Asn | Ile | Asn | Thr | Asn | Ile | Asn | Asp | Ile |
| 1940 |   |   |   |   | 1945 |   |   |   | 1950 |
| Asn | Ile | Asn | Thr | His | Val | Asn | Ser | Tyr | Lys | Glu | Asn | Asp | Lys | Lys |
| 1955 |   |   |   |   | 1960 |   |   |   | 1965 |
| Asn | Ile | Leu | Tyr | Asn | Asn | Asn | Ile | Asn | Asn | Met | Asn | Asn | Asp | Asn |
| 1970 |   |   |   |   | 1975 |   |   |   | 1980 |
| Ile | Asn | His | Asp | His | Tyr | Lys | Tyr | Ile | Cys | Asn | Ser | Asn | Ser | Asn |
| 1985 |   |   |   |   | 1990 |   |   |   | 1995 |
| Asn | Asn | Asn | Asn | Asn | Asn | Asn | Asn | Asn | Asn | Asn | Asn | Asn | Asn | Asn |
| 2000 |   |   |   |   | 2005 |   |   |   | 2010 |
| Asp | His | Tyr | Tyr | Tyr | Tyr | Asn | Cys | Cys | Arg | Asn | Glu | Glu | Tyr | Lys |
| 2015 |   |   |   |   | 2020 |   |   |   | 2025 |
| Tyr | Asn | Asp | Asn | Asn | Tyr | Ile | Asn | Ile | Gln | Asn | Lys | Lys | Asn | Asn |
| 2030 |   |   |   |   | 2035 |   |   |   | 2040 |
| Ile | Val | Asn | Asp | Asn | Thr | Ser | Asn | Ile | Ile | Lys | Ser | Gln | Tyr | Asn |
| 2045 |   |   |   |   | 2050 |   |   |   | 2055 |
| Asn | Thr | Asn | Lys | Asn | Met | Ile | Leu | Glu | Gln | His | Asn | Ile | Asn | Met |
| 2060 |   |   |   |   | 2065 |   |   |   | 2070 |
| Asn | Glu | Asp | Asn | Tyr | Asn | Gln | Ile | Asn | Ser | Asn | Leu | Cys | Leu | Leu |
| 2075 |   |   |   |   | 2080 |   |   |   | 2085 |

-continued

```
Lys Asn Asp Ser Ile Ser Thr Cys Cys Asp Asn Ile Asn Asn Asn
    2090            2095                2100

Asn Asn Asn Asn Asn Asn Lys Tyr Ser Asn Asn Glu Ile Asn Ser
    2105            2110                2115

Asn Glu Tyr Leu Tyr Tyr Lys Phe Asp Glu Gln Tyr Asp Lys Lys
    2120            2125                2130

Asn Asn Val Ser Ala Met Cys Asp Asn Ile Lys Asn Lys Gln His
    2135            2140                2145

Tyr Asn Asn Tyr Val Ala Tyr Asn Thr Asn Gly Ser Tyr Glu Asn
    2150            2155                2160

Met Ser Asn Phe Ser Ser Asn Asn Val Tyr Val Asn Asn Lys Cys
    2165            2170                2175

Pro Ser Tyr Asn Asn Asn Met Asn Asn Met Asn Asn Met Asn
    2180            2185                2190

Asn Asn Asn Cys Tyr Asn Tyr His Gly Tyr Asn Val Met Asn Thr
    2195            2200                2205

Lys Tyr Asn Lys Ala Gly Asn Lys Phe Ser Ser Val Gln Ile Asp
    2210            2215                2220

Thr Gln Met Asp Asn Pro Ile His Val Asp Lys Asn Lys Asn Asp
    2225            2230                2235

Asp Ile Leu Glu Arg Asn Ile Lys Gly Ser Ile Ile Asn Asn Asn
    2240            2245                2250

Asn Asp Ser Asn Asp Asp Asn Asn Asp Asp Asn Asn Asn Asp
    2255            2260                2265

Asn Asn Asn Asn Asp Asn Ala Ser Asn Asn Asn Asn Asp Thr Asn
    2270            2275                2280

Asn Ile Asn Tyr Leu Met Asn Ile Lys Asn Thr Asn Asn Phe Asp
    2285            2290                2295

Ser Thr Asn Asn Phe Asp Ser Thr Asn Asn Phe Asp Ser Thr Asn
    2300            2305                2310

Asn Phe Asp Ser Thr Asn Asn Phe Asp Ser Thr Asn Asn Phe Asn
    2315            2320                2325

Asn Arg Asn Asn Phe Asn Asn Arg Asn Asn Phe Asn Asn Arg Asn
    2330            2335                2340

Asn Phe Glu His Ile Asn Asn Ile Asn Lys Ile His His Ile Asp
    2345            2350                2355

Asn Glu Asn Asn Leu Cys Arg Glu Asp Glu Asn Asn His Asn Thr
    2360            2365                2370

Ile Leu Thr Asn Val Lys Asn Thr Thr Asn Lys Glu Tyr Ile Asn
    2375            2380                2385

Ile Cys Thr Asp His Leu Asn Leu Leu Lys Asn Tyr Asn Leu Asn
    2390            2395                2400

Asn Tyr Ile Asn Leu Leu Lys Ile Asn Lys Leu Asn Asp Tyr Tyr
    2405            2410                2415

Tyr Asn Ser Ile Ile Asn Lys Ser Gln Asp Gly Thr Cys Asn Thr
    2420            2425                2430

Phe Leu Gln Asn Ser Leu Asn Asn Gln Ser Asn Ile Ile Gln Asn
    2435            2440                2445

Asn Asn Ile Tyr Glu Asn Asn Gln Arg Ile Gln Leu Tyr Asn Tyr
    2450            2455                2460

Pro Ser Phe Glu Thr Tyr Asn Asn Asn Ile Ile Asn Thr Trp Asn
    2465            2470                2475

Gln Lys Asn Thr Asn Asn Ser Tyr Asn Ser Tyr Ile Pro Leu Ser
    2480            2485                2490
```

-continued

```
Asn Val Gln Cys Asn Trp Lys Asn His Ile Phe Asn Val Thr Gln
    2495                2500                2505

Asn Asn Ala His Ile Asn Asp Asn Lys Glu Tyr Asn Tyr Gln Lys
    2510                2515                2520

Tyr Pro Tyr Val Tyr Asn Asn Gln Ile Leu Ser Ile Asn His Gly
    2525                2530                2535

Lys Lys Glu Thr Asn Thr Leu Asn Tyr Leu Asn Cys Thr Gly Glu
    2540                2545                2550

Asn Glu Ile Thr Tyr Leu Asp Leu Asn Ser Asn Glu Gln Asn
    2555                2560                2565

Tyr Asn Asp His Asn Lys Asn Asn Pro Tyr Asn His Asp His
    2570                2575                2580

Asn Ile Ile Tyr Asn Asp Val Tyr Asn His Met Asn Pro Ser Tyr
    2585                2590                2595

Ile Tyr Asn Asn Ile Cys Thr Pro Thr Asn Phe Ile Gln Asp Leu
    2600                2605                2610

Ile Lys Thr Asn Lys Ile Asn Asn Ser Asn Tyr Leu Asn Ile
    2615                2620                2625

Phe Asn Asn Met Ile His Leu Gln Asn Met His Asn Glu Asn Asn
    2630                2635                2640

His Leu Phe Lys Lys Glu Lys Cys Asp Gln Ala Lys Pro Tyr Ser
    2645                2650                2655

Asn Thr Asp Val Leu Cys Thr Leu Lys Asn Asn Asn Leu Asn Glu
    2660                2665                2670

Asn Lys Asn Val Asn Ile Ile Asn Thr Ile Pro His Thr Leu Asn
    2675                2680                2685

Asn Tyr Tyr Asn Phe His Ile Leu Leu Asn Ile Leu Arg Arg Lys
    2690                2695                2700

Gln Leu Tyr His Asn Ser Phe Asn Gln Leu Ile Ser Lys Met Thr
    2705                2710                2715

Lys Asn Tyr Asn Ile Asn Ala Asn Asn Asn Asn Asn Asn Asp Asn
    2720                2725                2730

Ser Asn Leu Asn Asn Asn Asn Asn Asn Val Arg Tyr Asn Lys Arg
    2735                2740                2745

Asn Tyr Ser Ile Ser Ser Val Gly Phe Ser Asn Arg Ser Lys Arg
    2750                2755                2760

Trp Thr Ile Cys Pro Ser Tyr Ile Cys Cys Asn Ser Ala Leu Cys
    2765                2770                2775

Arg Phe Lys Leu Thr Cys Asn Phe Lys Phe Leu Gln Phe Asn Gln
    2780                2785                2790

Ala Tyr Asn Thr Phe Asn Ile Pro Tyr Ala Ile Tyr Asn Cys Tyr
    2795                2800                2805

Lys Asn Ile Met Asn Asn Tyr His Tyr Phe Thr Ser Thr Leu Cys
    2810                2815                2820

Pro Gln Gln Thr Tyr Leu Ser Lys His Ser Ala Gln Glu His Glu
    2825                2830                2835

Thr Ile Phe Asn Val Tyr Trp His Leu Leu Asn Asn Glu Lys Tyr
    2840                2845                2850

Lys Tyr Ile Gln Asn Ile Ile Leu Phe Leu Asp Ser Asn Leu Tyr
    2855                2860                2865

Thr Arg Ala Val Trp Leu Leu Lys Lys Gly Tyr Asn Met Asn Asp
    2870                2875                2880

Ile Glu Val Gln Lys Ala Glu Lys Lys Leu Ile Lys Leu Met Leu
```

-continued

```
            2885                2890                2895

Leu Val Phe Lys Phe Thr Tyr Asp Tyr Lys Asn Asp Asn Asn Lys
        2900                2905                2910

Tyr Glu Tyr Ile Lys Ser Phe Leu Tyr Ser Leu Arg Asn Asn His
        2915                2920                2925

Ile Asn Phe Glu Ile Met Asn Arg Phe Leu Phe Tyr Trp
        2930                2935                2940

<210> SEQ ID NO 20
<211> LENGTH: 327
<212> TYPE: PRT
<213> ORGANISM: Plasmodium falciparum

<400> SEQUENCE: 20

Met His Lys Glu Glu Lys Glu Lys Asp Lys Lys Asp Asn Asn Tyr
1               5                   10                  15

Asp Asn Asp Tyr His Asn Asp Tyr His Asn Asp Tyr His Asn Asp Tyr
            20                  25                  30

His Asn Asp Tyr Asp Asn Glu Asn Asp Cys Asn Asn Asn Glu Arg Glu
            35                  40                  45

Gly Ser Val His Gly Asp Asn Ile His Ala Tyr Glu Glu Gln Asn Tyr
50                  55                  60

Glu Asn Asp Ile Leu Asn Ile Ile Asn Lys Gln Met Asp Asn Ile Lys
65                  70                  75                  80

Ser Asn Asp Pro Ile Lys Asn Asn Ser Asn Asn Ser Tyr Asn Asn
                85                  90                  95

Phe Leu Asp Met Asn Phe Leu Glu Gln Asp Gln Leu Phe Leu Glu Asn
                100                 105                 110

Ile Asn Gln Asp Asn Val Val Ser Ala His Tyr Thr Ser Glu Tyr Asp
                115                 120                 125

Asn Asn Glu Lys Glu Lys Ser Asp Asp Leu Lys Asn Lys Leu Val His
130                 135                 140

Lys Asn Ile Ser Leu Asn Ile His Asn Ile Ile Ser Ser Ala Asn Leu
145                 150                 155                 160

Cys Ile Asp Ile Asn Leu Arg Leu Val Ala Val Ser Ile Arg Asn Ala
                165                 170                 175

Glu Tyr Asn Pro Ser Lys Ile Asn Thr Leu Ile Ile Arg Leu Asn Lys
                180                 185                 190

Pro Gln Cys Thr Ala Leu Ile Phe Lys Asn Gly Arg Ile Met Leu Thr
                195                 200                 205

Gly Thr Arg Thr Lys Lys Asp Ser Ile Met Gly Cys Lys Lys Ile Ala
            210                 215                 220

Lys Ile Ile Lys Ile Val Thr Lys Asp Lys Val Lys Phe Cys Asn Phe
225                 230                 235                 240

Lys Ile Glu Asn Ile Ile Ala Ser Ala Asn Cys Asn Ile Pro Ile Arg
                245                 250                 255

Leu Glu Val Leu Ala His Asp His Lys Glu Tyr Cys Asn Tyr Glu Pro
                260                 265                 270

Glu Leu Phe Ala Gly Leu Val Tyr Arg Tyr Lys Pro Thr Ser Asn Leu
                275                 280                 285

Lys Ser Val Ile Leu Ile Phe Val Ser Gly Lys Ile Ile Ile Thr Gly
                290                 295                 300

Cys Lys Ser Val Asn Lys Leu Tyr Thr Val Phe Gln Asp Ile Tyr Asn
305                 310                 315                 320

Val Leu Ile Gln Tyr Lys Asn
```

<210> SEQ ID NO 21
<211> LENGTH: 857
<212> TYPE: PRT
<213> ORGANISM: Plasmodium falciparum

<400> SEQUENCE: 21

```
Met Tyr Ala Asn Ser Glu Ile Asn Lys Leu Lys Asp Val Leu Lys Lys
1               5                   10                  15
Leu Pro Gln Glu Lys Asn Asp Asp Lys Lys Arg Glu Val Leu Lys Lys
                20                  25                  30
Val Ile Ala Tyr Met Thr Leu Gly Val Asp Val Ser Lys Leu Phe Pro
            35                  40                  45
Asp Ile Ile Met Ile Ser Ser Thr Asn Asp Ile Ile Gln Lys Lys Met
        50                  55                  60
Ile Tyr Leu Tyr Leu Asn Asn Tyr Ala Glu Thr Asn Ser Glu Leu Ser
65                  70                  75                  80
Leu Leu Thr Ile Asn Thr Leu Gln Lys Asp Ser Lys Asp Asp Asp Pro
                85                  90                  95
Ile Ile Arg Gly Leu Ala Leu Arg Thr Phe Cys Asn Leu Arg Ile Asn
            100                 105                 110
Asn Leu Phe Glu Tyr Ile Glu Gly Pro Leu Phe Asn Gly Leu Asn Asp
        115                 120                 125
Lys Asn Ser Tyr Val Arg Arg Ile Ala Ile Ile Ser Cys Val Lys Leu
130                 135                 140
Ile Lys Met Asn Pro Asp Leu Ser Ile Arg Asn Asp Ile Ile Lys Ile
145                 150                 155                 160
Leu Lys Asn Lys Leu Leu Asp Lys Asp Pro Gln Cys Ile Ile Asn Ser
                165                 170                 175
Val His Ala Leu Asn Glu Ile Leu Ile Asp Glu Gly Gly Leu Lys Val
            180                 185                 190
Asn Lys Glu Ile Val Phe Asn Met Leu Asn Lys Leu Ser His Phe Asn
        195                 200                 205
Glu Trp Gly Lys Ser Val Ile Leu Tyr Ile Val Ser Thr Tyr Ile Pro
210                 215                 220
Glu Asn Glu Asp Glu Met Tyr Asp Ile Met Asn Ile Leu Glu Asn His
225                 230                 235                 240
Ile Arg Asp Phe Ser Ser Thr Val Phe Leu Ala Cys Leu Lys Cys Phe
                245                 250                 255
Leu Asn Phe Ser Ile Asn Asp Thr Asn Leu Gln Ile Gln Ile Phe Gln
            260                 265                 270
Arg Met Lys Asp Pro Leu Leu Thr Leu Ile Ser Thr Ser Ser Asn Glu
        275                 280                 285
Ile Ala Tyr Ile Val Leu Leu His Thr Asn Leu Leu Leu His Glu Ala
290                 295                 300
Asn Lys Leu Asn Tyr Lys Ile Phe Asp Tyr Asp Tyr Lys His Phe Phe
305                 310                 315                 320
Phe Arg Tyr Asn Asp Leu Thr Tyr Ile Lys Asp Ile Lys Leu Asp Ile
                325                 330                 335
Leu Val Ser Val Ala Ser Lys Asn Asn Val Val Leu Ile Ile Asn Glu
            340                 345                 350
Leu Ser Glu Tyr Ile Ser Asp Ala Asn Val Glu Ile Ala Gln Lys Ala
        355                 360                 365
Ile Glu Ser Ile Gly Ser Ile Ala Leu Lys Ile Pro Lys Cys Ile Ser
```

-continued

```
                370                 375                 380
Arg Val Val Glu Leu Ser Leu Ser Asn Phe Met Thr Met Asn Tyr Ser
385                 390                 395                 400

Tyr Ile Cys Ser Ala Thr Ile Lys Ile Leu Val Asn Ile Leu Arg Lys
                405                 410                 415

Tyr Glu Glu Tyr Thr Lys Leu Ile Ile Glu Glu Ile Ile Lys His Gly
                420                 425                 430

Asn Arg Leu Ile Asp Asn Gly Gly Ile Ile Ser Tyr Ile Trp Ile Ile
                435                 440                 445

Gly Glu Tyr Cys Glu Tyr Ile Glu Glu Ala Pro Tyr Leu Leu Glu Glu
                450                 455                 460

Tyr Ile Asn Leu Arg Asn Cys Ser Tyr Leu Phe Met Leu Glu Leu Leu
465                 470                 475                 480

Thr Ala Cys Val Lys Val Leu Tyr Arg Arg Pro Ala Glu Met Lys Asn
                485                 490                 495

Ile Val Ser Thr Leu Phe Asp Asn Ile Leu Lys Asn Tyr Lys Tyr Pro
                500                 505                 510

Glu Leu Thr Asp Lys Met Phe Phe Tyr Lys Leu Leu Ser Tyr Asn
                515                 520                 525

Tyr Lys Glu Ala Phe His Ile Ile Ala Cys Lys Lys Ile Val Lys
                530                 535                 540

Asn Phe Ser Glu Ser Asn Glu Asn Leu Leu Leu Asp Lys Leu Tyr Asn
545                 550                 555                 560

Glu Phe Asn Thr Leu Ser Val Leu Tyr Lys Gln Pro Leu Asn Lys Phe
                565                 570                 575

Val Glu Tyr Ser Lys Ile Ala Phe Gly Ala Val Tyr Asp Pro Glu Glu
                580                 585                 590

Asn Ser Asp Ile Thr Lys Asp Ser Thr Ser Gln Leu Asn Gly Cys Asp
                595                 600                 605

Asn Thr Glu Asp Ile His Leu Asn Asn His Tyr Thr Ala Asp Gln Met
610                 615                 620

Tyr Asn Asn Val Ile Asp His Lys His Ala Ile His Asp Lys Asn Glu
625                 630                 635                 640

Asn Asn Asn Asn Asn Asn Asn Asn Asn Asn Asn Asn Asp Asn Asn
                645                 650                 655

Asn Leu Leu Asn Ile Asn Glu Asp Ile Leu Ile Met Asp Glu Gln Asn
                660                 665                 670

Ala Ile Thr Asn Gln Asn Asn Lys Tyr Ser Asn Asn Asn Asn Asn
                675                 680                 685

Asn Asn Asn Thr Leu Thr Asn Gln Glu Gln Lys Thr Asn Lys Asn Val
690                 695                 700

Ser Thr Asn Leu His Asp Val Ile Ile Asn Thr Glu Asn Asn Asn Gly
705                 710                 715                 720

Ile Ile Asn Leu Asp His Ile Tyr Asn Thr Ser Phe Lys Lys Leu
                725                 730                 735

Lys Asn Ile Ile Ile Asp Val Asp Ser Ile Asn Pro Glu Val Tyr Gln
                740                 745                 750

Thr Gln Trp Asn Ala Leu Pro Glu Gln Asn Asn Glu Lys Ile Phe Leu
                755                 760                 765

Arg Lys Asn Tyr Tyr Asn Leu Gln Leu Asp Thr Ile Asp Gln Leu Ile
                770                 775                 780

Ser Lys Tyr Asn Leu Ile Thr Leu Ala Ser Gly Glu Ile Asp Gln Cys
785                 790                 795                 800
```

```
Leu Lys Phe Tyr Met Tyr Ser Gln Leu Tyr Thr Lys His Tyr Ile Phe
            805                 810                 815
Ile Glu Leu Ile Phe Asn Lys Arg Asp Asn Ser Ile Asn Trp Ile Phe
        820                 825                 830
Lys Ser Glu Cys Asn Asp Glu Asn Leu Ile Glu Gln Phe Thr Asp Cys
    835                 840                 845
Phe Arg Asp Ile Phe Leu Asp Phe Met
    850                 855

<210> SEQ ID NO 22
<211> LENGTH: 164
<212> TYPE: PRT
<213> ORGANISM: Plasmodium falciparum

<400> SEQUENCE: 22

Met Lys Glu Lys Ile Glu Asn Val Asn Val His Leu Glu Lys Arg Ile
1               5                   10                  15
Ser Asn Ser Phe Gly Thr Gly Lys Lys Met Lys Phe His Lys
            20                  25                  30
Phe Leu Ser Leu Leu Glu Lys Gly Asn Lys Lys Tyr Tyr Leu Asn Thr
        35                  40                  45
Gln Tyr Val Lys Glu Asn Ala Tyr His Pro Lys Asp Phe Cys Asn Ser
    50                  55                  60
Ile Thr Arg Gln Met Ile Asn Tyr Leu Pro Lys Glu Leu Glu Ile Met
65                  70                  75                  80
Gly Asn Leu Glu Ile Tyr Gln Tyr Asn Ile Trp Leu Gly Asn Asn Lys
                85                  90                  95
Ser Thr Lys Leu Lys Thr Tyr Leu His His Asp Tyr His Asp Asn Ile
            100                 105                 110
Tyr Val Leu Leu Lys Gly Lys Lys Thr Phe Arg Ile Tyr Ser Pro Asn
        115                 120                 125
Phe Ala Tyr Arg Leu Lys Thr Asn Gly Lys Ile Phe Lys Val His Lys
    130                 135                 140
Asn Gly Leu Ile Thr Tyr Trp Pro Phe Ile Arg Ser Asp Gly Lys Leu
145                 150                 155                 160
Cys Met Asp Val

<210> SEQ ID NO 23
<211> LENGTH: 943
<212> TYPE: PRT
<213> ORGANISM: Plasmodium falciparum

<400> SEQUENCE: 23

Met Lys Lys Gly His Asn Leu Ser Arg Lys Glu Ile Arg Lys Leu Ala
1               5                   10                  15
Arg Lys Gln Ile Lys Lys Asn Lys Leu Leu Tyr Ser Lys Lys Lys Arg
            20                  25                  30
Lys Asn Ser Phe Leu Lys Lys Glu Lys Gln Val Ser Phe Ser Asn
        35                  40                  45
Asn Asp Gln Ile Ile Ile Asn Lys Asn His Glu Ser Asn Thr Asn Gln
    50                  55                  60
Phe Leu Ser Asp Ser Asp Lys Asn Leu Ile Lys Lys Asn Lys Ser Val
65                  70                  75                  80
Lys Asn Ser Lys Lys Thr Lys Lys Ile Lys Leu Asn Asp Asn Ser Asn
                85                  90                  95
Lys Ser Phe Asn Tyr Phe Asn Asn Lys Arg Asn Tyr Leu Glu Glu Gln
            100                 105                 110
```

```
Glu Lys Asp Asp Tyr Leu Leu Ser Tyr Leu Ser Lys Lys Leu Lys Ile
    115                 120                 125
Lys Asn Glu Asp Gly Ser Asn Lys Lys Asn Glu Asp Lys Leu Ile Lys
    130                 135                 140
Glu Leu Glu Lys Asp Gly Phe Asp Thr Ser Leu Leu Lys Leu Ala Asp
145                 150                 155                 160
Ile Ile Phe Asn Glu Ser Gln Asn Phe Leu Thr Lys Lys Lys Ile Gln
                165                 170                 175
Lys Gly Lys Asp Asp Glu Tyr Asn Glu Asp Gly Glu Tyr Asn Glu Asp
                180                 185                 190
Asp Glu Tyr Asn Glu Asp Gly Glu Tyr Asn Glu Asp Asp Glu Tyr Asn
                195                 200                 205
Val Asp Asp Glu Tyr Asn Glu Asp Asp Glu Tyr Asn Val Asp Asp Glu
                210                 215                 220
Tyr Asn Glu Asn Asp Glu Tyr Asn Glu Asp Gly Glu Asp Asn Leu Ser
225                 230                 235                 240
Gln Asp Asn Asp Lys Val Asn Asn Lys Asn Val Asp Asn Ile Leu Ser
                245                 250                 255
Gly Lys Glu Asn Glu Gln Pro Tyr Asn Lys Leu Gln Asp Asp Asn Ile
                260                 265                 270
Asp Asn Val Lys Asp Lys Lys Glu Ile Lys Lys Lys Lys Lys Lys Asp
                275                 280                 285
Lys Lys Lys Lys Lys Lys Lys Lys Leu Asp Lys His Ser Ser Asp
    290                 295                 300
Asn Asn Ile Asn Asn Asp Asn Pro Ile Val Glu Ile Lys Gln Lys Lys
305                 310                 315                 320
Lys Lys Lys Val Ser Phe Asn Tyr Glu Asn Asp Ile Lys Lys Met Glu
                325                 330                 335
Lys Phe Leu Met Ser Ser Leu Asn Lys Thr Ser Glu Phe Asn Ile Lys
    340                 345                 350
Ser Ile Ile Asp Asp Ile Cys Lys Tyr Phe His Asp Ile Asp Asn Val
                355                 360                 365
Lys Leu Lys Leu Cys Tyr Asn Asp Ile Leu Ile Lys Gln Ile Ser Thr
    370                 375                 380
Tyr Phe Lys Asn Val Asn Thr Thr Asp Ile His Ile Cys Met Cys Val
385                 390                 395                 400
Val Ile Ile Cys Val Leu Asn Asn Leu Leu Cys Glu Asn Ile Leu Tyr
                405                 410                 415
Asp Phe Leu Lys Asp Leu Thr Ala Ile Phe Lys Tyr Tyr Tyr Glu Asp
                420                 425                 430
Asn Val Asn Leu Met Lys Ile Val Glu Arg Glu Asn Glu Met Asn Asn
                435                 440                 445
Lys Ile Glu Thr Gln Ser Ile Asn Ser Val Asn Asp Thr Tyr Leu Leu
    450                 455                 460
Asn Arg Lys Asn Glu Asn Asn Met Leu Ser Asn Pro Gln Gly Asp Asn
465                 470                 475                 480
Tyr Lys Ile Ser Pro Lys Glu His Glu Lys Tyr Gln Asp Phe Lys Ile
                485                 490                 495
Leu Phe Arg Asn Leu Leu Lys Cys Phe Ser Leu Phe Tyr Ala Leu Ser
                500                 505                 510
Tyr Ile Glu Phe Asp Phe Ile Ile Asp Ile Ile Asn Ile Leu Cys Glu
                515                 520                 525
His Met Ser Ile Asn Asn Val Asp Asn Ile Ile Ile Val Leu Lys Ile
```

```
                530                 535                 540
Cys Gly Met Lys Leu Lys Glu Glu Asp Asp Asn Ile His Leu Lys His
545                 550                 555                 560

Ile Ser Glu Tyr Leu Lys Lys Gln Ile Glu Gln Tyr Ile Glu Cys Asn
                565                 570                 575

Asn Ile Leu Leu Glu Lys Ser Lys Leu Arg Phe Leu Ile Lys Asp Ile
                580                 585                 590

Glu Asp Leu Glu Asn Gly Lys Met Lys Phe His Phe Leu Asn Lys Phe
                595                 600                 605

Glu Phe Leu Phe Ser Val Leu Lys Glu Tyr Glu Asn Lys Tyr Val Tyr
                610                 615                 620

Lys Lys Thr Met Ile Ser Phe Ser Phe Ile Lys Val Phe Asn Thr Ile
625                 630                 635                 640

Ser Val Glu Asn Met His Asp Glu Lys Lys Arg Gly Lys Gln Lys Asn
                645                 650                 655

Lys Asn Lys Asn Lys Asn Ile Cys Asn Asp Leu His Thr Asn Ile Ser
                660                 665                 670

Asn Asn Gln Phe His Asp Ile Glu Asn Lys Thr Lys Ile Asn Lys Leu
                675                 680                 685

Asn Tyr Leu Ile Asp Gln Gln Phe Asn Glu Val His Phe Asn Lys
                690                 695                 700

Leu Leu Lys Lys Tyr Lys Ile Gln Gly Ile Leu Pro Lys Lys Ile Phe
705                 710                 715                 720

Leu Ile Ile Lys Tyr Ser Leu Asp Val Asp Glu Cys Val His Asn Leu
                725                 730                 735

Leu Ala Leu Leu Lys Lys Lys Asn Ile Pro His Val Ile Gln Thr
                740                 745                 750

Ile Ile Gln Ile Ile Leu Tyr Asn Lys Asn Tyr Lys Glu Ser Tyr Ala
                755                 760                 765

Lys Leu Leu Ser Asn Leu Ser His Val Asn Asn Arg Val Tyr Thr Phe
                770                 775                 780

Ser Leu Lys Thr Ile Phe Ile Asn Tyr Ile Lys Asn Ile Ser Asn Met
785                 790                 795                 800

Asp Ile Lys Asn Val Leu Phe Leu Ser Lys Leu Phe Thr Tyr Leu Leu
                805                 810                 815

Lys Glu Lys Leu Ile Asn Phe Leu Ile Phe Lys His Ile Lys Ile Glu
                820                 825                 830

Glu Met Lys Asn Gln Glu Lys Thr Asn Asp Glu Ile Asn Gln Asp Asp
                835                 840                 845

Thr Asn Ala Asn Ser Asn Ile Phe Phe Phe Leu Lys Thr Ile Phe Ile
850                 855                 860

Leu Ile Ser Leu Asp Asp His Lys Glu Asn Lys Leu Lys Asn Lys Asn
865                 870                 875                 880

Val Trp Thr Asn Ile Leu His Ile Leu Tyr Asn Gln Lys Leu Ser Thr
                885                 890                 895

Ser Leu Ile Tyr Ser Phe Lys Asn Ile Ile Lys Lys Tyr Ile Phe Asp
                900                 905                 910

Glu Val Lys Asn Ile His Lys Val Tyr Pro Lys Phe Asn Met Lys Tyr
                915                 920                 925

Ile Asp His Phe Tyr Lys Phe Leu Glu Lys Ile Gln Ile Leu Gln
                930                 935                 940

<210> SEQ ID NO 24
<211> LENGTH: 462
```

<212> TYPE: PRT
<213> ORGANISM: Plasmodium falciparum

<400> SEQUENCE: 24

```
Met Leu Lys Glu Phe Val Lys Asn Val Asn Val Arg Asn His Arg Tyr
1               5                   10                  15

Ile Ser Phe Tyr Ser Leu Arg Asn Gln Ser Arg Leu Asn Asp Ile Asp
                20                  25                  30

Asp Glu Thr Tyr Asn Met Leu Lys Ser Tyr Lys Asn Lys Asn Asp Ile
            35                  40                  45

Asn Leu Ser Leu Val His Asn Ile Met Pro Thr Tyr Met Lys Glu Tyr
50                  55                  60

Leu Ser Ile Asp Leu Asn Arg Asn Ile Phe Val Asn Asn Lys Asn Ile
65                  70                  75                  80

Glu Asn Leu Glu Tyr Ile Ala Leu Asn Ser Phe Asn Leu Gln Lys Lys
                85                  90                  95

Tyr Trp Gly Cys Leu Ile Ser Asn Val Ser Leu Asn Asn Asn Lys Ser
            100                 105                 110

Ile Asp Asp Tyr Phe Phe Ile Lys Leu Tyr Gly His Phe Leu Lys Lys
        115                 120                 125

Glu Cys Lys Ile Leu Arg Ile Asn Tyr Cys Leu Glu Gln Asn Ile Glu
130                 135                 140

Asn Asn Val Ser Asn Asp Ile Met Gln Asn Leu Tyr Asn Ile Ile Asn
145                 150                 155                 160

Ile Lys Asn Arg Asn Glu Pro Asn Tyr Asp Glu Ile Gln Lys Ile Ser
                165                 170                 175

Asn Asp Phe Asn Pro Asp Ile Ile Tyr Phe Asp Glu Ser Asn Asn Pro
            180                 185                 190

Tyr Asn Ile Asp Tyr Asp Arg Phe Ile Lys Gly Leu Lys Asn Lys Asn
        195                 200                 205

Asn Lys Ile His Asn Lys Pro Ile Ile Ile Thr Asn Met Asn Asn Lys
210                 215                 220

Ala Asn Leu Ile Ser Gln Asn Leu Ile Asn Ser Pro Phe Thr His Ser
225                 230                 235                 240

Asp Ile Val Phe Thr Tyr Phe Asn Glu Asn Phe Arg Ala His Asn Ser
                245                 250                 255

Phe Val Ile Phe Tyr Lys Lys Gly Tyr Lys Cys Val Asn Thr Asp Gly
            260                 265                 270

His Ile Ile Glu Tyr Asp Tyr Glu Lys Lys Leu Lys Tyr Ala Phe Asp
        275                 280                 285

Asp Ile Tyr Leu Asn Asn Ile Phe Phe Ser Phe Phe Thr Ser Phe Lys
290                 295                 300

Leu Met Lys Asn Glu Glu Phe Lys Glu Tyr Val Lys Gln Ile Lys Glu
305                 310                 315                 320

Asn Thr Tyr Ile Leu Tyr Lys Tyr Ile Asn Arg Lys Tyr Phe His Ile
                325                 330                 335

Gln Tyr Ser Gln Asn Asn Ser Phe Phe Asn Leu Asn Pro Ser Ser Cys
            340                 345                 350

Thr Phe Asn Ile Gln Glu Phe Tyr Leu Leu Cys Asn Lys Leu Asn Ile
        355                 360                 365

Tyr Phe Asp Ile Leu Lys Asp Lys Ser Ser Asn Gln Lys Ser Phe Asn
370                 375                 380

Ile Gly Thr Asn Asn Leu Thr Ser Leu Gly Leu Leu Thr His Asp Ile
385                 390                 395                 400
```

-continued

```
Lys Asn Val Ala Glu Phe Phe Asn Glu Ser Val Val Leu Tyr Phe Tyr
            405                 410                 415

Leu Lys Glu Lys Ser Lys Leu Thr Asn Met Ser Phe Ile Gln Tyr Ile
            420                 425                 430

Glu Asp Asn Ser Ser Ala Ser Asp Ile Tyr Ser Leu Ala Val Asp Ile
            435                 440                 445

Ser Ser Phe Ile Ser Ser Tyr Pro Ser Pro Tyr Thr Asn Glu
    450                 455                 460

<210> SEQ ID NO 25
<211> LENGTH: 594
<212> TYPE: PRT
<213> ORGANISM: Plasmodium falciparum

<400> SEQUENCE: 25

Met Gln Ser Asp Asn Lys Ile Glu Asp Asp Lys Lys Glu Ser Gly
1               5                   10                  15

His Glu Glu Asn Lys Asn Val Asp Lys Glu Tyr Ile Ser Asp Asn Gln
            20                  25                  30

Thr Asn Phe Asn Asn Asp Gln Glu Gly Val Asp His Asn Asn Leu Leu
        35                  40                  45

Cys Lys Gln Gln Ser Asp Asn Ser Lys Glu His Leu Asp Phe Asn Lys
    50                  55                  60

Tyr Asp Asn Leu Ser Lys Asp Ile Gln Glu Tyr Tyr Val Gly Val Pro
65                  70                  75                  80

Tyr Ser Trp Glu Tyr Val Glu Asp Ser Lys Ser Trp Phe Ile Val Glu
                85                  90                  95

Thr Ser Lys Asn Tyr Lys Phe Phe Tyr Asn Lys Lys Ser Asn Glu Lys
            100                 105                 110

Thr Trp Ile Cys Pro Glu Glu Val Gln Lys Leu Leu Asp Lys Gln Asn
        115                 120                 125

Lys Glu Glu Ser Asn Asp Ile Lys Ser Glu Glu Asn Asp Tyr Asn
    130                 135                 140

Cys Asp Asn Lys Lys Glu Asp Met Asp Asp Ile Leu Lys Ala Tyr Lys
145                 150                 155                 160

Glu Leu Leu Ile Glu Lys Glu Ile Asn Glu Phe Ser Lys Tyr Glu Asn
                165                 170                 175

Val Leu Ala Thr Ile Leu Tyr Asp Ser Arg Tyr Leu Asn Val Pro Lys
            180                 185                 190

Glu Met Arg Lys Glu Tyr Phe Asn Lys Leu Ile Lys Glu Ile Asn Glu
        195                 200                 205

Asn Lys Lys Asp Glu Leu Lys Ile Leu Ile Glu Asn Phe Gln Ser Leu
    210                 215                 220

Leu Lys Lys Lys Glu Glu His Phe Tyr Tyr Pro Phe Asn Glu His Asp
225                 230                 235                 240

Ala Ile Lys Val Leu Gln Asn His Lys Ala Tyr Asp Gly Asn Lys Thr
                245                 250                 255

Asn Asn Trp Val Asn Thr Arg Asn Lys Leu Leu Lys Asn Phe Leu Glu
            260                 265                 270

Lys Lys Asn Lys Glu Thr Glu Lys Val Glu Asp Lys Tyr Glu Asp
    275                 280                 285

Ala Leu Ile Asn Tyr Leu Glu Asn Glu Asn Pro Lys Glu Trp Ile Lys
    290                 295                 300

Ile Lys Asn His Leu Met Lys Leu Glu Lys Tyr Asp Ile Leu Ser Tyr
305                 310                 315                 320
```

```
Lys Arg Lys Asn Gln Ile Phe Glu Gln Val Ser Glu Asn Leu Leu Arg
                325                 330                 335

Glu Ile Lys Gln Lys Lys Arg Lys Tyr Lys Ser Gly Arg Glu Gln Lys
            340                 345                 350

Asp Tyr Glu Gly Tyr Glu Asn Asp Lys Gly Glu Tyr His Tyr Asp Asn
        355                 360                 365

Arg Arg Lys Tyr Ser Lys Lys Glu Phe Glu Asp Tyr Gln Lys Glu Lys
    370                 375                 380

Thr Ser Glu Lys Asn Leu Phe Ile Thr Ile Leu His Glu Lys Leu Lys
385                 390                 395                 400

Cys Pro Lys Val Asp Glu Glu Leu Leu Lys Thr Gly Tyr Asn Ser Ile
                405                 410                 415

Asp Asn Lys Asn Thr Phe Glu Asp Ile Cys Leu Leu Pro Arg Asp Ile
            420                 425                 430

Leu Asn Asp Glu Arg Tyr Lys Asn Ile Thr Leu Asn Asp Asn Glu Lys
        435                 440                 445

Phe Val Leu Tyr Lys Glu Phe Ile Asn Asn Tyr Ile Asp Ser Lys Lys
    450                 455                 460

Ile Ser Phe His Lys Leu Leu Ser Glu Leu Ser Ile Asn Cys Ile Asn
465                 470                 475                 480

Asn Thr Leu Asp Glu Ile Ile Leu Met Ile Asp Lys Asn Asn Lys Met
                485                 490                 495

Phe Lys Asp Ile Asn Lys Cys His Leu Glu Glu Asn Tyr Asn Lys Trp
            500                 505                 510

Arg Glu Tyr Lys Ile Lys Glu Ala Lys Asn Ile Phe Arg Asn Phe Leu
        515                 520                 525

Met Lys Phe Asn Tyr Ile Lys Tyr Asp Ser Asp Glu Tyr Asn Asn Tyr
    530                 535                 540

Lys Gln Leu Ile Asp Arg Leu Ser Gln Asp Val Ser Tyr Gln Arg Leu
545                 550                 555                 560

Asn Cys Val Pro Lys Glu Arg Glu Gln Ile Ile Leu Ser Arg Ile Glu
                565                 570                 575

Glu Leu Lys Glu Glu His Glu Leu Lys Asn Lys Asn Leu Ala Glu Arg Leu
            580                 585                 590

Asn Phe

<210> SEQ ID NO 26
<211> LENGTH: 1410
<212> TYPE: PRT
<213> ORGANISM: Plasmodium falciparum

<400> SEQUENCE: 26

Met Leu Lys Phe Ser Lys His Val Ser His Lys Ile Asn Thr Pro Tyr
1               5                   10                  15

Arg Phe Met Pro Tyr Ile Ile Asn Asn Ile Thr Asn Asn Leu Tyr Phe
                20                  25                  30

Ile Leu Leu His Asn Phe Ile Pro Tyr Lys Asn Lys His Ile Tyr Asn
            35                  40                  45

Lys Cys Asn Phe Tyr Ile Ile Asp Tyr Lys Gln Phe His Ile Leu Gln
        50                  55                  60

Asp Tyr Ile Ala Glu Lys Glu Lys Asn Thr Gly Asp Lys Ser Val Asn
65                  70                  75                  80

Tyr Gly Glu Gly Lys Ile Lys Gln Ile Arg His Ser Asn Asn Lys Asp
                85                  90                  95

Asn Ser Asn Asn Asn Asn Asn Asn Asn Asn Asn Asn Asn Ser Asn Asn
```

```
                    100                 105                 110
Asn Asn Asn Asn Asn Asn Ser Asn Asn Asn Asn Ser Asn Asn
                115                 120                 125
Asn Asn Ser Asn Asn Asn Asn Ser Lys Asn Ser Asn Asn
        130                 135                 140
Asn Asn Asn Tyr Asn Asp Tyr Lys Asp Gly Gln Asn Ile Val Ile
145                 150                 155                 160
Asn Thr Asn Tyr Thr Ser Ser Tyr Lys His Lys Lys Ser Val Asn
                165                 170                 175
Asn Ile Phe Ile Asn Asn Asp Val Phe Ser Ser Leu Gln Asn Ile Phe
            180                 185                 190
Leu Leu Ile Asn Lys Ile Asn Lys Asn Phe Phe Gln Arg Val Gln Pro
            195                 200                 205
Lys Phe Asp Gly Asn Gln Lys Gln Ile Ile Ile Asp Asn Val Val Tyr
        210                 215                 220
Ile Asn Lys His Pro Tyr Val Leu His Ile Leu Leu Asn Asn Asn
225                 230                 235                 240
Val Asn Ile Asn Ile Tyr Lys Glu Ile Asp Ile Leu Leu Ala Ser Glu
            245                 250                 255
Tyr Phe Ser His Leu Cys Asn Asn Ile Asn Asn Leu Asp Phe Phe Ser
            260                 265                 270
Leu Val Ser Leu Phe His Ile Tyr Ile Pro Lys Lys Lys Lys Asn
        275                 280                 285
Tyr Thr Ile Val Lys Asn Ala Asn Asp Ile Tyr Asn Ser Asn Asn Ser
        290                 295                 300
Tyr Asp Gly Ile Ile Lys Asp Arg Gln Glu Asn Ile Asp Glu Glu Glu
305                 310                 315                 320
Glu Lys Asn Gln Glu His Leu Asn Leu Ile Pro Phe Leu Asp Ile Ile
                325                 330                 335
Lys Asn Cys Ile Leu Lys Asn Ile Cys Ile Gln Ile Asn His Leu Met
                340                 345                 350
Thr Asn Val Lys Asn Asn Asn Glu His Lys Asp Asn Pro Ile Asn Val
            355                 360                 365
Asn Lys Lys Lys Lys Lys Val Thr Phe His Asp Ile Tyr Gly Glu Val
        370                 375                 380
Ile Asn Ile Leu Tyr Ile Lys Asp Asp Asp Ile Lys Asn Tyr Ile
385                 390                 395                 400
Asn Tyr Ile His Val Ile Leu Asp Thr Leu Tyr Lys Asn Ile His Lys
                405                 410                 415
His Ile His His Tyr Asn Tyr Thr Tyr Ser Ile Lys Leu Leu Arg Tyr
                420                 425                 430
Ile Asn Thr Ile Leu Ser Phe Asn Ile Asn His Ser Tyr Ile Ser Asn
            435                 440                 445
Gly Gln Lys Ile Arg Glu Glu Lys Asn Val Ser Arg Tyr Phe Ser
        450                 455                 460
Ser Leu Ile Asp Asn Asn Phe Leu Tyr Ile Arg Lys Glu Asn Phe Ser
465                 470                 475                 480
Phe Asn Tyr Val His Lys Asn Tyr Asn Ile Leu Tyr Asn Trp Asp Met
            485                 490                 495
Tyr Asn Thr Thr Asn Ile Asn Asn Asn Ile Asn His Asp Lys Asn Ile
            500                 505                 510
Gln Gln Tyr Thr Asn Asp Asp Asn Thr Thr Ile Tyr Ile Glu Asp Leu
        515                 520                 525
```

-continued

```
Asn Asn Leu Gln Asn Tyr Asn Leu Asn Lys Lys Leu Leu Tyr Lys Thr
        530                 535                 540

Asn Glu Asp Ile Tyr Asp Ile Ser Phe Met Pro Lys His Ile Glu His
545                 550                 555                 560

Asn Asn Asn Ile Leu Asn Asp Asn Asp Val Thr Trp Asn Asn Asn Ser
            565                 570                 575

Ser Ser Asn Tyr His His Pro Asn Val Tyr Lys Glu Gln Tyr Asp Lys
        580                 585                 590

Met Gly Thr Leu Pro Ile Ile Lys Asn Ser Pro Asn Glu Tyr Asn Leu
            595                 600                 605

Ile Ser Lys Asp Ile Glu Ser Tyr Lys Tyr Ile Ile Lys Phe Ser Ile
        610                 615                 620

Glu Leu Leu Tyr Ile Ile Val Lys Lys Ile Lys Tyr Val His His Thr
625                 630                 635                 640

Asn Thr Phe Ala Asp Glu Glu Ile Ile Leu Glu Ile Ile Asn Thr Leu
                645                 650                 655

Ile His Ile His His Thr Tyr His Thr Asp Ile Asn Asn Met Ile Asn
        660                 665                 670

Glu Lys Ser Leu Phe Leu Lys Asn Asn Ile Ile Asn Ser Glu Tyr Asn
            675                 680                 685

Asn Thr Tyr Ser Ile Tyr Phe Phe Leu Phe Leu Asp Phe Ile Phe Asn
690                 695                 700

Thr Leu Lys Lys Lys Tyr Ile Tyr Ile Ser His Asn Asp Asn His Met
705                 710                 715                 720

Asn Glu Ile Ile Thr Gln Tyr Tyr Tyr Lys Asn Glu Asn Phe Phe Lys
                725                 730                 735

Ile Leu Ser Leu Leu Ser Asn Ile Arg Tyr Leu Leu Thr Cys Asn Lys
            740                 745                 750

Arg Gln Pro Lys Asn Met Glu Pro Ser Thr His Asn Asn Thr Leu Cys
        755                 760                 765

Glu Asn His Lys Ile His Ile Ser His Gln Lys Ile Ile Glu Gly Thr
            770                 775                 780

Thr Asn Glu Lys Lys Lys Met Phe Ile Ser Lys Ile Asn Glu His Ile
785                 790                 795                 800

Tyr Gln Leu Thr Asn Asp Ile Ile Leu Phe Tyr Thr Glu Tyr Ser Asn
                805                 810                 815

Lys Met Asn Asn Asn His Arg Asn Tyr His Tyr Phe Gln Lys Asp
        820                 825                 830

Gly Ser Ser Tyr Asn Asn Thr Ile Asn Ile Gln Phe Tyr Ile Phe Tyr
            835                 840                 845

Leu Phe Asn Asp Val Tyr Leu Gln Asn Asn Tyr Ala Met Arg Lys Ile
850                 855                 860

Ile Phe Ser Tyr Phe Ser Asn Ser Tyr Lys Tyr Ile Tyr Ser Tyr Pro
865                 870                 875                 880

Leu Leu Asn Tyr Asn Ile Thr Tyr Leu Gln Tyr Ile Thr Ile Tyr Asn
                885                 890                 895

Phe Leu Lys Leu Phe Lys Asn Glu Ile Asn Glu Pro Ser Glu Glu Tyr
            900                 905                 910

Asp Asn Val Val Lys Ile Phe Ile Arg Leu Phe Asp Asn Asn Thr Tyr
        915                 920                 925

Gln Gln Ile Gly Val Gln Gln Asn Ile Asn Thr Thr Asn Ile Tyr
            930                 935                 940

Ile Gln His Asp Ile Lys Tyr Tyr Ile His Asn Leu Tyr Lys Ile Cys
945                 950                 955                 960
```

Tyr Phe Phe Ile Leu Ser Lys Lys Leu Ile Thr Asn Val Glu Phe Ile
            965                 970                 975

Asn Gln Ile Asn Ser Ile Phe Tyr Leu Asn Phe Tyr Met Ile Asn Gln
            980                 985                 990

Trp Val Gln Thr Glu Arg Gly Lys Asn Lys Leu Asn Asp Ser Gly His
            995                 1000                1005

Phe Thr Gln Leu Ile Asn Lys Cys Met Asn Lys Ile Ile Ile Ile
    1010                1015                1020

Phe Val Ile His Lys Tyr Trp Gln Ile Leu Lys Thr Glu Asp Thr
    1025                1030                1035

Ile Lys Tyr Leu Ser Thr Phe Ile Tyr Ala Thr His Asp Leu Ile
    1040                1045                1050

Ser Asn Glu Asn Lys Arg Lys Leu Leu Leu Tyr Ile Phe Pro Phe
    1055                1060                1065

Met Lys Glu Lys Lys His Glu Lys Val Leu Ile Gln Lys Tyr Tyr
    1070                1075                1080

Gln Ser Glu Lys Lys Asn Gln Ser Lys Asn Ile Pro Tyr Glu
    1085                1090                1095

Asn Asp Ile Ser Leu Thr Tyr Glu Lys Tyr Asn Glu Gln Thr Val
    1100                1105                1110

Glu Asp Tyr Lys Asn Asp Thr Val Leu Cys Pro Ser Asn Leu His
    1115                1120                1125

Val Gln Thr Asn Ile Asn Asn Lys Asn Lys Glu Gln Lys Gln Ile
    1130                1135                1140

Tyr Val Asn Tyr Asn Asn Tyr Phe Lys Asn Tyr Asp Ile Lys Asn
    1145                1150                1155

Thr Ser Lys Ile Asn His Asn Pro Ile His Ile Asn Val Lys Glu
    1160                1165                1170

Ile Ile Asn His Leu Glu Glu Asn Glu Asn Ile Lys Leu Ser Asn
    1175                1180                1185

Asp Glu Leu His Lys Ile Leu Lys Glu His Ile Asn Gln Met Asp
    1190                1195                1200

Ile Ile Lys Gln Glu Asn Met Leu Leu Lys Asn Lys Leu Asn Tyr
    1205                1210                1215

Ile Val Leu Asn Phe Glu Asn Phe Ile Ser Ser Tyr Ile His Asn
    1220                1225                1230

Ile Ile Ser Asn Lys Asn Ala His Val Leu Tyr Thr Lys Thr Asn
    1235                1240                1245

Ile Ser Val Asn Asn Asp Ser Ile Asn Glu Glu Thr Asn Lys Gln
    1250                1255                1260

Ile Ile Lys Glu Thr Phe Lys Glu Lys His Lys Glu Glu Gln Gln
    1265                1270                1275

Glu Tyr Ile His Val Tyr Asn Lys Thr Tyr His Glu Glu Lys Lys
    1280                1285                1290

Gln Glu Thr Lys Val Ser Ile Lys Phe Asn Tyr Gln Gln Met Asp
    1295                1300                1305

Val Lys Asn Glu Tyr Phe His Thr Leu Lys Lys Tyr Gln Thr Asn
    1310                1315                1320

His Ser Phe Lys Ile Asn Asn Ile Leu Ile Asn Met Tyr Met Tyr
    1325                1330                1335

Asn Pro Tyr Ile Cys Ala Lys Lys Asn Lys Asn Phe Phe Leu Ser
    1340                1345                1350

Lys Asn Lys Lys His Lys Lys Ile Ile Ile Leu Pro Tyr Asp Thr

-continued

```
                1355                1360                1365

Tyr Lys Asn Ile Lys Lys Ile Leu Thr Tyr Asp Asp His Asn Glu
            1370                1375                1380

Lys Thr Lys Ile Phe Lys Ser Leu Gln Asn Val Ile Tyr Leu Phe
        1385                1390                1395

Tyr Asp Arg Phe Lys Ala Leu Phe Glu Lys Ile Asn
    1400                1405                1410

<210> SEQ ID NO 27
<211> LENGTH: 1946
<212> TYPE: PRT
<213> ORGANISM: Plasmodium falciparum

<400> SEQUENCE: 27

Met Gly Phe His Asn Val Lys Asn Ile Ser Asp Ile Lys Glu Leu Lys
1               5                   10                  15

Ile Leu Gln Asn Asn Glu Arg Asn Val Asn Asn Phe Pro Gln Ile Cys
            20                  25                  30

Asn Asp Asn Ile Thr Leu Cys Val Asn Asn Ser Asn Glu Leu Tyr Leu
        35                  40                  45

Tyr Asn Lys Ser Ile Thr Ile Cys Asp Asn Asn Asn Ile Leu His
    50                  55                  60

Asn Tyr Lys Asn Glu Ile Val Asn Leu Ile Asn Asn Asn Asn Asn
65                  70                  75                  80

Thr Tyr Gln Asp Val Ser Asp Lys Cys Val Leu His Met Asp Cys Asp
                85                  90                  95

Asp Leu Tyr Val Ser Pro Asn Asn Val Glu Lys Asn Ile Tyr Gln
            100                 105                 110

Glu Asp Ile His Met Lys Asp Glu Asn Asp Leu Ser Leu Asn Cys
        115                 120                 125

Ile Asn Asn Thr His Leu Asn Glu Lys Ser Ile Ser Glu Thr Lys Glu
    130                 135                 140

Ile Ile Gly Lys Lys Val Arg Gln Asp Ile Ile His Thr Asn Asp Glu
145                 150                 155                 160

Asn Val Met Leu Glu Ile Gln Asp Asp Glu Asn Lys Leu Ile Arg
                165                 170                 175

Asn Val Glu Lys His Met Asp Gln Pro Ile Phe Ser Gly Ser Ser Met
            180                 185                 190

Ser Tyr Ser Phe Asp Lys Glu Lys Tyr Leu Tyr Arg Ser Asn Asp Met
        195                 200                 205

Ser Asp Thr Asn Tyr Val Cys Gln Asp Glu Ile His Ser Ile Ile Ser
    210                 215                 220

Pro Asp Glu Glu Lys Lys Asn Ser Leu Gln Ser Leu Ser Asn Gln Asn
225                 230                 235                 240

Leu Glu Ile Ala Tyr Glu Leu Thr Ser Asn Gly Asp Asp Glu Tyr Ile
                245                 250                 255

Ile Glu Asn Asn Glu Glu Asn Glu Glu Asn Asn Glu Glu Asn Asn
            260                 265                 270

Glu Glu Asn Asn Glu Glu Asn Asn Glu Glu Asn Asn Lys Glu Asn Asn
        275                 280                 285

Lys Glu Tyr Asn Asn Asp Asn Asn Asp Asn Tyr Ser Tyr Tyr Asn
    290                 295                 300

Ser Tyr Asn Asn Ser His Asn Asn Ser His Asn Asn Ser His Asn Asn
305                 310                 315                 320

Ser His Asn Asn Ser His Asn Asn Ser His Asn Asn Ser His Asn Asn
```

```
                    325                 330                 335
Ser His Asn Asn Ser His Asn Asn Ser His Asn Asn
                340                 345                 350
Ser His Asn Asn Ser His Asn Asn Ser His Asn Asn
                355                 360                 365
Ser His Asn Asn Ser His Asn Asn Ser Cys Asn Ile Ser Cys Tyr Asn
                370                 375                 380
Ser Asp Asp Asn Asp Asp Asp Lys Glu Ile Lys Asn Ile Leu Asn
385                 390                 395                 400
Val Leu Asn Asn Leu Arg Asn Tyr Lys Phe His Asp Thr Asp Asn Leu
                405                 410                 415
Asp Asn Asp Glu Asn Tyr Glu Ser Phe Asp Asn His Pro Asp Asp Tyr
                420                 425                 430
Lys Thr Ser Asn Lys Asp Met Asp Glu Asn Asp Lys Leu Asn Thr Asn
                435                 440                 445
Glu Met Asn Asn Met Tyr His Asp Gln Asn Ile Pro Phe Leu Lys Asn
                450                 455                 460
Glu Tyr Thr Tyr Asn Asn Val Leu Ser Lys Glu Asp Lys Glu Asn Ile
465                 470                 475                 480
Asp Leu Gln Lys Ile Lys Asp Lys Tyr Glu Lys Phe Thr Leu Asn Leu
                485                 490                 495
Asn Asn Gln Met Asp Asp Asn Asn Asn Lys Val Asn Gln Ile Asn
                500                 505                 510
Phe Asn Glu Asn Asn Lys Asn Asp Met Cys Gln Glu Lys Glu Lys
                515                 520                 525
Arg Gln Leu His Tyr Glu Thr Ser Gln Glu Glu Lys Lys Asn Met Ser
                530                 535                 540
Asn Glu Ile Ile Asn Asn Asp Asn Ser Thr Asn Gln Gln Val His Gly
545                 550                 555                 560
Lys Lys Lys Asp Leu Ile Asn Thr His Ile Tyr Ser Ser Lys Asn Asn
                565                 570                 575
Asn Asn His Ile His Asn Ser Asp Gln Glu Leu Ile Ile Phe Lys Asn
                580                 585                 590
Asn Ile Asn Cys Val Lys Asn Asn Glu Val Ile Ile Met Asp Asp Lys
                595                 600                 605
Asn Asn Cys His Ile Asn Asn Asn Ala Asn Asp His Phe Tyr Ile Tyr
                610                 615                 620
Lys Gln Thr Gln Asn Asn Tyr Asn Asp Ile Asn Gln Glu Lys Ile Lys
625                 630                 635                 640
Gln Ser Asn Ser Cys Asn Glu Glu Gln Asn Lys Val Lys Gly His Phe
                645                 650                 655
Asn Asn Ile Lys Glu Glu Leu Ala Ile Ser Ser Asn Asn Ser Ser Lys
                660                 665                 670
Asn Ser Glu Gln Val Arg Lys Lys Lys Leu Leu Lys Glu Asn Met Asn
                675                 680                 685
Asn Leu Asn Asn Val Asn Lys Asn Glu Glu Thr Asn Met Ile Tyr Asn
                690                 695                 700
Asn Lys Glu Thr Ile Met Asp Asn Glu Asn Val Tyr Ile Asn Thr Tyr
705                 710                 715                 720
Asn Asn Asn Asn Asn Asn Asn Asn Asn Asn Asn Asn Asn Asn Asp Ile
                725                 730                 735
Tyr Ser Asn Asn Asn Ile Tyr Asn Asn Asn Asn Cys Asn Asn Tyr
                740                 745                 750
```

-continued

```
Asp Val Cys Gly Asn Asp Val Gly Phe Ala Lys Ser Asn Ile Met Asn
        755                 760                 765

Val Asn Leu Glu Asn Tyr Asn Ile Ile Asp Ser Thr Lys Tyr Ile Phe
770                 775                 780

Gln Glu Asn Thr Lys Asp Ile Ser Asn Asp Ile Lys Thr Glu Met Lys
785                 790                 795                 800

Asn Ile Asn Leu Glu Asn Glu Asn Phe Glu Phe Asp Ser Tyr Leu
                    805                 810                 815

Asn Lys Leu Asn Asn Leu Lys Ser Met Leu His Gln Asn Glu Ser Asp
                820                 825                 830

Ser Glu Asn Tyr Asp Asp Glu Asn Gly Asp Ile Asn Ser Glu Glu Gln
            835                 840                 845

Asn Asp Ile Thr Asp Glu Gly Lys Lys Ser Val Val Asp Tyr Asp Lys
        850                 855                 860

Glu Leu Ser Thr Asp Val Asp Ile Asp Val Asp Val Asp Val Asp Val
865                 870                 875                 880

Asp Val Asp Val Asp Val Asp Glu Ser Ser Asn Gln Asn Ile Ser
                885                 890                 895

Asn Glu Lys Lys Asn Lys Glu Lys Lys Ile Lys Asn Asn Lys Asn Lys
                900                 905                 910

Asn Asp Asp Asp Asp Asn Asp Asp Asp Asp Asn Asp Asn
                915                 920                 925

Asp Asp Asn Asp Asn Asn Asp Asp Asn Asn Asp Asn Asp
930                 935                 940

Asn Asn Asp Asp Asn Asp Asn Asp Asn Asp Asn Asp Asn Asp Asn
945                 950                 955                 960

Asn Asp Asp Tyr Val His Tyr Val His Tyr Val His Tyr Asp Asp Asn
                965                 970                 975

Asn Asn Asn Asn Met Leu Val Gln Tyr Thr His Asn His His Asp Thr
                980                 985                 990

Ser Ser Gln Glu Asn Ile Gln His Thr Asn Tyr Lys His Asn Asn Tyr
        995                 1000                1005

Asn Val Leu Glu Asn Phe Thr Ile Asp Lys Gln Pro Ser Asp Asn
    1010                1015                1020

Asn His Asn Lys Asn Asn Tyr Arg Asp Asn Asn Arg Asn Lys Asn
    1025                1030                1035

Asn Tyr Arg Asp Asn Asn Arg Asn Lys Asn Asn Tyr Arg Asp Lys
    1040                1045                1050

Asn His Asn Ser Asn Asn Asn Lys Asn Asn Asn Lys Asn Lys Asn
    1055                1060                1065

Asn Asn Tyr Tyr Tyr Tyr Gln His Asn Asn Asn Leu Ser His Ile
    1070                1075                1080

Thr Val Leu Glu Lys Lys Asn Lys Ala Leu Asn Lys Gln Val Lys
    1085                1090                1095

Tyr Leu Glu Asn Lys Ile Leu Val Gln Lys Lys Lys Glu Met Ser
    1100                1105                1110

Phe Cys Lys Asn Lys Glu Lys Tyr Lys Lys Lys Ile Ser Leu
    1115                1120                1125

Ile Asn Glu Tyr Glu Lys Lys Leu Asp Asn Ile Ile Ile Asp Phe
    1130                1135                1140

Asn Lys Leu Lys Glu Asn Cys Ile Thr Lys Glu Lys Lys Leu Ala
    1145                1150                1155

Lys Met Glu Asp Ile Thr Lys Tyr Ile Asn Glu Gln Phe Ser Leu
    1160                1165                1170
```

-continued

```
Ser Lys Ile Gln Phe Glu Asn Lys Met Asn Glu Tyr Val Ile Phe
    1175                1180                1185
Leu Lys Lys Lys Asp Ser Glu Ile Tyr Met Leu Lys Glu Leu Ile
    1190                1195                1200
Lys Glu Lys Glu Lys Thr Ile Leu Tyr Asn Asp Asn Ile Leu Lys
    1205                1210                1215
Gln Tyr Lys Lys Asp Val Asp Asp Ile Leu Lys Glu Asn Ile Glu
    1220                1225                1230
Lys Ile Asp Asp Ile Lys Lys Lys Leu Lys Thr Gln Glu Glu Ile
    1235                1240                1245
Ile Ser Gln Lys Asp Arg Gln Ile Glu Thr Leu Glu Asn Asn Leu
    1250                1255                1260
Lys Ile Gly Lys Glu Lys Ile Asn Lys Phe Asp Asn Glu Ile Gln
    1265                1270                1275
Lys Leu Gln Tyr Lys Ile Asn Ile His Ile Glu Lys Glu Thr Glu
    1280                1285                1290
Ile Lys Lys Thr Asn Asp Ile Glu Lys Glu Lys Asn Thr Lys Leu
    1295                1300                1305
Ser Asn Lys Phe Asp Ile Ile Asn Lys Glu Asn Asn Asn Leu His
    1310                1315                1320
Asn Lys Ile Glu Thr Leu Leu Lys Asn Glu Lys Glu Ile Ser Thr
    1325                1330                1335
Glu Asn Val Lys Leu Ile Glu Thr Asn Lys Thr Leu Tyr Ile Glu
    1340                1345                1350
Asn Glu Lys Leu Ser Asn Asp Leu Lys Asn Thr Leu Lys Glu Lys
    1355                1360                1365
Glu Lys Ile Gln Glu Asn Tyr Asn Lys Ile Asn Lys Glu His Ile
    1370                1375                1380
Lys Ile Ile Glu Glu Leu Gln Ser Tyr Lys Glu Ile Lys Glu Lys
    1385                1390                1395
His Met Lys Glu Ile Thr Gln Ile Lys Glu Gln Ile His Asn Leu
    1400                1405                1410
Asp Lys His Ile Ala Gln Ile Gln Ile Glu Lys Asn Asn Phe Glu
    1415                1420                1425
Glu Ser Tyr Leu Lys Glu Lys Asn Glu Asn Glu Lys Met Ser Asn
    1430                1435                1440
Ile Leu Glu Glu Lys Tyr Lys Glu Leu Ser Thr Tyr Glu Ile Asp
    1445                1450                1455
Lys Asn Ile Asn Lys Ile Lys Ile Glu Asp Leu Glu Lys Asp Lys
    1460                1465                1470
Glu Asn Ile Leu Leu Thr Lys Asn Glu Glu Ile Asn Asn Leu Lys
    1475                1480                1485
Glu Glu Tyr Lys Met Val Gln Gln His Leu Glu Asp Thr Asn Val
    1490                1495                1500
Leu Tyr Glu Lys Gln Lys Leu Ala Ile Asp Thr Ile Thr Lys Glu
    1505                1510                1515
Lys Asn Asn Ile Ile Asn Glu Cys Asp Lys Ile Lys Asn Lys Asn
    1520                1525                1530
Lys Lys Leu Asn Asn Lys Leu Lys Glu Asn Gln Asn Asn Tyr Glu
    1535                1540                1545
His Thr Leu Asn Asn Ile Lys Lys Glu Asn Gln Gln Ile Ile Glu
    1550                1555                1560
Arg Glu Lys Lys Asn Phe Thr Gln Lys Val Glu Ser Leu Glu His
```

```
               1565                1570                1575

Ala Phe Lys Gln Ser Tyr Asn Gln Leu Lys Asp Gln Asn Glu Asn
    1580                1585                1590

Leu Gln Gln Gln Ile Lys Gln Leu Lys Asn Val Asn Gln Asp Ile
    1595                1600                1605

Lys Thr Asn Ser Lys Asn Leu Lys Asn Val Asn Glu Ile Leu Ile
    1610                1615                1620

Lys Glu Thr Lys Asn Tyr Ser Gln Gln Lys Glu Lys Phe Ile Lys
    1625                1630                1635

Gly Leu Lys Asn Ile Lys Gln Ala Tyr Ile Lys Leu Lys Asn Glu
    1640                1645                1650

Asn Gln Gln Leu Lys Ile Asn Ala Phe Glu Tyr Ile Lys Lys Asp
    1655                1660                1665

Val Gln Asp Asn Tyr Val Thr Leu Asn Val His Asn Asn Ile Leu
    1670                1675                1680

Asn Glu Gln Lys Lys Leu Phe Val Gln Ile Asp Ile Leu Lys Ser
    1685                1690                1695

Gln Val Asp Gln Lys Gln Asn Ile Ile Asn Asn Met Lys Glu Gln
    1700                1705                1710

Ile Glu Asp Val Asn His Lys Ile Ala Ser Ile Asn Lys Glu Lys
    1715                1720                1725

Glu Glu Leu Asn Thr Thr Ile Lys Ile Lys Asn Lys Ile Thr Glu
    1730                1735                1740

Asp Val Asn Leu Ser Val Glu Lys Leu Lys Ser Glu Leu Asn Ser
    1745                1750                1755

Lys Asp Asp Glu Val Lys Lys Arg Thr Ile Glu Ile Lys Gln Lys
    1760                1765                1770

Glu Arg Glu Tyr Lys Lys Leu Leu Asp Asp Tyr Lys Ile Glu Lys
    1775                1780                1785

Lys Asn Leu Val Thr Lys Tyr Glu Lys Glu Leu Asp Ser Tyr Met
    1790                1795                1800

Thr Lys Tyr Glu Phe Ala His Ala Lys Tyr Lys Gln Tyr Glu Glu
    1805                1810                1815

Glu Ile Lys Asp Leu Lys Asn Lys Leu Lys Leu Lys Asp Glu Val
    1820                1825                1830

Ile Glu Tyr Thr His Lys Glu Ile Glu Asn Ile Lys Glu Ser Phe
    1835                1840                1845

Cys Asn Glu Tyr Glu Asn Lys Ile Lys Thr Leu Val Glu Glu Lys
    1850                1855                1860

Asp Lys Glu Ile Asn Thr Val Gln Lys Lys Cys Lys Glu Leu Arg
    1865                1870                1875

Gln Asp Asn Thr Thr Asn Lys Asn Glu Ile Val Lys Leu Asn Lys
    1880                1885                1890

Met Leu Glu Glu Thr Asn Lys Lys Ile Lys Lys Arg Asp Met Glu
    1895                1900                1905

Met Tyr Ile Leu Leu Glu Glu Asn Lys Lys Gln Lys Glu Lys Ala
    1910                1915                1920

Ala Lys Lys Met Thr Lys Val Asn Ala Leu Leu Asn Asn Leu His
    1925                1930                1935

Lys Glu Tyr Thr Asp Asn Ile Pro
    1940                1945

<210> SEQ ID NO 28
<211> LENGTH: 75
```

```
<212> TYPE: PRT
<213> ORGANISM: Plasmodium falciparum

<400> SEQUENCE: 28

Met Glu Lys Asn Ile Leu Lys Lys Tyr Lys Ser Phe Asn Phe Val
1               5                   10                  15

Thr Asn Ile Lys Asn Asn Thr Glu Lys Glu Asn Ser Ile Lys Tyr Ala
            20                  25                  30

Gln Asn Ile Tyr Leu Ser Lys Ile Ser Lys Ser Asn Tyr Asn Val Lys
            35                  40                  45

Ser Asn Glu Asp Gln Ile Tyr Asp Asn Lys Leu Phe Leu Lys Tyr Trp
50                  55                  60

Ile Arg Lys Lys Arg Pro Gly Ala Arg Asn Trp
65                  70                  75

<210> SEQ ID NO 29
<211> LENGTH: 393
<212> TYPE: PRT
<213> ORGANISM: Plasmodium falciparum

<400> SEQUENCE: 29

Met Thr Asn Ile Ile Glu Cys Thr Phe Lys Thr Pro Pro Asp Asn Ala
1               5                   10                  15

Lys Thr Pro Asp Asn Ala Val Ile Trp Asn Gln Phe Gln Tyr Cys Asp
            20                  25                  30

Glu Lys Gly Trp Tyr Ser Leu Ser Asn His Asp Glu Ile Ala Leu Arg
            35                  40                  45

Pro Thr Thr Phe Asn Asp Lys Arg Ile Lys Phe Leu Val Gln Leu Pro
50                  55                  60

Glu Ile Pro Ser Glu Phe Glu Ser Ile Leu Ser Gly Arg Tyr Asp Ala
65                  70                  75                  80

Lys Ala Trp Gly Lys Glu Asp Cys Tyr Val Val Ile Glu Gly Glu Lys
                85                  90                  95

Asp Val His Ile Arg Leu Pro Gly Phe Lys Glu Lys Ile Asn Tyr Asn
            100                 105                 110

His Thr Glu Arg Phe Pro Thr Phe Leu Lys Asn Trp Lys Ile Ile Val
            115                 120                 125

Ser Ile Leu Asn Glu His Val Thr Leu Ile Arg Ile Asn Ala Glu Thr
            130                 135                 140

Ala Leu Ile Ile Asn Ile Asn Glu Lys Lys Asn Val Thr Val Lys Ser
145                 150                 155                 160

Val Asp Phe Asn Asn Gly Phe Leu Cys Val Asn Pro His Thr Asn Leu
                165                 170                 175

Ala Ile Ala Tyr Gly Asp Phe Ala Leu Ser Ser Leu Lys Lys Cys Glu
            180                 185                 190

Leu Ile Gln Asn Ile Pro His Glu Gly Gly Lys Trp Gly Phe Phe Thr
            195                 200                 205

His Leu Phe Lys Trp Gly His Ile Ile Pro Lys Glu Leu Glu Ile
            210                 215                 220

Lys Leu Pro Ser Pro Gly Leu Lys Leu Ile Gly Lys Lys Ile Asp Thr
225                 230                 235                 240

Leu Ala Ile Val Ser Ile Pro Pro Asn Ile His Ile His Val Lys Leu
                245                 250                 255

Asp Gly Pro Lys Cys Ile Arg Lys Leu Glu Tyr Gly Gln Asp Tyr Asn
            260                 265                 270

Ile Thr Ala Ile Lys Ser Ser Glu Ser Asp Val Asp Ile Tyr Ile Leu
```

-continued

```
                275                 280                 285
Phe Asp Gly His Leu Leu Lys Tyr Glu Phe Ser Phe Asp Ile Arg Leu
        290                 295                 300
Asn Lys Pro Glu Lys Gly Arg Ser Leu His Ser Ala Lys Leu Lys Cys
305                 310                 315                 320
Ile Asn Lys Ser Lys Glu Val Thr Ser Phe Ile Phe Gln Glu Thr Lys
                325                 330                 335
Asn Cys Lys Ile Leu Leu Gly Ser Asn Cys Pro Ser Asp Asn Leu Gly
            340                 345                 350
His Leu Leu Asn Ser Gln Thr Ile Ala Ile Phe Asp Ala Glu Ile Gly
                355                 360                 365
Glu Tyr Leu Ser His Pro Gln Gly Leu Gln Leu Thr Ser Val Phe Asn
        370                 375                 380
Thr Leu Ser Tyr Pro Leu Asp Lys Glu
385                 390

<210> SEQ ID NO 30
<211> LENGTH: 130
<212> TYPE: PRT
<213> ORGANISM: Plasmodium falciparum

<400> SEQUENCE: 30

Met Lys Val Ser Arg His Thr Val Leu Leu Asn Ile Ile Leu Ile Val
1               5                   10                  15
Ser Leu Leu Gly Cys Val Leu Thr Leu Asn Leu Phe Ser Ala Asn Asp
            20                  25                  30
Asp Lys Arg Ala Leu Lys Asp Ile Asp Arg Thr Leu Glu Lys Leu Leu
        35                  40                  45
Arg Lys Lys Gln Ile Ile Ile Ser Thr Ala Ala Val Ala Leu Ala Ile
    50                  55                  60
Thr Leu Gly Gly Leu Phe Gly Ser Leu Gly Tyr Lys Ser Trp Lys Asn
65                  70                  75                  80
Lys Asn Lys Ser Lys Asp Lys Val Asn Asp Gly Ser Asp Ser Glu Glu
                85                  90                  95
Leu Asp Met Gln Asn Thr Val Arg Asn Val Leu Val Thr Lys Tyr Ile
            100                 105                 110
Ile Glu His Pro Tyr Phe Lys Asn Glu Pro Leu Tyr Ile Tyr Ile Tyr
        115                 120                 125
Ile Asp
    130

<210> SEQ ID NO 31
<211> LENGTH: 1434
<212> TYPE: PRT
<213> ORGANISM: Plasmodium falciparum

<400> SEQUENCE: 31

Met Asn Asn Ile Arg Met Gln Phe Met Asn Lys Lys His Asn Asn Ser
1               5                   10                  15
Ala His Phe Glu Lys Phe Pro Cys Thr Thr Asn Ile Pro Tyr Ser Val
            20                  25                  30
Gln Asn Asn Phe Asn Leu Glu Lys Asp Thr Leu Ile Lys Asn Phe Glu
        35                  40                  45
Asp Lys Asn Glu His Ile Asn Lys Lys Ser Phe Asn Lys Asn Leu Gly
    50                  55                  60
Asn Leu Ile Tyr Asn Ile Ser Lys Leu Ile Leu His Asn Ser Asn Asn
65                  70                  75                  80
```

```
Asn Asn Ser Asp Gly Asn Asn Ile Asn Ser Lys Asn Ser Asp Thr Asn
                85                  90                  95

His Asn Ile Thr Asn Asn Lys Ser Ser Asn Asn Asn Thr Thr Asn His
            100                 105                 110

Asn Thr Thr Asn His Ser Ile Thr Asn Lys Asn Ile Thr Asn His Asn
            115                 120                 125

Ile Ala Asn Pro Asn Asn Asn Pro Asn Asp Asn Pro Lys Asn Asn
130                 135                 140

Tyr Lys Asp Lys Asn Asn Asn Lys Asn Asn Lys Asn Asn Asn Lys
145                 150                 155                 160

Asn Asn Asn Lys Asn Asn Lys Asn Asn Lys Asn Asn Asn Lys
                165                 170                 175

Asn Asn Asn Asn Asn Lys Asn Asn Leu Asn Ser Asn Ile Thr Cys Ser
                180                 185                 190

Glu Tyr Asn Leu Leu Ser Thr Asn Lys Lys Asn Gln Asp Ile Thr Gln
            195                 200                 205

Ala Leu Gly Asp His Ile Thr Ser Ile Thr Met Asn Asn Ile Glu Ser
210                 215                 220

Asn Asn Phe Leu Val Gly Asp Glu Asn Asn Gly Phe Tyr Gln Ile Leu
225                 230                 235                 240

Asn Asn Val Asp Tyr Asn Lys Lys Glu Lys Lys Asn Phe Ile Asn
            245                 250                 255

Asn Lys Cys Asn Ser Asn Ile His Met Asn Asn Ile Glu Asn Gln Leu
            260                 265                 270

Tyr Asn Asn Val Asn Asn Ile Ile Pro Met Val Ser Lys Asn Lys Tyr
            275                 280                 285

Asn Leu Phe Thr Asn Asn Glu Asn Tyr Asn Gln Glu Asn Asp Lys Tyr
            290                 295                 300

Asn Glu Lys Leu Phe Asn Asn Ser Val Asn Phe Cys Asn Ile Pro Asn
305                 310                 315                 320

Tyr Glu Gln Glu Lys Lys Lys Glu Ile Glu Gly Ser Glu Asn Tyr
                325                 330                 335

Lys Met Asn Asp Val Ser Gln Leu Thr Gln Met Asn Tyr Met Tyr Arg
            340                 345                 350

Asn Ile Asp Tyr Ser Lys Glu Lys Val Glu Glu Glu Ser Phe Glu Lys
            355                 360                 365

Asn Val Val Asp Phe Glu Glu Asn Val Pro Glu Phe Met Asn Glu Tyr
            370                 375                 380

Lys Leu Tyr Asn Glu Lys Val Lys His Asp Asn Ile Asn Asn Gln Ile
385                 390                 395                 400

Ile Lys Glu Ile Lys Lys Asn Lys Gly Asn Tyr Asn Phe Lys Asn Ile
                405                 410                 415

Val Ile Thr Asn Ile Phe Leu Gly Asn Ile Pro Pro Asn Ile Thr Glu
            420                 425                 430

Glu Arg Leu Lys Asn Val Leu Glu Ile Phe Gly Tyr Ile Ile His Ile
            435                 440                 445

Glu Tyr Lys Trp Ser Ile Asp Lys Trp Ser Tyr Ala Phe Val Tyr Phe
            450                 455                 460

Ile Asp Glu Lys Cys Ala Ile Asn Ala Val Asn Phe Leu Asn Gln Lys
465                 470                 475                 480

Lys Phe Phe Asp Asn Ser Pro Asn His Lys Leu Ile Cys Phe Ile Val
                485                 490                 495

Ser Lys Gln Ile Pro His Gln Asn Thr Met His Tyr Ser Lys Glu Asn
```

-continued

```
                500             505             510
Phe Ser Leu Leu Lys Asp Gly Pro Pro Gly Ala Asn Leu Phe Leu Tyr
        515                 520                 525
Gly Ile Pro Leu Lys Trp Thr Glu Leu Asn Leu Ile Gln Leu Val Asn
        530                 535                 540
Lys Tyr Gly His Val Val Gly Leu Arg Ile Pro Tyr Ile Ser Lys Glu
545                 550                 555                 560
Asn Asp Lys Lys Gln Gly Asn Arg Gly Phe Gly Phe Val Ser Tyr Asp
                565                 570                 575
Asn Lys Lys Ser Ala Ile Glu Ala Phe Glu Glu Leu Ser Lys Met Tyr
                580                 585                 590
Ile His Gly Lys Leu Leu Lys Val Gln Leu Lys Asn Gly Glu Glu His
                595                 600                 605
Leu Leu Pro Ala Lys Leu Lys Asn Ile Tyr Asn Thr Asn Lys Asn Lys
        610                 615                 620
Ala Lys Asp Val Thr Asn Leu Lys Thr Ala Gln Ser Leu Val Ser Thr
625                 630                 635                 640
Thr Asp Thr Leu Asn Thr Phe Asn Ser Leu Thr Ser Glu Val Lys
                        645                 650                 655
Lys Lys Leu Lys Asn Asn Lys Cys Ser Asn Asn Asn Met Lys Ser Ser
                660                 665                 670
Val Phe Ile Ser Asn Lys Asn Ile Asn Asn Asn Asn Asn Ser
                675                 680                 685
Thr Ile Tyr Asn Lys Ala Asn Asn Ser Asn Thr Gln His Leu Ser Ile
        690                 695                 700
Pro Asp Thr Asn Ser Ser Lys Ser Leu Leu Glu Asn Glu Tyr Lys Asn
705                 710                 715                 720
Lys Phe Pro Leu Asn Asn Ser Asn Asn Cys Asp Ser Val Pro Ser Ile
                725                 730                 735
Tyr Pro Lys Met Phe Thr Asn Tyr Ser Asp Lys Tyr Asp Leu Asn Val
                740                 745                 750
Thr Thr Glu Lys His Phe Pro Ile Tyr Ala Ser Lys Leu Pro Gln Asn
                755                 760                 765
Asn Gly Ala Asn Leu Cys Leu Ser Lys Glu Leu Asn Thr Gly Gly Glu
        770                 775                 780
Phe Cys Ser Tyr Thr Ile Asn Glu Asn Asn Ser Phe Glu Gly Lys Asp
785                 790                 795                 800
Thr Asn Lys Lys Asn Cys Gly Lys Met Leu Lys Glu Ala Asp Asp Ile
                805                 810                 815
Asn Lys Asn Glu Thr Phe Phe Leu Ile Lys Glu Asn Arg Glu Asn Lys
                820                 825                 830
Tyr Ser Asn Asn Lys Asp Asn Lys Gly Glu Gln Ile Asn Thr Gln Asn
                835                 840                 845
Asp Met Ala Leu Tyr Asn Asn Met Glu Ser Asn Met Ile Thr Tyr Lys
                850                 855                 860
Asn Met Glu Glu Asn Met Val Pro Asn Lys Asn Met Glu Thr Thr Phe
865                 870                 875                 880
Ser Tyr Phe Asn Met Cys Asp Asn Asn Asn Asn Asn Asn Ser
                        885                 890                 895
Lys Ser Asn Tyr Ser Asp Ser Lys Lys Val Thr Pro Asn Ser Asn Ser
                900                 905                 910
Asn Ser Asn Ser Asn Ser Ser Ser Ser Asn Ser Ser Ser Asn
        915                 920                 925
```

-continued

```
Asn Asn His Phe Glu Lys Arg Trp Asp Lys Asn Thr Trp Lys Lys Thr
            930                 935                 940

Ser Asn Ile Gln Ser Val Glu Glu Asn Asn Lys His Asp Asn Thr Phe
945                 950                 955                 960

Phe Asn Phe Ile Asp Lys Met Asp Thr Thr Arg Cys Gln Gly Gly Asn
                965                 970                 975

Ile Arg Asn Asn Lys Tyr Ser Asn Tyr Asn Tyr Ile Glu Glu Asn Asn
                980                 985                 990

Ser Glu Lys Asn Glu Ser Ser Lys Leu Asn Asn Phe Lys Asn Gln Phe
        995                 1000                1005

Gly Ala Asn Ser Lys Asn Leu Phe Phe Phe Asn Asn Ser Asn Glu
    1010                1015                1020

Ser Glu Asn Ser Asn Ile Asn Met Tyr Asn Lys Phe Phe Val Asn
    1025                1030                1035

Glu Asn Asn Leu Tyr Ser Val Asp Glu Lys Asn Glu Arg Gln Asn
    1040                1045                1050

Ile Pro Thr Glu Lys Asn Ile Glu Leu Thr Ile Asn Arg Ile Arg
    1055                1060                1065

Asn Glu Thr Pro Ser Ser Phe Asn Glu Lys Thr Lys Asn Ile Ser
    1070                1075                1080

Ser Phe Leu Asn Asp Ile Trp Tyr Asn Asn Gly Asn Asn Asn Ile
    1085                1090                1095

Ile Met Tyr Asn Lys Asn Ser Asn Val His Asp Asn Asn Asn Asn
    1100                1105                1110

Asn Asn Ile Ile His Asn Ser Asn Ser Met His Tyr His Ile Asn
    1115                1120                1125

Asp Ile His Thr Asn Met Lys Arg Asp Asn Tyr Glu Asn Asn Asn
    1130                1135                1140

Lys Trp Asn Asn Ile Lys Gly Asn Asn Ser Asn Glu Tyr Asn
    1145                1150                1155

Tyr Lys Lys Glu Asn Asn Asn Asn Asn Asn Met Phe Tyr Tyr Asn
    1160                1165                1170

Ile Asn Asn Asn Asn Asn Asn Asn Asn Asn Asn Asn Asn
    1175                1180                1185

Asn Asn Asn Ser Glu His Ile Ser Glu Ile Asp Val Lys Gln Leu
    1190                1195                1200

Asn Asn Ile Met Glu Lys Lys Lys Glu Tyr Leu Asn Ala Val Ser
    1205                1210                1215

Lys Glu Glu Gln Glu Asn Leu Asp Asp Asn Ile Ser Lys Asn Glu
    1220                1225                1230

Tyr Met Asn Asp Lys Gln Asn Lys Thr Thr Gln Tyr Phe Lys Asn
    1235                1240                1245

Met Lys Ile Leu Phe Thr Phe Leu Asn Ile Tyr Ala Lys Gln Asn
    1250                1255                1260

Ser Leu Asp Ile Asp Asp Phe Phe Asn Asp Glu Lys Asn Met His
    1265                1270                1275

Leu Phe Glu Met Leu Ile Asn Lys Lys Gln Phe Asp Lys Asn Asp
    1280                1285                1290

Leu Glu Tyr Leu Phe Asn Met Leu Gln Leu Lys Asn Asn Glu Lys
    1295                1300                1305

Glu Lys Met Lys Lys Glu Ile Leu Asn His Asn Glu Tyr Phe Lys
    1310                1315                1320

Glu Asn Tyr Asn His Asp Lys Ile Val Tyr Thr Lys Ser Asn Thr
    1325                1330                1335
```

```
Asn Met Leu Asn Met Asn Tyr Asn Thr Pro Asn Arg Tyr Gln Gln
    1340                1345                1350

Gly Asn Asn Ile Asn Thr Asn Pro Asn Val Ala Gln Arg Asn Glu
    1355                1360                1365

Asn Asn Tyr Tyr Gly Lys Asn Asn Asp Ala Pro Tyr Asp Leu Asp
    1370                1375                1380

Ile Asn Asn Ile Ile Tyr Thr Ser Asn Asn Phe Thr Asn Leu Asp
    1385                1390                1395

Lys Tyr Glu Asn Ser Asn Phe Asn Met Glu Ile Lys Lys Ile Asn
    1400                1405                1410

Asp Met Asn Ala Tyr Asp Asn Lys Phe Ile Pro Asn Val Gln Asn
    1415                1420                1425

Asn Val Asn Lys Tyr Met
    1430

<210> SEQ ID NO 32
<211> LENGTH: 62
<212> TYPE: PRT
<213> ORGANISM: Plasmodium falciparum

<400> SEQUENCE: 32

Met Lys Asn Arg Thr Arg Ile Leu Lys Asp Ser Asn Ile Gln Thr Phe
1               5                   10                  15

Asn Thr Cys Phe Asp Asn Ile Asn Leu Asn Cys Ala Ser Leu Lys Asn
            20                  25                  30

Lys Asn Leu Lys Asn Gly Pro Ser Phe Ser Phe Tyr Glu Tyr Ala
        35                  40                  45

His Asp Arg Ser Ile Leu Ser Leu Ser Leu Asp Glu Ser Gly
    50                  55                  60

<210> SEQ ID NO 33
<211> LENGTH: 229
<212> TYPE: PRT
<213> ORGANISM: Plasmodium falciparum

<400> SEQUENCE: 33

Met Lys Val Ser Lys Leu Val Leu Phe Ala His Ile Phe Phe Ile Ile
1               5                   10                  15

Asn Ile Leu Cys Gln Tyr Ile Cys Leu Asn Ala Ser Lys Val Asn Lys
            20                  25                  30

Lys Gly Lys Ile Ala Glu Glu Lys Lys Arg Lys Asn Ile Lys Asn Ile
        35                  40                  45

Asp Lys Ala Ile Glu Glu His Asn Lys Arg Lys Lys Leu Ile Tyr Tyr
    50                  55                  60

Ser Leu Ile Ala Ser Gly Ala Ile Ala Ser Val Ala Ala Ile Leu Gly
65                  70                  75                  80

Leu Gly Tyr Tyr Gly Tyr Lys Lys Ser Arg Glu Asp Asp Leu Tyr Tyr
                85                  90                  95

Asn Lys Tyr Leu Glu Tyr Arg Asn Gly Glu Tyr Asn Ile Lys Tyr Gln
            100                 105                 110

Asp Gly Ala Ile Ala Ser Thr Ser Glu Phe Tyr Ile Glu Pro Glu Gly
        115                 120                 125

Ile Asn Lys Ile Asn Leu Asn Lys Pro Ile Ile Glu Asn Lys Asn Asn
    130                 135                 140

Val Asp Val Ser Ile Lys Arg Tyr Asn Asn Phe Val Asp Ile Ala Arg
145                 150                 155                 160
```

```
Leu Ser Ile Gln Lys His Phe Glu His Leu Ser Asn Asp Gln Lys Asp
            165                 170                 175

Ser His Val Asn Asn Met Glu Tyr Met Gln Lys Phe Val Gln Gly Leu
            180                 185                 190

Gln Glu Asn Arg Asn Ile Ser Leu Ser Lys Tyr Gln Glu Asn Lys Ala
            195                 200                 205

Val Met Asp Leu Lys Tyr His Leu Gln Lys Val Tyr Ala Asn Tyr Leu
            210                 215                 220

Ser Gln Glu Glu Asn
225

<210> SEQ ID NO 34
<211> LENGTH: 291
<212> TYPE: PRT
<213> ORGANISM: Plasmodium falciparum

<400> SEQUENCE: 34

Met Ile Lys Val Leu Leu Ala Val Leu Phe Ile Leu Ile Lys Leu Glu
1               5                   10                  15

Asn Ile Ile Gly Gln Asp Glu Lys Ser Val Lys Asn Ile Cys Val Cys
            20                  25                  30

Asp Phe Thr Asp Lys Leu Asn Phe Leu Pro Leu Glu Lys Thr Lys Ile
        35                  40                  45

Leu Cys Glu Leu Lys Pro Gln Tyr Gly Glu Asp Ile Lys Ile Ile Ala
50                  55                  60

Asn Lys Glu Tyr Glu Ile Asn Cys Met Asn Asn Ser Lys Val Phe Cys
65                  70                  75                  80

Pro Leu Lys Asp Thr Phe Ile Asn Asn Thr Asn Ile Lys Leu Tyr Ser
                85                  90                  95

Pro Lys Leu His Phe Glu Ile Lys Asp Ile Thr His Lys Gly Lys Asn
            100                 105                 110

Ala Ala Leu Tyr Tyr Leu Lys Ile Asp Glu Glu Ala Ser Asp Ile Phe
        115                 120                 125

Phe Ser Cys Ser Ile Lys Pro Lys Gln Val Ser Gly Leu Leu Glu Gly
130                 135                 140

Glu Val Arg Val Asn Leu Lys Lys His Ile Asn Glu Glu Tyr Ser Ile
145                 150                 155                 160

Phe Asn Glu Glu Glu Asp Val His Val Cys Asp Phe Ser Lys Gly Asn
                165                 170                 175

Leu Asp Ile Thr Pro Ser Ala Gly Phe Tyr Leu Lys Asn Ser Arg Asn
            180                 185                 190

Val Ser Cys Ile Tyr Arg Val Ile Pro Asn Lys Leu Phe Leu Ile Lys
        195                 200                 205

Leu Pro Lys Leu Asp Ile Val Thr Glu Lys Leu Leu Pro Ser Ile Val
210                 215                 220

Asn Cys Leu Ser Glu Phe Ser Phe Ile Asn Phe Thr Leu Lys His Val
225                 230                 235                 240

Gln Glu Gly Asp Asn Tyr Ile Ser Phe Asn Val Ile Phe Gly Glu Phe
                245                 250                 255

Lys Lys His Phe Asn Leu Thr Cys Ser Leu Asp Leu Ser Asp Phe Gln
            260                 265                 270

Gln Glu Pro Cys Asn Leu Gly Lys Thr Ala Asn Ile Thr Phe Ile Phe
        275                 280                 285

Ser Lys Trp
    290
```

<210> SEQ ID NO 35
<211> LENGTH: 1026
<212> TYPE: PRT
<213> ORGANISM: Plasmodium falciparum

<400> SEQUENCE: 35

```
Met Ala Ile Asp Pro Glu Ser Phe Tyr Gly Lys Arg Lys Asn Cys Lys
1               5                   10                  15

Ser Thr Phe Glu Glu Asn Ile Glu Lys Tyr Lys Leu Leu Arg Lys Ile
            20                  25                  30

Lys Thr His Asp Glu Gly Cys Asp Arg Lys Asn Ile Lys Lys Arg Tyr
        35                  40                  45

Phe Tyr Lys Gln His Glu Val Leu Ser Tyr Tyr Asp Asp Leu Ile Asn
    50                  55                  60

Asp Lys Asn Ile Ser Gly Tyr Thr Asp Ile Ile Ile Tyr Thr Glu Glu
65                  70                  75                  80

Met Glu Asn Gly Lys Arg Cys Phe Ile Leu Glu Ser Phe Tyr Ser Phe
                85                  90                  95

Leu Lys Tyr Tyr Cys Phe Tyr Ala Met Ser Leu Asn Glu Ile Tyr Phe
            100                 105                 110

Val Lys Asn Glu Asn Ile Asn Lys Glu Asn Thr Ile Asn Glu Gln Ile
        115                 120                 125

Gln His Asp Ile Asp Asn Lys Asn Ser Ile Asn Gly Asn Pro Asp Met
    130                 135                 140

His Leu Tyr Glu Leu Ile Leu Thr Asn Glu Lys Arg Trp Leu Tyr Phe
145                 150                 155                 160

Asp Ile Glu Tyr Asp Ile Ile Asn Asn Tyr Glu Asn Lys Glu Ser Ile
                165                 170                 175

Leu Phe Ile Phe Leu Ile Glu Phe Cys Leu Phe Ile Tyr Ser Asn Phe
            180                 185                 190

Asn Ile Lys Ile Cys Leu Asn Asp Ile Leu Ile Leu Asp Ser Ser Thr
        195                 200                 205

Asn Lys Lys Val Ser Phe His Ile Ile Ile Lys Asn Ile His Thr Leu
    210                 215                 220

Asn Asn Asp Tyr Tyr Glu Tyr Leu Ile Asp Tyr Cys Asn Phe Tyr Ile
225                 230                 235                 240

Ser Gln Asn Glu Lys Glu Gln Lys Ser Gly Asn Pro Phe Tyr Asp Lys
                245                 250                 255

Tyr Lys Asn Lys Gln Tyr Lys Arg Asn His Asn Lys Gln Asn Glu Lys
            260                 265                 270

Asn Lys Pro Lys Glu His Ile Gln Glu Tyr Glu Gln Asn Tyr Leu Leu
        275                 280                 285

Phe Asp Asp Glu Asn Ser Ile Lys His Phe Val Asp Leu Phe Leu Asn
    290                 295                 300

His Ile Ser Asp His Ile Lys Tyr Cys Glu Asn Cys Phe Leu Val Asn
305                 310                 315                 320

His Thr Thr Val Tyr Ile Glu Cys Glu Asp Leu Val Glu Leu Asn Asn
                325                 330                 335

Asn Thr Ser Phe Val Asp Thr Asn Glu Ile Tyr Asn Asn Asn Lys Glu
            340                 345                 350

Ser Gln Asn Phe Ser Asp Glu Lys Glu Asn Asn His Ser Glu Glu Asn
        355                 360                 365

Asn His Cys Asp Glu Asn Asn His Cys Asp Glu Asn Asn His Cys Asp
    370                 375                 380
```

-continued

```
Glu Asn Asn His Cys Asp Lys Asn Asn Asn Cys Glu Glu Asn Asn His
385                 390                 395                 400

Cys Asp Asp Asp Leu Gln Lys Ile Ile Asn Asp Phe Ser Glu Val Thr
            405                 410                 415

Asp Ile Gln His Ile Asn Phe Asn Ser Thr Ser Ile Pro Phe Ile Gln
            420                 425                 430

Asn Met Asn Arg Asn Asn Cys Glu Glu Lys Lys Thr Lys Gly Tyr Phe
        435                 440                 445

His Leu Tyr Lys Asn Ser Leu Val Asp Ile Ile Thr His Tyr Ile Asn
    450                 455                 460

Tyr Leu Glu Lys Leu Lys Glu Gly Glu Lys Ser Tyr Cys Asn Tyr Ile
465                 470                 475                 480

Val Leu Leu Tyr Ala Phe Lys Arg Glu Asp Asn Ser Asp Gln Asn Leu
            485                 490                 495

Val Tyr Asp Met Asn Met Leu Asn Ile Lys Lys Asn Asn Phe Val Ser
            500                 505                 510

Lys Asn Asp Leu Ile Leu Asn Asp Cys Asp Asn Thr Asn Asn Asn Tyr
        515                 520                 525

Glu Glu Asn Asn Ser Leu Leu Ile Asn Glu Lys Glu Asn Ile Ile Ile
    530                 535                 540

Glu Asp Asp Lys Tyr Met Glu Glu Leu Ile Val Leu Phe Glu Asn Thr
545                 550                 555                 560

Pro Tyr Asn Tyr Glu His Asn Glu Tyr Lys Lys Asn Asn Asn Asn Lys
            565                 570                 575

Ile His Thr Leu Lys Cys Ile Ile Asp Ser Ser Val Tyr Ser Lys Asn
            580                 585                 590

Arg Asn Phe Arg Leu Ile Phe Ser Ser Lys Lys Asn Lys Lys Asn Lys
        595                 600                 605

Leu Leu Leu Ser Thr Lys Asn Val Lys Lys Tyr Gln Lys Thr Asp Ile
    610                 615                 620

Asn Asp Ile Ile Leu Lys Ser Leu Val Thr Phe Tyr Phe Lys Ser Asp
625                 630                 635                 640

Val Asn Tyr Lys Ile Asn Glu Gly Arg Phe Cys Asn Lys Asn Leu Leu
            645                 650                 655

Asn Asn Thr Met Asn Tyr Tyr Phe Glu Asn Leu Tyr Glu Lys Lys Gln
            660                 665                 670

Ile Asn Asn Asp Ile Asn Asp Ile Asn Ile Asn Asn Thr His Asn Ile
        675                 680                 685

Asn Asn Asn Asn Asn Asn Asn Asn Ile His Asn Ile Ile Ile Asn
    690                 695                 700

Asn Asn Asn Ile His Tyr Ile Asn Ser Asp Asn Ile Lys Asn Val Asp
705                 710                 715                 720

Phe Lys Phe Asn His Met Asn Ser Ser Asn Asn Ser Phe Lys Leu Leu
            725                 730                 735

Lys His Lys Asn Ile Cys Ile Pro Lys Asn Asn Thr Phe Asp Lys Tyr
            740                 745                 750

Val Ile Gln Asn Leu Glu His Phe His Asn Ile Leu Lys Ile Leu Phe
        755                 760                 765

Phe Trp Asn Phe Glu Leu Tyr Lys Asn Phe Arg Lys Asn Lys Ile Tyr
    770                 775                 780

Leu Asn Cys Phe Gln Asn Glu Ile Lys Lys Asp Tyr Phe Tyr Lys Ile
785                 790                 795                 800

Val Arg Ile Tyr Asn Asn Met Ala Phe Glu Asn Tyr Ile Lys Glu Asp
            805                 810                 815
```

```
Asn Ser Asn Met Lys Lys Tyr Asn Glu Thr Asn Glu His Thr Phe Glu
            820                 825                 830

Glu Lys Phe Ser Leu Glu Asn Ser Lys Lys Ile Cys Gln Leu Ser Asn
            835                 840                 845

Ile Ser Glu Lys Glu Asn Glu Ser Lys Asp Lys Asn Asn Glu Pro Asn
    850                 855                 860

Gln Asn Gln Lys Glu Lys Asn Asp Lys Asn Glu Pro Thr Tyr Asn Thr
865                 870                 875                 880

Lys Cys Asp Leu Lys Ile Glu Asp Lys Asn Tyr Ile Asn Ile Asn Asn
                885                 890                 895

Asn Val Gln Leu Lys Gly Ser Asn Lys Tyr Asn Thr Ile Cys Thr Lys
                900                 905                 910

Lys Lys Asn Ile Tyr Glu Tyr Asp Leu Asp Ser Tyr Asn Asn Leu Phe
                915                 920                 925

Leu Lys Ser Glu Asn Phe Tyr Ile Asp Leu Leu Asn Glu Tyr Lys Asn
                930                 935                 940

Val Phe Ser Lys Glu Ile Arg Gln Asp Asp Leu Ser Leu Leu Ile Lys
945                 950                 955                 960

Tyr Phe Val His Ser Phe Thr Ser Asn Asn Gly Glu Tyr Ile Ile Ser
                965                 970                 975

Leu Lys Asp Asn Lys Phe Cys Lys Asn Lys Asn Arg Ser His Lys Ser
                980                 985                 990

Asn His Ile Tyr Ile Ile Tyr Asn Tyr Lys Lys Lys Leu Phe Val Gln
                995                 1000                1005

Lys Cys Phe Asp His Glu Cys Ala His Tyr Ile Ser Glu Ile Tyr
    1010                1015                1020

Tyr Leu Trp
    1025

<210> SEQ ID NO 36
<211> LENGTH: 163
<212> TYPE: PRT
<213> ORGANISM: Plasmodium falciparum

<400> SEQUENCE: 36

Met Leu Met Lys Ile Ser Arg Tyr Phe Phe Leu Leu Tyr Leu Ile Lys
1               5                   10                  15

Ala His Leu Asp Phe Phe Leu Arg Tyr Arg Thr Gly Phe Ile Arg Ser
            20                  25                  30

Arg Leu Glu Thr Tyr Ile Gly Asn Ser Asp Val Arg Tyr Asn Lys Ser
        35                  40                  45

Phe Ile Asn Asn Arg Leu Leu Asn Glu His Ala His Cys Asp Ala Trp
    50                  55                  60

Ser Glu Trp Ser Ala Cys Ser Lys Thr Cys Asp Tyr Gly Ile Lys Ile
65                  70                  75                  80

Arg Val Lys Ile Ser Thr Asp Gln Thr Lys Ser Lys Ala Cys Ser Asn
                85                  90                  95

Ile Thr Glu Ser Thr Ile Cys His Glu His Ile Cys Pro Arg Thr Phe
            100                 105                 110

Glu Glu Ala Glu Glu Thr Tyr Leu His Asn Lys Glu Lys Glu Lys Lys
        115                 120                 125

Lys Lys Phe Arg Thr Arg Tyr Ile Leu Ile Phe Thr Ile Phe Ser Val
    130                 135                 140

Val Asn Ile Val Val Leu Leu Ile Cys Val Ile Leu Ser Ile Lys Lys
145                 150                 155                 160
```

Lys Ile Ile

<210> SEQ ID NO 37
<211> LENGTH: 245
<212> TYPE: PRT
<213> ORGANISM: Plasmodium falciparum

<400> SEQUENCE: 37

Met Lys Lys Lys Asn Asn Asn Lys Leu His Tyr Leu Asp Ser Lys Gly
1               5                   10                  15

Lys Leu Tyr Thr Ser Gly Leu Arg Ser Asp Thr Lys Glu Lys Tyr Gly
            20                  25                  30

Glu Ile Pro Ser Ser Asn Lys Asn His Asn Leu Ile Glu Lys Tyr Asn
        35                  40                  45

Glu Leu Gln Ser Leu Leu Ser Lys Glu Glu Glu Lys Tyr Asp Phe Val
    50                  55                  60

Lys Asn Glu Leu Gly Asp Leu Gln Lys Gln Lys Asp Leu Leu Lys Trp
65                  70                  75                  80

His Leu Cys Asn Asn Ile Lys Lys Leu Ser Met Lys Arg Ser Asp Tyr
                85                  90                  95

Lys Phe Lys Thr Glu Thr Lys Ser Lys Leu Glu Ser Lys Leu Lys Ser
            100                 105                 110

Leu Lys Asp Met Asn Lys Ile His Lys Phe Glu His Asp Thr Leu Glu
        115                 120                 125

Glu Leu Val His Lys Met Glu Gln Gly Leu Glu Thr Lys Met Tyr Ile
    130                 135                 140

Lys Asn Asp Ile Glu Asn Ile Phe Asn Glu Cys Ile Asn Lys Lys Asp
145                 150                 155                 160

Glu Tyr Leu Lys Asp Ile Thr Gln Glu Arg Ile Ser Val Phe Lys Glu
                165                 170                 175

Arg Lys Lys Arg Gln Asn Gln Leu Gln Lys Leu Leu Ile Met Lys
            180                 185                 190

Gln Glu Asn Asn Lys Asn Tyr Asn Ile Asn Tyr Leu Lys Lys Tyr Glu
        195                 200                 205

Ser Asn Leu Met Asn Glu Ile Asn Ser Tyr Lys Asn Tyr Lys Asp Phe
    210                 215                 220

Glu Thr Lys Ile Ala Met Asp Leu Ile Asp Asp His Ser Leu Asn Asp
225                 230                 235                 240

Leu Tyr Val Thr Trp
            245

<210> SEQ ID NO 38
<211> LENGTH: 163
<212> TYPE: PRT
<213> ORGANISM: Plasmodium falciparum

<400> SEQUENCE: 38

Met Leu Arg Cys Lys Ile Lys Gln Met Asp Val Leu Phe Phe Leu Leu
1               5                   10                  15

Asn Gly Lys Arg Tyr Asn Thr Ile Ile Arg Arg Glu Gln Ser Lys Glu
            20                  25                  30

Gly Lys Asn Cys Tyr Ile Lys Asp Glu Glu Leu Lys Lys Asn Phe Glu
        35                  40                  45

Lys Ile Ser Lys Gly Ser Pro Pro Arg Ala Lys Ile Asn Asn Ile Ile
    50                  55                  60

Asn Phe Leu Met Arg Ser Asn Ile Leu Ser Asn Thr Trp Ser Lys Leu

```
                65                  70                  75                  80
Glu Ile Ile Asp Glu Met Tyr Lys Arg Lys Ile Asp Lys Glu Leu Ser
                    85                  90                  95

Phe His Ile Asn Val Leu Tyr Gly Met Gly Ser Lys Gly Ile Asn Leu
                100                 105                 110

Asn Lys Lys Gly Ile Ile Pro Pro Ile Leu Phe Leu Pro Leu Ile Asp
                115                 120                 125

Tyr Glu Gln Phe Lys Tyr Phe Val Lys Val Met Gln Ile Ala Asp Arg
            130                 135                 140

Glu Lys Thr Tyr Asn Ile His Lys Gln Gln Glu Tyr Leu His Asn Phe
145                 150                 155                 160

Phe Lys Lys

<210> SEQ ID NO 39
<211> LENGTH: 478
<212> TYPE: PRT
<213> ORGANISM: Plasmodium falciparum

<400> SEQUENCE: 39

Met Tyr Val Leu Val Leu Ile His Met Cys Tyr His Phe Thr Met Lys
1               5                   10                  15

Arg Lys Lys Leu Phe Val Tyr Phe Ile Phe Leu Ser Phe Ile Ile Asn
                20                  25                  30

Phe Asn Phe Asn Ile Asn Ile Asn Phe Val Cys Ser Asn Val Ile Gln
            35                  40                  45

Asp Val Ile Ser Ile Gly Asn Val Asp Ile Cys Val Val Asn Val Asn
50                  55                  60

Ser Asp Glu Ala Gln Glu Cys Ile Leu Asn Asn Glu Phe Gly Lys Leu
65                  70                  75                  80

Leu Leu Phe Val Cys Asn Met Asn Asp Ala Phe Ser Thr Thr Ala Lys
                85                  90                  95

Thr His Pro Glu Asn Cys Pro Ser Arg Ala Phe Val Asn Gln Ser Asn
            100                 105                 110

Pro Thr Glu Asn Ser Pro Glu Val Asp Thr Tyr Ser Ile Tyr Pro Asn
        115                 120                 125

Leu Phe Gly Thr Asn Glu Asn Arg Leu Asn Asp Thr Tyr Ser Leu Tyr
    130                 135                 140

Ser Thr Pro Tyr Ser Asn Met Asp Ile Asp Phe Ser Cys Leu Cys Tyr
145                 150                 155                 160

Gly Asp Lys Gln Asp Lys Val Lys His Ile Met Arg Ile Asn Ile Lys
                165                 170                 175

Lys Thr Arg Lys Lys Ile Lys Gly Cys Asp Phe Gly Asn Ile Pro
            180                 185                 190

Ser Lys Arg Asp Leu Thr Asn Ser Leu Ser Leu Asn Glu Arg Ser Ser
        195                 200                 205

Cys Ile Ile His Ala Tyr Ser Asn Asp Val Leu Gly Ile Asn Cys Phe
    210                 215                 220

Lys Lys Glu Ile Asn Asn Ser Tyr Asn Asn Leu Glu Leu Asn Pro
225                 230                 235                 240

Ser Asn Cys Phe His Asp Val Tyr Phe Gly Ala Asp Leu Ile Leu Asn
                245                 250                 255

Ser Lys Asn Val Ile Pro Asn Ser Arg Val Ile Pro Asp Pro Ser Ser
            260                 265                 270

Asp Val Lys Leu Ser Arg Asn His Ser Phe Ser Ser Tyr Leu Ile Leu
        275                 280                 285
```

```
Pro Asn Asn Leu Thr Glu Asn Ile Lys Ile Ser Cys Thr Cys Lys Arg
    290                 295                 300
Asp Glu Phe Val Gly Thr Met Ile Ile Tyr Thr Lys Asn Ile Asn Ser
305                 310                 315                 320
Leu Met Phe Asp Asn Asn Asn Asn Asn Asp Glu Glu Gln Ile Phe
                325                 330                 335
Gln Asn Lys Tyr Met Lys Lys Glu Tyr Lys Lys Asp Glu Gly Asn
                340                 345                 350
Glu Tyr Asp Lys Lys Met Asn Thr Asp Asp Asn Tyr Ile Asn Asn Glu
                355                 360                 365
Glu His His Asn Asn Asn Gln Tyr Asn Asn Tyr Glu Asn Lys Ile Asn
                370                 375                 380
Asn Val Asn Tyr Asn Tyr Asp Asp Ile Ser Lys Tyr Ile Asn Glu His
385                 390                 395                 400
Tyr Lys Asn Tyr Asp His Glu Lys Asn Ser Lys Asn Ser Tyr Lys Thr
                405                 410                 415
Asn Thr Asn Ile His Asp Gln Tyr Asp Thr Tyr His Tyr Asn Asn Lys
                420                 425                 430
Tyr Asp Leu His Ser Asp Arg Thr Arg Ile Arg Thr Arg Thr Phe Trp
                435                 440                 445
Gln Asn Leu Phe Gly Leu Ser Ser Ser Lys Tyr Ile Leu Phe Asn Asn
                450                 455                 460
Phe Leu Ile Leu Phe Ile Phe Leu Ile Tyr Tyr Ser Thr
465                 470                 475

<210> SEQ ID NO 40
<211> LENGTH: 2416
<212> TYPE: PRT
<213> ORGANISM: Plasmodium falciparum

<400> SEQUENCE: 40

Met Lys Leu Ser Asn Asp Pro Asn Phe Gln Ile Asp Glu Asp Ser Leu
1               5                   10                  15
His Met Asn Asn Ile Asp Gln Asn Lys Ile Glu Glu Asp Val Ile Pro
                20                  25                  30
Asp Ser Lys Ala Val Ser Asp Tyr Asn Val Asn Asn Gln Glu Val Gln
                35                  40                  45
Arg Lys Ser Leu Ser Leu Lys Glu Asp Glu Lys Met Arg Ile Asn Ser
50                  55                  60
Val Gly Val Tyr Lys Val Lys Arg Glu Glu Tyr Lys Asn Asn Met His
65                  70                  75                  80
Pro Arg Asn Val Gln Gln Lys Asn Ile Asn Gln Met Tyr Lys Gln Tyr
                85                  90                  95
Lys Asn Ile Asn Thr Lys Val Tyr Asp Glu Asn Ile Glu Tyr His Arg
                100                 105                 110
Lys Asn Tyr Glu Glu Asn Leu Tyr Gly Ser Thr Lys Tyr Asp Arg Ile
                115                 120                 125
Glu Glu Leu Glu Asn Tyr Ile Asn Ile Asn Asn Val Thr Ser Val Cys
                130                 135                 140
Ser Leu Arg Ile Lys Leu Trp Glu Ala Leu Leu Leu Tyr Val Asn Asn
145                 150                 155                 160
Leu Asn Val Glu Phe Ile Tyr Phe Ile Ile Ser Cys Leu Lys Glu Ile
                165                 170                 175
Glu Val Tyr Trp Gly Gln Glu Ala Thr Glu Asn Leu His Glu Ile Ile
                180                 185                 190
```

```
Asn Leu Ile Asn Asp Lys Lys Tyr Lys Glu Val Ser Asn Lys Ile Arg
            195                 200                 205

Glu Thr Leu Ser Ser Leu Ser Val Thr Thr Gly Lys Ile Thr Asp Glu
            210                 215                 220

Asn Pro Phe Phe Tyr Thr Leu Ile Val Ser Ser Lys Arg Asp Glu Asn
225                 230                 235                 240

Arg Ser Asn Ser Thr Asn Asn Tyr Ser Asp Leu Thr Cys Glu Leu Asn
                245                 250                 255

Lys Ile Leu Gln Tyr Glu His Asn Arg Leu Ser Asn Gln Ile Asn Asn
            260                 265                 270

Lys Thr Leu Glu Tyr Lys Ile Glu Val Ser Asn Ala Arg Glu Ala
            275                 280                 285

Leu Leu Ala Cys Leu Ile Asn Pro Gln Ile Leu Ser Val Val Ile Val
            290                 295                 300

Asp Asn Leu Asn Ile Asp Glu Glu Arg Val Glu Glu Lys Asp Ile Tyr
305                 310                 315                 320

Asn Tyr Tyr Asn Asp Glu Asn Asn Ser Val Arg Asn His Ser Val Ala
                325                 330                 335

Asn Ser Tyr Val Tyr Asn Ser Ser Ile Val Asn Asn Val His Met Pro
            340                 345                 350

Ile Asn Lys Ser Asn Met Asn Asn Ile Ala Leu Asn Ala Leu Ala Leu
            355                 360                 365

Asn Asn Lys Asp Ile Tyr Met Lys Gly Met Met Gly Thr Ser Arg His
            370                 375                 380

His Asn Asn Asn Asn Asn Asn Asn Asn Asn Asn Asn Asn Asn Asn Asn
385                 390                 395                 400

Asn Asn Asn Asn Asn Asn Asn Asn Asn Asn Asn Asn Asn Asn Asn Asn
                405                 410                 415

Asn Asn Ser Gly Val Asn Asp Phe Arg Lys Asn Lys Ser Tyr Asn Tyr
            420                 425                 430

Ser Asn Asn Tyr Ile Asn Asn Asn Met Asn Leu Asn Lys Tyr Asn Asp
            435                 440                 445

Ser Asn Lys Lys Asn Ile Ile Asn Asn Val Asn Asn Leu Asn Asn Met
            450                 455                 460

Tyr Asn Leu Asn Asn Met Tyr Asn Met Tyr Asn Ile Cys Asn Ile Asn
465                 470                 475                 480

Tyr Asn Asn Asp Asn Ile Cys His His Gln Phe Lys Glu Tyr Lys Phe
                485                 490                 495

Asn Ile Ala Asp Phe Val Leu Gly Tyr Val Gln Leu Val Ser Ala Pro
            500                 505                 510

Leu Glu Lys Met Lys Lys Gly Phe Asn Ser Leu Val Ile Leu Ile Lys
            515                 520                 525

Ser Ile Ala Tyr Ile Arg Ser Ser Val Asp Ile Phe Cys Val Cys Thr
            530                 535                 540

Ser Ile Thr Leu Asp Ser Leu Gln Ser Val Asn Asn Met Ile Ile Arg
545                 550                 555                 560

Ile Phe Thr Thr His Asp Asp His Ser Asp Leu His Glu Ser Ile Leu
                565                 570                 575

Asp Gly Val Lys Lys Ile Lys Thr Pro Phe Phe Asn Ala Leu Lys
            580                 585                 590

Ala Tyr Ala Glu Arg Pro Ile Gly Val Phe His Ala Leu Ala Ile Ser
            595                 600                 605

Lys Gly Asn Ser Val Arg Arg Ser Arg Trp Ile Gln Ser Leu Leu Asp
```

-continued

```
            610                 615                 620
Phe Tyr Gly Val Asn Leu Phe Lys Ala Glu Ser Ser Ala Thr Cys Gly
625                 630                 635                 640

Gly Leu Asp Ser Leu Leu Asp Pro His Gly Ser Leu Lys Asp Ala Gln
                645                 650                 655

Ile Met Ala Ala Arg Ala Tyr Ser Ser Lys Tyr Cys Phe Phe Val Thr
                660                 665                 670

Asn Gly Thr Ser Ser Asn Lys Ile Val Met Gln Ala Leu Val Lys
                675                 680                 685

Pro Gly Asp Ile Ile Leu Val Asp Arg Ala Cys His Lys Ser His His
690                 695                 700

Tyr Gly Phe Val Leu Ser Gln Ala Phe Pro Cys Tyr Leu Asp Pro Tyr
705                 710                 715                 720

Pro Val Ser Lys Tyr Gly Ile Tyr Gly Ala Val Pro Ile Tyr Val Ile
                725                 730                 735

Lys Lys Thr Leu Leu Glu Tyr Arg Lys Ser Asn Lys Leu His Leu Val
                740                 745                 750

Arg Leu Ile Ile Leu Thr Asn Cys Thr Phe Asp Gly Ile Val Tyr Asn
                755                 760                 765

Val Lys Arg Val Met Glu Glu Cys Leu Ser Ile Lys Pro Asp Leu Ile
770                 775                 780

Phe Leu Phe Asp Glu Ala Trp Phe Ala Tyr Ala Cys Phe His Pro Ile
785                 790                 795                 800

Leu Lys Phe Arg Thr Ala Met Thr Val Ala Glu Lys Met Arg Ser Thr
                805                 810                 815

Glu Gln Lys Arg Ile Tyr Glu Lys Ile His Lys Leu Leu Lys Lys
                820                 825                 830

Phe Gly Asn Val Lys Ser Leu Asn Asp Val Pro Glu Glu Leu Leu
835                 840                 845

Lys Thr Arg Leu Tyr Pro Asn Pro Asn Glu Tyr Lys Val Arg Val Tyr
850                 855                 860

Ala Thr Gln Ser Ile His Lys Ser Leu Thr Ser Leu Arg Gln Gly Ser
865                 870                 875                 880

Val Ile Leu Ile Ser Asp Asp Asn Phe Glu Ser His Ala Tyr Thr Pro
                885                 890                 895

Phe Lys Glu Ala Tyr Tyr Thr His Met Ser Thr Ser Pro Asn Tyr Gln
                900                 905                 910

Ile Leu Ala Thr Leu Asp Ala Gly Arg Ala Gln Met Glu Leu Glu Gly
                915                 920                 925

Tyr Gly Leu Val Glu Lys Gln Thr Glu Ala Ala Phe Leu Ile Arg Lys
930                 935                 940

Glu Leu Ser Glu Asp Pro Ile Ile Ser Lys Tyr Phe Arg Ile Leu Asn
945                 950                 955                 960

Ala Asp Asp Leu Ile Pro Asp Arg Leu Arg Gln Cys Thr Val Ser Tyr
                965                 970                 975

Met Lys Arg Lys His Val Asn Asn Asn Asn Lys Lys Lys Asn Asn
                980                 985                 990

Gly Asp Asp Asp Asp Asn Asp Asp Asp Asn Asn Asn Asp Asp Asn Asn
                995                 1000                1005

Asn Asn  Asp Asp Asp Asn Asn  Asp Asp Asp Asn  Asn Asn Asp
    1010                1015                1020

Asp Asp Asn Asn Asn Asp Asp  Asp Asn Asn Asn  Asn Asp Ile
                1025                1030                1035
```

-continued

```
Asn His Asp Asn Asn His Asn Asn His Asn Val Gly Asn Gln
1040                1045                1050
Lys Lys Tyr Asn Asn Ser Leu Asn Ser Arg Cys Ser Ala Asp Glu
1055                1060                1065
Asp Ala Thr Gly Ser Tyr Ile Phe Asn Asn Asn Ile Lys Glu Ile
1070                1075                1080
Glu Asp Asn Thr Glu Ser Ala His Lys Ile Pro Ile Glu Tyr Val
1085                1090                1095
Asp Gly Lys Leu Phe Asn Val Ile Lys Tyr Pro His Glu Tyr Met
1100                1105                1110
Ser Glu Asp Asn Ser Pro Asn Asn Ile His Thr Asn Leu Gln Lys
1115                1120                1125
Ser Asn Met Lys Leu Leu Asn Asp Asn Asn Ile Glu Val Gly Arg
1130                1135                1140
Ile Leu Glu Ser Ser Asn Cys Phe Lys Tyr Ser His Asn Val Asn
1145                1150                1155
Met Cys Asn Val Leu Ile Asn Asn Ser Ser Tyr Arg Asn Asn Ser
1160                1165                1170
Asp Asn Lys Lys Asp Gly Ser Glu Lys Arg Tyr Val Tyr Asp Glu
1175                1180                1185
Tyr Asn Glu Ser Val Lys Glu Tyr Ser Pro Asn Asp Asp Thr Asn
1190                1195                1200
Tyr Asp Ala Thr Tyr Lys Gly Tyr Val Asn Gly His Val Asn Val
1205                1210                1215
Asn Met Asn Asn Leu Met Asn Gly Asp Asn Lys Cys Asp Trp Tyr
1220                1225                1230
Asp Thr Asn Asp Cys Asp Asp Asn Lys Asn Ile Tyr Cys Asp Lys
1235                1240                1245
Ala Asn Asn Ile Tyr Tyr Tyr Gly Asn Asn Tyr Lys Ser Lys Glu
1250                1255                1260
Glu Lys Arg Lys Lys Ala Asn Tyr Gly Ser Val Asn Ser Ile Cys
1265                1270                1275
Cys Asp Ser Thr Tyr Cys Met Asp Thr Ser Asp Asp Asn Leu Ser
1280                1285                1290
Ser Asn Glu Cys Ser Ser Tyr Ile Asp Asn Asn Asn Asn Asn Asn
1295                1300                1305
Asn Asn Asn Asn Asn Ile Asn Asn Asn Ser Asn Asn Asn Asn Ser
1310                1315                1320
Cys Ser Gly Asp Met Lys Asn Phe Leu Glu Tyr Phe Glu Arg Ser
1325                1330                1335
Trp Leu Ser Glu Asp Glu Phe Val Leu Asp Pro Thr Arg Ile Thr
1340                1345                1350
Leu Phe Thr Gly Tyr Ser Gly Ile Asp Gly Asp Thr Phe Lys Val
1355                1360                1365
Lys Trp Leu Met Asp Lys Tyr Gly Ile Gln Ile Asn Lys Thr Ser
1370                1375                1380
Ile Asn Ser Val Leu Phe Gln Thr Asn Ile Gly Thr Thr Gly Ser
1385                1390                1395
Ser Cys Leu Phe Leu Lys Ser Cys Leu Ser Leu Ile Ser Gln Glu
1400                1405                1410
Leu Asp Gln Lys Lys Ser Leu Phe Asn Glu Arg Asp Leu Asn Gln
1415                1420                1425
Phe Asn Glu Ser Val Tyr Asn Leu Val Tyr Asn Tyr Ile Asp Leu
1430                1435                1440
```

```
Ser Val Phe Ser Ala Phe His Pro Leu Phe Lys Lys Arg Tyr Glu
    1445            1450            1455

Asp Lys Asn Ile Phe Asn Asn Glu Gly Asp Leu Arg Lys Ala Phe
    1460            1465            1470

Tyr Leu Ala Tyr Glu Glu Asp Tyr Val Glu Tyr Ile Leu Leu Asn
    1475            1480            1485

Asn Leu Lys Asp Arg Ile Arg His Lys Glu Met Ile Val Ala Ala
    1490            1495            1500

Ser Phe Ile Ile Pro Tyr Pro Pro Gly Phe Pro Val Leu Val Pro
    1505            1510            1515

Gly Gln Ile Ile Ser Glu Glu Ile Val Asn Tyr Leu Ser Gly Leu
    1520            1525            1530

Ser Val Lys Glu Ile His Gly Tyr Asp Glu Asn Ile Gly Phe Arg
    1535            1540            1545

Cys Phe Tyr Asn Phe Ile Leu Asp Tyr Tyr Glu Thr Ile Asn Ile
    1550            1555            1560

Asn Asp Pro Tyr Ser Met Tyr Gln Pro Met Asp Lys Arg Leu Tyr
    1565            1570            1575

Glu Gln Leu Lys Glu Lys Tyr Leu His Ser Lys Lys Asp Leu His
    1580            1585            1590

Asp His Arg Leu Ser Asn Leu Tyr Met Tyr Asp Lys Glu Thr Met
    1595            1600            1605

Lys Met Lys Lys Val Tyr Ile His Asn Asn Gly Ser Tyr Ser Val
    1610            1615            1620

Asp Pro Tyr Gly Tyr Ile Ser Asp Leu Asn Glu Glu Glu Gly Val
    1625            1630            1635

Ile Ile Asn Ala Gln His Val Asn Asn Lys Lys Asp Ile Phe Phe
    1640            1645            1650

His Asn Lys Arg Glu Asn Lys Ile His Asn Asn Asn Asn Asn Asn
    1655            1660            1665

Asn Lys Lys Lys Thr His Val Asn Asn Lys Ser Asp Val Met Ile
    1670            1675            1680

Ile Ile Pro Ser Glu Asp His Leu Asn Pro His Ile Ile His Lys
    1685            1690            1695

Met Ser Asp Asn Asn Arg Lys Ile Ile Asn Thr Lys Asn Tyr Asn
    1700            1705            1710

Asn Ile Ile Asn Tyr Thr Ser Asn Ile Leu Asn Asn Lys Gln Asp
    1715            1720            1725

His Ala Phe Tyr Asn Ser Gly Ser Pro Arg Thr Ser Val Cys Ser
    1730            1735            1740

Asn His Lys Asn Ile Asn Thr Asn Gly Met Phe Asn Asn Leu Met
    1745            1750            1755

His Lys Asn Asp Glu Arg Gly Asn Asn Lys Ser Met Ser Lys His
    1760            1765            1770

Glu Lys Asn Asn His Ser Leu Tyr Leu Thr Asn Gly Val Asn Thr
    1775            1780            1785

Lys Ser His Lys Lys Met Tyr Ile Glu Ser Tyr Asn Pro Lys Gly
    1790            1795            1800

Asp Arg Glu Leu Asp Phe Gln Asn Lys Ser Thr Met Tyr Asn Asn
    1805            1810            1815

Met Asp Asp Val Ala Tyr His Gly Lys His Tyr His Ser Val Lys
    1820            1825            1830

Lys Asp Ile Ile Asn Asn Asp Thr Ser Leu Lys Glu Asn Arg Tyr
```

1835                1840                1845

Asn Lys Asn Ile Met Ser Cys Lys Thr Asn Asn Thr Gly Thr
    1850                1855                1860

Asn Ser Lys Asn Glu Arg Lys Lys Lys Ser Phe Gly Ile His
    1865                1870                1875

Met Ser Leu Ser Pro Asn Asn His Leu Lys Gly His Asp Thr
    1880                1885                1890

Ser Arg Tyr Ser Asp Ser Thr Ser Ile Cys Glu Asp Asn Ile Asn
    1895                1900                1905

Asp Asp Asn Ile Asp Asp Thr Gly His Lys Lys Met Asp Ala Ile
    1910                1915                1920

Asp Gly His Asn Ile Arg Asn Lys Lys Ser Asp Ile Lys Glu Ile
    1925                1930                1935

Leu Tyr Asn Asn Asn Asp Asn Asp Ile Tyr Gly Asn Ala Cys Asp
    1940                1945                1950

Val Ile Ala Cys Lys Glu Asn Met Tyr Ile Asn Glu Lys Asp Ser
    1955                1960                1965

Tyr Ser Asp Val Val Leu Ile Lys Arg Asn Asn Lys Ile Asn Lys
    1970                1975                1980

Asn Asp Gly Asn Tyr Tyr Tyr His Asn Asn Phe Ser Asn Asn Ser
    1985                1990                1995

Lys His Ser Asn Val Val Pro Ile Leu Asn Lys Gly Asn Val Leu
    2000                2005                2010

Leu Asn Asn Thr Asn Val Lys Lys Asn Asp Tyr Cys Val Ile Gln
    2015                2020                2025

Lys Asp Asn Lys Ile Met Ser Arg Asn Asn Met Ser Thr Lys Tyr
    2030                2035                2040

Ala Ser Ser Asn Glu Tyr Asn Lys Lys Lys Glu Glu Gly Ala Tyr
    2045                2050                2055

Tyr Ser Asp Ser Ser Lys Asn Ile His Asp Asn Leu Phe Leu Lys
    2060                2065                2070

Arg Lys Glu Asn Glu Asn Ile Glu His Ile Thr Lys Asp Val Met
    2075                2080                2085

Lys Lys Pro Leu Ile Gly Tyr Asn Lys Glu Glu Ile Lys Lys Ile
    2090                2095                2100

Asn Glu Phe Leu Lys Ile Asn Arg Arg Ile Ala Asp Glu His Met
    2105                2110                2115

Gly Asp Ile Gln Ile Lys Leu Asp Glu Glu Ile Leu Glu Arg Lys
    2120                2125                2130

Glu Glu Asp Met Tyr Asp Asn Lys Asn Asp Met Phe Asn Val Asn
    2135                2140                2145

Ile Lys Ser Asn Ile Glu Asp Val Ala Asp Asn Ser Pro Gln Met
    2150                2155                2160

Asn Ile Asp Lys Lys Asp Ile Ile Val Leu Ala Ser Asn Asn Asn
    2165                2170                2175

Tyr Cys Asp Ile Asn Asn Asn Asn Asn Asn Asn Cys Asn
    2180                2185                2190

Tyr Val Lys Lys Cys Glu Thr Asn Lys Cys Asp Ile Tyr Ile Thr
    2195                2200                2205

Lys Asp Asn Leu Glu Glu Ile Gln Lys Thr Asn Met Asn Ile Lys
    2210                2215                2220

Lys Asp Val Glu His Asp Ile Gly Glu Tyr Asn Phe Asp Ser Val
    2225                2230                2235

```
Ile Asn Gln Ser Val Asn Asn Ile Asn Ile Leu Ile Asp Lys
2240                2245                2250

Tyr Asn Cys Asn Asn Ile Lys Lys Leu Asn Asn Ser Asn Ile Cys
2255                2260                2265

Glu Asn Asn Asn Leu Leu Ser Asn Asp Asn Asn Tyr Ile Val Asn
2270                2275                2280

His Lys Val Tyr Ser Ser Ile Glu Asn Thr Asn Thr Leu Asn Cys
2285                2290                2295

Asn Asn Ile Lys Thr Asp Asn Asn Ser Asn Asn Asn Asn Asn Asn
2300                2305                2310

Met Pro Tyr Lys Glu Asn Lys Val Arg Gly Leu Ile Ile Cys Glu
2315                2320                2325

Asn Asp Ile Asn Lys Asn Thr Gly Arg Gln Leu Asn Thr Leu Asn
2330                2335                2340

Asn Asn Ser Tyr Ile Asn Asn Leu Ile Thr Asn Val Asp Asp Asp
2345                2350                2355

Thr Phe Val His Arg Glu Gly Asn Phe Phe Leu Gln Cys Glu Phe
2360                2365                2370

Thr Asn Ser Asp Ile Asn Cys Asn Met Tyr Glu Met Glu Thr Ser
2375                2380                2385

Leu Asn Asn Ile Cys Thr Asn Leu Gly Gly Val Ile Ile Lys Asn
2390                2395                2400

Asn Met Glu Tyr Asp Asp Cys Glu Thr Lys His Lys Trp
2405                2410                2415

<210> SEQ ID NO 41
<211> LENGTH: 843
<212> TYPE: PRT
<213> ORGANISM: Plasmodium falciparum

<400> SEQUENCE: 41

Met Lys Leu Arg Ile Leu Lys Lys His Tyr Tyr Val Val Phe Ile Leu
1               5                   10                  15

Leu Tyr Leu Tyr Asp Ile Ser Cys Phe Lys Cys Ile Arg Leu Asn Asn
                20                  25                  30

Arg Ser Ile Tyr Lys Asn Lys Tyr Lys Asn Asn Val His Ile Gly Thr
            35                  40                  45

Asn Glu Asn Ile Arg Ser Ile Glu Lys Tyr Ser Asn Val Leu Cys Asn
        50                  55                  60

Ser Ile Leu Cys Lys Asn Asp Lys Ile Ser Ser Phe Ile Asn Gln Arg
65                  70                  75                  80

Lys Asn Val Asp Asp Asp Glu Ser Glu Asn Asp Met Tyr Glu
                85                  90                  95

Ser Thr Thr Ala Gly Ser Ser Ser Glu Thr Asp Asn Glu Ser Asp Glu
                100                 105                 110

Glu Glu Asn Asp Ser Ser Asp Asn Asn Asn Ser Asp Glu Glu Gln Ile
            115                 120                 125

Glu Asn Ser Asn Asn Asn Asn Ser Asp Glu Glu Gln Asn Asp Ser Ser
        130                 135                 140

Ser Asn Asp Asn Asn Asp Glu Glu Asn Glu Glu Gln Asp Asp Val Met
145                 150                 155                 160

Asp Asn Asp Gln Asn Asp Lys Lys Ile Lys His Ser Phe Asn Leu Ala
                165                 170                 175

Asn Glu Ser Lys His Thr Lys Glu Glu Arg Val Lys Glu Glu Lys Lys
                180                 185                 190
```

```
Leu Lys Ile Tyr Asp Phe Ile Asn Asp Lys Glu Lys Arg Leu Asn Phe
    195                 200                 205

Asn Gly Asp Gln Lys Asp Glu Asp Asn Glu Glu Asn Asp Asp Lys Asp
    210                 215                 220

Glu Asn Thr Leu Glu Asn Arg Asn Ile Ile Ser Lys His Thr Ser Val
225                 230                 235                 240

Phe Pro Gly Leu Tyr Phe Ile Gly Ile Gly Tyr Asn Leu Leu Phe Gly
                245                 250                 255

Asn Pro Leu Gly Glu Ala Asp Ser Leu Ile Asp Pro Gly Tyr Arg Ala
                260                 265                 270

Gln Ile Tyr Leu Met Glu Trp Ala Leu Ser Lys Glu Gly Ile Ala Asn
            275                 280                 285

Asp Leu Ser Thr Leu Gln Pro Val Asn Gly Trp Ile Arg Lys Glu Asn
    290                 295                 300

Ala Cys Ser Arg Val Glu Ser Ile Thr Glu Cys Ser Ser Ile Ser Asp
305                 310                 315                 320

Tyr Thr Lys Ser Leu Ser Ala Glu Ala Lys Val Ser Gly Ser Tyr Trp
                325                 330                 335

Gly Ile Ala Ser Phe Ser Ala Ser Thr Gly Tyr Ser Ser Phe Leu His
                340                 345                 350

Glu Val Thr Lys Arg Ser Lys Lys Thr Phe Leu Val Lys Ser Asn Cys
            355                 360                 365

Val Lys Tyr Thr Ile Gly Leu Pro Pro Tyr Ile Pro Trp Asp Lys Thr
    370                 375                 380

Thr Ala Tyr Lys Asn Ala Val Asn Glu Leu Pro Ala Val Phe Thr Gly
385                 390                 395                 400

Leu Asp Lys Glu Ser Glu Cys Pro Ser Asp Val Tyr Glu Glu Asn Lys
                405                 410                 415

Thr Lys Ser Asn Cys Glu Asn Val Ser Leu Trp Met Lys Phe Phe Asp
                420                 425                 430

Ile Tyr Gly Thr His Ile Ile Tyr Glu Ser Gln Leu Gly Gly Lys Ile
            435                 440                 445

Thr Lys Ile Ile Asn Val Ser Thr Ser Ile Glu Gln Met Lys Lys
    450                 455                 460

Asn Gly Val Ser Val Lys Ala Lys Ile Gln Ala Gln Phe Gly Phe Gly
465                 470                 475                 480

Ser Ala Gly Gly Ser Thr Asp Val Asn Ser Asn Ser Ser Ala Asn
                485                 490                 495

Asp Glu Gln Ser Tyr Asp Met Asn Glu Gln Leu Ile Val Ile Gly Gly
                500                 505                 510

Asn Pro Ile Lys Asp Val Thr Lys Glu Glu Asn Leu Phe Glu Trp Ser
            515                 520                 525

Lys Thr Val Thr Asn His Pro Met Pro Ile Asn Ile Lys Leu Thr Pro
    530                 535                 540

Ile Ser Asp Ser Phe Asp Ser Asp Leu Lys Glu Ser Tyr Asp Lys
545                 550                 555                 560

Ala Ile Ile Tyr Tyr Ser Arg Leu Tyr Gly Leu Ser Pro His Asp Thr
                565                 570                 575

Met Gln Lys Asp Asp Lys Asp Ile Ile Lys Ile Leu Thr Asn Ala Asp
                580                 585                 590

Thr Val Thr Lys Asn Ser Ala Pro Pro Ile Asn Ala Gln Cys Pro His
            595                 600                 605

Gly Lys Val Val Met Phe Gly Phe Ser Leu Lys Gln Asn Phe Trp Asp
    610                 615                 620
```

```
Asn Thr Asn Ala Leu Lys Gly Tyr Asn Ile Glu Val Cys Glu Ala Gly
625                 630                 635                 640

Ser Asn Ser Cys Thr Ser Lys Gln Gly Ser Ser Asn Lys Tyr Asp Thr
            645                 650                 655

Ser Tyr Leu Tyr Met Glu Cys Gly Asp Gln Pro Leu Pro Phe Ser Glu
        660                 665                 670

Gln Val Ile Ser Glu Ser Thr Ser Thr Tyr Asn Thr Val Lys Cys Pro
        675                 680                 685

Asn Asp Tyr Ser Ile Leu Leu Gly Phe Gly Ile Ser Ser Ser Ser Gly
    690                 695                 700

Arg Ile Asn Ser Ala Glu Tyr Val Tyr Ser Thr Pro Cys Ile Pro Gly
705                 710                 715                 720

Met Lys Ser Cys Ser Leu Asn Met Asn Asn Asp Asn Gln Lys Ser Tyr
            725                 730                 735

Ile Tyr Val Leu Cys Val Asp Thr Thr Ile Trp Ser Gly Val Asn Asn
        740                 745                 750

Leu Ser Leu Val Ala Leu Asp Gly Ala His Gly Lys Val Asn Arg Ser
    755                 760                 765

Lys Lys Tyr Ser Asp Gly Glu Leu Val Gly Thr Cys Pro Leu Asp Gly
        770                 775                 780

Thr Val Leu Thr Gly Phe Lys Val Glu Phe His Thr Ser Ser Pro Tyr
785                 790                 795                 800

Val Gln Thr Pro Phe Glu Lys Cys Ala Lys Ser Leu Lys Ala Cys Ser
            805                 810                 815

Val His Gly Ser Gly His Ala Ile Gly Ile Gln Asn Phe Lys Ser Leu
        820                 825                 830

Phe Ile Tyr Met Leu Cys Lys Asn Asn Lys Trp
    835                 840

<210> SEQ ID NO 42
<211> LENGTH: 1346
<212> TYPE: PRT
<213> ORGANISM: Plasmodium falciparum

<400> SEQUENCE: 42

Met Phe Lys Lys Gly Pro Lys Asn Lys Lys Leu Lys Cys Lys Thr
1               5                   10                  15

Lys Lys Gln Ala Asn Asp Ser Phe Cys Asp Ser Ile Ile Tyr Pro Glu
            20                  25                  30

Lys Asp Met Val Asp Ile Leu Arg Gln Lys Glu Asn Leu Asn Lys Glu
        35                  40                  45

Asn Leu Asn Lys Glu Asn Leu Asn Glu Glu Asn Leu Asn Lys Glu Lys
    50                  55                  60

Leu Asn Glu Glu Asn Leu Asn Glu Glu Asn Cys Phe Leu Lys Lys Arg
65                  70                  75                  80

Thr Asp Glu Asn Asp Asn Lys Gln Ile Ile Asn Ser Asn Lys Tyr Ile
                85                  90                  95

Lys Asn Glu Leu Asp Asn Ile Leu Leu Ser Pro Asn Glu Ile Tyr Glu
            100                 105                 110

Lys Lys Asn Ile Gln Ile Asn Asp Lys Pro Ile Leu Glu Ser Ser Asn
        115                 120                 125

Asn Ile Asn Val Met Asp Ile Ser Glu Asn Thr Asp Ser Ile Tyr Gly
    130                 135                 140

Gln Asn Asn Asn Asn Asp Asn Asn Tyr Val Glu Pro Ile Lys Tyr Glu
145                 150                 155                 160
```

```
Lys Lys Glu Tyr Glu Ile Cys Asn Ser Asn Ser Ser Val Leu Lys Ser
                165                 170                 175
Ala Ser Asp Ser Asn Ile Asp Glu Gln Thr Asn Lys Asn Asn Asp Asn
            180                 185                 190
Tyr Lys Lys Glu Leu Ser Ile Ile Leu Asn Asn Glu Glu Ile Ile Ala
            195                 200                 205
Tyr Leu Lys Leu Asn Asn Lys Lys Asp Ile Asp Glu Lys Thr Asn Tyr
    210                 215                 220
Leu Phe Pro Ser Ile Asp Ile Asp His Lys Ser Tyr Ser Tyr Leu Glu
225                 230                 235                 240
Gln Gly Gln Asp Asp Tyr Leu Ile Glu Met Asp Lys Lys Ile Asp Lys
                245                 250                 255
Glu Ile Glu Asn Phe Gln Asn Thr Phe Asn His Phe Tyr Asn Leu Asp
                260                 265                 270
Asn Thr Asn Asn Lys Phe Asp Tyr Asn Asn Asp Asp Asn Asn Asn Asn
            275                 280                 285
Asp Glu Asn Asn Asp Asn Asn Asn Asn Asn Asn Asn Asn Asn Asn Asn
    290                 295                 300
Asp Asn Asn Asn Asn Asn Tyr Ile Asn Glu Gln Asn Lys Glu Glu Ile
305                 310                 315                 320
Thr Lys Asn Leu Asn Asn Asn Ile Leu Asn Thr Asn Glu Asn Asn
                325                 330                 335
Val Pro Asn Asn Met Leu Val Glu Lys Ile Asn Asp Thr Tyr Ile Gly
                340                 345                 350
Pro Lys Arg Gln Asn Lys Asn His Ile Phe Thr Tyr Lys Leu Lys Lys
            355                 360                 365
Asn Ile Tyr Gly Lys Ile Gln Lys Gln Lys Lys Cys Ser His Ser Thr
            370                 375                 380
Thr Lys Thr Arg His Tyr Thr Leu Leu Asn Asn Leu Phe Asn Ile Asn
385                 390                 395                 400
Lys Lys Asn Ile Leu Asp Asp Lys Lys Leu Gln Lys His Leu Arg Arg
                405                 410                 415
Lys Lys Lys Glu Lys Tyr Tyr Ile Phe Pro Tyr Asn Cys Gly Asn Thr
            420                 425                 430
Gln Ile Gln Leu Ile Thr Gly Tyr Ile Arg Cys Phe Lys Lys Tyr Ser
            435                 440                 445
Leu Tyr Lys Glu Phe Lys Lys His Glu Ile Arg Lys Asn Gln Lys Leu
    450                 455                 460
Asn Asn Glu Glu Val Lys Lys Leu Asn His Ile Asn Asn Met Gln Asn
465                 470                 475                 480
Glu Phe Glu Ile Ser Leu Leu Leu Cys Val Asn Val Ser Asn Cys Ile
                485                 490                 495
Ser Pro Ser Glu Phe Leu Glu His Phe Tyr Pro Tyr Asp Asn Phe Ile
            500                 505                 510
Phe Phe Leu Lys Val Leu Asn Thr Lys Ser Asn Glu Glu Tyr Met Ile
            515                 520                 525
Tyr Phe Leu Thr Phe His Ile Tyr Val Lys Gln Ile Met Lys Arg Ser
            530                 535                 540
Arg Thr Leu Thr Phe Phe Asn Met Lys Lys Lys Asn Val Lys Leu
545                 550                 555                 560
Tyr Leu Val Lys Asp Ile Thr Met Asn Arg Ile Ser Cys Ile Asn Lys
                565                 570                 575
Lys Lys Lys Lys Lys Lys Phe Ile Ile Asn Thr Asp Thr Phe Phe Glu
```

```
                580             585             590
Tyr Asn Glu Lys Lys Arg Asn Arg Ile Glu Asp Ser Ser Leu Ala
            595             600             605

Tyr Tyr His Met Arg Thr Lys Leu Tyr Glu Ile Gln Lys Lys Ala Phe
            610             615             620

Ile Asn Pro Leu Tyr Ile Ile Ser Gln Asn Lys Phe Gln Leu Ser Cys
625             630             635             640

Ala Val Cys Leu Glu Pro Leu Tyr Ser Glu Asn Leu Ser Lys Ile Ile
            645             650             655

Ser Tyr Ile Phe His Asn His Phe Glu Lys Asn Lys Asn Ile Thr Gly
            660             665             670

Ile Lys Lys Lys Lys Asp Ala Asp Asn Ile Ile Thr Ile Asp Lys Asp
            675             680             685

Lys Asn Val Pro Ser Asn Leu Lys Phe Lys Tyr Met Tyr Gly Lys Arg
            690             695             700

Asp Thr Thr Asn Phe Asn Asn Lys Glu Asn Phe Asn Asp Ser Leu Thr
705             710             715             720

Phe Glu Lys Gln Tyr Glu Asp Asn Lys Glu Ser Phe Lys Asn Ile Pro
            725             730             735

Ser Asp Asp Ile Leu Asn Lys Glu Ile Pro Cys Lys Glu Glu Leu Glu
            740             745             750

Tyr Asn Lys Glu Phe Lys Asp Phe Asn Lys Lys Tyr Asn Tyr Tyr
            755             760             765

Leu His Val Ile Arg Tyr Ile Ser Ser Ile Gln Asn Lys Tyr Asp Ser
            770             775             780

Glu Ile Lys Asn Lys Trp Lys Lys Gln Asn Asn Val Asp Thr Ile
785             790             795             800

Tyr Asp Asn Asn Lys Val Tyr Asn Val Cys Ile Asn Ile Leu Cys
            805             810             815

Gly His Ile Phe His Ser Asn Cys Leu Lys Lys Cys Cys Phe Thr Ser
            820             825             830

Cys Pro Ile Cys Arg Tyr Lys Gln Tyr Asn Tyr Gln Ile Ala Asn Cys
            835             840             845

Asp Ile Cys Glu Lys Asn Lys Asn Val Lys Ile Cys Leu Phe Cys Cys
850             855             860

Phe Ile Gly Cys Ser Ile Asn Tyr Glu Glu Gln Ser Lys Ile Lys Glu
865             870             875             880

Lys Lys Leu Lys Glu Lys His Lys Phe Ile Arg Lys Leu Tyr Leu
            885             890             895

Val Lys Arg Ile Leu Tyr Met Phe Ile Arg Ile Val Tyr Pro Phe Leu
            900             905             910

Gln Thr Cys His Lys Ile Tyr Leu His Gly Lys Cys Asn Met Ile Gln
            915             920             925

Gln Leu Glu Lys Lys Asn Lys Tyr Ile Lys Asn Ile Glu Ile Glu
            930             935             940

Met Asn Asp Ile Arg Tyr Asn Thr Leu Lys Ala Asn Asn Lys Val
945             950             955             960

Glu Gln Phe Pro Glu Ile Gln Ser Ile Lys Glu Asp Lys Asn Arg
            965             970             975

Asp Lys Asn Val Asn Lys Asn Ile Tyr Glu His Met Gly Ser Arg Lys
            980             985             990

Asn Lys His Arg Tyr Ser Met Asn Lys Phe Tyr Lys Tyr Ile Tyr Ile
            995            1000            1005
```

```
Arg Asn Ile Lys Asp Arg Leu Gln Gln Asn Tyr Ile Val Tyr Asn
    1010                1015                1020

Phe Lys Ser Asn Lys Ile Gly Ile Met Asn Lys Val His Phe Asn
    1025                1030                1035

Ile Ser Ser Tyr Lys Lys Lys Lys Ile Lys Lys Ile Asn Thr
    1040                1045                1050

Cys Asn Leu Tyr Ser Val Val Leu Asn Asn Ser Thr Glu Cys Thr
    1055                1060                1065

Leu Leu Thr Tyr Glu Lys Lys Lys Glu Lys Lys Lys Lys Lys
    1070                1075                1080

Lys Lys Lys Ser Asp Asn Lys Asn Asn Lys Asn Lys Lys Tyr Ile
    1085                1090                1095

Lys Gly Tyr Arg Lys Asn Asn Ile Asp His Ala Ile Glu His Phe
    1100                1105                1110

Tyr His Thr Asn His Asn Tyr Phe Tyr Asp Ile Ser Lys Asn Ser
    1115                1120                1125

Val Tyr Asp Tyr Ser Ser Gln Leu Tyr Thr Lys Thr Ile Ile Asn
    1130                1135                1140

Phe Lys Lys Glu Asp Lys Glu Asn Leu Asn Asp Met Tyr Ser Val
    1145                1150                1155

Asn Val Thr Asn His Asn Asp Glu Lys Glu Ile Ile Asp Lys Lys
    1160                1165                1170

Asn Ile Ile Met Tyr Ile Tyr Glu Tyr Asn Gln Leu Leu Cys Ala
    1175                1180                1185

Leu Leu Glu Ser Gln Arg Asn Asn Phe Leu Glu Ser Ile Ser Asp
    1190                1195                1200

Met Lys Lys Asn Tyr Glu Asn Ile Ser Lys Asp Asn Phe Asn Glu
    1205                1210                1215

Ala Asn Lys Ile Phe Lys Gln Leu Lys Thr Leu Gln Gln Lys Asn
    1220                1225                1230

Glu Asn Leu Lys Asn Asp Ile Lys Lys Lys Ile Ser Thr Leu His
    1235                1240                1245

Glu Lys Asn Ile Asn Asn Glu Asn Leu Lys Glu Leu Gln Asn
    1250                1255                1260

Leu Glu Leu Ile Asn Lys Lys Leu Ser Asp Asp Gln Lys Lys Glu
    1265                1270                1275

Ile Asn Asn Tyr Glu Met Lys Ala Glu Lys Lys Lys Ile Ile
    1280                1285                1290

Lys Glu Lys Gln Gln Ile Ile Arg Glu Leu Lys Gln Gln Ile Ala
    1295                1300                1305

Asp Leu Asn Phe His Lys Gln Ala Val Ser Lys Phe Ser Leu Ser
    1310                1315                1320

Gln Glu Thr Ala Asn Ser Ser Phe Met Ile Ala Glu Lys Ile Thr
    1325                1330                1335

Gln Asn Ser Arg Phe Lys Lys Trp
    1340                1345

<210> SEQ ID NO 43
<211> LENGTH: 1243
<212> TYPE: PRT
<213> ORGANISM: Plasmodium falciparum

<400> SEQUENCE: 43

Met Ile Thr Arg Lys Arg Lys Val Lys Leu Asp Asn Asn Asn Ile
1               5                   10                  15
```

```
Ser Ser Tyr Ile Asn Asn Asp Val Asn Lys Lys Asn Ser Tyr Lys
         20              25              30

Asn Asn Glu Glu Asn Pro Tyr Ser Lys Arg Lys Lys Ile Asn Glu
         35              40              45

Asp Glu His Arg Asn Ser Ser Thr Cys Asp Val Asn Tyr Asn Lys Cys
 50              55              60

Tyr Asn Asp Lys Asn Tyr Phe Thr Asp Glu Asn Ile Ser Asp Glu
 65              70              75              80

Gln Asn Thr Cys Asp Asn Asp Ser Glu Leu Ser Asp Leu Asn Asp Asp
                 85              90              95

Asp Tyr Val Tyr Gly Lys Arg Ser Asp Ala Ser Ser Tyr Tyr Lys
             100             105             110

Lys Arg Lys Lys Lys Lys Ile Ile Lys Arg Lys Asn Asn Asn
         115             120             125

Asn Asn Lys Thr Glu Ile Asn Lys Lys Val Lys Glu Lys Glu Lys
         130             135             140

Glu Lys Gln Ser Ser Asn Glu Asn Phe Pro Lys Lys Asp Glu Glu
 145             150             155             160

Lys Gln Pro Arg Lys Lys Phe Gln Lys Asn Thr Ile Leu Glu
             165             170             175

Lys Met His Asn Phe Ile Tyr Gln Lys Asn Glu Tyr Phe Asp Leu Asp
             180             185             190

Leu Phe Lys Tyr Leu Ser Thr Leu Thr Glu Arg Asp Glu Glu Lys Met
     195             200             205

Asn Glu His Phe Ser Tyr Phe Val Ile Ser Glu Phe Leu Asn Leu Met
 210             215             220

Arg Leu Cys Lys Arg Gly Lys Glu Asn Arg Asn Gln Gly Glu Val Glu
225             230             235             240

Lys Gln Asn Ile Asp Asp Asn Ile His Ile Asp Asp Asn Ile His Ile
             245             250             255

Asp Asp Asn Ile His Ile Asp Asp Asn Ile His Ile Asp Asn Ile
             260             265             270

His Ile Asp Glu His Ile Asp Cys Gln Asn Val Lys Asp Asn Met Ile
             275             280             285

Asn Ile Ser Glu Asn Ser Glu Ile Lys Lys Glu Lys Glu Ser Asp Ile
 290             295             300

Ser Cys Thr Glu Val Ser Asn Phe Ile Ser Lys Lys Ile Phe Asn Ile
305             310             315             320

Lys Glu Asn Ile Asp Leu Lys Cys Ile Leu Asn His Asp Asn Thr Asn
             325             330             335

Trp Arg Asn Ile Phe Phe Leu Glu Asp Ile Gln Ile His Leu Asn Asn
             340             345             350

Lys Lys Ile Lys Val Ser Pro Phe Ser Ser Glu Arg Val Val Asp Asn
             355             360             365

Ile Lys Lys Ser Tyr Leu Leu Lys Lys Lys Lys Asn Asn Phe His
             370             375             380

Ile Lys Gln Lys Val Lys Glu Gln Asn His Asp Phe Tyr Asn Tyr Leu
385             390             395             400

Glu Lys Ile Lys Ile Tyr Ile Asn Gly Gln Lys Lys Asn Arg Gln Glu
             405             410             415

Glu Ile Arg Glu Glu Arg Arg Gly Asn Asn Asn Phe Asp Ile Glu Cys
             420             425             430

Asn Ile Asn Arg Ile Glu Gly Asn Asn Ile Leu His Pro Asp Met Ile
             435             440             445
```

```
Val Phe Leu Tyr Phe Leu Leu Ile Cys Asn Ser Leu Ser Asn Asp Ile
450                 455                 460

Lys Glu Asn Thr Ser Glu Glu Asn Lys Ser Ile Thr Lys Asn Ile
465                 470                 475                 480

Asn Glu Glu Glu Thr Leu Asn Ile Glu Asn Ile Leu Asp Asn Leu Glu
                485                 490                 495

Glu Tyr Leu Ser Lys Asp Leu Ser Ser Glu Asn Ile Phe Leu Ser Leu
            500                 505                 510

Cys Cys Pro Ile Asn Tyr Met Asp Phe Ser Asp Ser Ile Asn Met Val
            515                 520                 525

Thr Tyr Leu Thr Phe Phe Leu Asn Glu Lys Asn Val Met Asp Lys Asn
530                 535                 540

Ile Tyr Asn Lys Asp Thr Tyr Pro Ile Asn Leu Ser Tyr Asn Asn Asn
545                 550                 555                 560

Ile Asn Asn Asn Ser Ile Ser Gly Glu Val Leu Tyr Asp Asp Lys
                565                 570                 575

Asn Arg Leu Glu Asn Asn Asn Tyr Asn Asn Asn Asn Asn Asn Asn
            580                 585                 590

Ser Ile Ser Gly Glu Glu Val Leu Tyr Asp Asp Lys Asn Thr Leu Lys
            595                 600                 605

Asn Asn Asn Tyr Asn Arg Ser Ile Ile Lys Asn Asp Val Thr Asn Phe
610                 615                 620

Arg Tyr Glu Asn Asn Asp Asn Ile Tyr Asn Glu Lys Ile Glu Asn Asn
625                 630                 635                 640

Ile Tyr Asn Leu Ile Asn Asp Met Met Met Lys Cys Ser Glu Ile Phe
                645                 650                 655

Glu Gly Asn Ile Leu Ser Ile Ser Ile Tyr Ser Tyr Leu Asn Ser Asp
            660                 665                 670

Ala Tyr Tyr Asn Ser Asp Lys Pro Gly Arg Asn Phe Ile Val Phe Tyr
            675                 680                 685

Phe Leu Ser Lys Tyr Leu Cys Lys Pro Val Phe Ile Asp Ile Ile Glu
            690                 695                 700

His Thr Tyr Met Cys Lys Lys Met Glu Trp Ile Lys Phe Asp Ser Leu
705                 710                 715                 720

Asn Ala Gly Lys Gly Lys Gly Lys Gly Lys Glu Tyr Ile Tyr Leu Leu
                725                 730                 735

Leu Cys Leu Leu Gly Asn Lys Ile Lys Ile Phe Ala Ile Ser Lys Tyr
            740                 745                 750

His Phe Phe Val Asn Ile Tyr Met Ala Leu Lys Asn Gln Arg Asn Lys
            755                 760                 765

Asp Ser Ser Asn Asn Ile Tyr Ser Phe Ile Lys Asn Glu Lys Arg Lys
            770                 775                 780

Glu Lys Lys Asn Gln Lys Lys Thr Gln Thr Lys Arg Gln Lys Phe Lys
785                 790                 795                 800

Lys Ile Phe Thr Tyr Thr Ser Ser Glu Tyr Ile Asn Asp Phe Ser Tyr
            805                 810                 815

Thr Ile Cys Ile Lys Asp Gln Lys Arg Tyr Leu Lys Ile Ala Leu Cys
            820                 825                 830

Phe Asn Asn Phe Lys Ile Lys Ile Ile Asp Ile Leu Asn Ile Val
            835                 840                 845

Asn Lys Glu Glu Asn Lys Ile Asn Ser Phe Ile Glu Lys Ser Lys Thr
850                 855                 860

Ile Asn Ile Ser Leu Gln Tyr Gly Asp Arg Glu His Tyr Glu Asn Phe
```

| | | 865 | | | 870 | | | 875 | | | 880 | |
|---|---|---|---|---|---|---|---|---|---|---|---|---|

Leu Phe Phe Asn Lys Asn Gln Lys Asn Ile Asn Gln Asn Met Gln Ser
                885               890             895

Phe Glu Gly Asn Ile Asn Glu Asn Asp Glu Leu Val His Arg Tyr Ser
         900              905             910

Trp Asn Lys Glu Met Lys Lys Lys Glu Asn Phe Phe Pro Thr Ser Trp
     915              920             925

Ser Asn His Asn Lys Asn Asp Asp Val Asn Asn His Asp Asp Ala Ile
 930             935             940

Asn Cys His Asn Val Asp Cys Ile Asn Asp Arg Asn Asn Asn Leu Tyr
945            950             955            960

Ile Ser Asp Lys Arg Lys Phe His Leu Glu Thr His Ser Asn Ile Arg
            965            970            975

Ser Gly Ile Lys Asn Asn Ile Tyr Asn Ile Ser Asn Asn Ile Cys Leu
         980              985             990

Ser Asn Ile Asn Lys Ile Asn Ile Arg Glu Glu Ile Ile Tyr Leu Gln
     995            1000           1005

His Gly Val Leu Ser Leu Cys Ser Phe Tyr Pro Cys Ile Asn Ser
 1010            1015           1020

Tyr Leu Leu Cys Leu Cys Ser Lys Asp Gly Asn Ile Val Ile Ile
 1025            1030           1035

Asp Ile Arg Asn Ser Lys Glu Leu Phe Tyr Phe Lys Arg Lys Thr
 1040            1045           1050

Glu Thr Cys Ser His Leu Lys Trp Tyr Arg Asn Ser Cys Ile Ser
 1055            1060           1065

Phe Gly Gln Asp Lys Gly Ser Ile Ile Asn Leu Phe Gln Asn Lys
 1070            1075           1080

Tyr Ile Leu Asn Ile Asp Lys Ser Phe Asn Thr Val Asp Asn
 1085            1090           1095

Ser Cys Leu Asn Ser Val Leu Ile Gly Asp His Met Tyr Leu Phe
 1100            1105           1110

Leu Tyr Asp Asp Asn Thr Ile Leu Lys Gly Lys Thr Lys Glu Asn
 1115            1120           1125

Ser Ser Lys Asn Lys Tyr Asn Glu Phe Phe Leu Trp Ser Thr Lys
 1130            1135           1140

Cys Val Asp Leu Glu Pro Ser Ile Leu Leu Glu Ile Ser Cys Met
 1145            1150           1155

Gln Lys Glu Asp Ile Tyr Ser Val Ser Met Ile Leu Leu Tyr Glu
 1160            1165           1170

Tyr Leu Lys Gly Leu Gln Asn Val Leu Asn Asp Gly Ile Lys Ile
 1175            1180           1185

Val Arg Ser Lys Lys Trp Asp Gln Gln Cys Thr Gly Lys Asn Arg
 1190            1195           1200

Ala Leu Thr Pro Lys Ser Ile Ser Tyr Ala Ser Phe Asp Glu Asn
 1205            1210           1215

Tyr Ile Ile Ala Tyr Gly Thr Ser Cys Gly Leu Ile His Ile Phe
 1220            1225           1230

Ser Gln Glu Lys Asp Glu Asn Asn Asn Val
 1235            1240

<210> SEQ ID NO 44
<211> LENGTH: 709
<212> TYPE: PRT
<213> ORGANISM: Plasmodium falciparum

```
<400> SEQUENCE: 44

Met Pro Leu Phe Lys Tyr Asp Leu Lys Ala Lys Glu Ile Ile Phe Met
1               5                   10                  15

Leu Asn Lys Ile Asn Phe Phe Ser Thr Val His Phe Cys Lys Ile Asp
            20                  25                  30

Val Lys Cys Ile Pro Ser Ser Phe Thr Asn Asn Tyr Asn Ile Asn Lys
        35                  40                  45

Ser Thr Tyr Met Asn Arg Lys Phe Ile Val Gly Asp Lys Asn Val Gly
    50                  55                  60

Arg Ile Asn Ser Asn Met Arg Leu Arg Lys Leu Lys Asp Lys Asn Met
65                  70                  75                  80

Val Ile Phe Trp Lys Lys Glu Asn Gly Asn Asn Ile Lys Lys Lys Lys
                85                  90                  95

Lys Lys Ser Gly Lys Lys Leu Phe Ala Ser Gly Phe Lys Lys Ser Val
            100                 105                 110

Ile Leu Asn Lys Phe His Ile Asp Leu Leu Asn Glu Glu Leu Lys Asn
        115                 120                 125

Val Glu Asn Glu Ile Asn Asn Lys Tyr Leu Thr Ser Asn Glu Glu Lys
    130                 135                 140

Glu Ile Ile Leu Arg Lys Ser Lys Tyr Ala Ser Gln Lys Phe Tyr Lys
145                 150                 155                 160

Ala Asn Glu Glu Glu Ile Lys Ile Ile Arg Lys Ser Glu Gly Gln Tyr
                165                 170                 175

Tyr Leu Pro Ile Glu Cys Glu Asn Ser Thr Ile Ile Arg Ile Val Asn
            180                 185                 190

Ile Asn Asp Lys Val Thr Ser Pro Ile Phe Arg Cys Val Arg Asn Ser
        195                 200                 205

Lys Phe Gly Leu Arg Lys Lys Glu Arg Thr Phe Phe Phe Tyr Tyr Ser
    210                 215                 220

Thr Phe Ile Cys Ser Phe Phe Thr Met Gly Ile Trp Gln Tyr Lys
225                 230                 235                 240

Lys Met Lys Lys Lys Phe Leu Ile Asn Tyr Ile Ser Asn Asn Leu
                245                 250                 255

Asn Asp Glu Ile Ile Asn Leu Asn Gly Thr Asn Phe Pro Trp Val Asn
            260                 265                 270

Asp Tyr Lys Thr Leu Lys Asp Glu Tyr Thr Gln Leu Ser Arg Asn Leu
        275                 280                 285

Leu Lys Tyr Glu Asn Lys Leu Val Ser Gly Tyr Asn Ile Leu Arg Asn
    290                 295                 300

Ile Tyr Val Asn Val Leu Ser Asn Tyr Glu Asn Trp Ile Pro Tyr Phe
305                 310                 315                 320

Asn Leu Ile Gly Met Tyr Lys Asn Tyr Ile Glu Thr Ser Asp Ser Val
                325                 330                 335

Ser Arg Met Asn Phe Lys Gly Met Glu Asn Ile Cys Val Asp Thr Asp
            340                 345                 350

Asp Tyr Leu Ser Lys Asn Arg Asn Asn Leu Tyr Asp Asn Ile Lys Arg
        355                 360                 365

Lys Glu Lys Glu Glu Tyr Lys Asn Ser Ile Glu Tyr Val Thr Val Asp
    370                 375                 380

Leu Asn Asn Ile Asp Asn Ile Tyr Glu Trp Leu Leu Lys Ile Arg Asn
385                 390                 395                 400

Glu Asn Ile Val Met Lys Leu Tyr Arg Lys Phe Phe Lys Arg Asn Glu
                405                 410                 415
```

```
Ile Ile Thr Asn Asp Glu Leu Lys Lys Leu Val Ile Glu Lys Tyr Lys
            420                 425                 430

Tyr Arg Lys Val Glu Ile Thr Gly Val Leu Asp Thr Thr Asn Glu Val
            435                 440                 445

Tyr Val Gly Pro Lys Ile Tyr Glu Lys Asp Ser Lys Gln Lys Tyr Phe
450                 455                 460

Tyr Val Ile Cys Pro Leu Phe Leu Lys Asn Gly Asn Cys Ile Leu Val
465                 470                 475                 480

Asn Arg Gly Leu Val Ser Asn Asp Ile Leu Glu Glu Lys Ile Asn Glu
                485                 490                 495

Ile Pro Lys Ile Val Thr Ile Arg Ala Val Leu Asp Pro Gly Glu Leu
            500                 505                 510

Tyr Glu Cys Ser Phe Lys Lys Ile Lys Asn Phe Ser Asn Lys Ser Ser
            515                 520                 525

Lys Lys Glu Ser Tyr Phe Tyr Tyr Asn Ile Glu Glu Ile Cys Asn
530                 535                 540

His Thr Asn Ile Ser Lys Phe Glu Gly Thr Ser Tyr Phe Ile Ala Asn
545                 550                 555                 560

Val Tyr Asp Ile Ile Phe His Glu Asp Tyr Leu Ser Asp Ile Gln Lys
                565                 570                 575

Tyr Asn Asn Asn Asn Val Gly Glu Glu Ser Asn Ser Pro Asp Lys
            580                 585                 590

Thr Asn Tyr Ile Asp Leu Asp Asn Val Asn Ile Asn Asn Ile Asp Ile
            595                 600                 605

Asn Gln Val Asp Arg Glu Thr Gln Glu Arg Ile Lys Arg Leu Thr Lys
            610                 615                 620

Ala Lys Ser Asn Val Ile Gln Lys Asp Lys Asn Tyr Val Asn Asn Leu
625                 630                 635                 640

Asp Asp Val Tyr Leu Ser Asp Ile Pro Tyr Lys Ser Arg Pro Phe Arg
                645                 650                 655

Tyr Asp Glu His Phe Ile His Lys Lys Lys Asp Tyr Val Lys Phe
            660                 665                 670

Tyr Ala Asp Glu Ser Thr His Phe Asn Tyr Ala Cys Gln Trp Phe Leu
            675                 680                 685

Phe Ser Phe Ile Phe Ser Thr Ile Ser Ile Phe Lys Phe Val Gln Phe
690                 695                 700

Lys Arg Trp Val Phe
705

<210> SEQ ID NO 45
<211> LENGTH: 182
<212> TYPE: PRT
<213> ORGANISM: Plasmodium falciparum

<400> SEQUENCE: 45

Met Asn Ala Leu Arg Arg Leu Pro Val Ile Cys Ser Phe Leu Val Phe
1               5                   10                  15

Leu Val Phe Ser Asn Val Leu Cys Phe Arg Gly Asn Asn Gly His Asn
            20                  25                  30

Ser Ser Ser Ser Leu Tyr Asn Gly Ser Gln Phe Ile Glu Gln Leu Asn
        35                  40                  45

Asn Ser Phe Thr Ser Ala Phe Leu Glu Ser Gln Ser Met Asn Lys Ile
    50                  55                  60

Gly Asp Asp Leu Ala Glu Thr Ile Ser Asn Glu Leu Val Ser Val Leu
65                  70                  75                  80
```

```
Gln Lys Asn Ser Pro Thr Phe Leu Glu Ser Ser Phe Asp Ile Lys Ser
                 85                  90                  95

Glu Val Lys Lys His Ala Lys Ser Met Leu Lys Glu Leu Ile Lys Val
            100                 105                 110

Gly Leu Pro Ser Phe Glu Asn Leu Val Ala Glu Asn Val Lys Pro Pro
            115                 120                 125

Lys Val Asp Pro Ala Thr Tyr Gly Ile Ile Val Pro Val Leu Thr Ser
            130                 135                 140

Leu Phe Asn Lys Val Glu Thr Ala Val Gly Ala Lys Val Ser Asp Glu
145                 150                 155                 160

Ile Trp Asn Tyr Asn Ser Pro Asp Val Ser Ser Glu Glu Ser Leu
                165                 170                 175

Ser Asp Asp Phe Phe Asp
            180
```

<210> SEQ ID NO 46
<211> LENGTH: 574
<212> TYPE: PRT
<213> ORGANISM: Plasmodium falciparum

<400> SEQUENCE: 46

```
Met Asn His Leu Gly Asn Val Lys Tyr Leu Ile Val Phe Leu Ile
1               5                   10                  15

Phe Phe Asp Leu Phe Leu Val Asn Gly Arg Asp Val Gln Asn Asn Ile
                20                  25                  30

Val Asp Glu Ile Lys Tyr Arg Glu Glu Val Cys Asn Asp Glu Val Asp
            35                  40                  45

Leu Tyr Leu Leu Met Asp Cys Ser Gly Ser Ile Arg Arg His Asn Trp
50                  55                  60

Val Asn His Ala Val Pro Leu Ala Met Lys Leu Ile Gln Gln Leu Asn
65                  70                  75                  80

Leu Asn Asp Asn Ala Ile His Leu Tyr Ala Ser Val Phe Ser Asn Asn
                85                  90                  95

Ala Arg Glu Ile Ile Arg Leu His Ser Asp Ala Ser Lys Asn Lys Glu
            100                 105                 110

Lys Ala Leu Ile Ile Ile Lys Ser Leu Leu Ser Thr Asn Leu Pro Tyr
            115                 120                 125

Gly Lys Thr Asn Leu Thr Asp Ala Leu Leu Gln Val Arg Lys His Leu
            130                 135                 140

Asn Asp Arg Ile Asn Arg Glu Asn Ala Asn Gln Leu Val Val Ile Leu
145                 150                 155                 160

Thr Asp Gly Ile Pro Asp Ser Ile Gln Asp Ser Leu Lys Glu Ser Arg
                165                 170                 175

Lys Leu Ser Asp Arg Gly Val Lys Ile Ala Val Phe Gly Ile Gly Gln
            180                 185                 190

Gly Ile Asn Val Ala Phe Asn Arg Phe Leu Val Gly Cys His Pro Ser
            195                 200                 205

Asp Gly Lys Cys Asn Leu Tyr Ala Asp Ser Ala Trp Glu Asn Val Lys
            210                 215                 220

Asn Val Ile Gly Pro Phe Met Lys Ala Val Cys Val Glu Val Glu Lys
225                 230                 235                 240

Thr Ala Ser Cys Gly Val Trp Asp Glu Trp Ser Pro Cys Ser Val Thr
                245                 250                 255

Cys Gly Lys Gly Thr Arg Ser Arg Lys Arg Glu Ile Leu His Glu Gly
            260                 265                 270
```

```
Cys Thr Ser Glu Leu Gln Glu Gln Cys Glu Glu Arg Cys Leu Pro
        275                 280                 285

Lys Arg Glu Pro Leu Asp Val Pro Asp Glu Pro Glu Asp Gln Pro
290                 295                 300

Arg Pro Arg Gly Asp Asn Phe Ala Val Glu Lys Pro Asn Glu Asn Ile
305                 310                 315                 320

Ile Asp Asn Asn Pro Gln Glu Pro Ser Pro Asn Pro Glu Glu Gly Lys
                325                 330                 335

Gly Glu Asn Pro Asn Gly Phe Asp Leu Asp Glu Asn Pro Glu Asn Pro
            340                 345                 350

Pro Asn Pro Asn Pro Asn Pro Asn Pro Asn Pro Asn Pro
        355                 360                 365

Asn Pro Asp Ile Pro Glu Gln Glu Pro Asn Ile Pro Glu Asp Ser Glu
370                 375                 380

Lys Glu Val Pro Ser Asp Val Pro Lys Asn Pro Glu Asp Asp Arg Glu
385                 390                 395                 400

Glu Asn Phe Asp Ile Pro Lys Lys Pro Glu Asn Lys His Asp Asn Gln
                405                 410                 415

Asn Asn Leu Pro Asn Asp Lys Ser Asp Arg Tyr Ile Pro Tyr Ser Pro
            420                 425                 430

Leu Ser Pro Lys Val Leu Asp Asn Glu Arg Lys Gln Ser Asp Pro Gln
        435                 440                 445

Ser Gln Asp Asn Asn Gly Asn Arg His Val Pro Asn Ser Glu Asp Arg
    450                 455                 460

Glu Thr Arg Pro His Gly Arg Asn Asn Glu Asn Arg Ser Tyr Asn Arg
465                 470                 475                 480

Lys His Asn Asn Thr Pro Lys His Pro Glu Arg Glu Glu His Glu Lys
                485                 490                 495

Pro Asp Asn Asn Lys Lys Lys Ala Gly Ser Asp Asn Lys Tyr Lys Ile
            500                 505                 510

Ala Gly Gly Ile Ala Gly Gly Leu Ala Leu Leu Ala Cys Ala Gly Leu
        515                 520                 525

Ala Tyr Lys Phe Val Val Pro Gly Ala Ala Thr Pro Tyr Ala Gly Glu
    530                 535                 540

Pro Ala Pro Phe Asp Glu Thr Leu Gly Glu Glu Asp Lys Asp Leu Asp
545                 550                 555                 560

Glu Pro Glu Gln Phe Arg Leu Pro Glu Glu Asn Glu Trp Asn
                565                 570

<210> SEQ ID NO 47
<211> LENGTH: 397
<212> TYPE: PRT
<213> ORGANISM: Plasmodium falciparum

<400> SEQUENCE: 47

Met Met Arg Lys Leu Ala Ile Leu Ser Val Ser Ser Phe Leu Phe Val
1               5                   10                  15

Glu Ala Leu Phe Gln Glu Tyr Gln Cys Tyr Gly Ser Ser Ser Asn Thr
                20                  25                  30

Arg Val Leu Asn Glu Leu Asn Tyr Asp Asn Ala Gly Thr Asn Leu Tyr
            35                  40                  45

Asn Glu Leu Glu Met Asn Tyr Tyr Gly Lys Gln Glu Asn Trp Tyr Ser
        50                  55                  60

Leu Lys Lys Asn Ser Arg Ser Leu Gly Glu Asn Asp Asp Gly Asn Asn
65                  70                  75                  80
```

```
Glu Asp Asn Glu Lys Leu Arg Lys Pro Lys His Lys Lys Leu Lys Gln
                85                  90                  95

Pro Ala Asp Gly Asn Pro Asp Pro Asn Ala Asn Pro Asn Val Asp Pro
            100                 105                 110

Asn Ala Asn Pro Asn Val Asp Pro Asn Ala Asn Pro Asn Val Asp Pro
        115                 120                 125

Asn Ala Asn Pro Asn Ala Asn Pro Asn Ala Asn Pro Asn Ala Asn Pro
    130                 135                 140

Asn Ala Asn Pro Asn Ala Asn Pro Asn Ala Asn Pro Asn Ala Asn Pro
145                 150                 155                 160

Asn Ala Asn Pro Asn Ala Asn Pro Asn Ala Asn Pro Asn Ala Asn Pro
                165                 170                 175

Asn Ala Asn Pro Asn Ala Asn Pro Asn Ala Asn Pro Asn Ala Asn Pro
            180                 185                 190

Asn Ala Asn Pro Asn Val Asp Pro Asn Ala Asn Pro Asn Ala Asn Pro
        195                 200                 205

Asn Ala Asn Pro Asn Ala Asn Pro Asn Ala Asn Pro Asn Ala Asn Pro
    210                 215                 220

Asn Ala Asn Pro Asn Ala Asn Pro Asn Ala Asn Pro Asn Ala Asn Pro
225                 230                 235                 240

Asn Ala Asn Pro Asn Ala Asn Pro Asn Ala Asn Pro Asn Ala Asn Pro
                245                 250                 255

Asn Ala Asn Pro Asn Ala Asn Pro Asn Ala Asn Pro Asn Ala Asn Pro
            260                 265                 270

Asn Lys Asn Asn Gln Gly Asn Gly Gln Gly His Asn Met Pro Asn Asp
        275                 280                 285

Pro Asn Arg Asn Val Asp Glu Asn Ala Asn Ala Asn Ser Ala Val Lys
    290                 295                 300

Asn Asn Asn Asn Glu Glu Pro Ser Asp Lys His Ile Lys Glu Tyr Leu
305                 310                 315                 320

Asn Lys Ile Gln Asn Ser Leu Ser Thr Glu Trp Ser Pro Cys Ser Val
                325                 330                 335

Thr Cys Gly Asn Gly Ile Gln Val Arg Ile Lys Pro Gly Ser Ala Asn
            340                 345                 350

Lys Pro Lys Asp Glu Leu Asp Tyr Ala Asn Asp Ile Glu Lys Lys Ile
        355                 360                 365

Cys Lys Met Glu Lys Cys Ser Ser Val Phe Asn Val Val Asn Ser Ser
    370                 375                 380

Ile Gly Leu Ile Met Val Leu Ser Phe Leu Phe Leu Asn
385                 390                 395

<210> SEQ ID NO 48
<211> LENGTH: 984
<212> TYPE: PRT
<213> ORGANISM: Plasmodium falciparum

<400> SEQUENCE: 48

Met Glu Gly Phe Val Ala Leu Leu Ser Phe Leu Val Val Leu Val Phe
1               5                   10                  15

Asn Lys Thr Ile Gly Tyr Asn Ile Lys Ser Gly Asn Thr Ser Asn Asn
                20                  25                  30

Ile Lys Tyr Val Asn Val Leu Asp Asn Asp Arg Asp Ile Asn Thr His
            35                  40                  45

Ser Val Leu Pro Glu Val Glu Asn Val Ile Glu Arg Lys Asp Ile Tyr
        50                  55                  60
```

-continued

```
Arg Gln Ile Asn Phe Met Glu Thr Phe Val Ser Ser Asn Asn Met Met
 65                  70                  75                  80

His Asp Arg Glu Lys His Thr Ser Asn Asp Ser Gly Ser Tyr Glu Ile
                 85                  90                  95

Thr Gly Ile Val Asp Gly Met Lys Ile Gly His Pro Ile Ser Val Ala
            100                 105                 110

Leu Gly Ser Gln Tyr Ser Asn Tyr Phe Asp Tyr Leu Gln Ile Val His
            115                 120                 125

Leu Asp Tyr Thr Asn Ser Arg Phe Ser Phe Thr Val Gly Glu Gly Lys
130                 135                 140

Tyr Tyr Leu Arg Thr Tyr Gly Ser Thr Tyr Met Thr Pro Ser Ala Ile
145                 150                 155                 160

Lys Ile Lys Val Pro Cys Glu Lys Cys Lys Phe Ile Asn Ser Glu Tyr
                165                 170                 175

Ser Gly Ile Ile Lys Ile Ile Pro Tyr Glu Thr Asn Asn Asn Leu Phe
            180                 185                 190

Ile Tyr Asn Trp Val Leu Gln Thr Ser Ser Pro Leu Ala Leu Glu Asn
            195                 200                 205

Ile Asn Thr Val Phe Ser Asp Glu Ala Asp Leu Ile His Gly Asn Ser
210                 215                 220

Leu Ser Glu Glu Phe Lys Ile Asp Ser Ser Ala Ala Ala Thr Ser Leu
225                 230                 235                 240

Asn Thr Phe Tyr Gly Ile Val Leu His Gly Ile Trp Ser Ser Glu Tyr
                245                 250                 255

Ala Glu Arg Leu Leu Thr Val Ile Ser Glu Phe Pro Asp Cys Val Lys
            260                 265                 270

Met Ser Ala His Asp Lys Asn Ala Arg Ser Lys Gln Arg Lys Asn Gln
            275                 280                 285

Lys Trp Ile Leu Val Asn Glu Asp Leu Gly Ser Phe Asp Met Lys Met
290                 295                 300

Glu Val Cys Glu Glu Val Asn Cys Asp Tyr Ser Ala Ile Ile His Val
305                 310                 315                 320

Ser Lys His Ala Phe Glu Tyr Ser Lys Lys Leu Val His Asn Arg Gly
                325                 330                 335

Arg Asn Gly Arg Tyr Tyr Ser Arg Arg Val Glu Lys Ile Leu Ile Arg
            340                 345                 350

Ala Leu Leu Ser Leu Asp Phe Ser Leu Phe Ile Thr Tyr Phe Gln Gln
            355                 360                 365

Lys His Gly Val Thr Leu Leu Asp Pro Gln Tyr Asp Tyr Glu Leu Ile
370                 375                 380

Thr Asn Met Ser Gly Tyr Ser Ser Asn Asn Tyr Gln Ser Trp Asn His
385                 390                 395                 400

Asn Leu Glu Glu Leu Val Glu Leu Ala Thr Ser Trp Asp Glu Tyr Pro
                405                 410                 415

Lys Gly Leu Gln Lys Val Gln Gly Leu Ser Tyr Leu Leu Arg Arg Lys
            420                 425                 430

Asn Gly Thr Lys His Pro Val Tyr Pro Thr Ala Pro Ala Val Ala Phe
            435                 440                 445

Pro Ala Gly Ser Gln Asn Asn Ser Phe Ile Glu Phe Met Glu Ser Ala
450                 455                 460

Phe Val Asn Tyr Val Asp Ile Ser His Leu Val Ile His Glu Val Ala
465                 470                 475                 480

His Phe Ile Trp Val Asn Thr Val Ser Lys Glu Leu Lys Glu Lys Trp
                485                 490                 495
```

```
Ile Gln Ile Gly Gln Trp Tyr Lys Glu Pro Leu Ser Pro Ser Glu Trp
                500                 505                 510

Ala Thr Lys Leu Glu Val Glu Phe Val Ser Ala Tyr Ala His Asp Lys
            515                 520                 525

Asn Pro Ala Glu Asp Phe Ala Glu Ser Met Ala Thr Tyr Val Leu Asn
        530                 535                 540

Ser Lys Leu Leu Asn Ser Arg Ser Phe Asp Lys Phe Lys Trp Ile Gln
545                 550                 555                 560

Asp Asn Leu Phe Gly Gly Phe Tyr Ile Thr Thr Gly Thr His Lys
                565                 570                 575

Phe Asp Val Ile Asn Leu Gly Asn Glu Val Tyr Phe Pro Gly Lys
                580                 585                 590

Val Thr Arg Val Arg Ala Lys Val Leu Gly Ser Pro Thr Glu Asp Lys
            595                 600                 605

Leu Val Lys Ile Tyr Ile Ser Leu Leu Ser Ser Asp Gly Ser Glu Gly
            610                 615                 620

Cys Ala Lys His Gly Tyr Ala Arg Ile Phe Ser Glu Gln Gln Thr Phe
625                 630                 635                 640

Arg Asp Leu Tyr Phe His Thr Glu Asp Arg Ser Pro Cys Ser His Lys
                645                 650                 655

Leu Tyr Gly Glu Phe Thr Met Asn Lys His Glu Ser Arg Gly Arg Trp
                660                 665                 670

Thr Ala Glu Ser Met Ile Phe Thr Gly Glu Asn Asn Ile Glu Arg Tyr
            675                 680                 685

Val Gly Leu Gly Ser Phe His Phe Tyr Leu Tyr Val Asn Asn Gln Asn
        690                 695                 700

Glu Asp Val Glu Lys Pro Ile Pro Leu Leu Asp Ser Ile Ser Ile Tyr
705                 710                 715                 720

Thr His Asn Ala Thr Glu Thr Asn Asp Ala Leu Leu Arg Leu His Val
                725                 730                 735

Met Val Leu Glu Asn Glu Leu Ile Lys Glu His Gly Gly Pro Tyr Ala
                740                 745                 750

Ser Phe Ala Ala His Glu Asn Lys Ser Tyr Ser Tyr Glu Ser Arg Thr
            755                 760                 765

Tyr Lys Met Tyr Pro Pro Glu Phe Asn Thr Leu Met Leu Lys Ala Asp
        770                 775                 780

Tyr Phe Ile Arg Asp Ile Asn Thr Arg Gly Phe Arg Glu Val Asn Met
785                 790                 795                 800

Asp Ser Cys Lys Ser Tyr Thr Asn Met Asp Thr Arg Asn Leu Lys Cys
                805                 810                 815

Phe Gln Val Leu Asn Pro Val Thr Ile Pro Lys Tyr Cys Ile Gly Ser
                820                 825                 830

Thr Tyr Phe Leu Arg Gln Val Ser Ile Glu Asp Ile Ala Gly Asn Leu
            835                 840                 845

Glu Thr Val Asn Ile Ser Ser Asp Lys Tyr Ser Ala Arg Leu His Pro
        850                 855                 860

Ile Gly Val Arg Asp Lys Gln Lys Pro Val Val Ser Asn Val Arg Val
865                 870                 875                 880

Ser Ser Lys Pro Ala Asn Glu Tyr His Asp Gly Glu Thr Ile Val Ser
                885                 890                 895

Leu Ser Phe Asn Val His Asp Asn Leu Ser Gly Val Tyr Tyr Ile Phe
            900                 905                 910

Val Tyr Leu Arg Asp Pro His Gly Gly Lys His Arg Ser Asp Ile Asp
```

```
                915                 920                 925
Arg Ala Ser Leu Pro Thr Gly Thr Glu Asn Lys Gln Ile Asn His Lys
        930                 935                 940

Ile Leu Leu Pro Lys Gly Ser Met Gly Gly Thr Trp Met Leu Glu Glu
945                 950                 955                 960

Ile Lys Ala Val Asp Ser Cys Lys Asn Glu Ser Arg Asn Ile Tyr Thr
                965                 970                 975

His Ser Val Tyr Val Gln Asn Asp
            980

<210> SEQ ID NO 49
<211> LENGTH: 16
<212> TYPE: PRT
<213> ORGANISM: Plasmodium yoelii

<400> SEQUENCE: 49

Lys Asp Asp Tyr Ser Lys Asn Asn Gly Lys Asp Ser Leu Val Cys Cys
1               5                   10                  15

<210> SEQ ID NO 50
<211> LENGTH: 16
<212> TYPE: PRT
<213> ORGANISM: Plasmodium yoelii

<400> SEQUENCE: 50

Cys Asn Leu Lys Tyr Leu Leu His His Thr Asn Ala Phe Leu Cys
1               5                   10                  15

<210> SEQ ID NO 51
<211> LENGTH: 9
<212> TYPE: PRT
<213> ORGANISM: Plasmodium berghei

<400> SEQUENCE: 51

Ile Asn Leu Gln Asn Leu Asn Tyr Ile
1               5

<210> SEQ ID NO 52
<211> LENGTH: 9
<212> TYPE: PRT
<213> ORGANISM: Plasmodium berghei

<400> SEQUENCE: 52

Ile Ala Val Glu Asn Cys Asn Asn Ile
1               5
```